United States Patent [19]
Hsu et al.

[11] Patent Number: 6,013,836
[45] Date of Patent: *Jan. 11, 2000

[54] INSECTICIDAL N'-SUBSTITUTED-N,N'-DISUBSTITUTEDHYDRAZINES

[75] Inventors: Adam Chi-Tung Hsu, Lansdale; Harold Ernest Aller, Norristown; Dat Phat Le, North Wales; Donald Wesley Hamp, Lansdale; Barry Weinstein, Dresher; Raymond August Murphy, Philadelphia, all of Pa.

[73] Assignee: Rohm and Haas Company, Philadelphia, Pa.

[*] Notice: This patent is subject to a terminal disclaimer.

[21] Appl. No.: 08/443,871

[22] Filed: May 22, 1995

Related U.S. Application Data

[63] Continuation-in-part of application No. 08/300,871, Jun. 10, 1994, application No. 08/261,588, Jun. 17, 1994, application No. 07/843,487, Feb. 28, 1992, and application No. 08/129,549, Sep. 29, 1993, Pat. No. 5,530,028, which is a continuation-in-part of application No. 07/984,189, Nov. 23, 1992, Pat. No. 5,344,958, said application No. 08/300,871, is a continuation of application No. 07/688,357, Mar. 12, 1991, abandoned, which is a continuation of application No. 07/384,079, Jul. 17, 1989, abandoned, which is a continuation of application No. 06/911,177, Sep. 14, 1986, abandoned, which is a continuation-in-part of application No. 06/789,797, Oct. 21, 1985, Pat. No. 4,985,461, said application No. 08/261,588, is a division of application No. 07/843,487, which is a division of application No. 07/715,843, Jun. 14, 1991, Pat. No. 5,117,057, which is a continuation of application No. 07/091,687, Aug. 31, 1987, abandoned, which is a continuation-in-part of application No. 07/024,660, Mar. 11, 1987, abandoned, which is a continuation-in-part of application No. 06/821,187, Jan. 22, 1986, abandoned, application No. 06/858,482, May 1, 1986, abandoned, application No. 06/911,177, Sep. 14, 1996, abandoned, application No. 06/911,928, Sep. 26, 1986, abandoned, and application No. 07/012,380, Feb. 19, 1987, abandoned, which is a continuation-in-part of application No. 06/885,508, Jul. 14, 1986, abandoned, and application No. 07/005,824, Feb. 4, 1987, abandoned, which is a continuation-in-part of application No. 06/835,073, Feb. 28, 1986, abandoned.

[51] Int. Cl.⁷ .......... A01N 33/26; A01N 43/653; A01N 43/36; A01N 43/40

[52] U.S. Cl. .......... 564/149; 514/350; 514/378; 514/383; 514/423; 514/427; 514/448; 514/459; 514/464; 514/466; 514/475; 514/514; 514/546; 514/548; 514/615; 548/266.8; 548/560; 548/563; 548/571; 546/272.1; 546/337; 549/72; 549/425; 549/553; 558/415; 560/138; 564/150

[58] Field of Search .......... 548/560, 563; 549/436, 553; 558/415; 560/138; 564/149, 150; 514/427, 464, 466, 475, 514, 546, 548, 615

[56] References Cited

U.S. PATENT DOCUMENTS

| | | | |
|---|---|---|---|
| 3,481,972 | 12/1969 | Trepanier | 560/468 |
| 3,884,874 | 5/1975 | Rosenberger et al. | 524/191 |
| 4,062,934 | 12/1977 | Tilly et al. | 424/9.43 |
| 4,189,482 | 2/1980 | Truener et al. | 514/194 |
| 4,317,741 | 3/1982 | Lederle et al. | 252/77 |
| 4,357,351 | 11/1982 | Fancher et al. | 514/588 |
| 4,547,524 | 10/1985 | Kaneko et al. | 514/594 |
| 4,564,611 | 1/1986 | Stahler et al. | 514/99 |
| 5,530,028 | 6/1996 | Lidert et al. | 514/649 |

FOREIGN PATENT DOCUMENTS 1575720  7/1969  France.

OTHER PUBLICATIONS

Bull Chem Soc., pp. 624–627, 1954.
Zhur. Obs. Khim. pp. 1719–1723, 1955.
J. Chem. Soc., pp. 4191–4198, 1952.
J. Chem. Soc., pp. 4793–4800, 1964.
J. Prakt. Chem., pp. 197–201, 1967.
CA 84: 1501681j, 1975.
J.A.C.S., pp. 1557–1564, 1972.
J.A.C.S., pp. 2556–2567, 1922.
J.A.C.S., pp. 1030–1035, 1926.
J.A.C.S., pp. 4677–4681, 1966.
J.A.C.S., pp. 7406–7416, 1972.
Aust. J. Chem., pp. 523–529, 1972.
J.A.C.S., pp. 4336–4340, 1961.
J.O.C., pp. 808–815, 1978.
Tetrahedron Letters, pp. 3575–3578, 1979.
Acta, Chim. Scand., pp. 95–102, 1963.
Chem. Berichte, pp. 954–962, 1923.
J. Chem. Soc., pp. 1531–1536, 1966.
Annalen der Chemie, p. 1–36, 1954.
Zhur. Obs. Khim., pp. 2806–2809, 1962.

*Primary Examiner*—Peter O'Sullivan
*Attorney, Agent, or Firm*—Thomas D. Rogerson; Clark R. Carpenter; Terence P. Strobaugh

[57] ABSTRACT

This invention relates to N'-substituted-N,N'-disubstitutedhydrazines of formula I

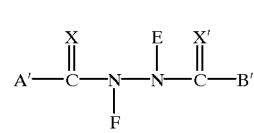

wherein X and X' are independently O, S, or NR; A' and B' are independently substituted or unsubstituted aryl or aromatic heterocycle; wherein F is alkyl, alkenyl, or aralkyl; and wherein E is a tertiary carbon containing organic radical having a total of at least four carbon and halogen atoms but not more than six halogen atoms, or a non-tertiary carbon containing non-haloalkyl organic or organometallic radical having at least five atoms other than hydrogen, oxygen and halogen which are useful as insecticides, compositions containing those compounds, methods of producing the compounds, and methods of their use. More particularly, the invention relates to insect growth regulating compounds and compositions, and methods of using such compounds and compositions. Compounds of the present invention are particularly suitable for controlling plant-destructive insects in crops of cultivated plants, ornamentals and forestry.

12 Claims, No Drawings

INSECTICIDAL N'-SUBSTITUTED-N,N'-DISUBSTITUTEDHYDRAZINES

BACKGROUND OF THE INVENTION

This application is a continuation-in-part of pending application Ser. No. 300,871 filed Jun. 10, 1994, which is a continuation of abandoned application Ser. No. 688,357 filed Mar. 12, 1991, which is a continuation of abandoned application Ser. No. 384,079 filed Jul. 17, 1989, which is a continuation of abandoned application Ser. No. 911,177 filed Sep. 14, 1986, which is a continuation-in-part of application Ser. No. 789,797, filed Oct. 21, 1985, now U.S. Pat. No. 4,985,461; and a continuation-in-part of pending application Ser. No. 261,588 filed Jun. 17, 1994, which is a division of pending application Ser. No. 843,487 filed Feb. 28, 1992, which is a division of application Ser. No. 715,843, filed Jun. 14, 1991, now U.S. Pat. No. 5,117,057, which is a continuation of abandoned application Ser. No. 091,687 filed Aug. 31, 1987, which is a continuation-in-part of abandoned application Ser. No. 024,660 filed Mar. 11, 1987, which is a continuation-in-part of abandoned application Ser. No. 821,187 filed Jan. 22, 1986, and a continuation-in-part of abandoned application Ser. No. 858,482 filed May 1, 1986, and a continuation-in-part of abandoned application Ser. No. 911,177, filed Sep. 14, 1986, and a continuation-in-part of abandoned application Ser. No. 911,928 filed Sep. 26, 1986, and a continuation-in-part of abandoned application Ser. No. 012,380 filed Feb. 19, 1987, which is a continuation-in-part of abandoned application Ser. No. 885,508 filed Jul. 14, 1986, and a continuation-in-part of abandoned application Ser. No. 005,824 filed Feb. 4, 1987, which is a continuation-in-part of abandoned application Ser. No. 835,073 filed Feb. 28, 1986; and a continuation-in-part of pending application Ser. No. 843,487; and continuation-in-part of pending application Ser. No. 129,549 filed Sep. 24, 1993, now U.S. Pat. No. 5,530,028, which is a continuation-in-part of application Ser. No. 984,189, filed Nov. 23, 1992, now U.S. Pat. No. 5,344,958.

This invention relates to N'-substituted-N,N'-disubstitutedhydrazines, which are useful as insecticides, compositions containing those compounds and methods of their use. More particularly, the invention relates to insect growth regulating compositions, and methods of using such compositions. Compounds of the present invention are particularly suitable for controlling plant-destructive insects in crops of cultivated plants, ornamentals and forestry.

The search for compounds which have a combination of excellent insecticidal activity and low undesirable toxicity is a continuing one because of factors such as the desire for compounds exhibiting greater activity, better selectivity, low undesirable environmental impact, low production cost and effectiveness against insects resistant to many known insecticides.

Certain hydrazine derivatives have been disclosed in the literature. However, none of the prior art literature suggests hydrazines derivatives having insect growth regulating characteristics.

U.S. Pat. No. 3,481,972 discloses 2-(beta-hydroxyethyl)-2-methyl acid hydrazine compounds of the formula $ZC(O)NHN(CH_3)CH_2CH_2OH$ where Z represents furyl, cyclohexyl, phenyl, benzyl, styryl, dihydrostyryl or substituted phenyl. The compounds are stated to be useful as pesticides for the control of such organisms as insects, arachnids, nematodes, fungi, plants and helminth organisms.

U.S. Pat. No. 4,062,934 discloses compounds of the formula

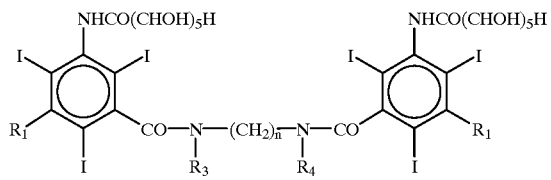

where $R_3$ and $R_4$ represent a hydrogen atom or a one to four alkyl and n is an integer from zero to four. These compounds are used as X-ray contrast media.

U.S. Pat. No. 4,189,482 discloses compounds of the formula

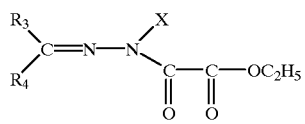

where $R_3$ is lower alkyl, or substituted or unsubstituted phenyl, benzyl, phenethyl, thienyl or furyl; $R_4$ is hydrogen or lower alkyl; and X is $-N_3$, $-CH_2-CH_2-OH$, $-CH_2CH_2$-halide and $-CH_2CH_2OSO_2CH_3$ as intermediates to penicillins having an imino substituted piperazindioncarbonylamino aceyl side chains.

U.S. Pat. No. 4,317,741 discloses a poly(oxyalkylated) hydrazine of the formula

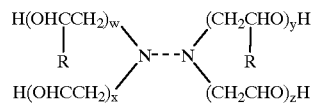

where R is hydrogen, $(C_1-C_4)$alkyl, phenyl or mixtures thereof and the sum of w, x, y and z is from about four to about 20. These compounds are used as corrosion inhibitors.

U.S. Pat. No. 4,357,351 discloses five specific compounds (Compound Nos. 400 and 402–404) of the formula

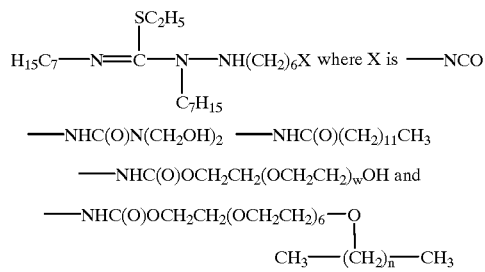

where n averages 7.7 and n' averages 11. These compounds are disclosed to have leptericidal activity. However, they are not claimed and it is not seen how these five compounds are included in the generic formula disclosed in the patent.

U.S. Pat. No. 4,547,524 discloses a class of benzoyl hydrazone derivatives which have insecticidal activity. However, the unsaturated carbon is bonded to hydrogen, lower alkyl, or phenyl, or forms part of a cyclohexane ring. Further the N'-substituent is not taught to include a tertiary carbon atom.

U.S. Pat. No. 4,564,611 discloses (di)thiophosphoric and -phosphonic acid derivatives having the formula

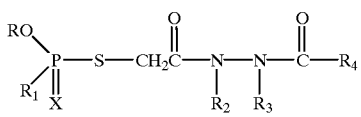

in which R denotes $(C_1-C_4)$-alkyl; $R_1$ denotes $(C_1-C_4)$-alkyl, $(C_1-C_4)$-alkoxy, $(C_1-C_4)$-alkylmercapto, $(C_1-C_4)$-alkylamino or di$(C_1-C_4)$alkylamino; $R_2$ and $R_3$ independently of one another denote hydrogen, $(C_1-C_4)$-alkyl, $(C_5-C_6)$-cycloalkyl, benzyl or furylmethyl; $R_4$ denotes $(C_1-C_4)$-alkyl, $(C_1-C_3)$-alkoxymethyl, $(C_1-C_3)$-alkylmercaptomethyl or phenyl and X denotes oxygen or sulfur, which have activity against sucking and biting insects, acarides and nematodes, and display good fungicidal activity. Insect growth regulating activity is not disclosed. Further, $R_2$ is not taught to include a tertiary carbon.

The Chemical Abstracts citation CA 84(21):150168j indicates that *Azerb Khim Zh,* 1975, (5), 47–8 discloses $Me_2CHCH_2CH=NN(Ac)CH_2CH_2OH$, $PhCH=NN(Ac)CH_2CH_2OH$ and $Me_2CHCH=NN(Ac)CH_2CH_2OH$ which have pesticidal activity.

In 88 *J.A.C.S,* 4677–4681 (1966) N'-t-butyl-N'-methylcarbonyl-N-benzoylhydrazine is disclosed. No biological activity is disclosed.

In 37 *Tetrahedron Letters,* 3575–3578 (1979), the result of an electron spin resonance study is reported. The hydrazyl radicals produced included PhC(O)N(t-Bu)NC(O)Ph and PhC(O)N(Et$_3$Si)NC(O)Ph. No utility was suggested for the radicals which were studied.

In 25 *Aust. J. Chem,* 523–529 (1972), several N,N'-dibenzoylhydrazine derivatives are disclosed including N'-i-propyl-; N'-n-propyl-; N'-(2-methylpropyl)-; N'-(3-methylbutyl)-; N'-benzyl- and N'-phenyl-N,N'-dibenzoylhydrazine in which one or both nitrogen atoms are alkylated or phenylated. No biological activity is disclosed for those compounds.

In 61 *Helv. Chim. Acta,* 1477–1510 (1978), several N,N'-dibenzoylhydrazine and hydrazide derivatives including N'-t-butyl-N-benzoyl-N'-(4-nitrobenzoyl)-hydrazine are disclosed. No biological activity is disclosed for those compounds.

In 44 *J.A.C.S.,* 2556–2567 (1922), isopropylhydrazine $(CH_3)_2CH-NH-NH_2$, symmetrical diisopropylhydrazine, dibenzoylisopropylhydrazine and certain derivatives are disclosed. No biological activity is disclosed for those compounds.

In 44 *J.A.C.S.,* 1557–1564 (1972), isopropyl, methyl and bornyl semicarbazides are disclosed. No biological activity is disclosed for those compounds.

In 48 *J.A.C.S.,* 1030–1035 (1926), symmetrical di-methylphenylmethylhydrazine and certain related compounds including 1,2-bis-methylphenylmethyl-4-phenyl-semicarbazide are disclosed. No biological activity is disclosed for those compounds.

In 27 *Bull. Chem. Soc. Japan,* 624–627 (1954), certain hydrazine derivatives including alpha,beta-dibenzoylphenylhydrazine are disclosed. No biological activity is disclosed for those compounds.

In *J. Chem. Soc.* (C), 1531–1536 (1966), N,N'-dibenzoylphenylhydrazine and N-acetyl-N'-benzoyl-p-nitrophenylhydrazine are disclosed. No biological activity is disclosed for those compounds.

In 56B *Chem. Berichte,* 954–962 (1923), symmetrical di-isopropylhydrazines, symmetrical diisobutyl- and certain derivatives including N,N'-diisobutyldibenzoyl-hydrazine are disclosed. No biological activity is disclosed for those compounds.

In 590 *Annalen der Chemie,* 1–36 (1954), certain N,N'-dibenzoylhydrazine derivatives are disclosed including N'-methyl- and N'-(2-phenyl)-isopropyl-N,N'-dibenzoylhydrazine. No biological activity is disclosed for those compounds.

In *J. Chem. Soc.* 4191–4198 (1952), N,N'-di-n-propylhydrazine, N,N'-dibenzoylhydrazine and bis-3,5-dinitrobenzoyl are disclosed. No biological activity is disclosed for those compounds.

In 32 *Zhur. Obs. Khim.,* 2806–2809 (1962), N'-2,4-methyl-2,4-pentadiene-N,N'-dibenzoylhydrazine is disclosed. No biological activity is disclosed.

In 17 *Acta. Chim. Scand.,* 95–102 (1963), 2-benzoylthiobenzoylhydrazide ($C_6H_5-CS-NHNH-CO-C_6H_5$) and certain hydrazone and hydrazine derivatives are disclosed including 1,2-dibenzoyl-benzylhydrazine. No biological activity is disclosed for those compounds.

In 25 *Zhur. Obs. Khim,* 1719–1723 (1955), N,N'-bis-cyclohexylhydrazine and N,N'-dibenzoylcyclohexylhydrazine are disclosed. No biological activity is disclosed for those compounds.

In *J. Chem. Soc.,* 4793–4800 (1964), certain dibenzoyl-hydrazine derivatives are disclosed including tribenzoylhydrazine and N,N'-dibenzoylcyclohexylhydrazine. No biological activity is disclosed for those compounds.

In 36 *J. Prakt. Chem.,* 197–201 (1967), certain dibenzoylhydrazine derivatives including N'-ethyl-; N'-n-propyl-; N'-isobutyl-; N'-neopentyl-; N'-n-heptyl-; and N'-cyclohexylmethyl-N,N'-dibenzoylhydrazines are disclosed. No biological activity is disclosed for those compounds.

In 26 *J.O.C.,* 4336–4340 (1961) N'-t-butyl-N,N'-di-(t-butoxycarbonyl)hydrazide is disclosed. No biological activity is disclosed.

In 41 *J.O.C.,* 3763–3765 (1976), N'-t-butyl-N-(phenylmethoxycarbonyl)-N'-(chlorocarbonyl)hydrazide is disclosed. No biological activity is disclosed.

In 94 *J.A.C.S.,* 7406–7416 (1972) N'-t-butyl-N,N'-dimethoxycarbonylhydrazide is disclosed. No biological activity is disclosed.

In 43 *J.O.C.,* 808–815 (1978), N'-t-butyl-N-ethoxycarbonyl-N'-phenylaminocarbonylhydrazide and N'-t-butyl-N-ethoxycarbonyl-N'-methylaminocarbonylhydrazide are disclosed. No biological activity is disclosed for those compounds.

In 39 *J. Econ. Ent.,* 416–417 (1946), certain N-phenyl-N'-acylhydrazines are disclosed and evaluated for their toxicity against codling moth larvae.

Compounds of the present invention are distinguished by their excellent insecticidal activity, particularly against insects of the orders Lepidoptera and Coleoptera, and most particularly by their insect growth regulating activity without material adverse impact on beneficial insects.

DETAILED DESCRIPTION OF THE INVENTION

This invention relates to compounds having the nucleus of the formula

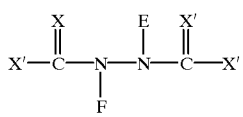

I wherein N is nitrogen; where X and X' are independently O, S, or NR, with R as defined below; wherein A' and B' are independently substituted or unsubstituted aryl or aromatic heterocycle; wherein F is hydrogen, alkyl, alkenyl, or aralkyl; wherein E is a tertiary carbon containing organic radical, a haloalkyl having a total of at least four carbon and halogen atoms but not more than six halogen atoms, or a non-tertiary carbon containing non-haloalkyl organic or organometallic radical having at least five atoms other than hydrogen, oxygen and halogen; provided that E is not a straight chain alkyl, —$CH_2CH_2N(CH_2CH_3)_2$, cyclohexyl, a six-membered cyclic containing organic radical, a cyclic aromatic radical, or an organic radical containing

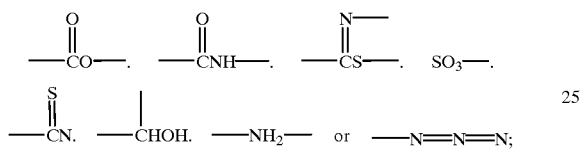

provided that E is not a sulfur or oxygen containing organic radical; provided that E does not have a chain length of non-hydrogen atoms greater than five; provided that when A' and B' are phenyl and F is hydrogen, then E is not neopentyl; provided that when A' is phenyl, F is hydrogen, and E is t-butyl, then B' is not 4-nitrophenyl; where organic radical is a radical comprising at least one carbon atom, but no metal atoms; and where organometallic radical is a radical containing a carbon-to-metal bond; or an agronomically acceptable salt thereof.

The invention also relates to a method of regulating insect growth which comprises contacting insects with a compound having the nucleus of Formula I, or an agronomically acceptable salt thereof.

Compounds of this invention with good insecticidal activity include those of Formula II:

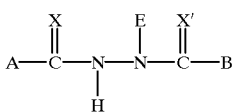

II wherein
X and X' are independently selected from O, S and NR, wherein R is selected from hydrogen and $(C_1-C_6)$alkyl;
E is selected from;
1. an unsubstituted tertiary-carbon containing $(C_4-C_{10})$ alkyl wherein the substituents are independently selected from 1 to 4 alkenyl, cyano, cycloalkyl, halogen, and phenyl and wherein the sum of non-hydrogen atoms in E is from 4 to 14, E does not have a chain length of non-hydrogen atoms greater than 5, and E does not contain more than one cyano group; and
2. an unsubstituted or substituted non-tertiary-carbon containing $(C_4-C_{10})$ alkyl wherein the substituents are independently selected from 1 to 4 alkenyl, cyano, cycloalkyl, halogen, phenyl, and trimethylsilyl and wherein the sum of non-hydrogen atoms in E is from 5 to 14, E does not have a chain length of non-hydrogen atoms greater than 5, and E does not contain more than one cyano group;

A and B are independently selected from;
1. unsubstituted or substituted naphthyl wherein the substituents are independently selected from 1 to 3 halo; nitro; $(C_1-C_4)$alkoxy; $(C_1-C_4)$alkyl; and amino;
2. unsubstituted or substituted phenyl wherein the substituents are independently selected from 1 to 5 halo; nitro; cyano; hydroxy; $(C_1-C_6)$alkyl; $(C_1-C_6)$ haloalkyl; $(C_1-C_6)$cyanoalkyl; $(C_1-C_6)$ hydroxyalkyl; $(C_1-C_6)$alkoxy; $(C_1-C_6)$haloalkoxy; $(C_1-C_6)$alkoxy$(C_1-C_6)$alkyl; $(C_1-C_6)$alkoxy $(C_1-C_6)$alkoxy; $(C_1-C_6)$alkylthio$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$ alkyl, or $(C_1-C_4)$alkoxy; $(C_2-C_6)$alkenyloxy; $(C_2-C_6)$alkenylcarbonyl; $(C_2-C_6)$ alkenyloxycarbonyloxy; $(C_2-C_6)$alkynyl optionally substituted with halo or $(C_1-C_4)$alkyl; carboxy; $(C_1-C_6)$alkylcarboxy$(C_1-C_6)$alkyl); $(C_1-C_6)$ alkylcarbonyl; $(C_1-C_6)$haloalkylcarbonyl; $(C_1-C_6)$ alkoxycarbonyl; $(C_1-C_6)$haloalkoxycarbonyl; $(C_1-C_6)$alkanoyloxy (—OCOR); $(C_1-C_6)$ alkoxycarbonyl$(C_1-C_6)$alkoxy; amino (—NRR'); carboxamido (—CONRR'); $(C_2-C_6)$ alkenylcarbonylamino; $(C_1-C_6)$ hydroxyalkylaminocarbonyl; aminocarbonyloxy (—OCONRR'); amido (—NRCOR'); alkoxycarbonylamino (—$NRCO_2R'$); thiocyanato; isothiocyanato; $(C_1-C_6)$thiocyanatoalkyl; $(C_1-C_6)$alkylthio; sulfoxide (—S(O)R); sulfonyl (—$SO_2R$); alkylsulfonyloxy (—$OSO_2R$); sulfonamide (—$SO_2NRR'$); alkylthiocarbonyl (—CSR); thioamido (—NRCSR'); unsubstituted or substituted phenyl wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino, and $(C_1-C_4)$dialkylamino having independently the stated number of carbon atoms in each alkyl group; unsubstituted or substituted phenoxy wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino, and $(C_1-C_4)$dialkylamino having independently the stated number of carbon atoms in each alkyl group; unsubstituted or substituted benzoyl wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino and $(C_1-C_4)$dialkylamino having independently the stated number of carbon atoms in each alkyl group; benzoyloxy$(C_1-C_6)$alkyl; phenylthio$(C_1-C_6)$alkyl wherein the phenyl ring is unsubstituted or substituted with 1 to 3 substituents independently selected from halo, cyano, nitro, $(C_1-C_4)$alkyl, $(C_1-C_4)$ haloalkyl, $(C_1-C_4)$alkoxy, carboxy, amino, $(C_1-C_4)$ alkylamino, and $(C_1-C_4)$dialkylamino having independently the stated number of carbon atoms in each alkyl group; imino (—CR=N—$R^2$) wherein $R^2$ is selected from hydroxy, $(C_1-C_4)$alkyl, $(C_1-C_4)$ alkoxy, amino (—NRR'), phenylamino, carbonyl (—COR), and benzoyl; acetylthiosemicarbazone; or when two adjacent positions on the phenyl ring are substituted with alkoxy groups, these groups, together with the carbon atoms to which they are attached, may be joined to form a 5 or 6 membered dioxolano or dioxano heterocyclic ring; and 3. unsubstituted or substituted five-membered heterocycle selected from furyl, thienyl, triazolyl, pyrrolyl, isopyrrolyl, pyrazolyl, isoimidazolyl, thiazolyl, isothiazolyl, oxazolyl, and isooxazolyl wherein the substituents are independently selected from 1 to 3 halo; nitro; hydroxy; $(C_1-C_6)$alkyl; $(C_1-C_6)$alkoxy; carboxy; $(C_1-C_6)$alkoxycarbonyl (—$CO_2R$); $(C_1-C_6)$alkylcarboxy$(C_1-C_6)$alkyl (—$RCO_2R'$); carboxamido (—CONRR'); amino (—NRR'); amido (—NRCOR'); $(C_1-C_6)$alkylthio; or unsubstituted or substituted phenyl wherein the substituents are independently selected from one to three halo, nitro, $(C_1-C_6)$alkyl, $(C_1-C_6)$haloalkyl; $(C_1-C_6)$alkoxy; $(C_1-C_6)$haloalkoxy; carboxy, $(C_1-C_4)$alkoxycarbonyl (—$CO_2R$); or amino (—NRR');

wherein R, R' and R'' are selected from hydrogen and $(C_1-C_6)$alkyl;

and agronomically acceptable salts thereof;

provided that when X and X' are O and A and B are unsubstituted phenyl, then E is other than isopropyl (—CH(CH$_3$)$_2$); 2-methylpropyl (—CH$_2$CH(CH$_3$)$_2$); 3-methylbutyl (—CH$_2$CH$_2$CH(CH$_3$)$_2$); neopentyl (2,2-dimethylpropyl; —CH$_2$C(CH$_3$)$_3$) or cyclohexylmethyl (—CH$_2$C$_6$H$_{11}$); or when X and X' are O, A is unsubstituted phenyl or phenyl substituted with 1 to 2 substituents independently selected from $(C_1-C_6)$alkyl, and B is unsubstituted phenyl or phenyl substituted with 1 to 2 substituents independently selected from halo, nitro, and $(C_1-C_6)$alkyl, then E is other than halo$(C_2-C_6)$ alkyl; or when X and X' are O, E is t-butyl (—C(CH$_3$)$_3$), and A is unsubstituted phenyl, then B is other than 4-nitrophenyl; and when one of A and B is an unsubstituted or substituted five-membered heterocycle the other of A and B is other than an unsubstituted or substituted five-membered heterocycle.

Because of their enhanced insecticidal activity, preferred compounds are those of Formula II wherein X and X' are independently selected from O and S; E is selected from (1) an unsubstituted or substituted tertiary-carbon containing $(C_3-C_{10})$ alkyl wherein the substituents are independently selected from 1 to 4 alkenyl, cyano, cycloalkyl, halogen, and phenyl and wherein the sum of non-hydrogen atoms in E is from 4 to 14, E does not have a chain length of non-hydrogen atoms greater than 5, and E does not contain more than one cyano group; (2) an unsubstituted or substituted non-tertiary-carbon containing $(C_4-C_{10})$ alkyl wherein the substituents are independently selected from 1 to 4 alkenyl, cyano, cycloalkyl, halogen, phenyl, and trimethylsilyl and wherein the sum of non-hydrogen atoms in E is from 5 to 14; and A and B are independently selected from (1) unsubstituted or substituted naphthyl wherein the substituents are independently selected from 1 to 3 halo; nitro; $(C_1-C_4)$ alkoxy; $(C_1-C_4)$alkyl; and amino; (2) unsubstituted or substituted phenyl wherein the substituents are independently selected from 1 to 5 halo; nitro; cyano; hydroxy; $(C_1-C_6)$ alkyl; $(C_1-C_6)$haloalkyl; $(C_1-C_6)$cyanoalkyl; $(C_1-C_6)$ hydroxyalkyl; $(C_1-C_6)$alkoxy; $(C_1-C_6)$haloalkoxy; $(C_1-C_6)$ alkoxy$(C_1-C_6)$alkyl; $(C_1-C_6)$alkoxy$(C_1-C_6)$alkoxy; $(C_1-C_6)$alkylthio$(C_1-C_6)$alkoxy; $(C_1-C_6)$alkanoyloxy $(C_1-C_6)$alkyl; $(C_2-C_6)$alkenyl optionally substituted with halo, cyano, $(C_1-C_4)$alkyl, or $(C_1-C_4)$alkoxy; $(C_2-C_6)$ alkenyloxy; $(C_2-C_6)$alkenylcarbonyl; $(C_2-C_6)$ alkenyloxycarbonyloxy; $(C_2-C_6)$alkynyl optionally substituted with halo or $(C_1-C_4)$alkyl; carboxy; $(C_1-C_6)$ alkylcarboxy$(C_1-C_6)$alkyl); $(C_1-C_6)$alkylcarbonyl; $(C_1-C_6)$ haloalkylcarbonyl; $(C_1-C_6)$alkoxycarbonyl; $(C_1-C_6)$ haloalkoxycarbonyl; $(C_1-C_6)$alkanoyloxy (—OCOR); $(C_1-C_6)$alkoxycarbonyl$(C_1-C_6)$alkoxy; amino (—NRR'); carboxamido (—CONRR'); $(C_2-C_6)$alkenylcarbonylamino; $(C_1-C_6)$hydroxyalkylaminocarbonyl; aminocarbonyloxy (—OCONRR'); amido (—NRCOR'); alkoxycarbonylamino (—NRCO$_2$R'); thiocyanato; isothiocyanato; $(C_1-C_6)$ thiocyanatoalkyl; $(C_1-C_6)$alkylthio; sulfoxide (—S(O)R); sulfonyl (—SO$_2$R); alkylsulfonyloxy (—OSO$_2$R); sulfonamide (—SO$_2$NRR'); alkylthiocarbonyl (—CSR); thioamido (—NRCSR'); unsubstituted or substituted phenyl wherein the substituents are independently selected from 1 to 3 halo, cyano, nitro, $(C_1-C_4)$alkyl, $(C_1-C_4)$haloalkyl, $(C_1-C_4)$ alkoxy, carboxy, amino, $(C_1-C_4)$alkylamino, and $(C_1-C_4)$ dialkylamino having independently the stated number of carbon atoms in each alkyl group; unsubstituted or substituted phenoxy wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$ alkylamino, and $(C_1-C_4)$dialkylamino having independently the stated number of carbon atoms in each alkyl group; unsubstituted or substituted benzoyl wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino and $(C_1-C_4)$ dialkylamino having independently the stated number of carbon atoms in each alkyl group; benzoyloxy$(C_1-C_6)$alkyl; phenylthio$(C_1-C_6)$alkyl wherein the phenyl ring is unsubstituted or substituted with 1 to 3 substituents independently selected from halo, cyano, nitro, $(C_1-C_4)$alkyl, $(C_1-C_4)$ haloalkyl, $(C_1-C_4)$alkoxy, carboxy, amino, $(C_1-C_4)$ alkylamino, and $(C_1-C_4)$dialkylamino having independently the stated number of carbon atoms in each alkyl group; imino (—CR=N—R$^2$) wherein R$^2$ is selected from hydroxy, $(C_1-C_4)$alkyl, $(C_1-C_4)$alkoxy, amino (—NRR'), phenylamino, carbonyl (—COR), and benzoyl; acetylthiosemicarbazone; or when two adjacent positions on the phenyl ring are substituted with alkoxy groups, these groups, together with the carbon atoms to which they are attached, may be joined to form a 5 or 6 membered dioxolano or dioxano heterocyclic ring; and agronomically acceptable salts thereof.

Because of their excellent insecticidal activity, more preferred compounds are those of Formula II wherein X and X' are O or S; F is branched $(C_3-C_8)$alkyl; A and B are the same or different unsubstituted naphthyl or unsubstituted or substituted phenyl wherein the substituents are independently selected from 1 to 5 halo; nitro; cyano; lower $(C_1-C_4)$alkyl; lower $(C_1-C_4)$haloalkyl; lower $(C_1-C_4)$cyanoalkyl; lower $(C_1-C_4)$alkoxy; lower $(C_1-C_4)$alkoxyalkyl having independently the stated number of carbon atoms in each alkyl group; carbonyl (—COR); lower $(C_1-C_4)$alkoxycarbonyl; lower $(C_1-C_4)$alkanoyloxy; thiocyanato; unsubstituted or substituted phenyl having one or two of the same or different halo, nitro, $(C_1-C_4)$alkyl, $(C_1-C_4)$alkoxy, carboxy, amino, $(C_1-C_4)$alkylamino or $(C_1-C_4)$dialkylamino having independently the stated number of carbon atoms in each alkyl group; or phenoxy where the phenyl ring is unsubstituted or substituted with one or two of the same or different halo, nitro, $(C_1-C_4)$alkyl, $(C_1-C_4)$alkoxy, carboxy, amino, $(C_1-C_4)$alkylamino or $(C_1-C_4)$dialkylamino having independently the stated number of carbon atoms in each alkyl group where R is hydrogen or ($C_1$–$C_4$)alkyl; and agronomically acceptable salts thereof.

Because of their outstanding insecticidal activity, even more preferred compounds are those of Formula II wherein X and X' are O; E is branched ($C_4$–$C_7$)alkyl; A and B are independently selected from unsubstituted or substituted phenyl wherein the substituents are independently selected from 1 to 3 halo, nitro, ($C_1$–$C_4$)alkyl, ($C_1$–$C_4$)alkoxy, or ($C_1$–$C_4$)haloalkyl; and agronomically acceptable salts thereof. Most preferred are those compounds of Formula II wherein X and X' are O, E is selected from tertiary butyl, neopentyl (2,2-dimethylpropyl), and 1,2,2-trimethylpropyl; A and B are independently selected from unsubstituted phenyl or substituted phenyl wherein the substituents are independently selected from 1 to 3 chloro, fluoro, bromo, iodo, nitro, methyl, ethyl, methoxy, trifluoromethoxy, and trifluoromethyl; and agronomically acceptable salts thereof.

The pattern of substitution on A and B, when A and B are substituted phenyl, affects the insecticidal activity. The preferred pattern are represented by Formula III:

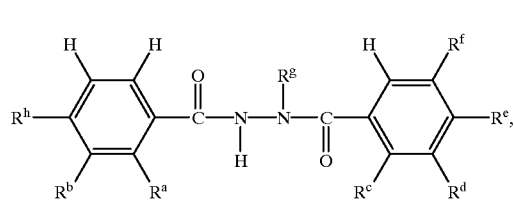

III

The more preferred substituent patterns for the left-side phenyl group of Formula III is wherein $R^a$ and $R^b$ are other than hydrogen and $R^h$ is hydrogen or wherein $R^h$ is other than hydrogen and $R^a$ and $R^b$ are hydrogen. The more preferred substituent pattern for the right-side phenyl group of Formula III is wherein $R^c$ and $R^e$ are hydrogen and wherein $R^d$ and $R^f$ are other than hydrogen. Preferred compounds of Formula III are wherein $R^a$ is selected from hydrogen, halo and ($C_1$–$C_6$)alkyl; $R^b$ is selected from hydrogen and unsubstituted or halo (preferably fluoro) substituted ($C_1$–$C_6$)alkoxy; $R^c$ is selected from hydrogen, halo, ($C_1$–$C_6$) alkyl, ($C_1$–$C_6$)alkoxy, ($C_1$–$C_6$)alkoxy($C_1$–$C_6$)alkyl, and nitro; $R^d$, $R^e$ and $R^f$ are each independently selected from hydrogen, bromo, chloro, fluoro, ($C_1$–$C_6$)alkyl, ($C_1$–$C_6$) alkoxy, and ($C_1$–$C_6$)alkoxy($C_1$–$C_6$)alkyl; $R^g$ is a branched ($C_4$–$C_6$)alkyl; $R^h$ is selected from hydrogen, ($C_1$–$C_6$)alkoxy, ($C_1$–$C_6$)alkyl, or when taken together with $R^b$ is methylenedioxy (—OCH$_2$O—), 1,2-ethylenedioxy (—OCH$_2$CH$_2$O—), 1,2-ethyleneoxy (—CH$_2$CH$_2$O—) or 1,3-propyleneoxy (—CH$_2$CH$_2$CH$_2$O—) wherein an oxo atom is located at the $R^b$ position; and the substituent pairs selected from $R^c$ and $R^d$, and $R^d$ and $R^e$, and $R^e$ and $R^f$ when taken together can be methylenedioxy or 1,2-ethylenedioxy; provided that one of $R^a$ and $R^b$ and $R^h$ must be other than hydrogen and that one of $R^c$ and $R^d$ and $R^e$ and $R^f$ must be other than hydrogen; and agronomically acceptable salts thereof.

The term "halo" should be understood as including chloro, fluoro, bromo and iodo. The term "alkyl" by itself or as a part of another substituent, unless otherwise stated, includes straight or branched chain groups such as methyl, ethyl, n-propyl, isopropyl, n-butyl, t-butyl, isobutyl, neopentyl and the like and, where indicated, higher homologues and isomers such as n-octyl, isooctyl and the like. The term "haloalkyl" by itself or as part of another substituent is an alkyl group of the stated number of carbon atoms having one or more halo atoms bonded thereto such as chloromethyl, 1- or 2-bromoethyl, trifluoromethyl and the like. Analogously, "cyanoalkyl" by itself or as part of another group is an alkyl group of the stated number of carbon atoms having one or more cyano groups bonded thereto; "haloalkoxy" by itself or as part of another group is an alkoxy group of the stated number of carbon atoms having one or more halo atoms bonded thereto such as difluoromethoxy, trifluoromethoxy, 2-fluoroethoxy, 2,2,2-trifluoroethoxy and the like. "Alkenyl" and "alkynyl" by themselves or as part of another substituent comprise straight and branched chain groups of the stated number of carbon atoms. "Alkadienyl" is a straight or branched chain alkenyl group comprising two carbon-to-carbon double bonds that can be conjugated such as 1,3-butadienyl, cumulated such as 1,2-propadienyl or isolated such as 1,4-pentadienyl.

The term "organic radical" should be understood to mean a radical comprising at least one carbon atom but no metal atoms. Examples of organic radicals include alkyl, alkenyl, alkynyl, cycloalkyl, cycloalkenyl, cycloalkynyl, aryl, heterocycles, esters, ethers, thio derivatives and amine derivatives.

The term "organometallic radical" should be understood to include radicals containing a carbon-to-metal bond. Examples of such radicals include trimethylsilyl.

The term "tertiary carbon" is meant to refer to a carbon having at least three carbon-to-carbon single bonds.

The term "aryl" should be understood to include those molecules which have a ring structure characteristic of benzene, naphthalene, phenanthrene and anthracene, that is either the six-carbon ring of benzene or the condensed six-carbon rings of other aromatic derivatives. Examples of aryl radicals include unsubstituted and substituted phenyl, benzyl and naphthalene.

The term "cyclic aromatic radical" should be understood to mean unsaturated cyclic compounds including heterocyclic compounds. Examples of cyclic aromatic radicals include aryl, indolyl, thienyl, furyl, pyrrolyl, triazolyl and tetrazolyl.

Representative examples of six-membered heterocycles having one, two, three or four nitrogen atoms and two to five nuclear carbon atoms include 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 3-pyrazinyl, 2-(1,3,5-triazinyl), 3-(1,2,4-triazinyl), 5-(1,2,4-triazinyl), 6-(1,2,4-triazinyl), 4-(1,2,3-triazinyl) and 5-(1,2,3-triazinyl).

Representative examples of five-membered heterocycles include 2-furyl; 3-furyl; 2-thienyl; 3-thienyl; 4-(1,2,3-triazolyl); 3-(1,2,4-triazolyl); 5-(1,2,4-triazolyl), 2-pyrrolyl; 2-oxazolyl; and the like.

Those N'-substituted-N,N'-diacylhydrazines of Formula I which possess acidic or basic functional groups may be further reacted to form novel salts with appropriate bases or acids. These salts also exhibit pesticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. The ammonium salts include those in which the ammonium cation has the formula NR$^5$R$^6$R$^7$R$^8$ wherein each of R$^5$, R$^6$, R$^7$ and R$^8$ are independently hydrogen, hydroxy, ($C_1$–$C_4$)alkoxy, ($C_1$–$C_{20}$)alkyl, ($C_3$–$C_8$)alkenyl, ($C_3$–$C_8$) alkynyl, ($C_2$–$C_8$)hydroxyalkyl, ($C_2$–$C_8$)alkoxyalkyl, ($C_2$–$C_6$)aminoalkyl, ($C_2$–$C_6$)haloalkyl, amino, ($C_1$–$C_4$) alkyl- or ($C_1$–$C_4$)dialkylamino, substituted or unsubstituted phenyl, substituted or unsubstituted phenylalkyl, having up to four carbon atoms in the alkyl moiety, or any two of $R^5$, $R^6$, $R^7$ or $R^8$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^5$, $R^6$, $R^7$ or $R^8$ can be taken together to form with the nitrogen atom a 5- or 6-membered aromatic heterocyclic ring, such as piperazole or pyridine. When $R^5$, $R^6$, $R^7$ or $R^8$ substituent in the ammonium group is a substituted phenyl or substituted phenylalkyl, the substituents on the phenyl and phenylalkyl will generally be selected from halo, ($C_1$–$C_8$)alkyl, ($C_1$–$C_4$)alkoxy, hydroxy, nitro, trifluoromethyl, cyano, amino, ($C_1$–$C_4$)alkylthio and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxy-ethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as hydrochloride, hydrobromide, sulfate, nitrate, perchlorate, acetate, oxalate and the like.

For insects to successfully grow, that is progress from one larval stage to the next larger larval stage or metamorphose to an adult stage, they must moult or shed the old cuticle. Compounds of this invention are insect growth regulators in that they interfere with this natural moulting and other growth-regulated processes.

Growth regulatory effects are not usually expressed rapidly after treatment. This is contrary to conventional insecticides, such as neurotoxins, respiratory poisons and the like, which affect vital processes and which are noted for rapidity of effect.

For example, compounds such as:

($R^1$)$_2$—P(X)X(CH$_2$)$_n$C(O)NHN(R")C(O)C$_5$H$_6$, where $R^1$=lower alkyl, alkoxy, thioalkyl and may be identical or different, X=O or S, n=0–5, and R"=t-butyl would constitute conventional, fast-acting, cholinesterase-inhibiting neurotoxins with efficacy anticipated against a comparatively broad range of insect orders and acarides as well as non-target organisms such as mammals, fish and birds. By contrast insect growth regulators as claimed herein would be somewhat less rapid in effect with activity being confined to particular insects which are largely pestiferous and including those strains resistant to organophosphate insecticides. Although somewhat slower to act than conventional cholinesterese-inhibiting neurotoxins, compounds of this invention are sufficiently rapid-acting so as to protect agricultural crops and are therefore superior to other known insect growth regulators which are quite slow to elicit effects.

The present inventors have found that the following parameters are important to yield compounds having the nucleus of Formula I which are insect growth regulators. A and B should have some bulk. However, if the bulk becomes too great, the compounds become less effective as insect growth regulators. Therefore, A and B should independently contain no more than about 21 non-hydrogen atoms.

The size of the moiety E of Formula I is important. E should have at least 4 non-hydrogen atoms. Oxygen containing radicals have been found to be generally not preferred. If oxygen is present, generally E should be bulkier. Moieties containing two oxygen atoms or one oxygen and one sulfur atom are less preferred. It is preferred that E have no greater than 10 non-hydrogen atoms. Preferably, E does not include a chain of greater than four or five non-hydrogen atoms but is highly branched.

The compounds of this invention or their precursors can be prepared according to the following processes. Process A can be used when preparing compounds according to Formula II below where X and X' are both oxygen and A and B are the same (for example, both A and B are phenyl or 4-chlorophenyl) or different (for example, A is 4-methylphenyl and B is 4-chlorophenyl).

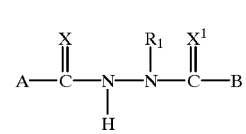
II wherein A and B are organic radicals attached to the carbon shown in Formula II by a carbon-to-carbon single bond and $R^1$ is other than hydrogen.

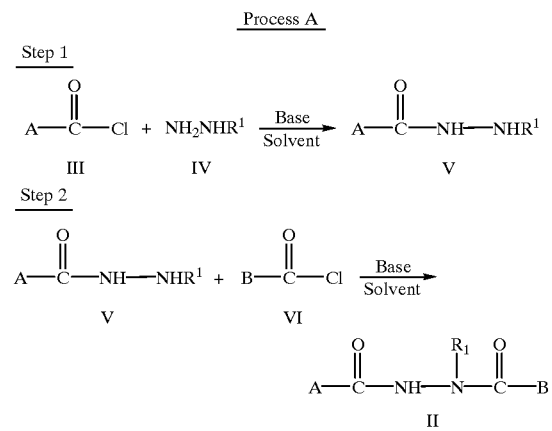

where $R^1$, A and B are as defined above for Formula II and X and X' are oxygen.

When $R^1$ is cyano substituted alkyl the intermediate Va may be made as follows:

Step 1a

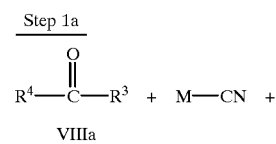
VIIIa

-continued

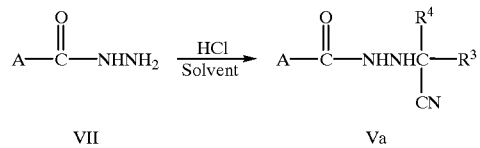

where M is K or Na, X and X' are oxygen, A and B are as defined above for Formula II, and $R_3$ and $R_4$ are the same or different hydrogen or $(C_2-C_9)$ straight or branched chain unsubstituted or substituted alkyl having one or two of the same or different $(C_3-C_6)$cycloalkyl;

Process B can be used when preparing compounds according to Formula II where X and X' are oxygen, and $R^1$, A and B are as defined above for Formula II.

Process B:
Method 1

Step 1

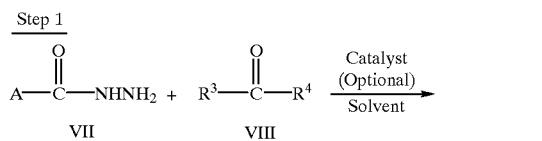

Step 2

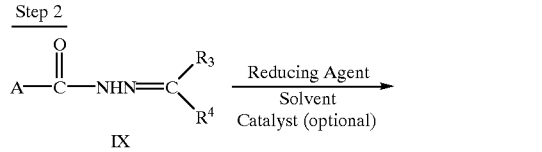

Step 3

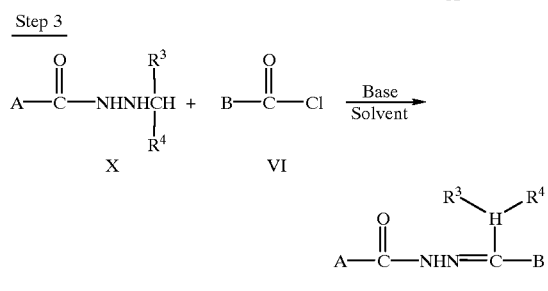

where X and X' are oxygen, A and B are as defined above for Formula II, and $R^3$ and $R^4$ are the same or different hydrogen or $(C_2-C_9)$ straight or branched chain unsubstituted or substituted alkyl having one or two of the same or different $(C_3-C_6)$cycloalkyl. As can be seen above, the intermediate product of Step 2, the compounds of Formula X, corresponds to the compounds of Formula V. In addition, the compound of Formula XI corresponds to the compounds of Formula II where X and X' are oxygen.

Method 2

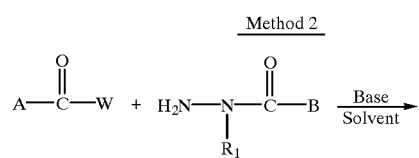

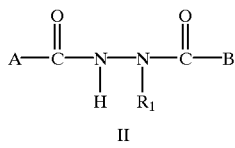

or

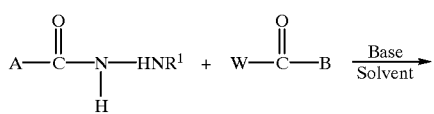

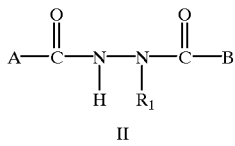

where $R^1$, A and B are as defined above for Formula II and W is a good leaving group such as halo, for example, chloro; an alkoxy, for example, ethoxy; methyl sulfonate ($—OSO_2CH_3$); or an ester, for example, acetate ($—OC(O)CH_3$).

Process C can be used when preparing compounds according to Formula II where A, B and $R^1$ are as defined for Formula II and one or both X and X' are sulfur.

Process C:

Step 1:

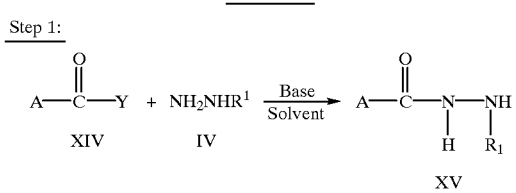

Step 2:

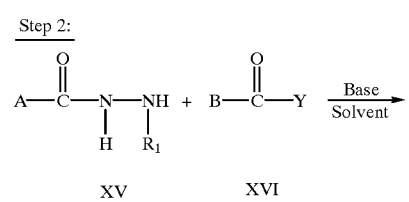

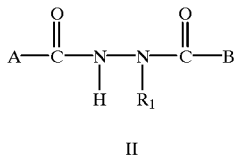

where A, B and $R^1$ are as defined above for Formula II and one or both X and X' are sulfur, and Y is a good leaving group such as carboxyalkylthio (for example, carboxymethylthio, $—SCH_2CO_2H$); alkylthio (for example, methylthio); or halo (for example, chloro).

Process D can be used when preparing compounds according to Formula II where X and X' are oxygen and $R^1$, A and B are as defined above for Formula II.

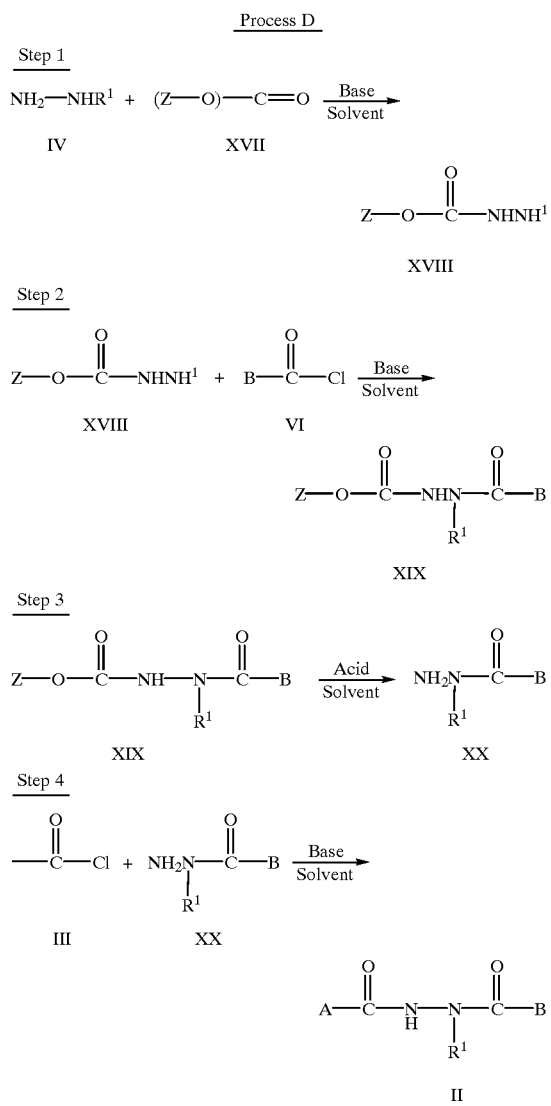

wherein A, B and $R^1$ are as defined above for Formula II and Z is t-butyl; ethyl; phenyl; or benzyl.

The starting materials for each process are generally commercially available, or can be prepared by generally customary and known methods.

Other compounds of this invention or their precursors can be prepared by reacting a suitably substituted hydrazine (Formula II) with an alkyl halide, allyl halide or phenylmethylhalide in the presence of a base in an inert or substantially inert solvent or mixture of solvents according to the following process:

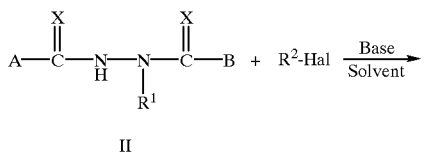

-continued

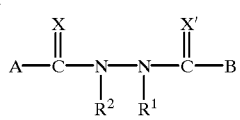

where X, X', $R^1$, $R^2$, A and B are as defined above for Formula II and Hal is halogen (chloro, fluoro or bromo).

Suitable bases for use in the above process include metal hydrides such as sodium hydride or potassium hydride; metal alkoxides such as sodium alkoxides or potassium alkoxides; sodium hydroxide; potassium hydroxide; or lithium diisopropyl amide. If desired, mixtures of these bases may be used. The preferred base is potassium t-butoxide.

Suitable solvents for use in the above process include ethers such as tetrahydrofuran (THF), glyme and the like; dimethylformamide (DMF); dimethylsulfoxide (DMSO); acetonitrile; or a mixture of water and benzene or toluene. If desired, mixtures of these solvents may be used. The preferred solvent is dimethylformamide.

The above process can be carried out at temperatures between about $-20°$ C. and about $100°$ C. Preferably, this reaction is carried out between about $-5°$ C. and about $50°$ C.

Preparation of the compounds of the present invention by the above process is preferably carried out at about atmospheric pressure although higher or lower pressures can be used if desired.

Substantially equimolar amounts of reactants are preferably used although higher or lower amounts can be used if desired.

Generally one equivalent of base is used per equivalent of starting material of Formula XXI.

The compounds of Formula XXI are generally commercially available or can be prepared by known procedures.

Modifications to the above process may be necessary to accommodate reactive functionalities of particular substituents. Such modifications would be apparent and known to those skilled in the art.

In process A, a compound of Formula III is reacted with a monosubstituted hydrazine of Formula IV or a corresponding acid addition salt such as the hydrochloride salt or the like in the presence of a base in an inert or substantially inert solvent or mixture of solvents to afford an intermediate product of Formula V which can be isolated or further reacted with a compound of Formula VI in the presence of a base in an inert or substantially inert solvent or mixture of solvents to afford the desired product of Formula II.

When A and B are the same, for example, both A and B are 4-chlorophenyl, two equivalents of a compound of Formula III or VI are reacted with a monosubstituted hydrazine of Formula IV in the presence of a base in an inert or substantially inert solvent or mixture of solvents to afford the desired product of Formula II.

Examples of the compounds of Formula III and/or Formula VI which can be used in the above processes include benzoyl chloride, 4-chlorobenzoyl chloride, 4-methylbenzoyl chloride, 3,5-dichlorobenzoyl chloride, 2-bromobenzoyl chloride, 3-cyanobenzoyl chloride, 3-toluoyl chloride, 4-toluoyl chloride, 4-ethylbenzoyl chloride, 2-nitrobenzoyl chloride, 2,3-dimethylbenzoyl chloride, 2-nitro-5-toluoyl chloride, cyclohexylcarbonyl chloride, n-butanoyl chloride, n-pentanoyl chloride, phenylacetyl chloride, 1-cyclohexenecarbonyl chloride, pivaloyl chloride, trichloroacetyl chloride, methacryloyl chloride and the like. The compounds of Formula III and/or Formula VI are generally commercially available or can be prepared by known procedures.

Examples of the compounds of Formula IV which can be used in the above processes include isopropylhydrazine, t-butylhydrazine, neopentylhydrazine, alphamethylneopentylhydrazine, isobutylhydrazine, isopentylhydrazine, isooctylhydrazine, 1,1-dimethyl-3-butenylhydrazine, (trimethylsilylmethyl)hydrazine, (1,1,1-trifluoro-2-propyl)hydrazine, (2,2,2-trifluoroethyl) hydrazine, (1-cyano-1-methyl)ethylhydrazine and the like. The compounds of Formula IV are generally commercially available or can be prepared by known procedures. For example, the Grignard reagent addition product of acetone azine in diethyl ether is hydrolyzed by the addition of an acid (such as oxalic acid), in a suitable solvent or mixture of solvents (such as ethanol and diethyl ether, 1:1) to afford the monosubstituted hydrazine of Formula IV.

Suitable solvents for use in the above processes include water; alcohols such as methanol, ethanol, isopropanol and the like; hydrocarbons such as toluene, xylene, hexane, heptane and the like; glyme; tetrahydrofuran; acetonitrile; pyridine; or haloalkanes such as methylene chloride or mixtures of these solvents.

Preferred solvents are water, toluene, methylene chloride or a mixture of these solvents.

Examples of bases for use in the above processes include tertiary amines such as triethylamine; pyridine; potassium carbonate; sodium carbonate; sodium bicarbonate; sodium hydroxide; or potassium hydroxide. Preferred bases are sodium hydroxide, potassium hydroxide or triethylamine.

In Process B, Method 1, a compound of Formula VII is reacted with a ketone or aldehyde of Formula VIII in an inert or substantially inert solvent or mixture of solvents and optionally in the presence of a catalyst to afford an intermediate product of Formula IX. The intermediate product of Formula IX is then further reacted with a reducing agent in an inert or substantially inert solvent or mixture of solvents to afford a second intermediate product of Formula X which can be isolated or further reacted with a compound of Formula VI in the presence of a base in an inert or substantially inert solvent or mixture of solvents to afford the desired product of Formula XI.

Examples of the compounds of Formula VII which can be used in the above Process B, Method 1, include benzoylhydrazine, 4-chlorobenzoylhydrazine, 2-methylbenzoylhydrazine, 4-methylbenzoylhydrazine, 3,5-dichlorobenzoylhydrazine and the like. The compounds of Formula VII are generally commercially available or can be prepared by known procedures.

Examples of the compounds of Formula VIII which can be used in the above Process B, Method 1, include 1,1,1-trimethylacetaldehyde, methylethylketone, diethylketone, trifluoroacetone, methacrolein, ethyl pyruvate and the like. The compounds of Formula VIII are generally commercially available or can be prepared by known procedures.

Optionally, a catalyst may be used in Step 1, Method 1 of Process B. Suitable catalysts generally include organic acids such as acetic acid, trifluoroacetic acid, oxalic acid and the like; mineral acids such as hydrochloric acid, sulfuric acid, nitric acid and the like; arylsulfonic acids such as toluenesulfonic acid; or pyridinium toluenesulfonate. Preferred catalysts are organic acids or arylsulfonic acids. Most preferred catalysts are acetic acid or trifluoroacetic acid.

Suitable solvents for use in the above Process B, Method 1, Step 1, include alcohols such as methanol, ethanol, isopropanol and the like; hydrocarbons such as toluene, benzene; ethers such as tetrahydrofuran (THF), glyme and the like; or dimethylformamide. Preferred solvents are alcohols and hydrocarbons. Most preferred solvents are alcohols such as methanol or ethanol.

Examples of suitable reducing agents for use in the above Process B, Method 1, Step 2, include hydrides such as sodium borohydride and derivatives thereof such as sodium cyanoborohydride, lithium aluminum hydride and derivatives thereof and the like; or diborane. Preferred reducing agents are sodium borohydride and derivatives thereof or lithium aluminum hydride and derivatives thereof. Most preferred as reducing agents are borane and diborane.

Optionally, in Process B, Method 1, Step 2, a catalyst may be included. Examples of suitable catalysts include organic acids such as acetic acid, trifluoroacetic acid; or mineral acids such as hydrochloric acid, sulfuric acid and the like. Preferred catalysts are organic acids or hydrochloric acid. Most preferred catalysts are acetic acid, trifluoroacetic acid or hydrochloric acid.

Suitable solvents for use in the above Process B, Method 1, Step 2, include alcohols such as methanol, ethanol, isopropanol and the like; ethers such as tetrahydrofuran (THF), diethylether, glyme and the like; or halohydrocarbons such as methylene chloride, chloroform and the like. Preferred solvents are alcohols and most preferred are methanol or ethanol.

Step 3 of Process B, Method I corresponds to Step 2 of Process A. Consequently, those bases and solvents suitable for use in Step 2 of Process A are suitable for use in Step 3, Method 1 of Process B including the preferred bases and solvents described above.

In Process B, Method 2, N'-substituted-N'-benzoylhydrazine of Formula XIII or N'-substituted-N-benzoylhydrazine of Formula XIIIa is reacted with a compound of Formula XII in the presence of a base in an inert or substantially inert solvent or mixture of solvents to afford the desired product of Formula II.

The compounds of Formula XII are generally commercially available or can be prepared from commercially available compounds by procedures well known to those skilled in the art as described below.

Examples of the compounds of Formula XIII which can be used in the above Process B, Method 2, include N'-t-butyl-N'-benzoylhydrazine; N'-t-butyl-N'-(3-methylbenzoyl)hydrazine; N'-t-butyl-N'-(4-chlorobenzoyl) hydrazine; N'-t-butyl-N'-(2-fluorobenzoyl)hydrazine; N'-isopropyl-N'-benzoylhydrazine; N'-neopentyl-N'-(4-chlorobenzoyl)hydrazine, N'-isopropyl-N-benzoylhydrazine; N'-sec-butyl-N-benzoylhydrazine; N'-(1-methyl)neopentyl-N-benzoylhydrazine; N'-neopentyl-N-benzoylhydrazine; N'-isobutyl-N-benzoylhydrazine; N'-(1,2,2-trimethylpropyl)-N-benzoylhydrazine; N'-diisopropylmethyl-N-benzoylhydrazine; N'-t-butyl-N-benzoylhydrazine; N'-t-butyl-N-(4-methylbenzoyl) hydrazine; N'-t-butyl-N-(4-chlorobenzoyl)hydrazine; N'-(1, 1-dimethyl-3-butenyl)-N'-benzoylhydrazine, N'-(trimethylsilylmethyl)-N'-(4-methylbenzoyl)hydrazine, N'-(1,1,1-trifluoro-2-propyl)-N'-(2,4-dichlorobenzoyl) hydrazine, N'-(1-cyano-1-methyl)ethyl-N'-(2-methylbenzoyl)hydrazine and the like.

Suitable solvents for use in the above Process B, Method 2, include water; hydrocarbons such as toluene, xylene, hexane, heptane and the like; alcohols such as methanol, ethanol, isopropanol, and the like; glyme; tetrahydrofuran; acetonitrile; pyridine; or haloalkanes such as methylene chloride; or mixtures of these solvents. Preferred solvents are water, toluene, methylene chloride or a mixture of these solvents.

Examples of bases suitable for use in the above Process C includes tertiary amines such as triethylamine; pyridine; potassium carbonate; sodium carbonate; sodium bicarbonate; sodium hydroxide; or potassium hydroxide. Preferred bases are sodium hydroxide, or triethylamine.

The compounds of Formula XII are commercially available, such as nicotinoyl chloride hydrochloride, isonicotinoyl chloride hydrochloride and ethyl picolinate or can be prepared from commercially available materials by procedures known to those skilled in the art.

The compounds of Formula XIII can be prepared by procedures known to those skilled in the art from commercially available reactants. By way of example, a suitably substituted hydrazine (such as t-butyl-hydrazine or (1,1,1-trifluoro-2-propyl)hydrazine) is reacted with an aldehyde or ketone (such as acetone) in the presence of a base (such as triethylamine) to afford a hydrazone which is then reacted with a benzoyl chloride in an inert or substantially inert solvent or mixture of solvents in the presence of a base (such as sodium hydroxide) to afford an N'-substituted-N'-benzoylhydrazone which is then reacted with an acid (such as hydrochloric acid) to afford the compound of Formula XIII. Alternatively, a suitable substituted hydrazine (such as t-butyl-hydrazine or (trimethylsilylmethyl)hydrazine) is reacted with di-tert-butyldicarbonate in an inert or substantially inert solvent or mixture of solvents (such as toluene/water) to afford an N'-t-butyl-N-t-butoxycarbonylhydrazine or an N'-(trimethylsilylmethyl)-N-t-butoxycarbonylhydrazine which is then reacted with a benzoylchloride in an inert or substantially inert solvent or mixture of solvents to afford N'-t-butyl-N'-benzoyl-N-t-butoxycarbonylhydrazine or an N'-(trimethylsilylmethyl)-N'-benzoyl-N-t-butoxycarbonylhydrazine which is then reacted with an acid to afford the desired compound of Formula XIII.

In Process C, a compound of Formula XIV is reacted with a monosubstituted hydrazine of Formula IV or a corresponding acid addition salt such as the hydrochloride salt or the like in the presence of a base in an inert or substantially inert solvent or mixture of solvents to afford an intermediate compound of Formula XV which can be isolated or further reacted with a compound of Formula XVI in the presence of a base in an inert or substantially inert solvent or mixture of solvents to afford the desired product of Formula I.

In Process D, a monosubstituted hydrazine of Formula IV or a corresponding acid addition salt, such as the hydrochloride salt or the like, is reacted with a compound of Formula XVII in the presence of a base in an inert or substantially inert solvent or mixture of solvents to afford an intermediate product of Formula XVIII. The intermediate product of Formula XVIII is then further reacted with a compound of Formula VI in the presence of a base in an inert or substantially inert solvent or mixture of solvents to afford a second intermediate product of Formula XIX. The second intermediate product of Formula XIX is then further reacted with an acid in an inert or substantially inert solvent or mixture of solvents to afford a third intermediate product of Formula XX. The third intermediate product of Formula XX is then further reacted with a compound of Formula III in the presence of a base in an inert or substantially inert solvent or mixture of solvents to afford the desired product of Formula II.

Examples of the compounds of Formula XVII which can be used in the above Process D include di-t-butyldicarbonate, diethyldicarbonate, diphenyldicarbonate, dibenzyldicarbonate and the like. The compounds of Formula XVII are generally commercially available or can be prepared by known procedures.

Suitable solvents for use in the above Process D, Steps 1, 2 and 4 include water; tetrahydrofuran; dioxane; toluene; alcohols such as methanol, ethanol and isopropanol; hexane; acetonitrile; pyridine; and haloalkanes such as methylene chloride; or mixtures of these solvents.

Preferred solvents are dioxane; toluene; tetrahydrofuran; pyridine; methylene chloride or water.

Most preferred solvents are dioxane; water or toluene.

Examples of the bases for use in the above Process D, Steps 1, 2 and 4 include tertiary amines such as triethylamine; pyridine; potassium carbonate, sodium carbonate; sodium bicarbonate; sodium hydroxide; and potassium hydroxide.

Preferred bases are sodium hydroxide; potassium hydroxide; pyridine or triethylamine.

Suitable solvents for use in the above Process D, Step 3 include alcohols such as methanol, ethanol and isopropanol; water; tetrahydrofuran; dioxane; and acetonitrile.

Preferred solvents are methanol or ethanol.

Examples of acids for use in the above Process D, Step 3 include concentrated hydrochloric acid or concentrated sulfuric acid.

When A and B are the same, for example, both A and B are unsubstituted phenyl, two equivalents of a compound Formula XIV or XVI are reacted with a monosubstituted hydrazine of Formula IV in the presence of a base in an inert or substantially inert solvent or mixture of solvents to afford the desired product of Formula II.

Examples of the compounds of Formula XIV and/or Formula XVI which can be used in the above Process C include 3-methyl-methylthio-thiobenzoate, 4-chloromethylthio-thiobenzoate, 4-methyl-methylthio-thiobenzoate, carboxymethylthiothiobenzoate and the like. The compounds of Formula XIV and/or Formula XVI are generally commercially available or can be prepared by known procedures.

Suitable solvents for use in the above Process C are generally polar high-boiling solvents such as dimethylformamide (DMF); glyme; tetrahydrofuran (THF); and pyridine. The preferred solvent is pyridine.

Suitable bases for use in the above Process C include tertiary amines such as triethylamine; and pyridine. The preferred base is pyridine.

The above Processes A and B, Method 1, can be carried out at temperatures between about −20° C. and about 100° C. Preferably, these reactions are carried out between about −5° C. and about 50° C.

The above Process B, Method 2, can be carried out at temperatures between about −50° C. and about 150° C. Preferably when W is a halo radical, the reaction is carried out between about 0° C. and about 30° C. When W is alkoxy, the reaction is preferably carried out between about 100° C. and about 150° C. When W is methyl sulfonate, the reaction is preferably carried out between about −20° C. to about 20° C. When W is an ester, the reaction is preferably carried out between about 0° C. and about 50° C.

Process C can be carried out at temperatures between about 10° C. and 200° C. Preferably, this reaction is carried out between about 70° C. and about 100° C.

Process D can be carried out at temperatures between about 0° C. and 100° C. Preferably, these reactions are carried out between about 0° C. and about 50° C.

Preparation of the compounds of the present invention by processes A, B, C and D are preferably carried out at about atmospheric pressure, although higher or lower pressures can be used if desired.

Substantially equimolar amounts of reactants are preferably used in processes A, B and C, although higher or lower amounts can be used if desired.

Generally, about one equivalent of base is used per equivalent of starting material of Formula III, VI, XII and/or XIV. Where the acid addition salt of the monosubstituted hydrazine of Formula IV is used, one additional equivalent of base is used. For example, in Process A, when substituents A and B are the same and a monosubstituted hydrazine is used, about two equivalents of base are used since about two equivalents of a suitably substituted benzoyl chloride of Formula III or VI are employed. In Process A, when substituents A and B are different and an acid addition salt of the monosubstituted hydrazines of Formula IV is used, about two equivalents of base are used in Step 1 and about one equivalent of base is used in Step 2.

Modifications to the above processes may be necessary to accommodate reactive functionalities of particular A and/or B substituents. Such modifications would be apparent and known to those skilled in the art.

It will be appreciated by those skilled in the art that electronic forces may give rise to more than one isomer of the compounds of Formula II such as enantiomers, conformers and the like. There may be a difference in properties such as physical characteristics and degree of biological activity between such isomers. Separation of a specific isomer can be accomplished by standard techniques well known to those skilled in the art such as silica gel chromatography.

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more hydroxy or carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme and the like; dioxane; tetrahydrofuran; alcohols such as methanol, ethanol, isopropanol and the like. When metal hydrides are used as reagents, useful solvents include nonhydroxylic solvents, for example, ethers such as dioxane, glyme, diethylether and the like; tetrahydrofuran; hydrocarbons such as toluene, xylene, hexane, pentane, heptane, octane and the like; dimethylformamide, and the like. When amines are used as reagents, useful solvents include alcohols, such as methanol or ethanol; hydrocarbons, such as toluene, xylene, hexane and the like; tetrahydrofuran; glyme; dioxane; or water. When ammonium salts are used as reagents, useful solvents include water; alcohols, such as methanol or ethanol; glyme; tetrahydrofuran; or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acid with a compound of Formula I having a basic functional group in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out at from about −10° C. to about 100° C., preferably at about room temperature.

The following examples will further illustrate this invention but are not intended to limit it in any way. In Table I, some N'-substituted-N,N'-disubstitutedhydrazines of the present invention that have been made are listed. The structure of these compounds was confirmed by NMR and in some cases by IR and/or elemental analysis. Specific illustrative preparation of the compounds of Examples 1, 3, 16, 44, 102, 103, 148, 220, 295, 324, 625, 635, 636, 637, 638, 639, 642, 646, 648, 654, 656, 659, 660, 682, 683, 688, 689, 691, 699, 702, 722, 723, 724, 727, 729, 733, 737, 738, 739, 743, 754, 755, 764, 765, 766, 767, 772, 778, 787, 802, 809, 822, 829, 837, 853, 855, 864, 870 to 873, 878, 880, 882, 883, 893, 905, 914, 918, 922, 923, 933, 941, 942, 944, 948, 1002, 1008, 1013 and 1015 to 1018 are described after Table I.

TABLE I

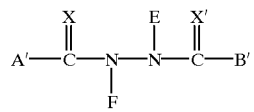

| Ex. # | C(X) | C(X') | E | F | A' | B' |
|---|---|---|---|---|---|---|
| 1 | C(O) | C(O) | —C(CH$_3$)$_3$ | H | —C$_6$H$_4$Cl-4 | —C$_6$H$_4$Cl-4 |
| 2 | C(O) | C(O) | —C(CH$_3$)$_3$ | H | —C$_6$H$_4$Cl-3 | —C$_6$H$_4$Cl-3 |
| 3 | C(O) | C(O) | —C(CH$_3$)$_3$ | H | —C$_6$H$_5$ | —C$_6$H$_5$ |
| 4 | C(O) | C(O) | —C(CH$_3$)$_3$ | H | —C$_6$H$_3$Cl$_2$-3,4 | —C$_6$H$_3$Cl$_2$-3,4 |
| 5 | C(O) | C(O) | —C(CH$_3$)$_3$ | H | —C$_6$H$_4$CH$_3$-4 | —C$_6$H$_4$CH$_3$-4 |
| 6 | C(O) | C(O) | —C(CH$_3$)$_3$ | H | —C$_6$H$_4$NO$_2$-4 | —C$_6$H$_4$NO$_2$-4 |
| 7 | C(O) | C(O) | —C(CH$_3$)$_3$ | H | —C$_6$H$_4$OCH$_3$-4 | —C$_6$H$_4$OCH$_3$-4 |
| 8 | C(O) | C(O) | —C(CH$_3$)$_3$ | H | —C$_6$H$_4$NO$_2$-3 | —C$_6$H$_4$NO$_2$-3 |
| 9 | C(O) | C(O) | —C(CH$_3$)$_3$ | H | —C$_6$H$_4$OCH$_3$-3 | —C$_6$H$_4$OCH$_3$-3 |
| 10 | C(O) | C(O) | —C(CH$_3$)$_3$ | H | —C$_6$H$_4$NO$_2$-2 | —C$_6$H$_4$NO$_2$-2 |
| 11 | C(O) | C(O) | —C(CH$_3$)$_3$ | H | —C$_6$H$_4$Cl-2 | —C$_6$H$_4$Cl-2 |
| 12 | C(O) | C(O) | —C(CH$_3$)$_3$ | H | —C$_6$H$_4$OCH$_3$-2 | —C$_6$H$_4$OCH$_3$-2 |
| 13 | C(O) | C(O) | —C(CH$_3$)$_3$ | H | —C$_6$H$_4$CH$_3$-4 | —C$_6$H$_5$ |
| 14 | C(O) | C(O) | —C(CH$_3$)$_3$ | H | —C$_6$H$_4$CN-4 | —C$_6$H$_4$CN-4 |
| 15 | C(O) | C(O) | —C(CH$_3$)$_3$ | H | —C$_6$H$_4$CH$_3$-4 | —C$_6$H$_4$Cl-4 |
| 16 | C(O) | C(O) | —C(CH$_3$)$_3$ | H | —C$_6$H$_5$ | —C$_6$H$_4$Cl-4 |

TABLE I-continued $$A'-\overset{X}{\underset{\|}{C}}-\underset{\underset{F}{|}}{N}-\overset{E}{\underset{}{N}}-\overset{X'}{\underset{\|}{C}}-B'$$

| Ex. # | C(X) | C(X') | E | F | A' | B' |
|---|---|---|---|---|---|---|
| 17 | C(O) | C(O) | —C(CH$_3$)$_3$ | H | —C$_6$H$_5$ | —C$_6$H$_4$Cl-3 |
| 18 | C(O) | C(O) | —C(CH$_3$)$_3$ | H | —C$_6$H$_5$ | —C$_6$H$_4$Cl-2 |
| 19 | C(O) | C(O) | —C(CH$_3$)$_3$ | H | —C$_6$H$_4$CH$_3$-3 | —C$_6$H$_4$CH$_3$-3 |
| 20 | C(O) | C(O) | —C(CH$_3$)$_3$ | H | —C$_6$H$_4$CH$_3$-2 | —C$_6$H$_4$CH$_3$-2 |
| 21 | C(O) | C(O) | —C(CH$_3$)$_3$ | H | —C$_6$H$_5$ | —C$_6$H$_4$CH$_3$-4 |
| 22 | C(O) | C(O) | —C(CH$_3$)$_3$ | H | —C$_6$H$_5$ | —C$_6$H$_4$CH$_3$-3 |
| 23 | C(O) | C(O) | —C(CH$_3$)$_3$ | H | —C$_6$H$_5$ | —C$_6$H$_4$CH$_3$-2 |
| 24 | C(O) | C(O) | —C(CH$_3$)$_3$ | H | —C$_6$H$_5$ | —C$_6$H$_4$OCH$_3$-4 |
| 25 | C(O) | C(O) | —C(CH$_3$)$_3$ | H | —C$_6$H$_5$ | —C$_6$H$_4$OCH$_3$-3 |
| 26 | C(O) | C(O) | —C(CH$_3$)$_3$ | H | —C$_6$H$_5$ | —C$_6$H$_4$OCH$_3$-2 |
| 27 | C(O) | C(O) | —C(CH$_3$)$_3$ | H | —C$_6$H$_5$ | —C$_6$H$_4$C(CH$_3$)$_3$-4 |
| 28 | C(O) | C(O) | —C(CH$_3$)$_3$ | H | —C$_6$H$_5$ | —C$_6$H$_4$CN-4 |
| 29 | C(O) | C(O) | —C(CH$_3$)$_3$ | H | —C$_6$H$_5$ | —C$_6$H$_4$NO$_2$-4 |
| 30 | C(O) | C(O) | —C(CH$_3$)$_3$ | H | —C$_6$H$_5$ | —C$_6$H$_4$NO$_2$-3 |
| 31 | C(O) | C(O) | —C(CH$_3$)$_3$ | H | —C$_6$H$_5$ | —C$_6$H$_4$NO$_2$-2 |
| 32 | C(O) | C(O) | —C(CH$_3$)$_3$ | H | —C$_6$H$_4$C(CH$_3$)$_3$-4 | —C$_6$H$_4$C(CH$_3$)$_3$-4 |
| 33 | C(O) | C(O) | —C(CH$_3$)$_3$ | H | —C$_6$H$_4$CH$_3$-4 | —C$_6$H$_3$Cl$_2$-3,4 |
| 34 | C(O) | C(O) | —C(CH$_3$)$_3$ | H | —C$_6$H$_5$ | —C$_6$H$_4$F-4 |
| 35 | C(O) | C(O) | —C(CH$_3$)$_3$ | H | —C$_6$H$_5$ | —C$_6$H$_4$F-3 |
| 36 | C(O) | C(O) | —C(CH$_3$)$_3$ | H | —C$_6$H$_5$ | —C$_6$H$_4$F-2 |
| 37 | C(O) | C(O) | —C(CH$_3$)$_3$ | H | —C$_6$H$_3$Cl$_2$-3,5 | —C$_6$H$_3$Cl$_2$-3,5 |
| 38 | C(O) | C(O) | —C(CH$_3$)$_3$ | H | —C$_6$H$_5$ | —C$_6$H$_3$Cl$_2$-2,4 |
| 39 | C(O) | C(O) | —CH(CH$_3$)$_2$ | H | —C$_6$H$_5$ | —C$_6$H$_5$ |
| 40 | C(O) | C(O) | —C(CH$_3$)$_3$ | H | —C$_6$H$_5$ | —C$_6$H$_4$CF$_3$-4 |
| 41 | C(O) | C(O) | —C(CH$_3$)$_3$ | H | —C$_6$H$_5$ | —C$_6$H$_4$CF$_3$-3 |
| 42 | C(O) | C(O) | —C(CH$_3$)$_3$ | H | —C$_6$H$_5$ | —C$_6$H$_4$CF$_3$-2 |
| 43 | C(O) | C(O) | —C(CH$_3$)$_3$ | H | —C$_6$H$_5$ | —C$_6$H$_3$F$_2$-2,5 |
| 44 | C(O) | C(O) | —CH$_2$C(CH$_3$)$_3$ | H | —C$_6$H$_5$ | —C$_6$H$_5$ |
| 45 | C(O) | C(O) | —C(CH$_3$)$_3$ | H | —C$_6$H$_5$ | —C$_6$H$_4$CN-3 |
| 46 | C(O) | C(O) | CH(CH$_3$)C$_2$H$_5$ | H | —C$_6$H$_5$ | —C$_6$H$_5$ |
| 47 | C(O) | C(O) | —C(CH$_3$)$_3$ | H | —C$_6$H$_5$ | —C$_6$H$_3$F$_2$-2,6 |
| 48 | C(O) | C(O) | —C(CH$_3$)$_3$ | H | —C$_6$H$_4$Cl-4 | —C$_6$H$_5$ |
| 49 | C(O) | C(O) | —C(CH$_3$)$_3$ | H | —C$_6$H$_5$ | —C$_6$H$_3$Cl$_2$-3,4 |
| 50 | C(O) | C(O) | —C(CH$_3$)$_3$ | H | —C$_6$H$_5$ | —C$_6$H$_3$Cl$_2$-3,5 |
| 51 | C(O) | C(O) | —C(CH$_3$)$_3$ | H | —C$_6$H$_5$ | —C$_6$H$_3$Cl$_2$-2,6 |
| 52 | C(O) | C(O) | —C(CH$_3$)$_3$ | H | —C$_6$H$_4$C(CH$_3$)$_3$-4 | —C$_6$H$_5$ |
| 53 | C(O) | C(O) | —C(CH$_3$)$_3$ | H | —C$_6$H$_4$Cl-2 | —C$_6$H$_5$ |
| 54 | C(O) | C(O) | —C(CH$_3$)$_3$ | H | 1-naphthyl | —C$_6$H$_5$ |
| 55 | C(O) | C(O) | —C(CH$_3$)$_3$ | H | 1-naphthyl | 1-naphthyl |
| 56 | C(O) | C(O) | —C(CH$_3$)$_3$ | H | —C$_6$H$_4$Cl-3 | —C$_6$H$_5$ |
| 57 | C(O) | C(O) | —C(CH$_3$)$_3$ | H | —C$_6$H$_4$Cl-4 | —C$_6$H$_3$Cl$_2$-3,4 |
| 58 | C(O) | C(O) | —C(CH$_3$)$_3$ | H | —C$_6$H$_4$Cl-2 | —C$_6$H$_3$Cl$_2$-3,4 |
| 59 | C(O) | C(O) | —C(CH$_3$)$_3$ | H | —C$_6$H$_4$CH$_3$-2 | —C$_6$H$_5$ |
| 60 | C(O) | C(O) | —C(CH$_3$)$_3$ | H | —C$_6$H$_5$ | —C$_6$H$_3$Cl-2-NO$_2$-4 |
| 61 | C(O) | C(O) | —C(CH$_3$)$_3$ | H | —C$_6$H$_5$ | —C$_6$H$_3$(NO$_2$)$_2$-3,5 |
| 62 | C(O) | C(O) | —C(CH$_3$)$_3$ | H | —C$_6$H$_5$ | —C$_6$H$_3$Cl$_2$-2,3 |
| 63 | C(O) | C(O) | —CHC(CH$_3$)$_3$<br>       |<br>       CH$_3$ | H | —C$_6$H$_5$ | —C$_6$H$_5$ |
| 64 | C(O) | C(O) | —C(CH$_3$)$_3$ | H | —C$_6$H$_5$ | —C$_6$H$_3$Cl-2-CH$_3$-5 |
| 65 | C(O) | C(O) | —C(CH$_3$)$_3$ | H | —C$_6$H$_5$ | —C$_6$H$_3$(CH$_3$)$_2$-3,5 |
| 66 | C(O) | C(O) | —C(CH$_3$)$_3$ | H | —C$_6$H$_5$ | —C$_6$H$_3$NO$_2$-2-CH$_3$-5 |
| 67 | C(O) | C(O) | —C(CH$_3$)$_3$ | H | —C$_6$H$_5$ | —C$_6$H$_3$CH$_3$-2-Cl-3 |
| 68 | C(O) | C(O) | —C(CH$_3$)$_3$ | H | —C$_6$H$_5$ | —C$_6$H$_3$Cl-3-CH$_3$-4 |
| 69 | C(O) | C(O) | —C(CH$_3$)$_3$ | H | —C$_6$H$_5$ | —C$_6$H$_3$NO$_2$-2-Cl-3 |
| 70 | C(O) | C(O) | —C(CH$_3$)$_3$ | H | —C$_6$H$_5$ | —C$_6$H$_3$OCH$_3$-3-NO$_2$-4 |
| 71 | C(O) | C(O) | —C(CH$_3$)$_3$ | H | —C$_6$H$_5$ | —C$_6$H$_3$NO$_2$-2-OCH$_3$-3 |
| 72 | C(O) | C(O) | —C(CH$_3$)$_3$ | H | —C$_6$H$_5$ | C$_6$H$_3$(NO$_2$)$_2$-2,4 |
| 73 | C(O) | C(O) | —C(CH$_3$)$_3$ | H | —C$_6$H$_4$Cl-4 | —C$_6$H$_4$Cl-2 |
| 74 | C(O) | C(O) | —C(CH$_3$)$_3$ | H | —C$_6$H$_4$Cl-4 | —C$_6$H$_4$Cl-3 |
| 75 | C(O) | C(O) | —C(CH$_3$)$_3$ | H | —C$_6$H$_4$Cl-4 | —C$_6$H$_4$CH$_3$-4 |
| 76 | C(O) | C(O) | —C(CH$_3$)$_3$ | H | —C$_6$H$_4$Cl-4 | —C$_6$H$_3$Cl$_2$-3,5 |
| 77 | C(O) | C(O) | —C(CH$_3$)$_3$ | H | —C$_6$H$_4$Cl-4 | —C$_6$H$_3$Cl$_2$-2,4 |
| 78 | C(O) | C(O) | —C(CH$_3$)$_3$ | H | —C$_6$H$_4$Cl-4 | —C$_6$H$_4$CF$_3$-4 |
| 79 | C(O) | C(O) | —C(CH$_3$)$_3$ | H | —C$_6$H$_5$ | —C$_6$H$_4$OSO$_2$CH$_3$-4 |

TABLE I-continued $$A'-\overset{X}{\underset{}{C}}-\underset{\underset{F}{|}}{N}-\overset{E}{N}-\overset{X'}{\underset{}{C}}-B'$$

| Ex. # | C(X) | C(X') | E | F | A' | B' |
|---|---|---|---|---|---|---|
| 80 | C(O) | C(O) | —C(CH$_3$)$_3$ | H | —C$_6$H$_5$ | —C$_6$H$_4$CH(CH$_3$)$_2$-4 |
| 81 | C(O) | C(O) | —C(CH$_3$)$_3$ | H | —C$_6$H$_5$ | —C$_6$H$_4$OCOCH$_3$-2 |
| 82 | C(O) | C(O) | —C(CH$_3$)$_3$ | H | —C$_6$H$_5$ | —C$_6$H$_4$CH$_2$CH$_3$-4 |
| 83 | C(O) | C(O) | —C(CH$_3$)$_3$ | H | —C$_6$H$_5$ | —C$_6$H$_4$Br-2 |
| 84 | C(O) | C(O) | —C(CH$_3$)$_3$ | H | —C$_6$H$_5$ | —C$_6$H$_4$OH-4 |
| 85 | C(O) | C(O) | —C(CH$_3$)$_3$ | H | —C$_6$H$_4$CH$_3$-4 | —C$_6$H$_4$CH$_3$-2 |
| 86 | C(O) | C(O) | —C(CH$_3$)$_3$ | H | —C$_6$H$_4$CH$_3$-4 | —C$_6$H$_4$CH$_3$-3 |
| 87 | C(O) | C(O) | —C(CH$_3$)$_3$ | H | —C$_6$H$_4$CH$_3$-4 | —C$_6$H$_3$Cl$_2$-2,4 |
| 88 | C(O) | C(O) | —C(CH$_3$)$_3$ | H | —C$_6$H$_4$CH$_3$-4 | —C$_6$H$_3$Cl$_2$-3,5 |
| 89 | C(O) | C(O) | —C(CH$_3$)$_3$ | H | —C$_6$H$_4$CH$_3$-4 | —C$_6$H$_4$Cl-2 |
| 90 | C(O) | C(O) | —C(CH$_3$)$_3$ | H | —C$_6$H$_4$CH$_3$-4 | —C$_6$H$_4$F-4 |
| 91 | C(O) | C(O) | —C(CH$_3$)$_3$ | H | —C$_6$H$_4$CH$_3$-4 | —C$_6$H$_4$CF$_3$-4 |
| 92 | C(O) | C(O) | —C(CH$_3$)$_3$ | H | —C$_6$H$_4$CH$_3$-4 | —C$_6$H$_4$Cl-3 |
| 93 | C(O) | C(O) | —C(CH$_3$)$_3$ | H | —C$_6$H$_4$Cl-4 | —C$_6$H$_4$CH$_2$Cl-3 |
| 94 | C(O) | C(O) | —C(CH$_3$)$_3$ | H | —C$_6$H$_4$Cl-4 | —C$_6$H$_4$CH$_2$Cl-4 |
| 95 | C(O) | C(O) | —C(CH$_3$)$_3$ | H | —C$_6$H$_4$Cl-4 | —C$_6$H$_4$CH$_3$-2 |
| 96 | C(O) | C(O) | —C(CH$_3$)$_3$ | H | —C$_6$H$_4$Cl-4 | —C$_6$H$_4$OCH$_3$-3 |
| 97 | C(O) | C(O) | —C(CH$_3$)$_3$ | H | —C$_6$H$_4$Cl-4 | —C$_6$H$_4$CH$_3$-3 |
| 98 | C(O) | C(O) | —C(CH$_3$)$_3$ | H | —C$_6$H$_4$F-4 | —C$_6$H$_4$F-4 |
| 99 | C(O) | C(O) | —C(CH$_3$)$_3$ | H | —C$_6$H$_4$F-3 | —C$_6$H$_4$F-3 |
| 100 | C(O) | C(O) | —C(CH$_3$)$_3$ | H | —C$_6$H$_4$F-2 | —C$_6$H$_4$F-2 |
| 101 | C(O) | C(O) | —C(CH$_3$)$_3$ | H | 2-naphthyl | 2-naphthyl |
| 102 | C(S) | C(O) | —C(CH$_3$)$_3$ | H | —C$_6$H$_4$Cl-4 | —C$_6$H$_5$ |
| 103 | C(O) | C(S) | —C(CH$_3$)$_3$ | H | —C$_6$H$_5$ | —C$_6$H$_5$ |
| 104 | C(O) | C(O) | —C(CH$_3$)$_3$ | H | —C$_6$H$_5$ | —C$_6$H$_4$Br-4 |
| 105 | C(O) | C(O) | —C(CH$_3$)$_3$ | H | —C$_6$H$_5$ | —C$_6$H$_4$Br-3 |
| 106 | C(O) | C(O) | —C(CH$_3$)$_3$ | H | —C$_6$H$_5$ | 4-butylphenyl |
| 107 | C(O) | C(O) | —C(CH$_3$)$_3$ | H | —C$_6$H$_4$CH$_2$CH$_3$-4 | —C$_6$H$_5$ |
| 108 | C(O) | C(O) | —C(CH$_3$)$_3$ | H | —C$_6$H$_3$Cl$_2$-3,4 | —C$_6$H$_5$ |
| 109 | C(O) | C(O) | —C(CH$_3$)$_3$ | H | —C$_6$H$_5$ | —C$_6$H$_4$COCH$_3$-4 |
| 110 | C(O) | C(O) | —CH$_2$C(CH$_3$)$_3$ | H | —C$_6$H$_5$ | —C$_6$H$_4$Br-2 |
| 111 | C(O) | C(O) | —CH$_2$C(CH$_3$)$_3$ | H | —C$_6$H$_5$ | C$_6$H$_4$NO$_2$-2 |
| 112 | C(O) | C(O) | —CH$_2$C(CH$_3$)$_3$ | H | —C$_6$H$_5$ | —C$_6$H$_4$OCH$_3$-2 |
| 113 | C(O) | C(O) | —C(CH$_3$)$_3$ | H | —C$_6$H$_5$ | —C$_6$H$_4$I-2 |
| 114 | C(O) | C(O) | CH$_2$CH(CH$_3$)$_2$ | H | —C$_6$H$_5$ | —C$_6$H$_5$ |
| 115 | C(O) | C(O) | —CH(CH$_3$)$_2$ | H | —C$_6$H$_5$ | —C$_6$H$_4$Br-2 |
| 116 | C(O) | C(O) | —CH(CH$_3$)$_2$ | H | —C$_6$H$_5$ | —C$_6$H$_3$Cl$_2$-3,4 |
| 117 | C(O) | C(O) | —C(CH$_3$)$_3$ | H | —C$_6$H$_5$ | —C$_6$H$_4$OC$_6$H$_5$-4 |
| 118 | C(O) | C(O) | —C(CH$_3$)$_3$ | H | —C$_6$H$_4$CF$_3$-4 | —C$_6$H$_5$ |
| 119 | C(O) | C(O) | —C(CH$_3$)$_3$ | H | —C$_6$H$_4$CF$_3$-4 | —C$_6$H$_3$Cl$_2$-3,4 |
| 120 | C(O) | C(O) | —CH | H | —C$_6$H$_5$ | —C$_6$H$_5$ |
| 121 | C(O) | C(O) | —C(CH$_3$)$_3$ | H | —C$_6$H$_5$ | —C$_6$H$_3$Cl-2-Br-4 |
| 122 | C(O) | C(O) | —C(CH$_3$)$_3$ | H | —C$_6$H$_5$ | —C$_6$H$_4$C$_6$H$_5$-4 |
| 123 | C(O) | C(O) | —C(CH$_3$)$_3$ | H | —C$_6$H$_5$ | —C$_6$H$_2$(OCH$_3$)$_3$-3,4,5 |
| 124 | C(O) | C(O) | —CHC(CH$_3$)$_3$ / —CH$_3$ | H | —C$_6$H$_5$ | —C$_6$H$_4$NO$_2$-2 |
| 125 | C(O) | C(O) | —C(CH$_3$)$_3$ | H | —C$_6$H$_5$ | —C$_6$H$_4$CH$_2$SCN-3 |
| 126 | C(O) | C(O) | —C(CH$_3$)$_3$ | H | —C$_6$H$_5$ | —C$_6$H$_4$CH$_2$CN-3 |
| 127 | C(O) | C(O) | —CHC(CH$_3$)$_3$ / —CH$_3$ | H | —C$_6$H$_5$ | —C$_6$H$_5$ |
| 128 | C(O) | C(O) | CH[CH(CH$_3$)$_2$]$_2$ | H | —C$_6$H$_5$ | —C$_6$H$_5$ |
| 129 | C(O) | C(O) | 1-cyclopropyl ethyl | H | —C$_6$H$_5$ | —C$_6$H$_5$ |
| 130 | C(O) | C(O) | —C(CH$_3$)$_3$ | H | —C$_6$H$_4$CH$_2$CH$_3$-4 | —C$_6$H$_4$CH$_3$-3 |
| 131 | C(O) | C(O) | —C(CH$_3$)$_3$ | H | —C$_6$H$_4$CH$_2$CH$_3$-4 | —C$_6$H$_4$Cl-4 |
| 132 | C(O) | C(O) | —C(CH$_3$)$_3$ | H | —C$_6$H$_4$CH$_2$CH$_3$-4 | —C$_6$H$_4$NO$_2$-2 |
| 133 | C(O) | C(O) | —C(CH$_3$)$_3$ | H | —C$_6$H$_5$ | —C$_6$H$_4$CH$_2$CH$_3$-3 |
| 134 | C(O) | C(O) | —C(CH$_3$)$_3$ | H | —C$_6$H$_4$CH$_2$CH$_3$-4 | —C$_6$H$_4$Br-3 |
| 135 | C(O) | C(O) | —C(CH$_3$)$_3$ | H | —C$_6$H$_4$CH$_2$CH$_3$-4 | —C$_6$H$_4$I-2 |

TABLE I-continued $$A'-\overset{\overset{X}{\|}}{C}-\underset{\underset{F}{|}}{N}-\overset{E}{N}-\overset{\overset{X'}{\|}}{C}-B'$$

| Ex. # | C(X) | C(X') | E | F | A' | B' |
|---|---|---|---|---|---|---|
| 136 | C(O) | C(O) | —CHC(CH₃)₃<br>   —CH₃ | H | —C₆H₅ | —C₆H₄Br-2 |
| 137 | C(O) | C(O) | —C(CH₃)₃ | H | —C₆H₅ | —C₆H₄CO₂CH₃-4 |
| 138 | C(O) | C(O) | —C(CH₃)₃ | H | —C₆H₄Br-2 | —C₆H₅ |
| 139 | C(O) | C(O) | —C(CH₃)₃ | H | —C₆H₄CF₃-2 | —C₆H₅ |
| 140 | C(O) | C(O) | —C(CH₃)₃ | H | —C₆H₅ | —C₆H₄I-3 |
| 141 | C(O) | C(O) | —C(CH₃)₃ | H | —C₆H₅ | —C₆H₄CH₂CH₃-2 |
| 142 | C(O) | C(O) | —C(CH₃)₃ | H | —C₆H₅ | —C₆H₄CH₂OCH₃-3 |
| 143 | C(O) | C(O) | 1-cyclohexyl ethyl | H | —C₆H₅ | —C₆H₅ |
| 144 | C(O) | C(O) | —C(CH₃)₃ | H | —C₆H₅ | C₆H₄OCH₂CH=CH₂-4 |
| 145 | C(O) | C(O) | —C(CH₃)₃ | H | —C₆H₄C₆H₅-4 | —C₆H₄C₆H₅-4 |
| 146 | C(O) | C(O) | —C(CH₃)₃ | H | —C₆H₅ | 2-nitro-5-(2-chloro-4-trifluoromethyl phenoxy)phenyl |
| 147 | C(O) | C(O) | —C(CH₃)₃ | H | 2-nitro-5-(2-chloro-4-trifluoromethyl phenoxy)phenyl | —C₆H₅ |
| 148 | C(O) | C(O) | —C(CH₃)₃ | H | C₆H₄(CH₂OC(O)C₆H₅)-2 | —C₆H₅ |
| 149 | C(O) | C(O) | —C(CH₃)₃ | H | —C₆H₅ | —C₆H₄SO₂CH₃-4 |
| 150 | C(O) | C(O) | —C(CH₃)₃ | H | —C₆H₅ | —C₆H₄OH-2 |
| 151 | C(O) | C(O) | —C(CH₃)₃ | H | —C₆H₅ | —C₆H₄SCH₃-4 |
| 152 | C(O) | C(O) | —C(CH₃)₃ | H | —C₆H₅ | —C₆H₃Br-3-CH₃-4 |
| 153 | C(O) | C(O) | —C(CH₃)₃ | H | —C₆H₅ | —C₆H₃CH₃-3-Br-4 |
| 154 | C(O) | C(O) | —C(CH₃)₃ | H | —C₆H₅ | —C₆H₃Br₂-2,4 |
| 155 | C(O) | C(O) | —CH(CH₃)₂ | H | —C₆H₅ | —C₆H₃Cl₂-2,6 |
| 156 | C(O) | C(O) | —CH₂C(CH₃)₃ | H | —C₆H₅ | —C₆H₃Cl₂-3,4 |
| 157 | C(O) | C(O) | —CHC(CH₃)₃<br>   —CH₃ | H | —C₆H₅ | —C₆H₄CN-4 |
| 158 | C(O) | C(O) | —CH₂C(CH₃)₃ | H | —C₆H₅ | —C₆H₄CH₂CH₃-4 |
| 159 | C(O) | C(O) | —C(CH₃)₃ | H | —C₆H₅ | —CH₂S—    —CH₃ |
| 160 | C(O) | C(O) | —C(CH₃)₃ | H | —C₆H₅ | —C₆H₄OC₆H₅-3 |
| 161 | C(O) | C(O) | —C(CH₃)₃ | H | —C₆H₅ | —C₆H₄(CH₂OC(O)CH₃)-3 |
| 162 | C(O) | C(O) | —C(CH₃)₃ | H | —C₆H₅ | —C₆H₄CH₂OH-4 |
| 163 | C(O) | C(O) | —C(CH₃)₃ | H | —C₆H₅ | —C₆H₄CHO-4 |
| 164 | C(O) | C(O) | —C(CH₃)₃ | H | —C₆H₅ | —C₆H₄CO₂H₄ |
| 165 | C(O) | C(O) | —CHC(CH₃)₃<br>   —CH₃ | H | —C₆H₅ | —C₆H₄OH-2 |
| 166 | C(O) | C(O) | —C(CH₃)₃ | H | —C₆H₅ | —C₆H₄CH=CCl₂-4 |
| 167 | C(O) | C(O) | —CHC(CH₃)₃<br>   —CH₃ | H | —C₆H₅ | —C₆H₄(OC(0)CH₃)-2 |
| 168 | C(O) | C(O) | —C(CH₃)₃ | H | —C₆H₃(OCH₃)₂-3,4 | —C₆H₅ |
| 169 | C(O) | C(O) | —C(CH₃)₃ | H | —C₆H₄CH₂Cl-2 | —C₆H₄CH₂Cl-2 |
| 170 | C(O) | C(O) | —C(CH₃)₃ | H | C₆H₄CH₂Cl-2 | —C₆H₅ |
| 171 | C(O) | C(O) | —C(CH₃)₃ | H | —C₆H₄NO₂-2 | —C₆H₅ |
| 172 | C(O) | C(O) | —C(CH₃)₃ | H | C₆H₄CH₂CH₂CH₃-4 | —C₆H₅ |
| 173 | C(O) | C(O) | —C(CH₃)₃ | H | —C₆H₃CH₃-2-CF₃-5 | —C₆H₄CH₃-2 |
| 174 | C(O) | C(O) | —C(CH₃)₃ | H | —C₆H₄Br-2 | —C₆H₄Br-2 |
| 175 | C(O) | C(O) | —C(CH₃)₃ | H | —C₆H₄CH₂CH₃-4 | —C₆H₄CH₂CH₃-3 |
| 176 | C(O) | C(O) | —C(CH₃)₃ | H | —C₆H₅ | —C₆H₄CH₂CH₂CH₃-4 |
| 177 | C(O) | C(O) | —C(CH₃)₃ | H | —C₆H₄CH₃-4 | —C₆H₄Br-3 |
| 178 | C(O) | C(O) | —C(CH₃)₃ | H | —C₆H₄CH₃-4 | —C₆H₃(CH₃)₂-3,5 |
| 179 | C(O) | C(O) | —C(CH₃)₃ | H | —C₆H₅ | —C₆H₄I-4 |
| 180 | C(O) | C(O) | —C(CH₃)₃ | H | —C₆H₄CH₃-4 | —C₆H₄CH₂CH₃-4 |
| 181 | C(O) | C(O) | —C(CH₃)₃ | H | —C₆H₄CH₂CH₃-4 | —C₆H₄CH₂CH₃-4 |

TABLE I-continued $$A'-\overset{\overset{X}{\|}}{C}-\underset{\underset{F}{|}}{N}-\overset{\overset{E}{|}}{N}-\overset{\overset{X'}{\|}}{C}-B'$$

| Ex. # | C(X) | C(X') | E | F | A' | B' |
|---|---|---|---|---|---|---|
| 182 | C(O) | C(O) | —C(CH₃)₃ | H | —C₆H₄CH₃-4 | —C₆H₄CH₂CH₃-3 |
| 183 | C(O) | C(O) | —C(CH₃)₃ | H | —C₆H₅ | C₆H₄CH(CH₃)₂-2 |
| 184 | C(O) | C(O) | —C(CH₃)₃ | H | —C₆H₄CH₂CH₃-3 | —C₆H₅ |
| 185 | C(O) | C(O) | —CHC(CH₃)₃ / —CH₃ | H | —C₆H₅ | —C₆H₄NO₂-3 |
| 186 | C(O) | C(O) | —CH₂C(CH₃)₃ | H | —C₆H₅ | —C₆H₄NO₂-3 |
| 187 | C(O) | C(O) | —CH₂C(CH₃)₃ | H | —C₆H₅ | —C₆H₄CH₃-3 |
| 188 | C(O) | C(O) | —CH₂C(CH₃)₃ | H | —C₆H₅ | —C₆H₄Cl-4 |
| 189 | C(O) | C(O) | —CH₂C(CH₃)₃ | H | —C₆H₅ | —C₆H₃(NO₂)₂-2,4 |
| 190 | C(O) | C(O) | —C(CH₃)₃ | H | —C₆H₄CH₂CH₃-4 | —C₆H₃Cl₂-2,4 |
| 191 | C(O) | C(O) | —C(CH₃)₃ | H | —C₆H₃Cl₂-314 | —C₆H₄Cl-4 |
| 192 | C(O) | C(O) | —C(CH₃)₃ | H | —C₆H₄(CH₂)₆CH₃-4 | —C₆H₄Cl-4 |
| 193 | C(O) | C(O) | —C(CH₃)₃ | H | C₆H₄CH₂CH₂CH₃-4 | —C₆H₄Cl-4 |
| 194 | C(O) | C(O) | —C(CH₃)₃ | H | —C₆H₄OCH₃-4 | —C₆H₄CH₃-3 |
| 195 | C(O) | C(O) | —C(CH₃)₃ | H | —C₆H₄OCH₃-4 | —C₆H₅ |
| 196 | C(O) | C(O) | —C(CH₃)₃ | H | —C₆H₄Cl-2 | —C₆H₄CH₃-3 |
| 197 | C(O) | C(O) | —C(CH₃)₃ | H | —C₆H₄Cl-2 | —C₆H₄NO₂-2 |
| 198 | C(O) | C(O) | —C(CH₃)₃ | H | —C₆H₄Cl-2 | —C₆H₄CH₃-4 |
| 199 | C(O) | C(O) | —C(CH₃)₃ | H | —C₆H₄Cl-2 | —C₆H₄CH₂CH₃-4 |
| 200 | C(O) | C(O) | —C(CH₃)₃ | H | —C₆H₄CH₂CH₃-4 | —C₆H₃(CH₃)₂-3,5 |
| 201 | C(O) | C(O) | —C(CH₃)₃ | H | —C₆H₄CH₂CH₃-4 | —C₆H₃CH₃-3-Cl-6 |
| 202 | C(O) | C(O) | —C(CH₃)₃ | H | —C₆H₅ | —C₆H₄(OC(O)CH₃)-3 |
| 203 | C(O) | C(O) | —C(CH₃)₃ | H | —C₆H₅ | —C₆H₄OH-3 |
| 204 | C(O) | C(O) | —C(CH₃)₃ | H | —C₆H₄CH₂CH₃-4 | —C₆H₃NO₂-2-CH₃-3 |
| 205 | C(O) | C(O) | —C(CH₃)₃ | H | —C₆H₄OCH₃-4 | —C₆H₃(CH₃)₂-3,5 |
| 206 | C(O) | C(O) | —C(CH₃)₃ | H | —C₆H₄OCH₃-4 | —C₆H₃Cl₂-2,4 |
| 207 | C(O) | C(O) | —C(CH₃)₃ | H | —C₆H₄Cl-2 | —C₆H₃Cl₂-2,6 |
| 208 | C(O) | C(O) | —C(CH₃)₃ | H | —C₆H₄Cl-2 | —C₆H₄Br-2 |
| 209 | C(O) | C(O) | —C(CH₃)₃ | H | —C₆H₄Cl-2 | —C₆H₃F₂-2,5 |
| 210 | C(O) | C(O) | —C(CH₃)₃ | H | —C₆H₄Cl-2 | —C₆H₄OCH₃-4 |
| 211 | C(O) | C(O) | —C(CH₃)₃ | H | —C₆H₄Cl-2 | —C₆H₄CH₃-2 |
| 212 | C(O) | C(O) | —C(CH₃)₃ | H | —C₆H₄F-2 | —C₆H₄Cl-4 |
| 213 | C(O) | C(O) | —C(CH₃)₃ | H | —C₆H₃Cl₂-2,4 | —C₆H₄Cl-4 |
| 214 | C(O) | C(O) | —C(CH₃)₃ | H | —C₆H₄Cl-2 | —C₆H₃Cl₂-2,4 |
| 215 | C(O) | C(O) | —C(CH₃)₃ | H | —C₆H₄Cl-2 | —C₆H₄OCH₃-3 |
| 216 | C(O) | C(O) | —C(CH₃)₃ | H | —C₆H₄Cl-2 | —C₆H₄Cl-3 |
| 217 | C(O) | C(O) | —C(CH₃)₃ | H | —C₆H₄Cl-2 | —C₆H₄CF₃-2 |
| 218 | C(O) | C(O) | —C(CH₃)₃ | H | —C₆H₄Cl-2 | —C₆H₄CF₃-3 |
| 219 | C(O) | C(O) | —C(CH₃)₃ | H | —C₆H₄Cl-2 | —C₆H₄CF₃-4 |
| 220 | C(O) | C(O) | —C(CH₃)₃ | H | —C₆H₄CH₃-3 | —C₆H₅ |
| 221 | C(O) | C(O) | —C(CH₃)₃ | H | —C₆H₄NO₂-3 | —C₆H₅ |
| 222 | C(O) | C(O) | —C(CH₃)₃ | H | —C₆H₃Cl₂-2,6 | —C₆H₅ |
| 223 | C(O) | C(O) | —C(CH₃)₃ | H | —C₆H₃F₂-2,4 | —C₆H₅ |
| 224 | C(O) | C(O) | —C(CH₃)₃ | H | —C₆H₄Cl-2 | —C₆H₄CN-4 |
| 225 | C(O) | C(O) | —C(CH₃)₃ | H | —C₆H₄Cl-2 | —C₆H₄F-4 |
| 226 | C(O) | C(O) | —C(CH₃)₃ | H | —C₆H₄Cl-2 | —C₆H₄Br-4 |
| 227 | C(O) | C(O) | —C(CH₃)₃ | H | —C₆H₄Cl-2 | —C₆H₄Cl-4 |
| 228 | C(O) | C(O) | —C(CH₃)₃ | H | —C₆H₄Cl-2 | —C₆H₄OCH₃-2 |
| 229 | C(O) | C(O) | —C(CH₃)₃ | H | —C₆H₄Cl-2 | —C₆H₄NO₂-4 |
| 230 | C(O) | C(O) | —C(CH₃)₃ | H | —C₆H₄Cl-2 | —C₆H₄F-2 |
| 231 | C(O) | C(O) | —C(CH₃)₃ | H | —C₆H₄Cl-2 | —C₆H₃F₂-2,6 |
| 232 | C(O) | C(O) | —C(CH₃)₃ | H | —C₆H₄NO₂-4 | —C₆H₅ |
| 233 | C(O) | C(O) | —C(CH₃)₃ | H | —C₆H₄CN-4 | —C₆H₅ |
| 234 | C(O) | C(O) | —C(CH₃)₃ | H | —C₆H₄OCH₃-3 | —C₆H₄OCH₃-3 |
| 235 | C(O) | C(O) | —C(CH₃)₃ | H | —C₆H₄OCH₃-3 | —C₆H₅ |
| 236 | C(O) | C(O) | —C(CH₃)₃ | H | —C₆H₄OCH₃-3 | —C₆H₄Cl-4 |
| 237 | C(O) | C(O) | —C(CH₃)₃ | H | —C₆H₄OCH₃-3 | —C₆H₄Cl₂-3,4 |
| 238 | C(O) | C(O) | —C(CH₃)₃ | H | C₆H₄OCH₃-2 | —C₆H₅ |
| 239 | C(O) | C(O) | —C(CH₃)₃ | H | —C₆H₄OCH₃-2 | —C₆H₄CH₃-3 |
| 240 | C(O) | C(O) | —C(CH₃)₃ | H | C₆H₄OCH₃-2 | —C₆H₃Cl₂-3,4 |
| 241 | C(O) | C(O) | —C(CH₃)₃ | H | —C₆H₄OCH₃-2 | —C₆H₄Cl-4 |
| 242 | C(O) | C(O) | —C(CH₃)₃ | H | —C₆H₄OCH₃-2 | —C₆H₄NO₂-2 |
| 243 | C(O) | C(O) | —C(CH₃)₃ | H | —C₆H₅ | —C₆H₄OCF₃-4 |
| 244 | C(O) | C(O) | —C(CH₃)₃ | H | —C₆H₄OCF₃-4 | —C₆H₅ |
| 245 | C(O) | C(O) | —C(CH₃)₃ | H | —C₆H₄OCF₃-4 | —C₆H₄CH₃-3 |

TABLE I-continued $$A'-\overset{\overset{X}{\|}}{C}-\underset{\underset{F}{|}}{N}-\overset{\overset{E}{|}}{N}-\overset{\overset{X'}{\|}}{C}-B'$$

| Ex. # | C(X) | C(X') | E | F | A' | B' |
|---|---|---|---|---|---|---|
| 246 | C(O) | C(O) | —C(CH₃)₃ | H | —C₆H₄OCF₃-4 | —C₆H₄Cl-4 |
| 247 | C(O) | C(O) | —C(CH₃)₃ | H | —C₆H₄OCF₃-4 | —C₆H₃Cl₂-3,4 |
| 248 | C(O) | C(O) | —C(CH₃)₃ | H | —C₆H₄CF₃-4 | —C₆H₄Cl-4 |
| 249 | C(O) | C(O) | —C(CH₃)₃ | H | —C₆H₄CF₃-4 | —C₆H₄CH₃-3 |
| 250 | C(O) | C(O) | C(CH₃)₂CH₂CH₂CH₂CH₃ | H | —C₆H₅ | —C₆H₅ |
| 251 | C(O) | C(O) | —C(CH₃)₃ | H | —C₆H₄OCH₂CH₃-4 | —C₆H₄CH₃-3 |
| 252 | C(O) | C(O) | —C(CH₃)₃ | H | —C₆H₄OCH₂CH₃-4 | —C₆H₃(CH₃)₂-3,5 |
| 253 | C(O) | C(O) | —C(CH₃)₃ | H | —C₆H₄OCH₂CH₃-4 | —C₆H₅ |
| 254 | C(O) | C(O) | —C(CH₃)₃ | H | —C₆H₄CH₂CH₃-4 | —C₆H₃NO₂-2-Cl-4 |
| 255 | C(O) | C(O) | —C(CH₃)₃ | H | —C₆H₃Cl-3-OCH₃-4 | —C₆H₅ |
| 256 | C(O) | C(O) | —C(CH₃)₃ | H | —C₆H₄SCH₃-4 | —C₆H₅ |
| 257 | C(O) | C(O) | —C(CH₃)₃ | H | C₆H₄OCH₂CH₂CH₂CH₃-4 | —C₆H₄Cl-4 |
| 258 | C(O) | C(O) | —C(CH₃)₃ | H | —C₆H₄SCH₃-2 | —C₆H₅ |
| 259 | C(O) | C(O) | —C(CH₃)₃ | H | —C₆H₃NO₂-2-Cl-4 | —C₆H₅ |
| 260 | C(O) | C(O) | —C(CH₃)₃ | H | —C₆H₃NO₂-2-Cl-4 | —C₆H₃NO₂-2-Cl-4 |
| 261 | C(O) | C(O) | —C(CH₃)₃ | H | —C₆H₃NO₂-2-Cl-4 | —C₆H₄C(CH₃)₃-4 |
| 262 | C(O) | C(O) | —C(CH₃)₃ | H | —C₆H₃NO₂-2-Cl-4 | —C₆H₄Cl-4 |
| 263 | C(O) | C(O) | —C(CH₃)₃ | H | —C₆H₄CH₃-4 | —C₆H₃CH₃-3-Cl-6 |
| 264 | C(O) | C(O) | —C(CH₃)₃ | H | —C₆H₃F₂-2,6 | C₆H₃F₂-2,6 |
| 265 | C(O) | C(O) | —C(CH₃)₃ | H | —C₆H₄OC₆H₅-4 | —C₆H₅ |
| 266 | C(O) | C(O) | —C(CH₃)₃ | H | —C₆H₄OC₆H₅-4 | —C₆H₄CH₃-4 |
| 267 | C(O) | C(O) | —C(CH₃)₃ | H | C₆H₄CH₂CH₂CH₂CH₃-4 | —C₆H₅ |
| 268 | C(O) | C(O) | —C(CH₃)₃ | H | C₆H₄CH₂CH₂CH₂CH₃-4 | —C₆H₄Cl-4 |
| 269 | C(O) | C(O) | —C(CH₃)₃ | H | —C₆H₄CH(CH₃)₂-4 | —C₆H₅ |
| 270 | C(O) | C(O) | —C(CH₃)₃ | H | C₆H₄CH(CH₃)₂-4 | —C₆H₄CH₃-3 |
| 271 | C(O) | C(O) | —C(CH₃)₃ | H | —C₆H₄OH-4 | —C₆H₅ |
| 272 | C(O) | C(O) | —C(CH₃)₃ | H | —C₆H₄CN-4 | —C₆H₅ |
| 273 | C(O) | C(O) | —C(CH₃)₃ | H | —C₆H₄CN-4 | —C₆H₄CH₃-3 |
| 274 | C(O) | C(O) | —C(CH₃)₃ | H | —C₆H₃CH₃-2-Cl-4 | —C₆H₅ |
| 275 | C(O) | C(O) | —C(CH₃)₃ | H | —C₆H₄CH₂CH₃-4 | —C₆H₄OCF₃-4 |
| 276 | C(O) | C(O) | —C(CH₃)₃ | H | —C₆H₅ | —C₆F₅-2,3,4,5,6 |
| 277 | C(O) | C(O) | —C(CH₃)₃ | H | —C₆F₅-2,3,4,5,6 | —C₆H₅ |
| 278 | C(O) | C(O) | —C(CH₃)₃ | H | —C₆H₄CN-4 | —C₆H₃Cl₂-3,4 |
| 279 | C(O) | C(O) | —C(CH₃)₃ | H | —C₆H₃CH₃-2-Cl-4 | —C₆H₄CH₃-3 |
| 280 | C(O) | C(O) | —C(CH₃)₃ | H | —C₆H₄CF₃-4 | —C₆H₃(CH₃)₂-3,5 |
| 281 | C(O) | C(O) | —C(CH₃)₃ | H | —C₆H₃CH₃-2-Cl-4 | —C₆H₃(CH₃)₂-3,5 |
| 282 | C(O) | C(O) | —C(CH₃)₃ | H | —C₆H₅ | —C₆H₄CH=CH₂-3 |
| 283 | C(O) | C(O) | —C(CH₃)₃ | H | —C₆H₄CH₂CH₃-4 | —C₆H₄CH=CH₂-3 |
| 284 | C(O) | C(O) | —C(CH₃)₃ | H | —C₆H₄CF₃-4 | —C₆H₄CH=CH₂-3 |
| 285 | C(O) | C(O) | —C(CH₃)₃ | H | —C₆H₄OH-4 | —C₆H₄CH₃-3 |
| 286 | C(O) | C(O) | —C(CH₃)₃ | H | C₆H₄OCH₂CH=CH₂-4 | —C₆H₄CH₃-3 |
| 287 | C(O) | C(O) | —C(CH₃)₃ | H | C₆H₄CH₂CH₂CH₃-4 | —C₆H₃Cl₂-3,4 |
| 288 | C(O) | C(O) | —C(CH₃)₃ | H | C₆H₄CH₂CH₂CH₃-4 | —C₆H₄CH₃-3 |
| 289 | C(O) | C(O) | —C(CH₃)₃ | H | —C₆H₄CH=CH₂-4 | C₆H₄CH=CH₂-4 |
| 290 | C(O) | C(O) | —C(CH₃)₃ | H | —C₆H₄CH=CH₂-4 | —C₆H₄CH₃-3 |
| 291 | C(O) | C(O) | —C(CH₃)₃ | H | —C₆H₃F₂-2,6 | —C₆H₃Cl₂-3,4 |
| 292 | C(O) | C(O) | —C(CH₃)₃ | H | —C₆H₃F₂-2,6 | —C₆H₄CH₃-3 |
| 293 | C(O) | C(O) | —C(CH₃)₃ | H | —C₆H₄CH₂Cl-2 | —C₆H₄Cl-4 |
| 294 | C(O) | C(O) | —C(CH₃)₃ | H | C₆H₄CH₂N(CH₂CH₃)₂-2 | —C₆H₄Cl-4 |
| 295 | C(O) | C(O) | —CHC(CH₃)₃<br>                —CH₃ | H | —C₆H₅ | —C₆H₅ |
| 296 | C(O) | C(O) | —C(CH₃)₃ | H | —C₆H₄Cl-4 | —C₆H₄Br-2 |
| 297 | C(O) | C(O) | —CHC(CH₃)₃<br>                —CH₃ | H | —C₆H₄CH₃-3 | —C₆H₄CH₃-3 |
| 298 | C(O) | C(O) | —CHC(CH₃)₃<br>                —CH₃ | H | —C₆H₄Br-2 | —C₆H₄Br-2 |

TABLE I-continued $$A'-\overset{X}{\underset{\|}{C}}-\underset{\underset{F}{|}}{N}-\overset{E}{N}-\overset{X'}{\underset{\|}{C}}-B'$$

| Ex. # | C(X) | C(X') | E | F | A' | B' |
|---|---|---|---|---|---|---|
| 299 | C(O) | C(O) | —C(CH$_3$)$_3$ | H | —C$_6$H$_4$Cl-4 | —C$_6$H$_3$(CH$_3$)$_2$-3,5 |
| 300 | C(O) | C(O) | —C(CH$_3$)$_3$ | H | —C$_6$H$_4$OCH$_3$-3 | —C$_6$H$_3$(CH$_3$)$_2$-3,5 |
| 301 | C(O) | C(O) | —C(CH$_3$)$_3$ | H | —C$_6$H$_4$Cl-4 | —C$_6$H$_4$F-4 |
| 302 | C(O) | C(O) | —C(CH$_3$)$_3$ | H | —C$_6$H$_4$CH$_2$CH$_3$-4 | —C$_6$H$_3$(CH$_3$)$_2$-3,5 |
| 303 | C(O) | C(O) | —C(CH$_3$)$_3$ | H | —C$_6$H$_4$CH=CH$_2$-4 | —C$_6$H$_3$(CH$_3$)$_2$-3,5 |
| 304 | C(O) | C(O) | —C(CH$_3$)$_3$ | H | C$_6$H$_4$(OC(O)CH$_3$)-4 | —C$_6$H$_3$(CH$_3$)$_2$-3,5 |
| 305 | C(O) | C(O) | —C(CH$_3$)$_3$ | H | —C$_6$H$_3$(CH$_3$)$_2$-3,5 | —C$_6$H$_5$ |
| 306 | C(O) | C(O) | —C(CH$_3$)$_3$ | H | —C$_6$H$_3$(CH$_3$)$_2$-3,5 | —C$_6$H$_4$CH$_3$-3 |
| 307 | C(O) | C(O) | —C(CH$_3$)$_3$ | H | —C$_6$H$_3$(CH$_3$)$_2$-3,5 | —C$_6$H$_4$CH$_2$CH$_3$-4 |
| 308 | C(O) | C(O) | —C(CH$_3$)$_3$ | H | C$_6$H$_4$CH=CHCH$_3$-4 | —C$_6$H$_4$CH=CHCH$_3$-4 |
| 309 | C(O) | C(O) | —C(CH$_3$)$_3$ | H | —C$_6$H$_4$CH(CH$_3$)$_2$-4 | —C$_6$H$_3$(CH$_3$)$_2$-3,5 |
| 310 | C(O) | C(O) | —C(CH$_3$)$_3$ | H | —C$_6$H$_4$CH$_2$CH$_3$-4 | —C$_6$H$_4$Br-2 |
| 311 | C(O) | C(O) | —C(CH$_3$)$_3$ | H | —C$_6$H$_3$Cl-3-CH$_3$-4 | —C$_6$H$_5$ |
| 312 | C(O) | C(O) | —C(CH$_3$)$_3$ | H | —C$_6$H$_3$Cl-3-CH$_3$-4 | —C$_6$H$_4$CH$_3$-3 |
| 313 | C(O) | C(O) | —C(CH$_3$)$_3$ | H | —C$_6$H$_3$Cl-3-CH$_3$-4 | —C$_6$H$_4$Cl-4 |
| 314 | C(O) | C(O) | —C(CH$_3$)$_3$ | H | —C$_6$H$_3$Cl-3-CH$_3$-4 | —C$_6$H$_3$Cl$_2$-3,4 |
| 315 | C(O) | C(O) | C(CH$_3$)$_2$CH$_2$CH$_3$ | H | —C$_6$H$_4$CH$_2$CH$_3$-4 | —C$_6$H$_4$NO$_2$-2 |
| 316 | C(O) | C(O) | —C(CH$_3$)$_3$ | H | —C$_6$H$_3$F$_2$-2,6 | —C$_6$H$_4$Cl-2 |
| 317 | C(O) | C(O) | —C(CH$_3$)$_3$ | H | —C$_6$H$_3$F$_2$-2,6 | —C$_6$H$_4$Cl-3 |
| 318 | C(O) | C(O) | —C(CH$_3$)$_3$ | H | —C$_6$H$_3$F$_2$-2,6 | —C$_6$H$_4$Cl-4 |
| 319 | C(O) | C(O) | —C(CH$_3$)$_3$ | H | —C$_6$H$_3$F$_2$-2,6 | —C$_6$H$_3$(CH$_3$)$_2$-3,5 |
| 320 | C(O) | C(O) | C(CH$_3$)$_2$CH$_2$CH$_3$ | H | —C$_6$H$_4$CH$_2$CH$_3$-4 | —C$_6$H$_3$(CH$_3$)$_2$-3,5 |
| 321 | C(O) | C(O) | —C(CH$_3$)$_3$ | H | —C$_6$H$_4$CF$_3$-3 | —C$_6$H$_4$Cl-4 |
| 322 | C(O) | C(O) | —C(CH$_3$)$_3$ | H | —C$_6$H$_4$CF$_3$-3 | —C$_6$H$_3$(CH$_3$)$_2$-3,5 |
| 323 | C(S) | C(O) | —C(CH$_3$)$_3$ | H | —C$_6$H$_5$ | —C$_6$H$_4$Cl-4 |
| 324 | C(S) | C(O) | —C(CH$_3$)$_3$ | H | —C$_6$H$_5$ | —C$_6$H$_4$CH$_3$-3 |
| 325 | C(O) | C(O) | —C(CH$_3$)$_3$ | H | —C$_6$H$_3$NO$_2$-2-OCH$_3$-3 | —C$_6$H$_4$CH$_3$-3 |
| 326 | C(O) | C(O) | —C(CH$_3$)$_3$ | H | —C$_6$H$_3$Br-3-CH$_3$-4 | —C$_6$H$_5$ |
| 327 | C(O) | C(O) | —C(CH$_3$)$_3$ | H | —C$_6$H$_4$Cl-4 | —C$_6$H$_4$CO$_2$CH$_3$-4 |
| 328 | C(O) | C(O) | —C(CH$_3$)$_3$ | H | —C$_6$H$_4$CH$_2$CH$_3$-4 | C$_6$H$_4$CO$_2$Cl#34 |
| 329 | C(O) | C(O) | —C(CH$_3$)$_3$ | H | —C$_6$H$_5$ | —C$_6$H$_4$NH$_2$--3 |
| 330 | C(O) | C(O) | —C(CH$_3$)$_3$ | H | —C$_6$H$_5$ | —C$_6$H$_4$NH$_2$--2 |
| 331 | C(O) | C(O) | —C(CH$_3$)$_3$ | H | —C$_6$H$_4$F-4 | —C$_6$H$_5$ |
| 332 | C(O) | C(O) | —CHC(CH$_3$)$_3$<br>  —CH$_3$ | H | —C$_6$H$_4$CH$_3$-4 | —C$_6$H$_4$NO$_2$-2 |
| 333 | C(O) | C(O) | —C(CH$_3$)$_3$ | H | —C$_6$H$_4$OH-3 | —C$_6$H$_5$ |
| 334 | C(O) | C(O) | —C(CH$_3$)$_3$ | H | —C$_6$H$_4$CH$_2$CH$_3$-4 | —C$_6$H$_3$Cl$_2$-3,5 |
| 335 | C(O) | C(O) | —C(CH$_3$)$_3$ | H | C$_6$H$_4$OCH$_2$CH=CH$_2$-3 | —C$_6$H$_5$ |
| 336 | C(O) | C(O) | —CHC(CH$_3$)$_3$<br>  —CH$_3$ | H | —C$_6$H$_4$CH$_3$-4 | —C$_6$H$_3$(CH$_3$)$_2$-3,5 |
| 337 | C(O) | C(O) | —CHC(CH$_3$)$_3$<br>  —CH$_3$ | H | —C$_6$H$_4$CH$_3$-4 | —C$_6$H$_3$NO$_2$-2-CH$_3$-3 |
| 338 | C(O) | C(O) | —CHC(CH$_3$)$_3$<br>  —CH$_3$ | H | —C$_6$H$_4$CH$_3$-4 | —C$_6$H$_3$NO$_2$-2-CH$_3$-5 |
| 339 | C(O) | C(O) | —CHC(CH$_3$)$_3$<br>  —CH$_3$ | H | —C$_6$H$_4$CH$_3$-4 | —C$_6$H$_4$CH$_3$-3 |
| 340 | C(O) | C(O) | —CHC(CH$_3$)$_3$<br>  —CH$_3$ | H | —C$_6$H$_4$CH$_3$-4 | —C$_6$H$_4$I-2 |
| 341 | C(O) | C(O) | —C(CH$_3$)$_3$ | H | —C$_6$H$_4$Cl-4 | —C$_6$H$_4$F-2 |

TABLE I-continued $$A'-\overset{\overset{X}{\|}}{C}-\overset{\overset{E}{|}}{N}-\overset{\overset{X'}{\|}}{N}-\overset{\overset{X'}{\|}}{C}-B'$$
$$\phantom{A'-\overset{\overset{X}{\|}}{C}-\overset{}{N}}\overset{}{|}\phantom{-\overset{\overset{X'}{\|}}{C}-B'}$$
$$\phantom{A'-\overset{\overset{X}{\|}}{C}-\overset{}{N}}F\phantom{-\overset{\overset{X'}{\|}}{C}-B'}$$

| Ex. # | C(X) | C(X') | E | F | A' | B' |
|---|---|---|---|---|---|---|
| 342 | C(O) | C(O) | —C(CH₃)₃ | H | —C₆H₄CH₂CH₃-4 | —C₆H₃Cl₂-3,4 |
| 343 | C(O) | C(O) | —C(CH₃)₃ | H | —C₆H₄CH₂CH₃-4 | —C₆H₄F-2 |
| 344 | C(O) | C(O) | —C(CH₃)₃ | H | C₆H₄OC(O) N(CH₃)₂-3 | —C₆H₅ |
| 345 | C(O) | C(O) | —C(CH₃)₃ | H | C₆H₄CCO₂CH=CH₂-3 | —C₆H₅ |
| 346 | C(O) | C(O) | —C(CH₃)₃ | H | —C₆H₄CO₂CH₃-4 | —C₆H₄Cl-4 |
| 347 | C(O) | C(O) | —C(CH₃)₃ | H | —C₆H₄CO₂CH₃-4 | —C₆H₃(CH₃)₂-3,5 |
| 348 | C(O) | C(O) | —C(CH₃)₃ | H | —C₆H₄CO₂CH₃-4 | —C₆H₄CH₃-3 |
| 349 | C(O) | C(O) | —C(CH₃)₃ | H | —C₆H₄CO₂H₄ | —C₆H₄CH₃-3 |
| 350 | C(O) | C(O) | —C(CH₃)₃ | H | —C₆H₃NH₂-2-OCH₃-3 | —C₆H₄CH₃-3 |
| 351 | C(O) | C(O) | —C(CH₃)₃ | H | —C₆H₄NH₂-4 | —C₆H₄Cl-4 |
| 352 | C(O) | C(O) | —C(CH₃)₃ | H | —C₆H₄NHCO₂CH₃-4 | —C₆H₄Cl-4 |
| 353 | C(O) | C(O) | —C(CH₃)₃ | H | —C₆H₄NHC(O)CH₃-4 | —C₆H₄Cl-4 |
| 354 | C(O) | C(O) | —C(CH₃)₃ | H | —C₆H₃NHC(O)CH₃-2-OCH₃-3 | —C₆H₄CH₃-3 |
| 355 | C(O) | C(O) | —C(CH₃)₃ | H | —C₆H₄OC₆H₅-3 | —C₆H₅ |
| 356 | C(O) | C(O) | —C(CH₃)₃ | H | —C₆H₄OC₆H₅-3 | —C₆H₄CH₃-3 |
| 357 | C(O) | C(O) | —C(CH₃)₃ | H | —C₆H₄C(O)CH₃-4 | —C₆H₄CH₃-3 |
| 358 | C(O) | C(O) | —C(CH₃)₃ | H | —C₆H₄OCH₂OCH₃-4 | —C₆H₅ |
| 359 | C(O) | C(O) | —C(CH₃)₃ | H | C₆H₄OC(O)N(CH₃)₂-4 | —C₆H₅ |
| 360 | C(O) | C(O) | —C(CH₃)₃ | H | C₆H₄OCH₂CO₂CH₃-4 | —C₆H₅ |
| 361 | C(O) | C(O) | —C(CH₃)₃ | H | C₆H₄CH₂OC(O)CH₃-4 | —C₆H₅ |
| 362 | C(O) | C(O) | —C(CH₃)₃ | H | —C₆H₄CH₂SCN-4 | —C₆H₅ |
| 363 | C(O) | C(O) | —C(CH₃)₃ | H | —C₆H₄CH₂OH-4 | —C₆H₅ |
| 364 | C(O) | C(O) | —C(CH₃)₃ | H | —C₆H₄Br-4 | —C₆H₄Br-4 |
| 365 | C(O) | C(O) | —C(CH₃)₃ | H | —C₆H₄OCH₂SCH₃-4 | —C₆H₅ |
| 366 | C(O) | C(O) | —C(CH₃)₃ | H | C₆H₄OCH₂C(CH₃)₂-4 | —C₆H₅ |
| 367 | C(O) | C(O) | —C(CH₃)₃ | H | —C₆H₄CH₂CN-4 | —C₆H₅ |
| 368 | C(O) | C(O) | —C(CH₃)₃ | H | —C₆H₄CH---CHCH₃-4 (epoxide) | —C₆H₅ |
| 369 | C(O) | C(O) | —C(CH₃)₃ | H | C₆H₄C(CH₃)=NNHC(O)NH₂-4 | —C₆H₄CH₃-3 |
| 370 | C(O) | C(O) | —C(CH₃)₃ | H | —C₆H₄C₆H₅-4 | —C₆H₄CH₃-3 |
| 371 | C(O) | C(O) | —C(CH₃)₃ | H | —C₆H₄CN-3 | —C₆H₄CH₃-3 |
| 372 | C(O) | C(O) | —C(CH₃)₃ | H | —C₆H₄NH₂-3 | —C₆H₄CH₃-3 |
| 373 | C(O) | C(O) | —C(CH₃)₃ | H | C₆H₄C(O)NHC(CH₃)₂CH₂OH-4 | —C₆H₄CH₃-3 |
| 374 | C(O) | C(O) | —C(CH₃)₃ | H | C₆H₄CH(OH)CH₃-4 | —C₆H₄CH₃-3 |
| 375 | C(O) | C(O) | —C(CH₃)₃ | H | C₆H₄NHC(O)C(CH₃)=CH₂-3 | —C₆H₄CH₃-3 |
| 376 | C(O) | C(O) | —C(CH₃)₃ | H | —C₆H₄CO₂H-3 | —C₆H₄CH₃-3 |
| 377 | C(O) | C(O) | —C(CH₃)₃ | H | —C₆H₄CH₂Cl-3 | —C₆H₄CH₃-3 |
| 378 | C(O) | C(O) | —C(CH₃)₃ | H | —C₆H₄CH₂CH₃-4 | —C₆H₃(CH₃)₂-2,3 |
| 379 | C(O) | C(O) | —C(CH₃)₃ | H | —C₆H₃(CH₃)₂-2,3 | —C₆H₄CH₃-3 |
| 380 | C(O) | C(O) | —C(CH₃)₃ | H | —C₆H₅ | —C₆H₃(CH₃)₂-2,3 |
| 381 | C(O) | C(O) | —C(CH₃)₃ | H | —C₆H₄CH₃-4 | —C₆H₃(CH₃)₂-2,3 |
| 382 | C(O) | C(O) | —CHC(CH₃)₃ / CH₃ | H | —C₆H₄CH₃-4 | —C₆H₄CH₃-2 |
| 383 | C(O) | C(O) | —CHC(CH₃)₃ / CH₃ | H | —C₆H₄CH₃-4 | —C₆H₄CF₃-2 |
| 384 | C(O) | C(O) | —CHC(CH₃)₃ / CH₃ | H | —C₆H₄CH₃-4 | —C₆H₅ |
| 385 | C(O) | C(O) | —C(CH₃)₃ | H | —C₆H₄OCH₂OCH₃-4 | —C₆H₄CH₃-3 |
| 386 | C(O) | C(O) | —C(CH₃)₃ | H | —C₆H₄C(CH₃)=CH₂-4 | —C₆H₄CH₃-3 |
| 387 | C(O) | C(O) | —C(CH₃)₃ | H | —C₆H₅ | 1-naphthyl |
| 388 | C(O) | C(O) | —C(CH₃)₃ | H | 1-naphthyl | —C₆H₄CH₃-3 |

TABLE I-continued $$\underset{F}{A'-\overset{\overset{X}{\|}}{C}-N-\overset{E}{N}-\overset{\overset{X'}{\|}}{C}-B'}$$

| Ex. # | C(X) | C(X') | E | F | A' | B' |
|---|---|---|---|---|---|---|
| 389 | C(O) | C(O) | —C(CH₃)₃ | H | —C₆H₄NCS-4 | —C₆H₄CH₃-3 |
| 390 | C(O) | C(O) | —C(CH₃)₃ | H | —C₆H₃(CH₃)₂-3,5 | —C₆H₃(CH₃)₂-3,5 |
| 391 | C(O) | C(O) | —C(CH₃)₃ | H | —C₆H₃Cl₂-2,4 | —C₆H₃Cl₂-2,4 |
| 392 | C(O) | C(O) | —C(CH₃)₃ | H | —C₆H₄F-2 | —C₆H₄Br-2 |
| 393 | C(O) | C(O) | —C(CH₃)₃ | H | —C₆H₄F-2 | —C₆H₄CH₃-3 |
| 394 | C(O) | C(O) | —C(CH₃)₃ | H | —C₆H₃(CH₃)₂-2,3 | —C₆H₃(CH₃)₂-2,3 |
| 395 | C(O) | C(O) | —C(CH₃)₃ | H | —C₆H₄F-2 | —C₆H₄NO₂-2 |
| 396 | C(O) | C(O) | —C(CH₃)₃ | H | —C₆H₄F-2 | —C₆H₅ |
| 397 | C(O) | C(O) | —C(CH₃)₃ | H | —C₆H₃CH₃-2-Cl-3 | —C₆H₄CH₃-3 |
| 398 | C(O) | C(O) | —C(CH₃)₃ | H | —C₆H₃CH₃-2-Cl-3 | —C₆H₅ |
| 399 | C(O) | C(O) | CH(CH₃)CH₂C(CH₃)₃ | H | —C₆H₄CH₃-4 | —C₆H₃(CH₃)₂-3,5 |
| 400 | C(O) | C(O) | CH(CH₃)CH₂C(CH₃)₃ | H | —C₆H₄CH₃-4 | —C₆H₃Cl₂-3,4 |
| 401 | C(O) | C(O) | —C(CH₃)₃ | H | —C₆H₄Br-4 | —C₆H₅ |
| 402 | C(O) | C(O) | —C(CH₃)₃ | H | —C₆H₃Cl₂-2,3 | —C₆H₄Br-2 |
| 403 | C(O) | C(O) | —C(CH₃)₃ | H | —C₆H₃Cl₂-2,3 | —C₆H₅ |
| 404 | C(O) | C(O) | —C(CH₃)₃ | H | —C₆H₄F-2 | —C₆H₃(CH₃)₂-3,5 |
| 405 | C(O) | C(O) | —C(CH₃)₃ | H | —C₆H₃Cl₂-2,3 | —C₆H₄CH₃-3 |
| 406 | C(O) | C(O) | —C(CH₃)₃ | H | —C₆H₅ | 2-naphthyl |
| 407 | C(O) | C(O) | —C(CH₃)₃ | H | 2-naphthyl | —C₆H₄CH₃-3 |
| 408 | C(O) | C(O) | —C(CH₃)₃ | H | —C₆H₅ | —C₆H₄CCF₃-3 |
| 409 | C(O) | C(O) | —C(CH₃)₃ | H | —C₆H₄NCS-4 | —C₆H₅ |
| 410 | C(O) | C(O) | —C(CH₃)₃ | H | —C₆H₃F₂-2,6 | —C₆H₃Cl₂-2,4 |
| 411 | C(O) | C(O) | —C(CH₃)₃ | H | —C₆H₃F₂-2,6 | —C₆H₃Cl₂-3,5 |
| 412 | C(O) | C(O) | —C(CH₃)₃ | H | —C₆H₄CH₃-4 | —C₆H₃(CF₃)₂-3,5 |
| 413 | C(O) | C(O) | —C(CH₃)₃ | H | —C₆H₅ | —C₆H₃(CF₃)₂-3,5 |
| 414 | C(O) | C(O) | CH(CH₃)C(CH₃)(CH₂CH₃)₂ | H | —C₆H₄CH₃-4 | —C₆H₅ |
| 415 | C(O) | C(O) | CH(CH₃)C(CH₃)(CH₂CH₃)₂ | H | —C₆H₄CH₃-4 | —C₆H₃(CH₃)₂-3,5 |
| 416 | C(O) | C(O) | CH(CH₃)C(CH₃)(CH₂CH₃)₂ | H | —C₆H₄CH₃-4 | —C₆H₄NO₂-2 |
| 417 | C(O) | C(O) | —CHC(CH₃)₃ / —CH₃ | H | —C₆H₄CH₂CH₃-4 | —C₆H₃(CH₃)₂-3,5 |
| 418 | C(O) | C(O) | —CHC(CH₃)₃ / —CH₃ | H | —C₆H₄CH₂CH₃-4 | —C₆H₃NO₂-2-CH₃-5 |
| 419 | C(O) | C(O) | —C(CH₃)₃ | H | —C₆H₅ | —C₆H₃Cl-3-F-4 |
| 420 | C(O) | C(O) | —C(CH₃)₃ | H | —C₆H₄Cl-4 | —C₆H₃Cl-3-F-4 |
| 421 | C(O) | C(O) | —CH(CH₃)₂ | H | —C₆H₄CH₂CH₃-4 | —C₆H₃(CH₃)₂-3,5 |
| 422 | C(O) | C(O) | —C(CH₃)₃ | H | —C₆H₄Cl-4 | —C₆H₃(CF₃)₂-3,5 |
| 423 | C(O) | C(O) | —C(CH₃)₃ | H | —C₆H₃(CH₃)₂-2,3 | —C₆H₃Cl₂-314 |
| 424 | C(O) | C(O) | —C(CH₃)₃ | H | —C₆H₄CH₃-4 | —C₆H₃CH₃-2-Cl-3 |
| 425 | C(O) | C(O) | —C(CH₃)₃ | H | —C₆H₃Cl-3-F-4 | —C₆H₅ |
| 426 | C(O) | C(O) | —C(CH₃)₃ | H | C₆H₃(CH₃)₂-2,6 | —C₆H₄CH₃-3 |
| 427 | C(O) | C(O) | —C(CH₃)₃ | H | —C₆H₃(CH₃)₂-2,6 | —C₆H₃(CH₃)₂-3,5 |
| 428 | C(O) | C(O) | —C(CH₃)₃ | H | —C₆H₃(CH₃)₂-2,3 | —C₆H₄Br-2 |
| 429 | C(O) | C(O) | —C(CH₃)₃ | H | —C₆H₃(CH₃)₂-2,3 | —C₆H₃(CH₃)2-3,5 |
| 430 | C(O) | C(O) | —C(CH₃)₃ | H | —C₆H₃(CH₃)2-2,3 | —C₆H₄Cl-3 |
| 431 | C(O) | C(O) | —C(CH₃)₃ | H | —C₆H₄OCF₃-3 | —C₆H₅ |
| 432 | C(O) | C(O) | —C(CH₃)₃ | H | —C₆H₄CCF₃-3 | —C₆H₄CH₃-3 |
| 433 | C(O) | C(O) | —C(CH₃)₃ | H | —C₆H₃(CH₃)₂-2,3 | —C₆H₃CH₃-2-Cl-3 |
| 434 | C(O) | C(O) | —CHC(CH₃)₃ / —CH₃ | H | —C₆H₄CH₂CH₃-4 | —C₆H₃Cl₂-2,4 |
| 435 | C(O) | C(O) | CH(CH₃)C(CH₃)(CH₂CH₃)₂ | H | —C₆H₄CH₃-4 | —C₆H₃NO₂-2-CH₃-5 |
| 436 | C(O) | C(O) | CH(CH₃)C(CH₃)(CH₂CH₃)₂ | H | —C₆H₄CH₃-4 | —C₆H₃NO₂-2-CH₃-3 |
| 437 | C(O) | C(O) | —C(CH₃)₃ | H | —C₆H₃F₂-2,6 | —C₆H₄Br-2 |

TABLE I-continued $$\underset{A'}{\overset{X}{\underset{\|}{C}}}-\underset{\underset{F}{|}}{N}-\underset{}{N}\overset{E}{\underset{}{}}-\underset{\|}{\overset{X'}{C}}-B'$$

| Ex. # | C(X) | C(X') | E | F | A' | B' |
|---|---|---|---|---|---|---|
| 438 | C(O) | C(O) | —C(CH₃)₃ | H | —C₆H₃CH₃-2-Cl-3 | —C₆H₃(CH₃)₂-3,5 |
| 439 | C(O) | C(O) | —C(CH₃)₃ | H | —C₆H₃CH₃-2-Cl-3 | —C₆H₃Cl-3-F-4 |
| 440 | C(O) | C(O) | —C(CH₃)₃ | H | —C₆H₃(CH₃)₂-2,3 | —C₆H₃Cl-3-F-4 |
| 441 | C(O) | C(O) | —C(CH₃)₃ | H | —C₆H₄CH₂CH₃-4 | —C₆H₃Cl-3-F-4 |
| 442 | C(O) | C(O) | —C(CH₃)₃ | H | —C₆H₃(CH₃)₂-3,4 | —C₆H₅ |
| 443 | C(O) | C(O) | —C(CH₃)₃ | H | —C₆H₃(CH₃)₂-3,4 | —C₆H₄CH₃-3 |
| 444 | C(O) | C(O) | —C(CH₃)₃ | H | —C₆H₃(CH₃)₂-314 | —C₆H₄Cl-2 |
| 445 | C(O) | C(O) | —C(CH₃)₃ | H | —C₆H₃(CH₃)₂-3,4 | —C₆H₃Cl₂-2,4 |
| 446 | C(O) | C(O) | —C(CH₃)₃ | H | —C₆H₃(CH₃)₂-3,4 | —C₆H₄Br-2 |
| 447 | C(O) | C(O) | —C(CH₃)₃ | H | —C₆H₃(CH₃)₂-3,4 | —C₆H₃(CH₃)₂-3,5 |
| 448 | C(O) | C(O) | —C(CH₃)₃ | H | —C₆H₃(CH₃)₂-3,4 | —C₆H₄NO₂-2 |
| 449 | C(O) | C(O) | —C(CH₃)₃ | H | —C₆H₃(CH₃)₂-3,4 | —C₆H₃(CH₃)₂-3,4 |
| 450 | C(O) | C(O) | —C(CH₃)₃ | H | —C₆H₅ | —C₆H₃(CH₃)₂-3,4 |
| 451 | C(O) | C(O) | —C(CH₃)₃ | H | —C₆H₄CH₂CH₃-4 | —C₆H₃(CH₃)₂-3,4 |
| 452 | C(O) | C(O) | —C(CH₃)₃ | H | —C₆H₃F-2-Cl-6 | —C₆H₄CH₃-3 |
| 453 | C(O) | C(O) | CH(CH₂CH₃)C(CH₃)₃ | H | —C₆H₄CH₃-4 | —C₆H₅ |
| 454 | C(O) | C(O) | —C(CH₃)₃ | H | —C₆H₄CH₂Cl-4 | —C₆H₅ |
| 455 | C(O) | C(O) | —C(CH₃)₃ | H | —C₆H₃(OCH₃)₂-2,3 | —C₆H₅ |
| 456 | C(O) | C(O) | —C(CH₃)₃ | H | —C₆H₃(OCH₃)₂-2,3 | —C₆H₄Cl-4 |
| 457 | C(O) | C(O) | —C(CH₃)₃ | H | —C₆H₃(OCH₃)₂-2,3 | —C₆H₄Br-2 |
| 458 | C(O) | C(O) | —C(CH₃)₃ | H | —C₆H₃Cl-3-F-4 | —C₆H₃Cl₂-3,4 |
| 459 | C(O) | C(O) | —C(CH₃)₃ | H | —C₆H₄C(CH₃)₃-4 | —C₆H₃(CH₃)₂-3,4 |
| 460 | C(O) | C(O) | —C(CH₃)₃ | H | —C₆H₄C(CH₃)₃-4 | —C₆H₃(CH₃)₂-3,5 |
| 461 | C(O) | C(O) | —C(CH₃)₃ | H | —C₆H₄C(CH₃)₃-4 | —C₆H₃Cl₂-2,4 |
| 462 | C(O) | C(O) | —C(CH₃)₃ | H | —C₆H₄C(CH₃)₃-4 | —C₆H₄NO₂-2 |
| 463 | C(O) | C(O) | —C(CH₃)₃ | H | —C₆H₄C(CH₃)₃-4 | —C₆H₄Br-2 |
| 464 | C(O) | C(O) | —C(CH₃)₃ | H | —C₆H₄C(CH₃)₃-4 | —C₆H₄CH₃-3 |
| 465 | C(O) | C(O) | —C(CH₃)₃ | H | —C₆H₄C(CH₃)₃-4 | —C₆H₄Cl-2 |
| 466 | C(O) | C(O) | —C(CH₃)₃ | H | —C₆H₄C(CH₃)₃-4 | —C₆H₃Cl₂-3,4 |
| 467 | C(O) | C(O) | —C(CH₃)₃ | H | —C₆H₃(CH₃)₂-3,4 | —C₆H₃Cl₂-3,4 |
| 468 | C(O) | C(O) | —C(CH₃)₃ | H | —C₆H₃(CH₃)₂-3,4 | —C₆H₄F-4 |
| 469 | C(O) | C(O) | —C(CH₃)₃ | H | —C₆H₄C(CH₃)₃-4 | —C₆H₄F-4 |
| 470 | C(O) | C(O) | CH(CH₂CH₃)C(CH₃)₃ | H | —C₆H₄CH₃-4 | —C₆H₄NO₂-2 |
| 471 | C(O) | C(O) | CH(CH₂CH₃)C(CH₃)₃ | H | —C₆H₄CH₃-4 | —C₆H₃NO₂-2-CH₃-5 |
| 472 | C(O) | C(O) | CH(CH₂CH₃)C(CH₃)₃ | H | —C₆H₄CH₃-4 | —C₆H₃(CH₃)₂-3,5 |
| 473 | C(O) | C(O) | —C(CH₃)₃ | H | —C₆H₃NH₂-2-OCH₃-3 | —C₆H₅ |
| 474 | C(O) | C(O) | —C(CH₃)₃ | H | 1-naphthyl | —C₆H₃Cl₂-2,4 |
| 475 | C(O) | C(O) | —C(CH₃)₃ | H | 1-naphthyl | —C₆H₄Br-2 |
| 476 | C(O) | C(O) | —C(CH₃)₃ | H | —C₆H₃CH₃-2-NO₂-3 | —C₆H₅ |
| 477 | C(O) | C(O) | —C(CH₃)₃ | H | —C₆H₃CH₃-2-NO₂-3 | —C₆H₄CH₃-3 |
| 478 | C(O) | C(O) | —C(CH₃)₃ | H | —C₆H₃CH₃-2-NO₂-3 | —C₆H₄Cl-4 |
| 479 | C(O) | C(O) | —C(CH₃)₃ | H | —C₆H₃CH₃-2-NO₂-3 | —C₆H₃Cl₂-2,4 |
| 480 | C(O) | C(O) | —C(CH₃)₃ | H | —C₆H₃CH₃-2-Br-3 | —C₆H₅ |
| 481 | C(O) | C(O) | —C(CH₃)₃ | H | —C₆H₃CH₃-2-Br-3 | —C₆H₄CH₃-3 |
| 482 | C(O) | C(O) | —C(CH₃)₃ | H | —C₆H₃CH₃-2-Br-3 | —C₆H₄Cl-4 |
| 483 | C(O) | C(O) | —C(CH₃)₃ | H | —C₆H₃CH₃-2-Br-3 | —C₆H₃Cl₂-2,4 |
| 484 | C(O) | C(O) | —C(CH₃)₃ | H | —C₆H₃CH₃-2-NH₂-3 | —C₆H₄CH₃-3 |
| 485 | C(O) | C(O) | —C(CH₃)₃ | H | —C₆H₄CH₃-2 | —C₆H₄Br-2 |
| 486 | C(O) | C(O) | —C(CH₃)₃ | H | —C₆H₄CH₃-2 | —C₆H₄NO₂-2 |
| 487 | C(O) | C(O) | —C(CH₃)₃ | H | —C₆H₄CH₃-2 | —C₆H₄Cl-3 |
| 488 | C(O) | C(O) | —C(CH₃)₃ | H | —C₆H₄CH₃-2 | —C₆H₄Cl-4 |
| 489 | C(O) | C(O) | —C(CH₃)₃ | H | —C₆H₄CH₃-2 | —C₆H₄CH₃-3 |
| 490 | C(O) | C(O) | —C(CH₃)₃ | H | —C₆H₄CH₃-2 | —C₆H₃(CH₃)₂-3,5 |
| 491 | C(O) | C(O) | —C(CH₃)₃ | H | —C₆H₄CH₃-2 | —C₆H₃Cl₂-3,4 |
| 492 | C(O) | C(O) | —C(CH₃)₃ | H | —C₆H₄CH₃-2 | —C₆H₃Cl₂-3,5 |
| 493 | C(O) | C(O) | —C(CH₃)₃ | H | —C₆H₃CH₃-2-F-3 | —C₆H₅ |
| 494 | C(O) | C(O) | —C(CH₃)₃ | H | —C₆H₃CH₃-2-F-3 | —C₆H₄CH₃-3 |
| 495 | C(O) | C(O) | —C(CH₃)₃ | H | —C₆H₃F-2-Cl-6 | —C₆H₅ |
| 496 | C(O) | C(O) | —C(CH₃)₃ | H | —C₆H₃F-2-Cl-6 | —C₆H₃Cl₂-2,4 |
| 497 | C(O) | C(O) | —C(CH₃)₃ | H | —C₆H₃F-2-Cl-6 | —C₆H₄F-4 |
| 498 | C(O) | C(O) | —C(CH₃)₃ | H | —C₆H₄CH₂CH₂Cl-4 | —C₆H₃(CH₃)₂-3,5 |
| 499 | C(O) | C(O) | —C(CH₃)₃ | H | —C₆H₂F₃-2,4,6 | —C₆H₅ |
| 500 | C(O) | C(O) | —C(CH₃)₃ | H | —C₆H₂F₃-2,4,6 | —C₆H₃Cl₂-2,4 |
| 501 | C(O) | C(O) | —C(CH₃)₃ | H | —C₆H₂F₃-2,4,6 | —C₆H₄Br-2 |

TABLE I-continued $$\underset{F}{A'-\overset{\overset{X}{\|}}{C}-N-\overset{\overset{E}{|}}{N}-\overset{\overset{X'}{\|}}{C}-B'}$$

| Ex. # | C(X) | C(X') | E | F | A' | B' |
|---|---|---|---|---|---|---|
| 502 | C(O) | C(O) | —C(CH$_3$)$_3$ | H | —C$_6$H$_2$F$_3$-2,4,6 | —C$_6$H$_3$(CH$_3$)$_2$-3,5 |
| 503 | C(O) | C(O) | —C(CH$_3$)$_3$ | H | —C$_6$H$_3$NO$_2$-2-Cl-3 | —C$_6$H$_5$ |
| 504 | C(O) | C(O) | —C(CH$_3$)$_3$ | H | —C$_6$H$_3$NO$_2$-2-Cl-3 | —C$_6$H$_4$Br-2 |
| 505 | C(O) | C(O) | —C(CH$_3$)$_3$ | H | —C$_6$H$_3$NO$_2$-2-Cl-3 | —C$_6$H$_4$NO$_2$-2 |
| 506 | C(O) | C(O) | —C(CH$_3$)$_3$ | H | —C$_6$H$_3$NO$_2$-2-Cl-3 | —C$_6$H$_4$CH$_3$-3 |
| 507 | C(O) | C(O) | —C(CH$_3$)$_3$ | H | —C$_6$H$_3$NO$_2$-2-Cl-3 | —C$_6$H$_4$Cl-3 |
| 508 | C(O) | C(O) | —C(CH$_3$)$_3$ | H | —C$_6$H$_3$NO$_2$-2-Cl-3 | —C$_6$H$_3$Cl$_2$-2,4 |
| 509 | C(O) | C(O) | —C(CH$_3$)$_3$ | H | —C$_6$H$_3$NO$_2$-2-Cl-3 | —C$_6$H$_3$Cl$_2$-3,5 |
| 510 | C(O) | C(O) | —C(CH$_3$)$_3$ | H | —C$_6$H$_3$NO$_2$-2-Cl-3 | —C$_6$H$_3$(CH$_3$)$_2$-3,5 |
| 511 | C(O) | C(O) | —C(CH$_3$)$_3$ | H | —C$_6$H$_4$CH$_2$CH$_3$-4 | —C$_6$H$_3$F$_2$-2,3 |
| 512 | C(O) | C(O) | —C(CH$_3$)$_3$ | H | —C$_6$H$_4$CH$_2$CH$_3$-4 | —C$_6$H$_3$Cl$_2$-2,3 |
| 513 | C(O) | C(O) | —C(CH$_3$)$_3$ | H | —C$_6$H$_3$F$_2$-2,3 | —C$_6$H$_5$ |
| 514 | C(O) | C(O) | —C(CH$_3$)$_3$ | H | —C$_6$H$_3$Cl$_2$-2,3 | —C$_6$H$_4$NO$_2$-2 |
| 515 | C(O) | C(O) | —C(CH$_3$)$_3$ | H | —C$_6$H$_5$ | —C$_6$H$_3$F$_2$-2,3 |
| 516 | C(O) | C(O) | —C(CH$_3$)$_3$ | H | —C$_6$H$_3$Cl$_2$-2,3 | —C$_6$H$_3$(CH$_3$)$_2$-3,5 |
| 517 | C(O) | C(O) | —C(CH$_3$)$_3$ | H | —C$_6$H$_3$Cl$_2$-2,3 | —C$_6$H$_3$Cl$_2$-2,4 |
| 518 | C(O) | C(O) | —C(CH$_3$)$_3$ | H | —C$_6$H$_3$Cl$_2$-2,3 | —C$_6$H$_3$Cl$_2$-3,5 |
| 519 | C(O) | C(O) | —C(CH$_3$)$_3$ | H | —C$_6$H$_3$Cl$_2$-2,3 | —C$_6$H$_4$Cl-3 |
| 520 | C(O) | C(O) | —C(CH$_3$)$_3$ | H | —C$_6$H$_3$Cl$_2$-2,3 | C$_6$H$_3$(CH$_3$)$_2$-2,3 |
| 521 | C(O) | C(O) | —C(CH$_3$)$_3$ | H | —C$_6$H$_3$F$_2$-2,3 | —C$_6$H$_4$Br-2 |
| 522 | C(O) | C(O) | —C(CH$_3$)$_3$ | H | —C$_6$H$_3$(CH$_3$)$_2$-2,3 | —C$_6$H$_4$Cl-4 |
| 523 | C(O) | C(O) | —C(CH$_3$)$_3$ | H | —C$_6$H$_3$(CH$_3$)$_2$-2,3 | C$_6$H$_3$Cl$_2$-2,4 |
| 524 | C(O) | C(O) | —C(CH$_3$)$_3$ | H | —C$_6$H$_3$(CH$_3$)$_2$-2,3 | —C$_6$H$_3$F$_2$-2,6 |
| 525 | C(O) | C(O) | —C(CH$_3$)$_3$ | H | —C$_6$H$_3$(CH$_3$)$_2$-2,3 | —C$_6$H$_3$F$_2$-2,4 |
| 526 | C(O) | C(O) | —C(CH$_3$)$_3$ | H | —C$_6$H$_3$(CH$_3$)$_2$-2,3 | —C$_6$H$_4$OCH$_3$-3 |
| 527 | C(O) | C(O) | —C(CH$_3$)$_3$ | H | —C$_6$H$_3$(CH$_3$)$_2$-2,3 | —C$_6$H$_4$OCH$_3$-2 |
| 528 | C(O) | C(O) | —C(CH$_3$)$_3$ | H | —C$_6$H$_3$(CH$_3$)$_2$-2,3 | —C$_6$H$_4$CH$_3$-2 |
| 529 | C(O) | C(O) | —C(CH$_3$)$_3$ | H | —C$_6$H$_3$(CH$_3$)$_2$-2,3 | —C$_6$H$_4$CH$_3$-4 |
| 530 | C(O) | C(O) | —C(CH$_3$)$_3$ | H | —C$_6$H$_3$CH$_3$-2-Cl-3 | —C$_6$H$_3$Cl$_2$-2,4 |
| 531 | C(O) | C(O) | —C(CH$_3$)$_3$ | H | —C$_6$H$_4$CH$_2$CH$_2$Cl-4 | —C$_6$H$_5$ |
| 532 | C(O) | C(O) | —C(CH$_3$)$_3$ | H | —C$_6$H$_4$CH$_2$CH$_2$Cl-4 | —C$_6$H$_3$Cl$_2$-2,4 |
| 533 | C(O) | C(O) | —C(CH$_3$)$_3$ | H | —C$_6$H$_3$F-3-CH$_3$-4 | —C$_6$H$_3$(CH$_3$)$_2$-3,5 |
| 534 | C(O) | C(O) | —C(CH$_3$)$_3$ | H | —C$_6$H$_3$F-3-CH$_3$-4 | —C$_6$H$_3$F$_2$-3,5 |
| 535 | C(O) | C(O) | —C(CH$_3$)$_3$ | H | —C$_6$H$_5$F-3-CH$_3$-4 | —C$_6$H$_4$CH$_3$-3 |
| 536 | C(O) | C(O) | —C(CH$_3$)$_3$ | H | —C$_6$H$_3$F-3-CH$_3$-4 | —C$_6$H$_3$Cl$_2$-3,5 |
| 537 | C(O) | C(O) | —C(CH$_3$)$_3$ | H | —C$_6$H$_3$F-3-CH$_3$-4 | —C$_6$H$_4$NO$_2$-2 |
| 538 | C(O) | C(O) | —C(CH$_3$)$_3$ | H | —C$_6$H$_3$F-3-CH$_3$-4 | —C$_6$H$_3$Cl$_2$-2,4 |
| 539 | C(O) | C(O) | —C(CH$_3$)$_3$ | H | —C$_6$H$_4$CH$_2$CH$_3$-4 | —C$_6$H$_3$F$_2$-3,5 |
| 540 | C(O) | C(O) | —C(CH$_3$)$_3$ | H | —C$_6$H$_3$(CH$_3$)$_2$-2,3 | —C$_6$H$_4$I-2 |
| 541 | C(O) | C(O) | —C(CH$_3$)$_3$ | H | —C$_6$H$_4$CH$_2$CH$_2$OH-4 | —C$_6$H$_3$(CH$_3$)$_2$-3,5 |
| 542 | C(O) | C(O) | —C(CH$_3$)$_3$ | H | —C$_6$H$_2$F$_2$-2,6—CH$_3$-3 | —C$_6$H$_5$ |
| 543 | C(O) | C(O) | —C(CH$_3$)$_3$ | H | —C$_6$H$_2$F$_2$-2,6—CH$_3$-3 | —C$_6$H$_4$CH$_3$-3 |
| 544 | C(O) | C(O) | —C(CH$_3$)$_3$ | H | —C$_6$H$_2$F$_2$-2,6—CH$_3$-3 | —C$_6$H$_3$Cl$_2$-2,4 |
| 545 | C(O) | C(O) | —C(CH$_3$)$_3$ | H | —C$_6$H$_4$Cl-4 | —C$_6$H$_3$(CH$_3$)$_2$-2,3 |
| 546 | C(O) | C(O) | —CHC(CH$_3$)$_3$ / —CH$_3$ | H | —C$_6$H$_3$(CH$_3$)$_2$-2,3 | —C$_6$H$_3$(CH$_3$)$_2$-3,5 |
| 547 | C(O) | C(O) | —CHC(CH$_3$)$_3$ / —CH$_3$ | H | —C$_6$H$_3$(CH$_3$)$_2$-2,3 | —C$_6$H$_4$CH$_3$-3 |
| 548 | C(O) | C(O) | —C(CH$_3$)$_3$ | H | —C$_6$H$_3$F-2-Cl-6 | —C$_6$H$_3$F$_2$-2,3 |
| 549 | C(O) | C(O) | —C(CH$_3$)$_3$ | H | C$_6$H$_3$F$_2$-2,3 | —C$_6$H$_4$NO$_2$-2 |
| 550 | C(O) | C(O) | —C(CH$_3$)$_3$ | H | —C$_6$H$_3$F$_2$-2,3 | —C$_6$H$_4$CH$_3$-3 |
| 551 | C(O) | C(O) | —C(CH$_3$)$_3$ | H | —C$_6$H$_3$F$_2$-2,3 | —C$_6$H$_3$(CH$_3$)$_2$-3,5 |
| 552 | C(O) | C(O) | —C(CH$_3$)$_3$ | H | —C$_6$H$_3$F$_2$-2,3 | —C$_6$H$_3$Cl$_2$-2,4 |
| 553 | C(O) | C(O) | —C(CH$_3$)$_3$ | H | —C$_6$H$_3$(CH$_3$)$_2$-2,3 | —C$_6$H$_3$F$_2$-2,3 |
| 554 | C(O) | C(O) | —C(CH$_3$)$_3$ | H | —C$_6$H$_3$(CH$_3$)$_2$-2,3 | —C$_6$H$_3$Cl$_2$-2,3 |
| 555 | C(O) | C(O) | —C(CH$_3$)$_3$ | H | —C$_6$H$_3$(CH$_3$)$_2$-2,3 | —C$_6$H$_3$(CH$_3$)$_2$-3,4 |
| 556 | C(O) | C(O) | —C(CH$_3$)$_3$ | H | —C$_6$H$_3$(CH$_3$)$_2$-213 | —C$_6$H$_4$NO$_2$-2 |
| 557 | C(O) | C(O) | —C(CH$_3$)$_3$ | H | —C$_6$H$_4$CH$_2$CH$_3$-4 | —C$_6$H$_3$CH$_3$-2-Cl-5 |
| 558 | C(O) | C(O) | —C(CH$_3$)$_3$ | H | —C$_6$H$_3$(CH$_3$)$_2$-2,3 | —C$_6$H$_5$ |
| 559 | C(O) | C(O) | —C(CH$_3$)$_3$ | H | —C$_6$H$_5$ | —C$_6$H$_3$CH$_3$-2-Cl-5 |
| 560 | C(O) | C(O) | —C(CH$_3$)$_3$ | H | —C$_6$H$_3$F$_2$-2,6 | —C$_6$H$_3$CH$_3$-2-Cl-5 |
| 561 | C(O) | C(O) | —C(CH$_3$)$_3$ | H | —C$_6$H$_3$(CH$_3$)$_2$-2,3 | —C$_6$H$_3$CH$_3$-2-Cl-5 |
| 562 | C(O) | C(O) | —C(CH$_3$)$_3$ | H | —C$_6$H$_3$CH$_3$-2-Cl-3 | —C$_6$H$_3$CH$_3$-2-Cl-5 |

TABLE I-continued $$A'-\overset{\overset{X}{\|}}{C}-\underset{\underset{F}{|}}{N}-\overset{\overset{E}{\|}}{N}-\overset{\overset{X'}{\|}}{C}-B'$$

| Ex. # | C(X) | C(X') | E | F | A' | B' |
|---|---|---|---|---|---|---|
| 563 | C(O) | C(O) | —C(CH₃)₃ | H | —C₆H₃F₂-2,6 | —C₆H₃Cl-2-CH₃-5 |
| 564 | C(O) | C(O) | —C(CH₃)₃ | H | —C₆H₃(CH₃)₂-2,3 | —C₆H₃Cl-2-CH₃-5 |
| 565 | C(O) | C(O) | —C(CH₃)₃ | H | —C₆H₃CH₃-2-Cl-3 | —C₆H₃Cl-2-CH₃-5 |
| 566 | C(O) | C(O) | —C(CH₃)₃ | H | —C₆H₄Cl-4 | —C₆H₃CH₃-2-Cl-5 |
| 567 | C(O) | C(O) | —C(CH₃)₃ | H | —C₆H₄Cl-4 | —C₆H₃Cl-2-CH₃-5 |
| 568 | C(O) | C(O) | —C(CH₃)₃ | H | —C₆H₃F-2-Cl-4 | —C₆H₅ |
| 569 | C(O) | C(O) | —C(CH₃)₃ | H | —C₆H₃F-2-Cl-4 | —C₆H₄CH₃-3 |
| 570 | C(O) | C(O) | —C(CH₃)₃ | H | —C₆H₃F-2-Cl-4 | —C₆H₃(CH₃)₂-3,5 |
| 571 | C(O) | C(O) | —C(CH₃)₃ | H | —C₆H₃F-2-Cl-4 | —C₆H₃Cl₂-3,5 |
| 572 | C(O) | C(O) | —C(CH₃)₃ | H | —C₆H₃F-2-Cl-4 | —C₆H₄Br-2 |
| 573 | C(O) | C(O) | —C(CH₃)₃ | H | —C₆H₃F-2-Cl-4 | —C₆H₄NO₂-2 |
| 574 | C(O) | C(O) | —C(CH₃)₃ | H | —C₆H₃Cl-2-CH₃-3 | C₆H₃Cl₂-2,4 |
| 575 | C(O) | C(O) | —C(CH₃)₃ | H | —C₆H₃Cl-2-CH₃-3 | —C₆H₅ |
| 576 | C(O) | C(O) | —C(CH₃)₃ | H | —C₆H₃Cl-2-CH₃-3 | —C₆H₄CH₃-3 |
| 577 | C(O) | C(O) | —C(CH₃)₃ | H | —C₆H₃Cl-2-CH₃-3 | —C₆H₃(CH₃)₂-3,5 |
| 578 | C(O) | C(O) | —C(CH₃)₃ | H | —C₆H₃Cl-2-CH₃-3 | —C₆H₃Cl₂-3,5 |
| 579 | C(O) | C(O) | —C(CH₃)₃ | H | —C₆H₃Br-2-CH₃-3 | —C₆H₃(CH₃)₂-3,5 |
| 580 | C(O) | C(O) | —C(CH₃)₃ | H | —C₆H₃Br-2-CH₃-3 | —C₆H₃Cl₂-2,4 |
| 581 | C(O) | C(O) | —C(CH₃)₃ | H | —C₆H₃Br-2-CH₃-3 | —C₆H₄CH₃-3 |
| 582 | C(O) | C(O) | —C(CH₃)₃ | H | —C₆H₃Br-2-CH₃-3 | —C₆H₃Cl₂-3,5 |
| 583 | C(O) | C(O) | —C(CH₃)₃ | H | —C₆H₃Br-2-CH₃-3 | —C₆H₄Br-2 |
| 584 | C(O) | C(O) | —C(CH₃)₃ | H | —C₆H₃(CH₃)₂-2,3 | —C₆H₄Cl-2 |
| 585 | C(O) | C(O) | —C(CH₃)₃ | H | —C₆H₃(CH₃)₂-2,3 | —C₆H₄CF₃-2 |
| 586 | C(O) | C(O) | —C(CH₃)₃ | H | —C₆H₃(CH₃)₂-2,3 | —C₆H₄CH₂CH₃- |
| 587 | C(O) | C(O) | —C(CH₃)₃ | H | —C₆H₃(CH₃)₂-2,3 | —C₆H₃Cl₂-3,5 |
| 588 | C(O) | C(O) | —C(CH₃)₃ | H | —C₆H₃F₂-2,6 | —C₆H₃-3-F-4 |
| 589 | C(O) | C(O) | —C(CH₃)₃ | H | —C₆H₄Cl-4 | —C₆H₃F₂-3,5 |
| 590 | C(O) | C(O) | —C(CH₃)₃ | H | —C₆H₃(CH₃)₂-2,3 | —C₆H₃F₂-3,5 |
| 591 | C(O) | C(O) | —C(CH₃)₃ | H | —C₆H₃CH₃-2-Cl-3 | —C₆H₃F₂-3,5 |
| 592 | C(O) | C(O) | —C(CH₃)₃ | H | —C₆H₅ | —C₆H₃F₂-3,5 |
| 593 | C(O) | C(O) | —C(CH₃)₃ | H | —C₆H₄CH₂CH₃-4 | —C₆H₃(CH₃)₂-2,5 |
| 594 | C(O) | C(O) | —C(CH₃)₃ | H | —C₆H₃F₂-2,6 | —C₆H₃F₂-3,5 |
| 595 | C(O) | C(O) | —C(CH₃)₃ | H | —C₆H₃CH₃-2-Cl-3 | —C₆H₃Cl₂-3,5 |
| 596 | C(O) | C(O) | —C(CH₃)₃ | H | —C₆H₃(CH₃)₂-2,3 | C₆H₃(CH₃)₂-2,5 |
| 597 | C(O) | C(O) | —C(CH₃)₃ | H | —C₆H₄Br-2 | —C₆H₃(CH₃)₂-3,5 |
| 598 | C(O) | C(O) | —C(CH₃)₃ | H | —C₆H₃Br-2-CH₃-3 | —C₆H₄Cl-3 |
| 599 | C(O) | C(O) | —C(CH₃)₃ | H | —C₆H₃Cl-2-CH₃-3 | —C₆H₄Cl-3 |
| 600 | C(O) | C(O) | —C(CH₃)₃ | H | —C₆H₃Br-2-CH₃-3 | —C₆H₄NO₂-2 |
| 601 | C(O) | C(O) | —C(CH₃)₃ | H | —C₆H₃Cl-2-CH₃-3 | —C₆H₄NO₂-2 |
| 602 | C(O) | C(O) | —C(CH₃)₃ | H | —C₆H₃(CH₃)₂-2,3 | —C₆H₃NO₂-2-CH₃-3 |
| 603 | C(O) | C(O) | —C(CH₃)₃ | H | C₆H₃(CH₃)₂-2,3 | —C₆H₃NO₂-2-CH₃-5 |
| 604 | C(O) | C(O) | —C(CH₃)₃ | H | —C₆H₃F₂-2,6 | —C₆H₅ |
| 605 | C(O) | C(O) | —C(CH₃)₃ | H | —C₆H₃(CH₃)₂-2,6 | C₆H₃Cl₂-2,4 |
| 606 | C(O) | C(O) | —C(CH₃)₃ | H | —C₆H₂(CH₃)₃-2,4,6 | —C₆H₃(CH₃)₂-3,5 |
| 607 | C(O) | C(O) | —C(CH₃)₃ | H | —C₆H₂(CH₃)₃-2,4,6 | —C₆H₃Cl₂-2,4 |
| 608 | C(O) | C(O) | —C(CH₃)₃ | H | —C₆H₃F₂-2,6 | —C₆H₄CH₃-4 |
| 609 | C(O) | C(O) | —C(CH₃)₃ | H | —C₆H₃F₂-2,6 | —C₆H₃Cl₂-2,5 |
| 610 | C(O) | C(O) | —C(CH₃)₃ | H | —C₆H₂(CH₃)₃-2,4,6 | —C₆H₄Cl-4 |
| 611 | C(O) | C(O) | —C(CH₃)₃ | H | —C₆H₂(CH₃)₃-2,4,6 | —C₆H₄CH₃-3 |
| 612 | C(O) | C(O) | —C(CH₃)₃ | H | —C₆H₂(CH₃)₃-2,4,6 | —C₆H₃Cl₂-3,4 |
| 613 | C(O) | C(O) | —C(CH₃)₃ | H | —C₆H₄CC(O)CH₃-2 | —C₆H₄OC(O)CH₃-2 |
| 614 | C(O) | C(O) | —C(CH₃)₃ | H | —C₆H₄OH-2 | —C₆H₄OH-2 |
| 615 | C(O) | C(O) | —C(CH₃)₃ | H | —C₆H₃(CH₃)₂-2,4 | —C₆H₄CH₃-3 |
| 616 | C(O) | C(O) | —C(CH₃)₃ | H | —C₆H₃(CH₃)₂-2,4 | —C₆H₃Cl₂-2,4 |
| 617 | C(O) | C(O) | —C(CH₃)₃ | H | —C₆H₃(CH₃)₂-2,4 | —C₆H₃(CH₃)₂-3,5 |
| 618 | C(O) | C(O) | —C(CH₃)₃ | H | —C₆H₃(CH₃)₂-2,4 | —C₆H₃Cl₂-3,5 |
| 619 | C(O) | C(O) | —C(CH₃)₃ | H | —C₆H₃(CH₃)₂-2,4 | —C₆H₄Br-3 |
| 620 | C(O) | C(O) | —C(CH₃)₃ | H | —C₆H₃(CH₃)₂-2,4 | —C₆H₃Cl₂-3,4 |
| 621 | C(O) | C(O) | —C(CH₃)₃ | H | —C₆H₃Br-2-CH₃-3 | —C₆H₅ |
| 622 | C(O) | C(O) | —C(CH₃)₃ | H | 3,4-methylenedioxy | —C₆H₅ |
| 623 | C(O) | C(O) | —C(CH₃)₃ | H | 3,4-methylenedioxy | —C₆H₄Cl-4 |
| 624 | C(O) | C(O) | —C(CH₃)₃ | H | 314-methylenedioxy | —C₆H₄CH₃-3 |
| 625 | C(O) | C(O) | —C(CH₃)₃ | H | 4-(4,4-dimethyl-2-oxazinyl)phenyl | —C₆H₄CH₃-3 |
| 626 | C(O) | C(O) | —C(CH₃)₃ | H | 2-pyrolylphenyl | —C₆H₅ |
| 627 | C(O) | C(O) | —C(CH₃)₃ | H | 2-pyrolylphenyl | —C₆H₄CH₃-3 |
| 628 | C(O) | C(O) | —C(CH₃)₃ | H | —C₆H₃(CH₃)₂-2,3 | —C₆H₃Br-2-Cl-5 |
| 629 | C(O) | C(O) | —C(CH₃)₃ | H | —C₆H₃CH₃-2-Cl-3 | —C₆H₄Cl-3 |
| 630 | C(O) | C(O) | —C(CH₃)₃ | H | —C₆H₃CH₃-2-Cl-3 | —C₆H₄F-3 |

TABLE I-continued $$A'-\overset{X}{\underset{\|}{C}}-\underset{\underset{F}{|}}{N}-\overset{E}{N}=\overset{X'}{\underset{\|}{C}}-B'$$

| Ex. # | C(X) | C(X') | E | F | A' | B' |
|---|---|---|---|---|---|---|
| 631 | C(O) | C(O) | —C(CH₃)₃ | H | —C₆H₃CH₃-2-Cl-3 | —C₆H₄Br-2 |
| 632 | C(O) | C(O) | —C(CH₃)₃ | H | —C₆H₃CH₃-2-Cl-3 | —C₆H₃CH₃-2-Cl-3 |
| 633 | C(O) | C(O) | —C(CH₃)₃ | H | —C₆H₃CH₃-2-Cl-3 | —C₆H₂(CH₃)₂-3,5—Cl-4 |
| 634 | C(O) | C(O) | —CHC(CH₃)₃ / —CH₃ | H | —C₆H₅ | —C₆H₃CH₃-2-Cl-3 |
| 635 | C(O) | C(O) | —C(CH₃)₃ | CH₃ | —C₆H₅ | —C₆H₅ |
| 636 | C(O) | C(O) | —C(CH₃)₃ | CH₂—C₆H₅ | —C₆H₅ | —C₆H₅ |
| 637 | C(O) | C(O) | —C(CH₃)₃ | CH₂CH=CH₂ | —C₆H₅ | —C₆H₅ |
| 638 | C(O) | C(O) | —C(CH₃)₃ | CH₂OCH₃ | —C₆H₅ | —C₆H₅ |
| 639 | C(O) | C(O) | —C(CH₃)₃ | —CH₂SCH₃ | —C₆H₅ | —C₆H₅ |
| 640 | C(O) | C(O) | —C(CH₃)₃ | —CH₂C≡CH | —C₆H₅ | —C₆H₅ |
| 641 | C(O) | C(O) | —C(CH₃)₃ | —CH₂C≡CH | —C₆H₄CH₃-4 | —C₆H₄CH₃-3 |
| 642 | C(O) | C(O) | —C(CH₃)₃ | —CH₂C≡CH | —C₆H₅ | —C₆H₃(CH₃)₂-3,5 |
| 643 | C(O) | C(O) | —C(CH₃)₃ | —CH₂C≡CH | —C₆H₅ | —C₆H₃Cl₂-2,4 |
| 644 | C(O) | C(O) | —C(CH₃)₃ | —CH₂C≡CH | —C₆H₅ | —C₆H₃Cl₂-3,4 |
| 645 | C(O) | C(O) | —C(CH₃)₃ | CH₂C₆H₄Br-4 | —C₆H₅ | —C₆H₅ |
| 646 | C(O) | C(O) | —C(CH₃)₃ | H | —C₆H₁₁ | —C₆H₅ |
| 647 | C(O) | C(O) | —C(CH₃)₃ | H | —CH₂CH₂CH₃ | —C₆H₄Cl-4 |
| 648 | C(O) | C(O) | —C(CH₃)₃ | H | —CH₂CH₂CH₂CH₃ | —C₆H₅ |
| 649 | C(O) | C(O) | —C(CH₃)₃ | H | —CH₂CH₂CH₂CH₃ | —C₆H₄Cl-4 |
| 650 | C(O) | C(O) | —C(CH₃)₃ | H | —CH₂CH₂CH₂CH₃ | —C₆H₄CH₃-4 |
| 651 | C(O) | C(O) | —C(CH₃)₃ | H | —CH₂CH₂CH₃ | —C₆H₅ |
| 652 | C(O) | C(O) | —C(CH₃)₃ | H | —CH₂CH₂CH₂CH₃ | —C₆H₄F-4 |
| 653 | C(O) | C(O) | —C(CH₃)₃ | H | —CH₂CH₂CH₂CH₃ | —C₆H₄CF₃-4 |
| 654 | C(O) | C(O) | —C(CH₃)₃ | H | —CH₂C₆H₅ | —C₆H₅ |
| 655 | C(O) | C(O) | —C(CH₃)₃ | H | —C(CH₃)₃ | —C₆H₄Cl-4 |
| 656 | C(O) | C(O) | —C(CH₃)₃ | H | cyclohex-1-enyl | —C₆H₅ |
| 657 | C(O) | C(O) | —C(CH₃)₃ | H | —CH₂Cl | —C₆H₅ |
| 658 | C(O) | C(O) | —C(CH₃)₃ | H | —CHCl₂ | —C₆H₅ |
| 659 | C(O) | C(O) | —C(CH₃)₃ | H | —CCl₃ | —C₆H₅ |
| 660 | C(O) | C(O) | —C(CH₃)₃ | H | —C(CH₃)₂CH₂Cl | —C₆H₅ |
| 661 | C(O) | C(O) | —C(CH₃)₃ | H | —C(Cl)=CCl₂ | —C₆H₅ |
| 662 | C(O) | C(O) | —C(CH₃)₃ | H | CH₂CH₂CH₂CH₂CH₃ | —C₆H₃Cl₂-3,4 |
| 663 | C(O) | C(O) | —C(CH₃)₃ | H | CH₂CH₂CH₂CH₂CH₃ | —C₆H₄CH₃-3 |
| 664 | C(O) | C(O) | —C(CH₃)₃ | H | —C(CH₃)=CH₂ | —C₆H₅ |
| 665 | C(O) | C(O) | —C(CH₃)₃ | H | cyclobutanyl | —C₆H₅ |
| 666 | C(O) | C(O) | —C(CH₃)₃ | H | 2-norbornyl | —C₆H₄CH₃-3 |
| 667 | C(O) | C(O) | —C(CH₃)₃ | H | cyclohex-3enyl | —C₆H₄CH₃-3 |
| 668 | C(O) | C(O) | —C(CH₃)₃ | H | —CH₂CO₂—CH₂CH₃ | —C₆H₄Cl₂-3,4 |
| 669 | C(O) | C(O) | —C(CH₃)₃ | H | —CHCO₂—CH₂CH₃ / —CH₂OH | —C₆H₄Cl₂-3,4 |
| 670 | C(O) | C(O) | —C(CH₃)₃ | H | 3-acetyl-2,2-dimethylcyclobutyl-methyl | —C₆H₄CH₃-3 |
| 671 | C(O) | C(O) | —C(CH₃)₃ | H | —CH=CHCH₂CH₃ | —C₆H₄CH₃-3 |
| 672 | C(O) | C(O) | —C(CH₃)₃ | H | —CH₂CH₂CH=CH₂ | —C₆H₄CH₃-3 |
| 673 | C(O) | C(O) | —C(CH₃)₃ | H | CH₂CH₂CH₂CO₂CH₃ | —C₆H₄CH₃-3 |
| 674 | C(O) | C(O) | —C(CH₃)₃ | H | —CH(CH₃)₂ | —C₆H₃(CH₃)₂-3,5 |
| 675 | C(O) | C(O) | —C(CH₃)₃ | H | 2-propenyl | —C₆H₃(CH₃)₂-3,5 |
| 676 | C(O) | C(O) | —C(CH₃)₃ | H | —CH(CH₃)₂ | —C₆H₄Br-2 |
| 677 | C(O) | C(O) | —C(CH₃)₃ | H | —CH(CH₃)₂ | —C₆H₅ |
| 678 | C(O) | C(O) | —C(CH₃)₃ | H | 3,4-E-dihydroxy cyclohexane | —C₆H₄CH₃-3 |
| 679 | C(O) | C(O) | —C(CH₃)₃ | H | 3,4-Z-dihydroxy cyclohexane | —C₆H₄CH₃-3 |
| 680 | C(O) | C(O) | —C(CH₃)₃ | H | O CH₃ | —C₆H₄CH₃-3 |
| 681 | C(O) | C(O) | —C(CH₃)₃ | H | 2-methylcyclohex-2,5-dienyl | —C₆H₄CH₃-3 |
| 682 | C(O) | C(O) | —C(CH₃)₃ | H | —C₆H₅ | CH₂CH₂CH₂CH₂CH₃ |
| 683 | C(O) | C(O) | —C(CH₃)₃ | H | —C₆H₅ | cyclohexenyl |
| 684 | C(O) | C(O) | —C(CH₃)₃ | H | —C₆H₃Cl₂-3,5 | —CH₂CH₂Br |

TABLE I-continued $$A'-\overset{X}{\underset{\|}{C}}-\underset{\underset{F}{|}}{N}-\overset{E}{\underset{}{N}}-\overset{X'}{\underset{\|}{C}}-B'$$

| Ex. # | C(X) | C(X') | E | F | A' | B' |
|---|---|---|---|---|---|---|
| 685 | C(O) | C(O) | —C(CH₃)₃ | H | —C₆H₃Cl₂-3,5 | —CH₂Cl |
| 686 | C(O) | C(O) | —C(CH₃)₃ | H | —C₆H₃Cl₂-3,5 | —CH(CH₃)Br |
| 687 | C(O) | C(O) | —C(CH₃)₃ | H | —C₆H₃Cl₂-3,5 | —CH=CH₂ |
| 688 | C(O) | C(O) | —C(CH₃)₃ | H | —C₆H₅ | —C(CH₃)₃ |
| 689 | C(O) | C(O) | —C(CH₃)₃ | H | —C₆H₅ | —CH₂C₆H₅ |
| 690 | C(O) | C(O) | —C(CH₃)₃ | H | —C₆H₃Cl₂-3,4 | —CH₃ |
| 691 | C(O) | C(O) | —C(CH₃)₃ | H | —C₆H₅ | 2-trifluoromethyl-1-propenyl |
| 692 | C(O) | C(O) | —C(CH₃)₃ | H | —C₆H₄Cl-4 | —C(CH₃)₃ |
| 693 | C(O) | C(O) | —C(CH₃)₃ | H | —C₆H₄Cl-4 | —CH=CHC₆H₅ |
| 694 | C(O) | C(O) | —C(CH₃)₃ | H | —C₆H₄Cl-4 | —CH₂C₆H₅ |
| 695 | C(O) | C(O) | —C(CH₃)₃ | H | —C₆H₃NO₂-2-Cl-4 | —CH=CHC₆H₄CF₃-3 |
| 696 | C(O) | C(O) | —C(CH₃)₃ | H | —C₆H₃NO₂-2-Cl-4 | —CH=CHC₆H₄CN-4 |
| 697 | C(O) | C(O) | —C(CH₃)₃ | H | —C₆H₃NO₂-2-Cl-4 | —CH=CHC₆H₄Cl-4 |
| 698 | C(O) | C(O) | —C(CH₃)₃ | H | —C₆H₅ | cyclohexenyl |
| 699 | C(O) | C(O) | —C(CH₃)₃ | H | —C₆H₅ | —C(CH₃)=CH₂ |
| 699 | C(O) | C(O) | —C(CH₃)₃ | H | —C₆H₅ | 2-phenylcyclopropyl |
| 701 | C(O) | C(O) | —C(CH₃)₃ | H | —C₆H₃Cl₂-3,4 | cyclopropyl |
| 702 | C(O) | C(O) | —C(CH₃)₃ | H | —C₆H₄Cl-4 | cyclobutyl |
| 703 | C(O) | C(O) | —C(CH₃)₃ | H | —C₆H₅ | 2-(3-furyl)ethenyl |
| 704 | C(O) | C(O) | —C(CH₃)₃ | H | —C₆H₅ | —CHCO₂CH₂CH₂-CH₂OH |
| 705 | C(O) | C(O) | —C(CH₃)₃ | H | —C₆H₃(CH₃)₂-2,3 | 3-cyclohexenyl |
| 706 | C(O) | C(O) | —C(CH₃)₃ | H | —C₆H₃(CH₃)₂-2,3 | 1-(4-chlorophenyl)-2-methyl-2-propyl |
| 707 | C(O) | C(O) | —C(CH₃)₃ | H | —C₆H₅ | 2-methylcyclohex-2,5-dienyl |
| 708 | C(O) | C(O) | —C(CH₃)₃ | H | —C₆H₅ | —CC—C₆H₅ |
| 709 | C(O) | C(O) | —C(CH₃)₃ | H | —C₆H₅ | —CH(CH₃)CH₂CH₃ |
| 710 | C(O) | C(O) | —C(CH₃)₃ | H | —C₆H₅ | 1-phenyl-2-methyl-1-butyl |
| 711 | C(O) | C(O) | —C(CH₃)₃ | H | —C₆H₅ | 3-acetyl-2,2-dimethylcyclobutyl-methyl |
| 712 | C(O) | C(O) | —C(CH₃)₃ | H | —C₆H₅ | —CH=CHCH₂CH₃ |
| 713 | C(O) | C(O) | —C(CH₃)₃ | H | —C₆H₅ | —CH₂CH₂CH=CH₂ |
| 714 | C(O) | C(O) | —C(CH₃)₃ | H | —C₆H₅ | CH₂CH₂CH₂CO₂CH₃ |
| 715 | C(O) | C(O) | —C(CH₃)₃ | H | —C₆H₅ | —CH₂OCH₃ |
| 716 | C(O) | C(O) | —C(CH₃)₃ | H | —C₆H₃(CH₃)₂-2,3 | 2-propenyl |
| 717 | C(O) | C(O) | —C(CH₃)₃ | H | —C₆H₄CH₂CH₃-4 | 2-propenyl |
| 718 | C(O) | C(O) | —C(CH₃)₃ | H | —C₆H₃(CH₃)₂-2,3 | —CH(CH₃)₂ |
| 719 | C(O) | C(O) | —C(CH₃)₃ | H | —C₆H₃(CH₃)₂-2,3 | —C(CH₃)₃ |
| 720 | C(O) | C(O) | —C(CH₃)₃ | H | —C₆H₃(CH₃)₂-2,3 | 2-but-1-enyl |
| 721 | C(O) | C(O) | —C(CH₃)₃ | H | —C₆H₃(CH₃)₂-2,3 | 2-pent-2-enyl |
| 722 | C(O) | C(O) | —C(CH₃)₃ | H | —C₆H₅ | 4-pyridyl |
| 723 | C(O) | C(O) | —C(CH₃)₃ | H | 2-pyridyl | C₆H₅ |
| 724 | C(O) | C(O) | —C(CH₃)₃ | H | —C₆H₅ | 3-pyridyl |
| 725 | C(O) | C(O) | —C(CH₃)₃ | H | 3-pyridyl | —C₆H₃Cl₂-3,4 |
| 726 | C(O) | C(O) | —C(CH₃)₃ | H | 3-pyridyl | —C₆H₅ |
| 727 | C(O) | C(O) | —C(CH₃)₃ | H | 2-pyridyl | —C₆H₄NO₂-2 |
| 728 | C(O) | C(O) | —C(CH₃)₃ | H | 2-pyridyl | —C₆H₄CH₂CH₃-4 |
| 729 | C(O) | C(O) | —C(CH₃)₃ | H | 2-pyridyl | —C₆H₄Br-2 |
| 730 | C(O) | C(O) | —C(CH₃)₃ | H | —C₆H₄CH₂CH₃-4 | 2-pyridyl |
| 731 | C(O) | C(O) | —C(CH₃)₃ | H | —C₆H₄OCF₃-4 | 2-pyridyl |
| 732 | C(O) | C(O) | —C(CH₃)₃ | H | 2-pyridyl | —C₆H₄CH₃-3 |
| 733 | C(O) | C(O) | —C(CH₃)₃ | H | 2-pyridyl | —C₆H₃Cl₂-3,4 |
| 734 | C(O) | C(O) | —C(CH₃)₃ | H | 5-propyl-2-pyridyl | —C₆H₅ |
| 735 | C(O) | C(O) | —C(CH₃)₃ | H | —C₆H₅ | 2-pyrazinyl |
| 736 | C(O) | C(O) | —C(CH₃)₃ | H | 2-pyridyl | —C₆H₃(CH₃)₂-3,5 |
| 737 | C(O) | C(O) | —C(CH₃)₃ | H | 3-bromo-2-pyridyl | —C₆H₄Cl-4 |
| 738 | C(O) | C(O) | —C(CH₃)₃ | H | 2-pyrazinyl | —C₆H₅ |
| 739 | C(O) | C(O) | —C(CH₃)₃ | H | 4-pyridyl | —C₆H₅ |
| 740 | C(O) | C(O) | —C(CH₃)₃ | H | 2-pyridyl | —C₆H₄OCH₃-4 |
| 741 | C(O) | C(O) | —C(CH₃)₃ | H | 2-pyridyl | —C₆H₄I-2 |
| 742 | C(O) | C(O) | —C(CH₃)₃ | H | 2-pyridyl | —C₆H₃Cl₂-2,4 |
| 743 | C(O) | C(O) | —C(CH₃)₃ | H | 2-pyridyl | —C₆H₄F-4 |
| 744 | C(O) | C(O) | —C(CH₃)₃ | H | 2-pyridyl | —C₆H₄CF₃-2 |
| 745 | C(O) | C(O) | —C(CH₃)₃ | H | 2-pyridyl | —C₆H₄NO₂-3 |
| 746 | C(O) | C(O) | —C(CH₃)₃ | H | 4-pyridyl | C₆H₄CH₃-3 |

TABLE I-continued $$A'-\underset{\underset{}{\overset{\overset{X}{\|}}{C}}}{}-\underset{\underset{F}{|}}{N}-\underset{\underset{}{\overset{\overset{E}{}}{N}}}{}-\underset{\underset{}{\overset{\overset{X'}{\|}}{C}}}{}-B'$$

| Ex. # | C(X) | C(X') | E | F | A' | B' |
|---|---|---|---|---|---|---|
| 747 | C(O) | C(O) | —C(CH$_3$)$_3$ | H | 2-pyridyl | —C$_6$H$_4$Cl-2 |
| 748 | C(O) | C(O) | —C(CH$_3$)$_3$ | H | 2-pyridyl | —C$_6$H$_4$OCH$_3$-3 |
| 749 | C(O) | C(O) | —C(CH$_3$)$_3$ | H | 2-pyridyl | —C$_6$H$_4$F-4 |
| 750 | C(O) | C(O) | —C(CH$_3$)$_3$ | H | —C$_6$H$_5$ | 2-methanesulfonyl-5-pyridyl |
| 751 | C(O) | C(O) | —C(CH$_3$)$_3$ | H | 4-pyrimidinyl | —C$_6$H$_4$F-4 |
| 752 | C(O) | C(O) | —C(CH$_3$)$_3$ | H | —C$_6$H$_5$ | 4-pyrimidinyl |
| 753 | C(O) | C(O) | —C(CH$_3$)$_3$ | H | 2-pyridyl | —C$_6$H$_3$(CH$_3$)$_2$-2,3 |
| 754 | C(O) | C(O) | —C(CH$_3$)$_3$ | H | —C$_6$H$_5$ | 2-pyridyl |
| 755 | C(O) | C(O) | —C(CH$_3$)$_3$ | H | —C$_6$H$_5$ | 2-pyridyl |
| 756 | C(O) | C(O) | —C(CH$_3$)$_3$ | H | N | —C$_6$H$_4$CH$_3$-3 |
| 757 | C(O) | C(O) | —C(CH$_3$)$_3$ | H | —C$_6$H$_3$(CH$_3$)$_2$-2,3 | 2-Cl-3-pyridyl |
| 758 | C(O) | C(O) | —C(CH$_3$)$_3$ | H | 2-pyridyl | —C$_6$H$_3$Cl-2-CH$_3$-5 |
| 759 | C(O) | C(O) | —C(CH$_3$)$_3$ | H | 2-Cl-3-pyridyl | —C$_6$H$_3$Cl-2-CH$_3$-5 |
| 760 | C(O) | C(O) | —C(CH$_3$)$_3$ | H | 2-thiomethyl-3-pyridyl | —C$_6$H$_4$CH$_3$-3 |
| 761 | C(O) | C(O) | —C(CH$_3$)$_3$ | H | 2-thiomethyl-3-pyridyl | —C$_6$H$_3$Cl$_2$-3,4 |
| 762 | C(O) | C(O) | —C(CH$_3$)$_3$ | H | 2-Cl-3-pyridyl | —C$_6$H$_5$ |
| 763 | C(O) | C(O) | —C(CH$_3$)$_3$ | H | 2-pyridyl | —C$_6$H$_3$Cl-2-F-3 |
| 764 | C(O) | C(O) | —C(CH$_3$)$_3$ | H | —C$_6$H$_5$ | 2-furyl |
| 765 | C(O) | C(O) | —C(CH$_3$)$_3$ | H | —C$_6$H$_5$ | 2-thienyl |
| 766 | C(O) | C(O) | —C(CH$_3$)$_3$ | H | 2-thienyl | —C$_6$H$_5$ |
| 767 | C(O) | C(O) | —C(CH$_3$)$_3$ | H | 2-furyl | —C$_6$H$_5$ |
| 768 | C(O) | C(O) | —C(CH$_3$)$_3$ | H | —C$_6$H$_4$CH$_3$-3 | 2-thienyl |
| 769 | C(O) | C(O) | —C(CH$_3$)$_3$ | H | 2-thienyl | —C$_6$H$_5$CH$_3$-4 |
| 770 | C(O) | C(O) | —C(CH$_3$)$_3$ | H | 2-furyl | —C$_6$H$_4$CH$_3$-3 |
| 771 | C(O) | C(O) | —C(CH$_3$)$_3$ | H | —C$_6$H$_4$CH$_3$-4 | 2-furyl |
| 772 | C(O) | C(O) | —C(CH$_3$)$_3$ | H | —C$_6$H$_4$CH$_3$-4 | 2,5-di-Cl-3-thienyl |
| 773 | C(O) | C(O) | —C(CH$_3$)$_3$ | H | —C$_6$H$_3$Cl$_2$-3,4 | 2-thienyl |
| 774 | C(O) | C(O) | —C(CH$_3$)$_3$ | H | 3-thienyl | —C$_6$H$_5$ |
| 775 | C(O) | C(O) | —C(CH$_3$)$_3$ | H | 3-thienyl | —C$_6$H$_4$CH$_3$-3 |
| 776 | C(O) | C(O) | —C(CH$_3$)$_3$ | H | 3-thienyl | —C$_6$H$_3$Cl$_2$-3,4 |
| 777 | C(O) | C(O) | —C(CH$_3$)$_3$ | H | 3-thienyl | —C$_6$H$_4$Cl-4 |
| 778 | C(O) | C(O) | —C(CH$_3$)$_3$ | H | N-methyl-2-pyrolyl | —C$_6$H$_5$ |
| 779 | C(O) | C(O) | —C(CH$_3$)$_3$ | H | N-methyl-2-pyrolyl | —C$_6$H$_4$Cl-4 |
| 780 | C(O) | C(O) | —C(CH$_3$)$_3$ | H | N-methyl-2-pyrolyl | —C$_6$H$_4$CH$_3$-3 |
| 781 | C(O) | C(O) | —C(CH$_3$)$_3$ | H | 3-furyl | —C$_6$H$_5$ |
| 782 | C(O) | C(O) | —C(CH$_3$)$_3$ | H | 3-furyl | —C$_6$H$_4$CH$_3$-2 |
| 783 | C(O) | C(O) | —C(CH$_3$)$_3$ | H | 3-furyl | —C$_6$H$_4$Cl-4 |
| 784 | C(O) | C(O) | —C(CH$_3$)$_3$ | H | 3-furyl | —C$_6$H$_3$Cl$_2$-2,4 |
| 785 | C(O) | C(O) | —C(CH$_3$)$_3$ | H | 3-furyl | —C$_6$H$_4$CH$_3$-3 |
| 786 | C(O) | C(O) | —C(CH$_3$)$_3$ | H | —C$_6$H$_3$F$_2$-2,6 | 2-thienyl |
| 787 | C(O) | C(O) | —C(CH$_3$)$_3$ | H | 4-3H-triazolyl | —C$_6$H$_4$CH$_3$-3 |
| 788 | C(O) | C(O) | —C(CH$_3$)$_3$ | H | —C$_6$H$_3$Cl-2-OCH$_3$-3 | 2-furyl |
| 789 | C(O) | C(O) | —C(CH$_3$)$_3$ | H | 3-methyl-2-thienyl | —C$_6$H$_4$CH$_3$-3 |
| 790 | C(O) | C(O) | —C(CH$_3$)$_3$ | H | —C$_6$H$_5$ | 3-methyl-2-thienyl |
| 791 | C(O) | C(O) | —C(CH$_3$)$_3$ | H | 3,5-dimethyl-4-oxazolyl | —C$_6$H$_5$ |
| 792 | C(O) | C(O) | —C(CH$_3$)$_3$ | H | —C$_6$H$_4$CH$_2$CH$_3$-4 | 2-phenyl-4-triazolyl |
| 793 | C(O) | C(O) | —C(CH$_3$)$_3$ | H | —C$_6$H$_5$ | 4,4-dimethyl-2-oxazolyl |
| 794 | C(O) | C(O) | —C(CH$_3$)$_3$ | H | 3,5-thiomethyl-4-1,2-oxazolyl | —C$_6$H$_5$ |
| 795 | C(O) | C(O) | —CH(CH$_3$)CF$_3$ | H | —C$_6$H$_3$(CH$_3$)$_2$-2,3 | —C$_6$H$_3$Cl$_2$-2,4 |
| 796 | C(O) | C(O) | —CH(CH$_3$)CF$_3$ | H | —C$_6$H$_3$(CH$_3$)$_2$-2,3 | —C$_6$H$_3$(CH$_3$)$_2$-3,5 |
| 797 | C(O) | C(O) | —CH(CH$_3$)CF$_3$ | H | —C$_6$H$_3$(CH$_3$)$_2$-2,3 | —C$_6$H$_3$NO$_2$-2-CH$_3$-5 |
| 798 | C(O) | C(O) | —CH(CH$_3$)CF$_3$ | H | —C$_6$H$_5$ | —C$_6$H$_5$ |
| 799 | C(O) | C(O) | —CH$_2$CF$_3$ | H | —C$_6$H$_3$Cl$_2$-3,4 | —C$_6$H$_3$Cl$_2$-3,4 |
| 800 | C(O) | C(O) | —CH$_2$CF$_3$ | H | —C$_6$H$_4$Cl-4 | —C$_6$H$_4$Cl-4 |
| 801 | C(O) | C(O) | —CH$_2$CF$_3$ | H | —C$_6$H$_5$ | —C$_6$H$_5$ |
| 802 | C(O) | C(O) | —C(CH$_3$)$_2$CN | H | —C$_6$H$_5$ | —C$_6$H$_5$ |
| 803 | C(O) | C(O) | —C(CH$_3$)$_2$CN | H | —C$_6$H$_5$ | —C$_6$H$_4$Cl-4 |
| 804 | C(O) | C(O) | —C(CH$_3$)$_2$CN | H | —C$_6$H$_4$CH$_3$-4 | —C$_6$H$_4$CH$_3$-3 |
| 805 | C(O) | C(O) | —C(CH$_3$)$_2$CN | H | —C$_6$H$_5$ | —C$_6$H$_4$CH$_3$-3 |
| 806 | C(O) | C(O) | —C(CH$_3$)$_2$CN | H | —C$_6$H$_4$Cl-4 | —C$_6$H$_4$Cl-4 |
| 807 | C(O) | C(O) | —C(CH$_3$)$_2$CN | H | —C$_6$H$_4$CH$_3$-4 | —C$_6$H$_3$(CH$_3$)$_2$-3,5 |
| 808 | C(O) | C(O) | —C(CH$_3$)$_2$CN | H | —C$_6$H$_4$CH$_3$-4 | —C$_6$H$_4$F-4 |
| 809 | C(O) | C(O) | —C(CH$_3$)$_2$CN | H | —C$_6$H$_4$CH$_3$-4 | —C$_6$H$_4$CH$_3$-4 |

TABLE I-continued $$A'-\overset{\overset{X}{\|}}{C}-\underset{\underset{F}{|}}{N}-\overset{\overset{E}{|}}{N}-\overset{\overset{X'}{\|}}{C}-B'$$

| Ex. # | C(X) | C(X') | E | F | A' | B' |
|---|---|---|---|---|---|---|
| 810 | C(O) | C(O) | C(CH₃)(CH₂CH₃)CN | H | —C₆H₅ | —C₆H₅ |
| 811 | C(O) | C(O) | —C(CH₃)₂CN | H | 2-thienyl | —C₆H₄CH₃-3 |
| 812 | C(O) | C(O) | —C(CH₃)₂CN | H | —C₆H₄C₂H₅-4 | —C₆H₃(CH₃)₂-3,5 |
| 813 | C(O) | C(O) | —C(CH₃)₂CN | H | —C₆H₄CH₃-2 | —C₆H₃(CH₃)₂-3,5 |
| 814 | C(O) | C(O) | —C(CH₃)₂CN | H | —C₆H₄Cl-4 | —C₆H₄CH₃-3 |
| 815 | C(O) | C(O) | —C(CH₃)₂CN | H | —C₆H₃F₂-2,6 | —C₆H₄Cl-4 |
| 816 | C(O) | C(O) | —C(CH₃)₂CN | H | —C₆H₄CH₃-2 | —C₆H₄CH₃-3 |
| 817 | C(O) | C(O) | —C(CH₃)₂CN | H | —C₆H₄NO₂-2 | —C₆H₄CH₃-3 |
| 818 | C(O) | C(O) | —C(CH₃)₂CN | H | —C₆H₄Cl-2 | —C₆H₄CH₃-3 |
| 819 | C(O) | C(O) | —C(CH₃)₂CO₂CH₃ | H | —C₆H₅ | —C₆H₅ |
| 820 | C(O) | C(O) | C(CH₃)₂CH₂CH=CH₂ | H | —C₆H₄CH₃-4 | —C₆H₄CH₃-4 |
| 821 | C(O) | C(O) | C(CH₃)₂CH₂CH=CH₂ | H | —C₆H₄CH₃-3 | —C₆H₄CH₃-3 |
| 822 | C(O) | C(O) | C(CH₃)₂CH₂CH=CH₂ | H | —C₆H₅ | —C₆H₅ |
| 823 | C(O) | C(O) | —CH₂Si(CH₃)₃ | H | —C₆H₄C₂H₅-4 | —C₆H₃NO₂-2-CH₃-5 |
| 824 | C(O) | C(O) | —CH₂Si(CH₃)₃ | H | —C₆H₄Cl-4 | —C₆H₄Cl-4 |
| 825 | C(O) | C(O) | —CH₂Si(CH₃)₃ | H | —C₆H₄CH₃-2 | —C₆H₄CH₃-2 |
| 826 | C(O) | C(O) | —CH₂Si(CH₃)₃ | H | —C₆H₄NO₂-2 | —C₆H₄NO₂-2 |
| 827 | C(O) | C(O) | —CH₂Si(CH₃)₃ | H | —C₆H₅ | —C₆H₅ |
| 828 | C(O) | C(O) | —CH₂Si(CH₃)₃ | H | —C₆H₄C₂H₅-4 | —C₆H₃(CH₃)₂-3,5 |
| 829 | C(O) | CH₂ | —C(CH₃)₃ | H | —C₆H₅ | —C₆H₅ |
| 830 | C(O) | CH₂ | —C(CH₃)₃ | H | —C₆H₅ | —C₆H₄Cl-4 |
| 831 | C(O) | CH₂ | —C(CH₃)₃ | H | —C₆H₅ | —C₆H₃Cl₂-2,4 |
| 832 | C(O) | CH₂ | —C(CH₃)₃ | H | —C₆H₅ | —C₆H₃Cl₂-3,4 |
| 833 | C(O) | CH₂ | —C(CH₃)₃ | H | —C₆H₅ | —C₆H₄CF₃-4 |
| 834 | C(O) | CH₂ | —C(CH₃)₃ | H | —C₆H₅ | —C₆H₄CO₂CH₃-4 |
| 835 | C(O) | CH₂ | —C(CH₃)₃ | H | —C₆H₅ | —C₆H₄NO₂-2 |
| 836 | C(O) | CH₂ | —C(CH₃)₃ | H | —C₆H₅ | —C₆H₄F-4 |
| 837 | C(O) | CH₂ | —C(CH₃)₃ | H | 2-furyl | —C₆H₅ |
| 838 | C(O) | CH₂ | —C(CH₃)₃ | H | —C₆H₅ | —C₆H₄Br-2 |
| 839 | C(O) | CH₂ | —C(CH₃)₃ | H | —C₆H₅ | —C₆H₄CN-2 |
| 840 | C(O) | CH₂ | —C(CH₃)₃ | H | 2-thienyl | —C₆H₅ |
| 841 | C(O) | CH₂ | —C(CH₃)₃ | H | —C₆H₄CH₃-4 | —C₆H₄CN-4 |
| 842 | C(O) | CH₂ | —C(CH₃)₃ | H | —C₆H₄CH₃-4 | —C₆H₅ |
| 843 | C(O) | CH₂ | —C(CH₃)₃ | H | —C₆H₅ | —C₆H₄NO₂-3 |
| 844 | C(O) | CH₂ | —C(CH₃)₃ | H | —C₆H₅ | —C₆H₄OCH₃-4 |
| 845 | C(O) | CH₂ | —C(CH₃)₃ | H | —C₆H₅ | —C₆H₄OCH₃-3 |
| 846 | C(O) | CH₂ | —C(CH₃)₃ | H | —C₆H₅ | —C₆H₄CH₃-3 |
| 847 | C(O) | CH₂ | —C(CH₃)₃ | H | —C₆H₄CH₃-4 | —C₆H₄CH₃-3 |
| 848 | C(O) | CH₂ | —C(CH₃)₃ | H | —C₆H₅ | —C₆H₄CH₃-4 |
| 849 | C(O) | CH₂ | —C(CH₃)₃ | H | —C₆H₄CH₃-4 | —C₆H₄CH₃-4 |
| 850 | C(O) | CH₂ | —C(CH₃)₃ | H | —C₆H₃Cl₂-3,4 | —C₆H₅ |
| 851 | C(O) | CH₂ | —C(CH₃)₃ | H | —C₆H₃Cl₂-3,4 | —C₆H₄CH₃-4 |
| 852 | C(O) | CH₂ | —C(CH₃)₃ | H | 2-pyridyl | —C₆H₅ |
| 853 | C(O) | CH₂ | —C(CH₃)₃ | H | —C₆H₅ | 2-pyridyl |
| 854 | C(O) | CH₂ | —C(CH₃)₃ | H | —C₆H₅ | —C₆H₄CH₃-2 |
| 855 | CH₂ | C(O) | —C(CH₃)₃ | H | —C₆H₅ | —C₆H₅ |
| 856 | CH₂ | C(O) | —C(CH₃)₃ | H | —C₆H₅ | —C₆H₄F-4 |
| 857 | CH₂ | C(O) | —C(CH₃)₃ | H | —C₆H₅ | —C₆H₄Br-2 |
| 858 | CH₂ | C(O) | —C(CH₃)₃ | H | —C₆H₅ | —C₆H₃Cl₂-3,4 |
| 859 | CH₂ | C(O) | —C(CH₃)₃ | H | —C₆H₅ | —C₆H₄CH₃-2 |
| 860 | CH₂ | C(O) | —C(CH₃)₃ | H | —C₆H₄CH₃-3 | —C₆H₃Cl₂-2,3 |
| 861 | CH₂ | C(O) | —C(CH₃)₃ | H | —C₆H₄CH₃-3 | —C₆H₅ |
| 862 | CH₂ | C(O) | —C(CH₃)₃ | H | —C₆H₄CH₃-3 | 2-thienyl |
| 863 | C(H) | C(O) | —C(CH₃)₃ | H | 2-pyridyl | —C₆H₅ |
| 864 | C(H) | C(O) | —C(CH₃)₃ | — | —C₆H₅ | —C₆H₅ |
| 865 | C(H) | C(O) | —C(CH₃)₃ | — | —C₆H₅ | —C₆H₄F-4 |
| 866 | C(H) | C(O) | —C(CH₃)₃ | — | —C₆H₅ | —C₆H₃Cl₂-3,4 |
| 867 | C(H) | C(O) | —C(CH₃)₃ | — | —C₆H₅ | —C₆H₄Br-2 |
| 868 | C(H) | C(O) | —C(CH₃)₃ | — | —C₆H₄CH₃-3 | —C₆H₅ |
| 869 | C(H) | C(O) | —C(CH₃)₃ | — | —C₆H₅ | 2-thienyl |
| 870 | C(O) | CH₂ | —C(CH₃)₃ | H | —C₆H₅ | —CH₂C₆H₅ |
| 871 | C(O) | CH₂ | —C(CH₃)₃ | H | —C₆H₅ | —CO₂CH₂CH₃ |
| 872 | C(O) | C(O) | —C(CH₃)₃ | H | —N(H)C₆H₅CH₃-4 | —C₆H₅ |
| 873 | C(O) | C(O) | —C(CH₃)₃ | H | —C(O)C₆H₅ | —C₆H₅ |
| 874 | C(O) | C(O) | —C(CH₃)₃ | H | —C(O)C₆H₅ | —C₆H₄CH₃-3 |
| 875 | C(O) | C(O) | —C(CH₃)₃ | H | —C₆H₃(CH₃)₂-2,3 | —C(O)C₆H₅ |

TABLE I-continued $$A'-\overset{X}{\underset{\|}{C}}-\underset{\underset{F}{|}}{N}-\overset{E}{\underset{\|}{N}}-\overset{X'}{\underset{\|}{C}}-B'$$

| Ex. # | C(X) | C(X') | E | F | A' | B' |
|---|---|---|---|---|---|---|
| 876 | C(O) | C(O) | —C(CH₃)₃ | H | —C₆H₄CH₃-4 | —C(O)C₆H₅ |
| 877 | C(O) | C(O) | —C(CH₃)₃ | H | —C₆H₄C₂H₅-4 | —C(O)C₆H₅ |
| 878 | C(O) | C(O) | —C(CH₃)₃ | H | —C₆H₅ | —C(O)C₆H₅ |
| 879 | C(O) | C(O) | —C(CH₃)₃ | H | —C₆H₃(CH₃)₂-2,3 | 2-methyl-1-phenyl-1-propyl |
| 880 | C(O) | C(O) | —C(CH₃)₃ | H | 2-(1,2,3,4-tetrahydro0 naphthyl | —C₆H₄CH₃-3 |
| 881 | C(O) | C(O) | —C(CH₃)₃ | H | —C₆H₄Cl-4 | —CH₂C₆H₅ |
| 882 | C(O) | C(O) | —C(CH₃)₃ | H | —C₆H₅ | —CHClC₆H₅ |
| 883 | C(O) | C(O) | —C(CH₃)₃ | H | —C₆H₅ | —CH₂C₆H₅ |
| 884 | C(O) | C(O) | —C(CH₃)₃ | H | —C₆H₄Cl-4 | —CHClC₆H₅ |
| 885 | C(O) | C(O) | —C(CH₃)₃ | H | —C₆H₁₃(CH₃)₂-2,3 | —CH₂C₆H₅ |
| 886 | C(O) | C(O) | —C(CH₃)₃ | H | —C₆H₄C₂H₅-4 | —CH₂C₆H₅ |
| 887 | C(OC(O)CH₃) | C(O) | —C(CH₃)₃ | — | —C₆H₅ | —C₆H₅ |
| 888 | C(OCO₂CH₃) | C(O) | —C(CH₃)₃ | — | —C₆H₅ | —C₆H₅ |
| 889 | C(OC(O)CH₂OCH₃) | C(O) | —C(CH₃)₃ | — | —C₆H₅ | —C₆H₅ |
| 890 | C(OCO₂CH=CH₂) | C(O) | —C(CH₃)₃ | — | —C₆H₅ | —CH5 |
| 891 | C(OC(O)CH=CHCH₃) | C(O) | —C(CH₃)₃ | — | —C₆H₅ | —C₆H5 |
| 892 | C(OC(O)CH=C(CH₃)₂) | C(O) | —C(CH₃)₃ | — | —C₆H₅ | —C₆H5 |
| 893 | C(OC(O)-2-furyl | C(O) | —C(CH₃)₃ | — | —C₆H₅ | —C₆H₅ |
| 894 | C(OC(O)CH(CH₃)=CH₂) | C(O) | —C(CH₃)₃ | — | —Chd 6H₄C₂H₅-4 | —C₆H₃(CH₃)₂-3,5 |
| 895 | C(OC(O)CH₃) | C(O) | —C(CH₃)₃ | — | —C₆H₄C₂H₅-4 | —C₆H₃(CH₃)₂-3,5 |
| 896 | C(OCO₂CH₃) | C(O) | —C(CH₃)₃ | — | —C₆H₄C₂H₅-4 | —C₆H₃(CH₃)₂-3,5 |
| 897 | C(OC(O)CH₂OCH₃) | C(O) | —C(CH₃)₃ | — | —C₆H₄C₂H₅-4 | —C₆H₃(CH₃)₂-3,5 |
| 898 | C(OCO₂CH=CH₂) | C(O) | —C(CH₃)₃ | — | —C₆H₄C₂H₅-4 | —C₆H₃(CH₃)₂-3,5 |
| 899 | C(OC(O)-2-furyl | C(O) | —C(CH₃)₃ | — | —C₆H₄C₂H₅-4 | —C₆H₃(CH₃)₂-3,5 |
| 900 | C(OC(O)CH₂CH₃) | C(O) | —C(CH₃)₃ | — | —C₆H₄C₂H₅-4 | —C₆H₃(CH₃)₂-3,5 |
| 901 | C(OC(O)CH₃) | C(O) | —C(CH₃)₃ | — | —C₆H₃(CH₃)₂-2,3 | —C₆H₄CH₃-3 |
| 902 | C(OCO₂CH₃) | C(O) | —C(CH₃)₃ | — | —C₆H₃(CH₃)₂-2,3 | —C₆H₄CH₃-3 |
| 903 | C(OC(O)-2-furyl | C(O) | —C(CH₃)₃ | — | —C₆H₃(CH₃)₂-2,3 | —C₆H₄CH₃-3 |
| 904 | C(OC₂H₅) | C(O) | —C(CH₃)₃ | — | —C₆H₃(CH₃)₂-2,3 | —C₆H₃Cl₂-2,4 |
| 905 | C(OCH₃) | C(O) | —C(CH₃)₃ | — | —C₆H₃(CH₃)₂-2,3 | —C₆H₃Cl₂-2,4 |
| 906 | C(OCH₃) | C(O) | —C(CH₃)₃ | — | —C₆H₅ | —C₆H₅ |
| 907 | C(OC(O)CH=CH₂) | C(O) | —C(CH₃)₃ | — | —C₆H₅-4 | —C₆H₃(CH₃)₂-2,3 |
| 908 | C(OC(O)CH=CH₂) | C(O) | —C(CH₃)₃ | — | —C₆H₅ | —C₆H₅ |
| 909 | C(OC(O)C₆H₄C₂H₅-4) | C(O) | —C(CH₃)₃ | — | —C₆H₅ | —C₆H₅ |
| 910 | C(OC(O)CH₂CH=CH₂) | C(O) | —C(CH₃)₃ | — | —C₆H₅ | —C₆H₅ |
| 911 | C(OC(O)CH=C(CH₃)₂) | C(O) | —C(CH₃)₃ | — | —C₆H₅ | —C₆H₅ |
| 912 | C(OC(O)CH₃) | C(O) | —C(CH₃)₃ | — | —C₆H₅ | —C₆H₃Cl₂-2,4 |
| 913 | C(OC(O)CCH₃=CH₂) | C(O) | —C(CH₃)₃ | — | —C₆H₅ | —C₆H₃Cl₂-2,4 |
| 914 | SO₂ | C(O) | —C(CH₃)₃ | H | —C₆H₅ | —C₆H₅ |
| 915 | SO₂ | C(O) | —C(CH₃)₃ | H | —C₆H₅CH₃-4 | —C₆H₅ |
| 916 | SO₂ | C(O) | —C(CH₃)₃ | H | —C₆H₄F-4 | —C₆H₅ |
| 917 | C(O) | SO₂ | —C(CH₃)₃ | H | —C₆H₅ | —C₆H₄F-4 |
| 918 | C(O) | SO₂ | —C(CH₃)₃ | H | —C₆H₅ | —C₆H₅ |
| 919 | C(O) | SO₂ | —C(CH₃)₃ | H | —C₆H₅ | —C₆H₄CH₃-4 |
| 920 | C(O) | SO₂ | —C(CH₃)₃ | H | 2-pyridyl | —C₆H₅ |
| 921 | C(O) | SO₂ | —C(CH₃)₃ | H | —C₆H₅ | 2-thienyl |
| 922 | C(O) | P(O)CH₃ | —C(CH₃)₃ | H | —C₆H₅ | —NHC₆H₄Cl-2 |
| 923 | P(O)CH₃ | C(O) | —C(CH₃)₃ | H | —C₆H₅ | —C₆H₅ |
| 924 | C(O) | C(O) | —CH₃ | H | —C₆H₄Cl-4 | —C₆H₄Cl-4 |
| 925 | C(O) | C(O) | —CH₃ | H | —C₆H₂Cl₂-3,5 | —C₆H₂Cl₂-3,5 |
| 926 | C(O) | C(O) | —C(CH₃)₃ | H | —CH₂CH₂CH₂CH₃ | —CH₂CH₂CH₂CH₃ |
| 927 | C(O) | C(O) | —C(CH₃)₃ | H | heptyl | heptyl |
| 928 | C(O) | C(O) | —C(CH₃)₃ | H | —CH₂Cl | —CH₂Cl |
| 929 | C(O) | C(O) | —C(CH₃)₃ | H | —CH₂CH₂CH₂CH₃ | 2-furyl |
| 930 | C(O) | C(O) | —C(CH₃)₃ | H | —OCH₂CH₃ | —CH₂CH₂CH₂CH₃ |
| 931 | C(O) | C(O) | —C(CH₃)₃ | H | —OCH₂CH₃ | —C₆H₄Cl-4 |
| 932 | C(O) | C(O) | —C(CH₃)₃ | H | —C₆H₅ | —OCH₂CH₃ |
| 933 | C(O) | C(O) | —C(CH₃)₃ | H | CH(C₆H₅)CH(CH₃)CH₂CH₃ | —C₆H₄CH₃-3 |
| 934 | C(O) | C(O) | —C(CH₃)₃ | H | —OC₆H₅ | —C₆H₅ |
| 935 | C(O) | C(O) | —C(CH₃)₃ | H | —C₆H₅ | —OC₆H₅ |
| 936 | C(O) | C(O) | —C(CH₃)₃ | H | —C₆H₅ | —OC₆H₄NO₂-4 |
| 937 | C(O) | C(O) | —C(CH₃)₃ | H | —CH=C(CH₃)₂ | —CH=C(CH₃)₂ |
| 938 | C(O) | C(O) | —C(CH₃)₃ | H | —CCl=CCl₂ | —CCl=CCl₂ |
| 939 | C(O) | C(O) | —C(CH₃)₃ | H | —CH=CHC₆H₅ | —CH=CHC₆H₅ |

TABLE I-continued $$A'-\overset{\overset{X}{\|}}{C}-\underset{\underset{F}{|}}{N}-N-\overset{\overset{X'}{\|}}{C}-B'$$
(with E on the second N)

| Ex. # | C(X) | C(X') | E | F | A' | B' |
|---|---|---|---|---|---|---|
| 940 | C(O) | C(O) | —C(CH$_3$)$_3$ | H | —C$_6$H$_4$CH$_3$-4 | —C≡CC$_6$H$_5$ |
| 941 | C(O) | C(O) | —C(CH$_3$)$_3$ | H | —C≡CC$_6$H$_5$ | —C$_6$H$_4$CH$_3$-5 |
| 942 | C(O) | C(O) | —C(CH$_3$)$_3$ | H | —C$_6$H$_3$(CH$_3$)$_2$-2,3 | —C≡CC$_6$H$_5$ |
| 943 | C(O) | C(O) | —C(CH$_3$)$_3$ | H | cyclohexyl | cyclohexyl |
| 944 | C(O) | C(O) | —C(CH$_3$)$_3$ | H | 3,4-epoxy cyclohexyl | —C$_6$H$_4$CH$_3$-3 |
| 945 | C(O) | C(O) | —C(CH$_3$)$_3$ | H | —C$_6$H$_4$Cl | —C$_6$H$_4$C$_6$H$_5$-4 |
| 946 | C(O) | C(O) | —C(CH$_3$)$_3$ | H | —H$_6$H$_5$ | 1,2,3,4-tetrahydro- |
| 947 | C(O) | C(O) | —C(CH$_3$)$_3$ | H | 2-azolidinyl | —C$_6$H$_4$CH$_3$-3 |
| 948 | C(O) | C(O) | —C(CH$_3$)$_3$ | H | 2,2-dimethyl-4-keto-2,3-dihydro-pyranyl | —CH$_4$CH$_3$-3 |
| 949 | C(O) | C(O) | —C(CH$_3$)$_3$ | H | 2-furyl | 2-furyl |
| 950 | C(O) | C(O) | —C(CH$_3$)$_3$ | H | 2-thienyl | 2-thienyl |
| 951 | C(O) | C(O) | —C(CH$_3$)$_3$ | H | azolidinyl | azolidinyl |
| 952 | C(O) | C(O) | —C(CH$_3$)$_3$ | H | —C$_6$H$_5$ | —N(CH$_2$CH$_3$)$_2$ |
| 953 | C(O) | C(O) | —C(CH$_3$)$_3$ | H | —C$_6$H$_5$ | —NHC$_6$H$_4$Cl-4 |
| 954 | C(O) | C(O) | —C(CH$_3$)$_3$ | H | —N(CH$_2$CH$_3$)$_2$ | —N(CH$_2$CH$_3$)$_2$ |
| 955 | C(O) | C(O) | 1,2-diphenyl-ethyl | H | —C$_6$H$_5$ | —C$_6$H$_5$ |
| 956 | C(O) | C(O) | cyclopentyl | H | —C$_6$H$_5$ | —C$_6$H$_5$ |
| 957 | C(O) | C(O) | cyclohexyl | H | —C$_6$H$_5$ | —C$_6$H$_5$ |
| 958 | C(O) | C(O) | 2-methyl cyclohexyl | H | —C$_6$H$_5$ | —C$_6$H$_5$ |
| 959 | C(O) | C(O) | 2-methylphenyl | H | —C$_6$H$_5$ | —C$_6$H$_5$ |
| 960 | C(O) | C(O) | cyclopenyl-phenylmethyl | H | —C$_6$H$_5$ | —C$_6$H$_5$ |
| 961 | C(O) | C(O) | —C$_6$H$_5$ | H | —C$_6$H$_5$ | —C$_6$H$_5$ |
| 962 | C(O) | C(O) | —C$_6$H$_5$ | H | —C$_6$H$_3$Cl$_2$-3,5 | —C$_6$H$_3$Cl$_2$3,5 |
| 963 | C(O) | C(O) | —C$_6$G$_4$Cl | H | —C$_6$H$_5$ | —C$_6$H$_5$ |
| 964 | C(O) | C(O) | —C$_6$H$_4$Cl-4 | H | —C$_6$H$_5$ | —C$_6$H$_5$ |
| 965 | C(O) | C(O) | —CH$_2$C$_6$H$_5$ | H | —C$_6$H$_5$ | —C$_6$H$_5$ |
| 966 | C(O) | C(O) | —CH$_2$C$_6$H$_5$ | H | —C$_6$H$_3$Cl$_2$-3,5 | —CH$_2$Cl |
| 967 | C(O) | C(O) | —CH$_2$C$_6$H$_5$ | H | —C$_6$H$_3$Cl$_2$03,5 | —C$_6$H$_3$Cl$_2$-3,5 |
| 968 | C(O) | C(O) | 6-Cl-3-pyridizinyl | H | —C$_6$H$_5$ | —H$_6$H$_5$ |
| 969 | C(O) | C(O) | —CH$_2$C(CH$_3$)=CH$_2$ | H | —C$_6$H$_4$CH$_3$-4 | —C$_6$H$_5$ |
| 970 | C(O) | C(O) | —CH$_2$C(CH$_3$)=CH$_2$ | H | —C$_6$H$_4$CH$_3$-4 | —C$_6$H$_4$CH$_3$-3 |
| 971 | C(O) | C(O) | C(CH$_3$)=CHCH$_2$CH$_2$CH(CH$_3$)CH$_2$CH$_3$ | H | —C$_6$H$_5$ | —C$_6$H$_4$Br-2 |
| 972 | C(O) | C(O) | C(CH$_3$)=CHCH$_2$CH$_2$CH(CH$_3$)CH$_2$CH$_3$ | H | —C$_6$H$_5$ | —C$_6$H$_4$NO$_2$-2 |
| 973 | C(O) | C(O) | —CH$_2$C(CH$_3$)$_2$Br | H | —C$_6$H$_4$CH$_3$-4 | —C$_6$H$_4$CH$_3$-3 |
| 974 | C(O) | C(O) | —CH(CH$_3$)CO$_2$CH$_2$CH$_3$ | H | —C$_6$H$_4$CH$_3$-4 | —C$_6$H$_5$ |
| 975 | C(O) | C(O) | —CH(CH$_3$)CO$_2$CH$_2$CH$_3$ | H | —C$_6$H$_4$CH$_3$-4 | —C$_6$H$_4$NO$_2$-2 |
| 976 | C(O) | C(O) | —CH(CH$_3$)CH$_2$N(CH$_3$)$_2$ | H | —C$_6$H$_4$CH$_3$-4 | —C$_6$H$_3$(CH$_3$)$_2$-3,5 |
| 977 | C(O) | C(O) | —CH(CH$_3$)C(CH$_3$)$_2$OH | H | —C$_6$H$_4$CH$_3$-4 | —C$_6$H$_5$ |
| 978 | C(O) | C(O) | —CH(CH$_3$)C(CH$_3$)$_2$OH | H | —C$_6$H$_4$CH$_3$-4 | —C$_6$H$_3$(CH$_3$)$_2$-3,5 |
| 979 | C(S) | C(O) | —C(CH$_3$)$_3$ | H | —C$_6$H$_5$ | —C$_6$H$_5$ |
| 980 | C(S) | C(O) | —C(CH$_3$)$_3$ | H | —C$_6$H$_5$ | —C$_6$H$_4$Br-2 |
| 981 | C(S) | C(O) | —C(CH$_3$)$_3$ | H | —C$_6$H$_5$ | —C$_6$H$_3$Cl$_2$-2,4 |
| 982 | C(S) | C(O) | —C(CH$_3$)$_3$ | H | —C$_6$H$_5$ | —C$_6$H$_3$Cl$_2$-3,4 |
| 983 | C(S) | C(O) | —C(CH$_3$)$_3$ | H | —C$_6$H$_5$ | —C$_6$H$_3$F$_2$-2,6 |
| 984 | C(S) | C(O) | —C(CH$_3$)$_3$ | H | —C$_6$H$_5$ | —C$_6$H$_5$CH$_3$-4 |
| 987 | C(S) | C(O) | —C(CH$_3$)$_3$ | H | —C$_6$H$_5$ | —NHCH$_2$CH$_3$ |
| 988 | C(S) | C(O) | —C(CH$_3$)$_3$ | H | —C$_6$H$_5$ | —NHCH$_2$CH$_2$CH$_3$ |
| 989 | C(S) | C(O) | —C(CH$_3$)$_3$ | H | —C$_6$H$_5$ | NHCH$_2$CH$_2$CH$_3$ |
| 990 | C(O) | C(O) | —C(CH$_3$)$_3$ | H | —CH$_2$CH$_2$CH$_3$ | CH$_2$CH$_2$CH$_3$ |
| 991 | C(O) | C(O) | —C(CH$_3$)$_3$ | H | —C$_6$H$_5$ | —CH$_2$Cl |
| 992 | C(O) | C(O) | —C(CH$_3$)$_3$ | H | —C(CH$_3$)$_2$Br | —C$_6$H$_5$ |
| 993 | C(O) | C(O) | —C(CH$_3$)$_3$ | H | —CH$_2$CH$_2$CH$_2$CH$_3$ | —OC$_2$H$_5$ |
| 994 | C(O) | C(O) | —C(CH$_3$)$_3$ | H | —C$_6$H$_4$Cl-4 | —OC$_2$H$_5$ |
| 995 | C(O) | C(O) | —C(CH$_3$)$_3$ | H | —C$_6$H$_3$F$_2$-2,6 | —OC$_2$H$_5$ |
| 996 | C(O) | C(O) | —C(CH$_2$)$_2$C$_6$H$_5$ | H | —C$_6$H$_5$ | —C$_6$H$_5$ |
| 997 | C(O) | C(O) | —C(CH$_2$)$_2$C$_6$H$_5$ | H | —C$_6$H$_5$ | —C$_6$H$_4$Cl-4 |
| 998 | C(O) | C(O) | —C(CH$_2$)$_2$C$_6$H$_5$ | H | —C$_6$H$_5$ | —C$_6$H$_3$Cl$_2$-3,4 |
| 999 | C(O) | C(O) | —C(CH$_3$)$_3$ | H | —NH$_2$ | —C$_6$H$_4$Cl-4 |
| 1000 | C(O) | C(O) | —C(CH$_3$)$_3$ | H | —NHSO$_2$C$_6$H$_5$ | —C$_6$H$_4$CH$_3$-3 |
| 1001 | C(O) | C(O) | —C(CH$_3$)$_3$ | H | —NHSO$_2$C$_6$H$_4$Cl-2 | —C$_6$H$_4$CH$_3$-3 |
| 1002 | C(O) | C(O) | —C(CH$_3$)$_3$ | H | —NHSO$_2$C$_6$H$_4$Cl-4 | —C$_6$H$_4$CH$_3$-3 |

TABLE I-continued $$A'-\overset{\overset{X}{\|}}{C}-\underset{\underset{F}{|}}{N}-\overset{E}{\underset{}{N}}-\overset{\overset{X'}{\|}}{C}-B'$$

| Ex. # | C(X) | C(X') | E | F | A' | B' |
|---|---|---|---|---|---|---|
| 1003 | C(O) | C(O) | —C(CH$_3$)$_3$ | H | NHSO$_2$C$_6$H$_4$CH$_3$-4 | —C$_6$H$_4$CH$_3$-3 |
| 1004 | C(O) | C(O) | —C(CH$_3$)$_3$ | H | —C$_6$H$_5$ | —NHCH$_2$CH$_2$CH$_3$ |
| 1005 | C(O) | C(O) | —C(CH$_3$)$_3$ | H | —C$_6$H$_5$Cl-3 | —NHCH$_2$CH$_2$CH$_3$ |
| 1006 | C(O) | C(O) | —C(CH$_3$)$_3$ | H | —C$_6$H$_4$CH$_3$-3 | —NHC$_6$H$_5$ |
| 1007 | C(O) | C(O) | —C(CH$_3$)$_3$ | H | —C$_6$H$_4$CH$_3$-3 | —NHCH$_2$CH$_2$CH$_3$ |
| 1008 | C(O) | C(O) | C(CH$_3$)$_2$C(O)NH$_2$ | H | —NHC(O)C$_6$H$_4$Cl-4 | —C$_6$H$_4$CH$_3$-3 |
| 1009 | C(O) | C(O) | C(CH$_3$)$_2$C(O)NH$_2$ | H | NHC(O)C$_6$H$_4$CH$_3$-2 | —C$_6$H$_4$CH$_3$-3 |
| 1010 | C(O) | C(O) | C(CH$_3$)$_2$C(O)NH$_2$ | H | —C$_6$H$_4$NO$_2$-2 | —C$_6$H$_4$CH$_3$-3 |
| 1011 | C(O) | C(O) | C(CH$_3$)$_2$C(O)NH$_2$ | H | —C$_6$H$_4$Cl-2 | —C$_6$H$_4$CH$_3$-3 |
| 1012 | C(H) | C(O) | —C(CH$_3$)$_3$ | — | —C$_6$H$_5$CH$_3$-2 | —NHCH$_2$CH$_2$CH$_3$ |
| 1013 | C(H) | C(O) | —C(CH$_3$)$_3$ | — | —C(Cl)=C(Cl)CO$_2$H | —C$_6$H$_4$CH$_3$-3 |
| 1014 | C(H) | C(O) | —C(CH$_3$)$_3$ | — | —C(Br)=C(Br)CO$_2$H | —C$_6$H$_4$CH$_3$-3 |
| 1015 | C(CH$_3$)$_3$ | C(O) | —C(CH$_3$)$_3$ | — | —C(O)C$_2$H$_5$ | —C$_6$H$_4$CH$_3$-3 |
| 1016 | C(CH$_3$)$_3$ | C(O) | —C(CH$_3$)$_3$ | — | —CH$_3$ | —C$_6$H$_4$CH$_3$-3 |
| 1017 | CH(CH$_3$)$_2$ | C(O) | —C(CH$_3$)$_3$ | H | —CH$_3$ | —C$_6$H$_4$CH$_3$-3 |
| 1018 | CH(CH$_3$)$_2$ | C(O) | —C(CH$_3$)$_3$ | H | —CN | —C$_6$H$_5$ |

EXAMPLE NO. 1

Preparation of N'-t-butyl-N,N'-(4-chlorobenzoyl)hydrazine

A suspension of t-butylhydrazine hydrochloride (12.5 g, 0.1 mole) in toluene (100 ml) at 0–5° C. was treated slowly with 1 equivalent of NaOH solution, prepared from diluting 8 g of 50% NaOH commercially available solution to 20 ml of the volume with H$_2$O. At 0 to 5° C. with mechanical stirring, 2 equivalents of 4-chlorobenzoyl chloride (35.9 g, 0.2 mole) and 2 equivalents of NaOH (16 g of 50% NaOH diluted with H$_2$O to 40 ml) were added dropwise separately and simultaneously from dropping funnels. The exothermic reaction was cooled down by an ice-water bath through the entire addition. After the addition was completed, the resulting suspension was stirred at room temperature (RT) for one hour. The white precipitate (p.p.t.) was collected by suction-filtration and washed with a small amount of toluene and 100 ml of H$_2$O. The material was then air-dried, then crystallized from 95% aqueous CH$_3$OH to afford 24.65 g of N'-t-butyl-N,N'-(4-chlorobenzoyl)hydrazine as needles: m.p. 246–248° C.

Additional product can be obtained by concentrating the mother liquor of crystallization.

EXAMPLE NO. 3

Preparation of N'-t-butyl-N,N'-dibenzoyl-hydrazine

To a stirred suspension of t-butylhydrazine hydrochloride (1.24 g, 10 mmoles) in toluene (50 ml) at room temperature, was added dropwise a solution of 50% aqueous sodium hydroxide (0.8 g, 10 ml). After 15 minutes, the reaction mixture was cooled to 5° C. and solutions of benzoyl chloride (2.82 gm, 20 ml) in toluene (7 ml) and 50% aqueous sodium hydroxide (1.6 g) were added dropwise and simultaneously from separate addition funnels while maintaining the temperature below 10° C. Following the addition, the reaction mixture was warmed to room temperature and stirred for 1 hr. The reaction mixture was diluted with ether and the product isolated by filtration. The product was washed with water and ether and dried. The product was recrystallized from ethermethanol to afford N'-t-butyl-N,N'-dibenzoylhydrazine as a white powder: m.p. 174–176° C.

EXAMPLE NO. 16

Preparation of N'-t-butyl-N'-(4-chlorobenzoyl)-N-benzoylhydrazine

To a stirred suspension of t-butylhydrazine hydrochloride (1.24 g, 10 mmoles) in toluene (30 ml) at room temperature was added dropwise a 50% aqueous solution of sodium hydroxide (0.8 g, 10 mmole). After 15 min., the reaction mixture was cooled to 5° C. and a solution of benzoyl chloride (1.42 g, 10 mmoles) in toluene (5 ml) and a solution of aqueous 50% sodium hydroxide (0.8 g, 10 mmole) were added dropwise simultaneously from separate addition funnels while maintaining the temperature at or below 10°. Following the addition, the reaction mixture was warmed to room temperature and stirred for 1 hr. The reaction mixture was diluted with toluene washed with water. The organic layer was separated, dried over anhydrous magnesium sulfate, and the solvent removed under vacuum to afford a yellow oil which slowly solidifies on standing. The product was recrystallized from ether-hexane to afford white crystals.

To a stirred solution of the monobenzoylated compound (1.92 g, 10 mmoles) in toluene (30 ml) at 5° C., were added dropwise simultaneously from separate addition funnels, solutions of p-chlorobenzoyl chloride (1.75 g, 10 mmoles) in toluene (5 ml) and aqueous 50% sodium hydroxide solution (0.8 g) while maintaining the temperature below 10° C. Following the addition, the reaction mixture was warmed to room temperature and stirred for 1 hr. The mixture was then diluted with hexane and the precipitated product isolated by filtration. The product was washed with water and hexane and dried. The crude product was recrystallized from ether-methanol to afford N'-t-butyl-N'-(4-chlorobenzoyl)-N-benzoylhydrazine as a white powder: m.p. 201–204° C.

EXAMPLE NO. 44

Preparation of N'-neopentyl-N,N'-dibenzoylhydrazine

A solution of benzoylhydrazine (1.36 g, 10 mmoles), 1,1,1-trimethylacetaldehyde (0.86 g, 10 mmoles), and acetic acid (catalytic amount) in methanol are stirred at room temperature until hydrazone formation is complete. The reaction mixture is brought to a pH of 4 and sodium cyanoborohydride (0.75 g, 12.5 mmoles) is added slowly portionwise (the reaction is connected to an aqueous sodium hydroxide trap). Upon completion, the reaction is diluted with excess aqueous sodium hydroxide and the methanol is removed under vacuum. The product is partitioned into methylene chloride and washed with aqueous base and water. The organic layer is separated and dried over anhydrous magnesium sulfate. The magnesium sulfate is filtered, and the methylene chloride removed under vacuum to afford the product as a yellow oil which solidifies on standing. The crude 2-neopentyl-1-benzoylhydrazine is benzoylated directly.

To a stirred solution of the 2-neopentyl-1-benzoylhydrazine in toluene (40 ml) at 5° C., were added dropwise and simultaneously solutions of benzoyl chloride (1.4 g, 10 mmoles) in toluene (5 ml) and aqueous 50% sodium hydroxide solution (0.8 g) while maintaining the temperature below 10° C. After the addition, the reaction mixture was warmed to room temperature and stirred for 1 hour. The reaction mixture was diluted with hexane and the precipitated product isolated by filtration. The product was washed with water and hexane and dried. The crude product was recrystallized from methanol to afford N'-neopentyl-N,N'-dibenzoylhydrazine as a white powder: m.p. 237–239° C.

EXAMPLE NO. 102

Preparation of N'-t-butyl-N'-benzoyl-N-4-chlorothiobenzolyhydrazine

A mixture of 4-chloro-methylthio-thiobenzoate (3.0 g, 0.015 mol) and t-butyl hydrazine hydrochloride (2.0 g, 0.016 mol) in 5 ml of pyridine was heated at 90° C. for 18 hours. The mixture was poured into 0.1 N HCl/ether. The layers were separated and the organic extracts were washed with 3 portions of 0.1N HCl followed by saturated aqueous NaHCO. After the extracts were dried over anhydrous magnesium sulfate, the solvents were removed under vacuum to afford 1.9 g of a brown solid. Chromatography on silica gel using ether (25%)-methylene chloride (25%)-hexane as eluant afforded 0.8 g of a golden yellow solid. The solid was dissolved in 3 ml of methylene chloride and treated with pyridine (1 ml) and benzoyl chloride (0.6 ml). After 24 hours at 23° C., the reaction mixture was poured onto 0.1N HCl/ether. The organic layer was washed with saturated aqueous sodium bicarbonate and was dried over anhydrous magnesium sulfate. Evaporation of solvents gave a yellow oil which was chromatographed on silica gel using ether (25%)-methylene chloride (25%)-hexane as eluant to give 0.15 g of N'-t-butyl-N'-benzoyl-N-4-chlorothiobenzoylhydrazine as a yellow solid: m.p. 160–162° C.

EXAMPLE NO. 103

Preparation of N'-t-butyl-N'-thiobenzoyl-N-benzoylhydrazine

A mixture of N'-t-butyl-N-benzoyl hydrazine (60% purity, 1.0 g, 0.0031 mol) and S-(thiobenzoyl)-thioglycolic acid (1.0 g, 0.0047 mol) in 3 ml of pyridine was heated at about 90° C. for 24 hours. The dark colored mixture was cooled and poured into 0.1 N HCl/ether. The organic layer was washed with three 15 ml portions of 0.1 N HCl followed by saturated aqueous sodium bicarbonate. The organic extracts were dried over anhydrous magnesium sulfate. Evaporation of the solvents afforded 0.5 g of a brown oil which was recrystallized from ether-hexane to yield 0.2 g of N'-t-butyl-N'-thiobenzoyl-N-benzoylhydrazine as a tan solid m.p. 169–171° C.

EXAMPLE NO. 148

Preparation of N'-t-butyl-N-(2-hydroxy-methylbenzoyl)-N'-benzoylhydrazine t-Butylhydrazine (0.1 mol) in 75 ml ethanol was treated with 50% aqueous sodium hydroxide (0.11 mol). Phthalide (0.1 mol) was added and the mixture was refluxed for 5 days. After cooling, water was added and the crude product was isolated by filtration. Filtration through silica gel afforded N'-t-butyl-N-(2-hydroxymethylbenzoyl)hydrazine (3.0 g). m.p. 116–118° C.

0.7 g of N'-t-butyl-N-(2-hydroxymethylbenzoyl) hydrazine and 1.1 g benzoyl chloride are combined in 10 ml of 5% NaOH and stirred at room temperature for 1.5 hours. The solids are filtered off, washed with water, then ether, to afford 0.6 g of white solid N'-t-butyl-N-(2-(benzoyloxymethyl)benzoyl)-N'-benzoylhydrazine. m.p. 190–191° C.

EXAMPLE NO. 220

Preparation of N-(3-toluoyl)-N'-t-butyl-N'-benzoylhydrazine

Step 1

To a stirred suspension of t-butylhydrazine (51 g) in a mixture of dioxane and water (2:1) (150 ml) was added sodium hydroxide (32 g of a 50% aqueous solution). After 10 min., the solution was cooled to 5° C. and di-t-butyldicarbonate (42 g) was added dropwise so as to maintain the reaction temperature below 10° C. The reaction mixture was warmed and stirred 2 hours at room temperature. The reaction mixture was filtered, washed with water and dried to afford N-t-butyloxycarbonyl-N'-t-butylhydrazine (74 g) as a white crystalline solid. m.p. 69–71° C.

Step 2

To a stirred solution of N-t-butyloxycarbonyl-N'-t-butylhydrazine (61 g) in toluene (120 ml) was added benzoyl chloride (45 g) and sodium hydroxide (31 g of a 50% aqueous sodium hydroxide solution) dropwise and simultaneously. After stirring for 1 hour at room temperature, the solid N-t-butyloxycarbonyl-N'-t-butyl-N'-benzoylhydrazine was filtered, washed with water, hexane and dried to afford 52 g of product. m.p. 167–170° C.

Step 3

The N-t-butoxycarbonyl-N'-t-butyl-N'-benzoylhydrazine (52 g, 0.18 mol) was stirred at room temperature in a methanolic hydrochloric acid solution for 4 days. The reaction mixture was neutralized with saturated aqueous sodium bicarbonate. The white precipitate was filtered, washed with water and dried in vacuo to give 30 g of N'-t-butyl-N'-benzoylhydrazine. m.p. 124–125° C.

Step 4

To a stirred mixture of N'-t-butyl-N'-benzoylhydrazine (1.0 g) in 15 ml toluene and aqueous sodium hydroxide (0.5 g of 50% NaOH) was added 3-toluoylchloride (0.9 g). After stirring for 2 hours, the product was isolated by filtration to give N'-t-butyl-N-(3-toluoyl)-N'-benzoylhydrazine in good yield. m.p. 111–114° C.

EXAMPLE NO. 295

Preparation of N'-(1,1-dimethylethyl)-N,N'-dibenzoylhydrazine

To a gentle refluxing solution of ethyl magnesium bromide (150 ml of 1M solution) was added acetone azine (20 g) dissolved in diethyl ether (80 ml). The solution was refluxed for three days. Upon cooling, a saturated solution of ammonium chloride (75 ml) was added. The aqueous layer was separated and washed twice with diethyl ether (150 ml). The combined ether extracts were dried over anhydrous magnesium sulfate, filtered and the ether removed at reduced pressure. The product was distilled through a vigreux column at 3 torr and collected in a dry ice/acetone cooled receiving flask. The boiling point was 40–50°. 15 g of product was collected.

Oxalic acid (17 g) was dissolved in a solution of ethanol:diethyl ether (1:1) (150 ml) and water (3.3 g) was added. To this acid solution was added the hydrazone (13 g) dissolved in diethyl ether (30 ml). The solution was stirred for 24 hours then filtered. The solid is washed once with diethyl ether. The filtrate was concentrated and combined with the solid to afford a 77% yield (16.3 g) of the hydrazine oxalate.

The 1,1-dimethylethylhydrazine oxalate (2 g) was dissolved in toluene and neutralized with 50% aqueous sodium hydroxide. To this solution was added benzoyl chloride (4.02 g) and sodium hydroxide (50% Aq. solution) (2.45 g) at 25° C. The reaction mixture was warmed to room temperature and stirred 3 hours. The mixture was diluted with hexane and filtered to afford the product as a white solid (0.5 g).

EXAMPLE NO. 324

Preparation of N'-t-butyl-N-(thio-benzoyl)-N'-(3-toluoyl)hydrazine

S-(thiobenzoyl)thioglycolic acid (3.0 g) was dissolved in 20 ml pyridine, treated with t-butyl hydrazine hydrochloride (excess, ca. 4 g) and then was heated at ca. 120° C. for 14 hours. Water (120 ml) was added and the mixture was extracted with ether. The organic extracts were dried over anhydrous magnesium sulfate, filtered and evaporated to give crude N'-t-butyl-N-(thiobenzoyl)hydrazine as a viscous yellow oil.

N't-butyl-N-(thiobenzoyl)hydrazine (ca. 1 g), m-toluoyl chloride (approx. 0.7 g) and 50% aqueous sodium hydroxide (6 drops) were mixed in 1 ml water and 10 ml toluene at 23° C. After stirring for 3 hours, ether-hexane was added and the product was isolated by filtration (0.25 g). m.p. 165–168° C.

EXAMPLE NO. 344

Preparation of N'-t-butyl-N-[3-(N,N-dimethylcarbamoyl)benzoyl])-N'-benzoylhydrazine N-(3-hydroxybenzoyl)-N'-t-butyl-N'-benzoylhydrazine (0.2 g) was stirred in tetrahydrofuran (15 ml) at 23° C. Solid potassium t-butoxide (0.1 g) was added and the solution went from clear colorless to cloudy yellow. After stirring 10 minutes at room temperature, N,N-dimethylcarbamoyl chloride was added dropwise (0.1 g). With the addition the solution turned colorless and a precipitate appeared. Saturated aqueous NaHCO3 and ether were added, the layers separated and the organic dried over magnesium sulfate, filtered and rotavapped to afford an oily solid.

EXAMPLE NO. 625

Preparation of N'-t-butyl-N-(4-(4,4-dimethyloxazol-2-yl)benzoyl)-N'-(3-toluoyl)hydrazine 1.2 g of N'-t-butyl-N-(4-carbomethoxybenzoyl)-N'-(3-toluoyl)hydrazine was heated in 2 ml of 2-amino-2-methyl-1-propanol at 90–100° C. for 5 hours. After cooling, the mixture was diluted with ether/methylene chloride and washed with 0.1 N HCl. The organic layer was evaporated to afford 1.0 g of the corresponding amide.

The amide in 10 ml of chloroform was treated with 0.25 g of thionyl chloride and stirred at 23° C. for 1.5 hours. Saturated aqueous sodium bicarbonate was added and the layers separated. Evaporation of the organic layer afforded the product as a foam.

EXAMPLE NO. 635

Preparation of N-methyl-N'-t-butyl-N,N'-dibenzoylhydrazine

To a stirred solution of N'-t-butyl-N,N'-dibenzoylhydrazine (2.5 g, 0.008 M) in dimethylformamide (DMF) (30 ml) at room temperature under nitrogen was added portionwise sodium hydride (60% oil dispersion) (0.4 g, 0.009 M). The mixture was stirred at room temperature for 0.5 hours, and then methyl iodide (1.0 g, 0.008 M) was added dropwise. The reaction mixture was allowed to stir for 1 hour. The mixture was then diluted with water (50 ml), neutralized with 10% HCl, and the product extracted into methylene chloride (50 ml). The methylene chloride layer was washed with water (5×20 ml), dried over anhydrous magnesium sulfate, and the methylene chloride removed under vacuum to afford N-methyl-N'-t-butyl-N,N'-dibenzoylhydrazine as an oil.

EXAMPLE NO. 636

Preparation of N-benzyl-N'-t-butyl-N,N'-dibenzoylhydrazine

To a stirred solution of N'-t-butyl-N,N'-dibenzoylhydrazine (2 g, 0.006 M) in DMF (25 ml) at room temperature under nitrogen was added portionwise sodium hydride (60% oil dispersion) (0.3 g, 0.007 M). The mixture was stirred at room temperature for 0.5 hours, and then benzyl bromide (1.2 g, 0.007 M) was added dropwise. The reaction mixture was warmed to 60° C. and allowed to stir for 2 hours. The mixture was then diluted with water (50 ml), neutralized with 10% HCl, and the product extracted into methylene chloride (50 ml). The methylene chloride layer was washed with water (5×20 ml), dried over anhydrous magnesium sulfate, and the methylene chloride removed under vacuum to afford N-benzyl-N'-t-butyl-N,N'-dibenzoylhydrazine as an oil.

EXAMPLE NO. 637

Preparation of N-allyl-N'-t-butyl-N,N'-dibenzoylhydrazine

To a stirred solution of N'-t-butyl-N,N'-dibenzoylhydrazine (3 g, 0.011 M) in DMF (30 ml) at room temperature under nitrogen was added portionwise sodium hydride (60% oil dispersion) (0.5 g, 0.012 M). The mixture was stirred at room temperature for 0.5 hours, and then allyl iodide (1.8 g, 0.01 M) was added dropwise. The reaction mixture was warmed to 60° C. and stirred for 2 hours. The mixture was then diluted with water (50 ml), neutralized with 10% HCl, and the product extracted into methylene chloride (50 ml). The methylene chloride layer was washed with water (5×20 ml), dried over anhydrous magnesium sulfate, and the methylene chloride removed under vacuum to afford N-allyl-N'-t-butyl-N,N'-dibenzoylhydrazine as an oil.

EXAMPLE NO. 638

Preparation of N-methoxymethyl-N'-t-butyl-N-N'-dibenzoylhydrazine

N'-t-butyl-N,N'-dibenzoylhydrazine (2 g, 0.007 M) was stirred at room temperature in a two phase system of toluene-50% sodium hydroxide with 100 mg of phase transfer catalyst (tetra-n-butylammonium hydrogen sulfate). Methoxymethyl chloride (1.2 g, 0.015 M) was added dropwise and the mixture was stirred 3 hours. The layers were separated and the toluene layer was washed several times with water (until the water washes were neutral). The toluene solution was dried over anhydrous magnesium sulfate and the toluene removed under vacuum to afford N-methoxymethyl-N'-t-butyl-N,N'-dibenzoylhydrazine as a thick oil.

EXAMPLE NO. 639

Preparation of N-methylthiomethyl-N'-t-butyl-N,N'-dibenzoylhydrazine

To a stirred suspension of sodium hydride (a 50% oil dispersion washed 2 times with 20 ml pentane) (0.21 g, 0.0043 M) in dry DMF (20 ml) under nitrogen at room temperature, was added N'-t-butyl-N,N'-dibenzoylhydrazine (1 g, 0.0034 M) portionwise as a solid. The mixture was stirred at room temperature for ½ hour and methylthiomethylchloride (0.34 g, 0.0035M) was added dropwise. The resulting mixture was heated at 50° C. overnight, cooled, diluted with methylene chloride and washed repeatedly with water. The organic layer was dried over anhydrous magnesium sulfate and the methylene chloride removed under vacuum. The oily residue was chromatographed on silica gel using methylene chloride to afford N-methylthiomethyl-N'-t-butyl-N,N'-dibenzoylhydrazine as an oil (60% yield).

EXAMPLE NO. 642

Preparation of N-(2-propynyl)-N'-t-butyl-N-benzoyl-N'-(3,5-dimethylbenzoyl)hydrazine To a stirred suspension of N'-t-butyl-N-benzoyl-N'-(3,5-dimethylbenzoyl)hydrazine (1.5 g) in dimethylformamide (DMF) (20 ml) was added sodium hydride (200 mg of 60% oil dispersion) portionwise. After 15 min., propargyl bromide (0.6 g) was added to the reaction mixture dropwise and the reaction stirred for 1 hour. The reaction mixture was diluted with ethyl acetate (50 ml) and washed with water (5×20 ml). The organic layer was then dried over magnesium sulfate and the solvent removed under vacuum to afford N-(2-propynyl)-N'-t-butyl-N-benzoyl-N'-(3,5-dimethylbenzoyl)hydrazine as a yellow amorphous solid. The product, N-(2-propynyl)-N'-t-butyl-N-benzoyl-N'-(3,5-dimethylbenzoyl)hydrazine, was purified by column chromatography on silica gel (solvent system:methylene chloride) to afford a 70% yield as a white solid.

EXAMPLE NO. 646

Preparation of N'-t-butyl-N-cyclohexyl-carbonyl-N'-benzoylhydrazine

To a stirred suspension of t-butylhydrazine hydrochloride (2.0 g, 0.016M) in toluene (30 ml) was added 50% sodium hydroxide (1.3 g, 0.016M). After 15 minutes, the mixture was cooled to 5° C. and cyclohexanecarbonylchloride (2.4 g, 0.016 M) and 50% sodium hydroxide (1.3 g, 0.016M) were added separately and simultaneously so as to maintain the reaction temperature below 10° C. After the addition, the reaction mixture was allowed to warm to room temperature and stirred for 1 hr. The mixture was diluted with hexane and the solid product isolated by filtration. This product (1.5 g, 0.008M) was dissolved in a stirred mixture of toluene (30 ml) and cooled on ice. To this mixture was added benzoylchloride (1.1 g, 0.008 M) and 50% sodium hydroxide (0.6 g, 0.008M) simultaneously. After addition, the mixture was stirred for ½ hr., diluted with hexane and the solid product, N'-t-butyl-N-cyclohexylcarbonyl-N'-benzoylhydrazine, isolated by filtration.

EXAMPLE NO. 648

Preparation of N'-t-butyl-N-valeryl-N'-benzoylhydrazine

To a stirred suspension of t-butylhydrazine hydrochloride (24.8 g, 0.20 mole) in toluene (150 ml) at 5° C. was added one equivalent of NaOH, prepared by diluting 16 g of 50% aqueous (aq.) NaOH to 30 ml. After addition, valeryl chloride (24 g, 0.2 mole) and another one equivalent of NaOH solution (30 ml) were dropwise added separately and simultaneously. The reaction mixture was warmed to room temperature and stirred for 40 min. The two phase mixture was separated and the organic layer was washed with water and brine. The organic layer was dried over $Na_2SO_4$ and concentrated under vacuum to give a colorless oil.

To a stirred solution of 1-t-butyl-2-valerylhydrazine (4 g, 0.023M) in toluene (40 ml) at 5° C. was added benzoyl chloride (3.4 g, 0.024M) and 50% aq. sodium hydroxide (0.98 g, 0.024M). After addition, the mixture was warmed to room temperature and stirred 2.5 hr. The mixture was diluted with ethyl acetate (50 ml) and washed with water (2×25 ml) and brine (1×25 ml). The organic layer was dried over magnesium sulfate and concentrated under vacuum to afford N'-t-butyl-N-valeryl-N'-benzoylhydrazine as a yellow oil.

EXAMPLE NO. 654

Preparation of N'-t-butyl-N-phenyl-acetyl-N'-benzoylhydrazine

To a stirred suspension of t-butylhydrazine hydrochloride (2.0 g, 0.016M) in toluene (30 ml) was added 50% sodium hydroxide (1.3 g, 0.016M). After 15 minutes, the mixture was cooled to 5° C. and phenylacetyl chloride (2.4 g, 0.016M) and 50% sodium hydroxide (1.3 g, 0.016M) were added separately and simultaneously so as to maintain the reaction temperature below 10° C. After the addition, the reaction mixture was allowed to warm to room temperature and stirred for 1 hr. The mixture was diluted with hexane and the solid product isolated by filtration. This product (3.2 g, 0.015M) was dissolved in a stirred mixture of toluene (30 ml) and cooled on ice. To this mixture was added benzoylchloride (2.2 g, 0.016M) and 50% sodium hydroxide (1.3 g, 0.016M) simultaneously. After addition, the mixture was stirred for ½ hr., diluted with hexane and the solid product, N'-t-butyl-N-phenylacetyl-N'-benzoylhydrazine, isolated by filtration.

EXAMPLE NO. 656

Preparation of N'-t-butyl-N-cyclo-hexenylcarbonyl-N'-benzoylhydrazine

To a stirred suspension of t-butylhydrazine hydrochloride (0.86 g, 0.007M) in toluene (30 ml) was added 50% sodium hydroxide (0.55 g, 0.007M). After 15 minutes, the mixture was cooled to 5° C. and cyclohexenylcarbonyl chloride (1.0 g, 0.007M) and 50% sodium hydroxide (0.55 g, 0.007M) were added separately and simultaneously so as to maintain the reaction temperature below 10° C. After the addition, the reaction mixture was allowed to warm to room temperature and stirred for 1 hr. The mixture was diluted with hexane and the solid product isolated by filtration. This product (1.2 g, 0.006M) was dissolved in toluene (30 ml) and cooled on ice while stirring. To this mixture was added benzoylchloride (1.0 g, 0.007M) and 50% sodium hydroxide (1.3 g, 0.007M) simultaneously. After addition, the mixture was stirred for ½ hr., diluted with hexane and the solid product, N'-t-butyl-N-cyclohexenylcarbonyl-N'-benzoylhydrazine, isolated by filtration.

EXAMPLE NO. 659

Preparation of N'-t-butyl-N-(beta-chloropivaloyl)-N'-benzoylhydrazine

To a stirred suspension of tert-butylhydrazine hydrochloride (200 g, 1.61 mole) in acetone (400 ml) was dropwise added triethylamine (200 g, 1.98 mole). After addition, the mixture was refluxed for 3 hours while periodically adding magnesium sulfate (100 g total). The mixture was cooled to room temperature and funnel filtered. The filtrate was dried over magnesium sulfate and concentrated under vacuum at 5° C. until a slurry formed. The mixture was diluted with ethyl acetate (100 ml) and was filtered. The filtrate was distilled yielding a yellow oil (b.p. 121–127° C.).

Into a stirred suspension of 1-t-butyl-2-acetonehydrazone (43 g, 0.34 mole) in toluene (250 ml) at 5° C. was added 10% aq. sodium hydroxide (200 ml, 0.50 mole). After addition, benzoylchloride (70 g, 0.50 mole) was added dropwise to this mixture. Stirring was continued for 2 hours at 5° C. and 72 hours at room temperature. The mixture was diluted with ethyl acetate (300 ml) and washed with water (3×200 ml) and brine (200 ml). The organic layer was dried over magnesium sulfate and concentrated at 35° C. under vacuum to afford a yellow oil.

A mixture of 1-t-butyl-1-benzoyl-2-acetone hydrazone (90 g, approximately 60% pure, approximately 0.3 mole), ethanol (500 ml, 200 proof) and 10% aq. hydrochloric acid (500 ml) was stirred overnight at room temperature. The mixture was concentrated under vacuum to a thick slurry. The slurry was suction filtered with a water wash (400 ml). The solids were air-dried overnight.

The solids were dissolved in a water (200 ml) and methanol (100 ml) solution on a steam bath. The mixture stood at room temperature overnight. The mixture was suction filtered and rinsed with cold water (100 ml) and the solids were air dried overnight. The solids were dissolved in 10% aq. hydrochloric acid (300 ml) and were washed with ethyl acetate (3×300 ml). The ethyl acetate washes were combined and extracted with 10% aq. hydrochloric acid (250 ml). The 10% aq. hydrochloric acid layers were combined and were neutralized with 50% aq. sodium hydroxide while being stirred. Stirring was continued for 1 hour at room temperature. The mixture was suction filtered and rinsed with water (100 ml) and the solids were air-dried yielding a white solid (m.p. 125–126° C.).

To a stirred solution of 1-t-butyl-1-benzoylhydrazine (1 g, 0.005M) in toluene (40 ml) cooled to 5° C. was added 3-chloro-2,2-dimethylpropionylchloride (1.2 g, 0.007M) and 50% aq. sodium hydroxide (0.45 g, 0.0056M) so as to maintain the temperature below 10° C. The mixture was warmed to room temperature and stirred 1 hr. The mixture was diluted with hexane (40 ml) and water (10 ml). The white solid product N'-t-butyl-N-(beta-chloropivaloyl)-N'-benzoylhydrazine was isolated by suction filtration, washed with 50 ml hexane and 50 ml water and dried.

EXAMPLE NO. 661

Preparation of N'-t-butyl-N-(1,2,2-trichlorovinyl)carbonyl-N'-benzoylhydrazine

To a stirred suspension of tert-butylhydrazine hydrochloride (200 g, 1.61 mole) in acetone (400 ml) was dropwise added triethylamine (200 g, 1.98 mole). After addition, the mixture was refluxed for 3 hours while periodically adding magnesium sulfate (100 g total). The mixture was cooled to room temperature and funnel filtered. The filtrate was dried over magnesium sulfate and concentrated under vacuum at 5° C. until a slurry formed. The mixture was diluted with ethylacetate (100 ml) and was filtered. The filtrate was distilled yielding a lightly yellow tinted oil (b.p. 121–127° C.).

To a stirred suspension of 1-t-butyl-2-acetonehydrazone (43 g, 0.34 mole) in toluene (250 ml) at 5° C. was added 10% aq. sodium hydroxide (200 ml, 0.50 mole). After addition, benzoylchloride (70 g, 0.50 mole) was added dropwise to the mixture. Stirring was continued for 2 hours at 5° C. and 72 hours at room temperature. The mixture was diluted with ethyl acetate (300 ml) and washed with water (3×200 ml) and brine (200 ml). The organic layer was dried over magnesium sulfate and concentrated at 35° C. under vacuum yielding a yellow oil.

A mixture of 1-t-butyl-1-benzoyl-2-acetone hydrazone (90 g, approximately 60% pure, approximately 0.3 mole), ethanol (500 ml, 200 proof) and 10% aq. hydrochloric acid (500 ml) was stirred overnight at room temperature. The mixture was concentrated under vacuum to a thick slurry. The slurry was suction filtered and washed with water (400 ml). The solids were air-dried overnight.

The solids were dissolved in a water (200 ml) and methanol (100 ml) solution on a steam bath. The mixture stood at room temperature overnight. The mixture was suction filtered and rinsed with cold water (100 ml) and the solids were air dried overnight. The solids were dissolved in 10% aq. hydrochloric acid (300 ml) and were washed with ethyl acetate (3×300 ml). The ethyl acetate washes were combined and extracted with 10% aq. hydrochloric acid (250 ml). The 10% aq. hydrochloric acid layers were combined and were neutralized with 50% aq. sodium hydroxide while being stirred. Stirring was continued for 1 hour at room temperature. The mixture was suction filtered and rinsed with water (100 ml) and the solids were air-dried yielding a white solid (m.p. 125–126° C.).

To a stirred solution of 1-t-butyl-1-benzoylhydrazine (1.5 g, 0.008 M) in methylene chloride at 5° C. was added, simultaneously and separately, trichloroacryloylchloride (1.7 g, 0.009 M) and triethylamine (0.9 g, 0.009 M). After addition, the reaction was warmed to room temperature and stirred for 3 h. The flask's contents were diluted with 50 ml methylene chloride and washed with water (3×75 ml) and brine solution (1×75 ml). The organic layer was dried over magnesium sulfate and the solvent removed under vacuum to afford N'-t-butyl-N-(1,2,2-trichlorovinyl)carbonyl-N'-benzoylhydrazine as a white solid product.

EXAMPLE 682

Preparation of N'-t-butyl-N-benzoyl-N'-n-pentanecarbonylhydrazine

To a stirred suspension of t-butylhydrazine hydrochloride (1 g, 0.008M) in toluene (30 ml) at room temperature was added dropwise a 50% aqueous solution of sodium hydroxide (0.64 g, 0.008M). After 15 min., the reaction mixture was cooled to 5° C. and a solution of benzoyl chloride (1.12 g, 0.008M) in toluene (5 ml) and a solution of aqueous 50% sodium hydroxide (0.64 g, 0.008M) were added dropwise simultaneously from separate addition funnels while maintaining the temperature at or below 10° C. Following the addition, the reaction mixture was warmed to room temperature and stirred for 1 hr. The reaction was diluted with hexane and the solid N'-t-butyl-N'-benzoylhydrazine was isolated by filtration.

To a stirred solution of the monobenzoylated compound (1.4 g, 0.0073M) in toluene (30 ml) at 5° C., were added dropwise simultaneously from separate addition funnels, solutions of hexanoyl chloride (1 g, 0.0073 M) in toluene (5 ml) and aqueous 50% sodium hydroxide solution (0.58 g, 0.0073 M) while maintaining the temperature below 10° C. Following the addition, the reaction mixture was warmed to room temperature and stirred for 1 hr. The mixture was then diluted with hexane and the solid product isolated by filtration. The product was washed with water and hexane and dried. The crude product was recrystallized from ether-methanol to afford N'-t-butyl-N-benzoyl-N'-n-pentanecarbonylhydrazine as a white powder. m.p. 117–118° C.

EXAMPLE 683

Preparation of N'-t-butyl-N-benzoyl-N'-cyclohexanecarbonylhydrazine

To a stirred suspension of t-butylhydrazine hydrochloride (1 g, 0.008M) in toluene (30 ml) at room temperature was added dropwise a 50% aqueous solution of sodium hydroxide (0.6 g, 0.008M). After 15 min., the reaction mixture was cooled to 5° C. and a solution of benzoyl chloride (1.12 g, 0.008M) in toluene (5 ml) and a solution of aqueous 50% sodium hydroxide (0.64 g, 0.008M) were added dropwise and simultaneously from separate addition funnels while maintaining the temperature at or below 10° C. Following the addition, the reaction mixture was warmed to room temperature and stirred for 1 hr. The reaction was diluted with hexane and the solid N'-t-butyl-N-benzoylhydrazine was isolated by filtration.

To a stirred solution of the monobenzoylated compound (1.4 g, 0.0073M) in toluene (30 ml) at 5° C., were added dropwise and simultaneously from separate addition funnels, solutions of cyclohexanecarbonyl chloride (1.1 g, 0.0073M) in toluene (5 ml) and aqueous 50% sodium hydroxide solution (0.58 g, 0.0073M) while maintaining the temperature below 10° C. Following the addition, the reaction mixture was warmed to room temperature and stirred for 1 hr. The mixture was then diluted with hexane and the solid product isolated by filtration. The product was washed with water and hexane and dried. The crude product was recrystallized from ether-methanol to afford N'-t-butyl-N-benzoyl-N'-cyclohexanecarbonylhydrazine as a white powder. m.p. 202–204° C.

EXAMPLE 688

Preparation of N'-t-butyl-N-benzoyl-N'-pivaloylhydrazine

To a stirred suspension of t-butylhydrazine hydrochloride (2 g, 0.016M) in toluene (50 ml) at room temperature was added dropwise a 50% aqueous solution of sodium hydroxide (1.28 g, 0.016M). After 15 min., the reaction mixture was cooled to 5° C. and a solution of benzoyl chloride (2.3 g, 0.017M) in toluene (5 ml) and a solution of aqueous 50% sodium hydroxide (1.36 g, 0.017M) were added dropwise simultaneously from separate addition funnels while maintaining the temperature at or below 10° C. Following the addition, the reaction mixture was warmed to room temperature and stirred for 1 hr. The reaction mixture was diluted with hexane and the solid N'-t-butyl-N-benzoylhydrazine was isolated by filtration.

To a stirred solution of the monobenzoylated compound (2 g, 0.010M) in pyridine (15 ml) was added pivaloyl chloride (1.8 g, 0.015M) and a catalytic amount of 4-dimethylamino pyridine. The mixture was heated to 60° C. and stirred for approximately 1 hr., cooled and diluted with methylene chloride. The organic layer was washed with 10% HCl (3×25 ml) and water (50 ml), dried over magnesium sulfate and the solvent removed under vacuum. The solid product was recrystallized from methanol-ether to afford N'-t-butyl-N-benzoyl-N'-pivaloylhydrazine in 60% yield as a white solid. m.p. 217–220° C.

EXAMPLE 689

Preparation of N'-t-butyl-N-benzoyl-N'-phenylacetylhydrazine

To a stirred suspension of t-butylhydrazine hydrochloride (1 g, 0.008M) in toluene (30 ml) at room temperature was added dropwise a 50% aqueous solution of sodium hydroxide (0.64 g, 0.008M). After 15 min., the reaction mixture was cooled to 5° C. and a solution of benzoyl chloride (1.12 g, 0.008 M) in toluene (5 ml) and a solution of aqueous 50% sodium hydroxide (0.64 g, 0.008 M) were added dropwise simultaneously from separate addition funnels while maintaining the temperature at or below 10° C. Following the addition, the reaction mixture was warmed to room temperature and stirred for 1 hr. The reaction was diluted with hexane and the solid N'-t-butyl-N-benzoylhydrazine was isolated by filtration.

To a stirred solution of the monobenzoylated compound (1.5 g, 0.0078M) in toluene (30 ml) at 5° C., were added dropwise and simultaneously from separate addition funnels, solutions of phenylacetyl chloride (1.2 g, 0.008M) in toluene (5 ml) and aqueous 50% sodium hydroxide solution (0.63 g, 0.0078 M) while maintaining the temperature below 10° C. Following the addition, the reaction mixture was warmed to room temperature and stirred for 1 hr. The mixture was then diluted with hexane and the solid product isolated by filtration. The product was washed with water and hexane and dried. The crude product was recrystallized from ether-methanol to afford N'-t-butyl-N-benzoyl-N'-phenylacetylhydrazine as a white powder. m.p. 167–169° C.

EXAMPLE 691

Preparation of N'-t-butyl-N-benzoyl-N'-(beta-trifluoromethylcrotonyl)hydrazine

N'-t-butyl-N-benzoylhydrazine (1.0 g,) in 2 ml toluene was added dropwise to a solution of beta-trifluoromethylcrotonyl chloride (prepared by addition of oxalyl chloride (1.3 g) to a solution of 1.5 g beta-trifluoromethylcrotonic acid in 5 ml toluene at 23° C.). After 30 min. at 23° C., the reaction mixture was partitioned between saturated aqueous sodium bicarbonate (20 ml) and ether (20 ml). The ether layer was evaporated under reduced pressure to about 10 ml and the excess hydrazine was removed by filtration. The filtrate was evaporated to give N'-t-butyl-N-benzoyl-N'-(beta-trifluoromethylcrotonyl) hydrazine as a colorless oil.

EXAMPLE 699

Preparation of N'-t-butyl-N-benzoyl-N'-methacryloylhydrazine

N'-t-butyl-N-benzoylhdyrazine (0.9 g) suspended in 10 ml toluene and 1 ml $H_2O$ containing 0.3 g 50% sodium hydroxide was treated with 1.2 g of methacryloyl chloride at 23° C. After 18 hours, 5 ml of hexane was added and N'-t-butyl-N-benzoyl-N'-methacryloylhydrazine was collected by filtration. m.p. 148–152° C.

EXAMPLE 702

Preparation of N'-t-butyl-N'-cyclobutane-carbonyl-N-(4-chlorobenzoyl)hydrazine

To a stirred solution of N'-t-butyl-N-(4-chlorobenzoyl) hydrazine (2.0 g, 8.8 mmole) in toluene (35 ml) at 5° C. was added cyclobutanecarboxylic acid chloride (1.25 g, 10.5 mmole) in one portion. To the above mixture was dropwise added 50% NaOH solution (0.85 g, 10.6 mmole). After addition, the ice water bath was removed and the reaction mixture was stirred at room temperature overnight.

The mixture was diluted with hexane (30 ml) and $H_2O$ (30 ml) and stirred for another 30 min. The solid product was collected by suction-filtration and washed with $H_2O$ (100 ml) and hexane (100 ml) to yield 1.5 g of N'-t-butyl-N'-cyclobutanecarbonyl-N-(4-chlorobenzoyl)hydrazine.

EXAMPLE 722

Preparation of N'-t-butyl-N-benzoyl-N'-isonicotinoylhydrazine

N'-t-butyl-N-benzoylhydrazine (1.0 g, 0.0052 mol) was suspended in 20 ml of toluene. Isonicotinoyl chloride hydrochloride (0.93 g, 0.0052 mol) was added and then a solution of sodium hydroxide (1.25 g of 50% aqueous NaOH) in 5 ml of water was added dropwise. After stirring at 23° C. for 2 hours, the solids were removed by filtration, washed with water and dried in air. The crude product was chromatographed on silica gel using 5% methanol/methylene chloride as eluant to afford pure N'-t-butyl-N-benzoyl-N'-isonicotinoylhydrazine. m.p. >210° C.

EXAMPLE 723

Preparation of N'-t-butyl-N-(2-pyridine-carbonyl)-N'-benzoylhydrazine

A solution of N'-t-butyl-N-(2-pyridinecarbonyl)-hydrazine (1.0 g, 0.00518 mol) in 20 ml of toluene at 23° C. was treated sequentially with 50% sodium hydroxide (1.3 g) and benzoyl chloride (0.728 g). The mixture was stirred overnight. The solids were removed by filtration and washed with water to afford N'-t-butyl-N-(2-pyridinecarbonyl)-N'-benzoylhydrazine.

EXAMPLE 724

Preparation of N'-t-butyl-N-benzoyl-N'-nicotinoylhydrazine

A solution of N'-t-butyl-N-benzoylhydrazine (2.0 g) and nicotinoyl chloride hydrochloride in 20 ml of methylene chloride at 23° C. was treated dropwise with triethylamine (4 ml). The reaction mixture was stirred at 23° C. for 0.5 hours. Solids were removed by filtration. The filtrate was diluted with 10N HCl and ether. The layers were separated and the organic layer was washed with 10N HCl. The aqueous layer was neutralized with solid sodium bicarbonate and extracted with ether. The ether extracts were treated with charcoal and then dried with magnesium sulfate. Evaporation of solvents afforded a yellow oil which was chromatographed on silica gel using as eluant a mixture of 10% $CH_3OH$, 40% $CH_2Cl_2$, 50% $Et_2O$ to afford N'-t-butyl-N-benzoyl-N'-nicotinoylhydrazine as a yellow foam. m.p. 60–63° C.

EXAMPLE 727

Preparation of N'-t-butyl-N-(2-pyridinecarbonyl)-N'-(2-nitrobenzoyl)hydrazine

A solution of N'-t-butyl-N-(2-pyridinecarbonyl)-hydrazine (1.0 g, 0.00518 mol) in 20 ml of toluene was treated dropwise simultaneously with a solution of sodium hydroxide (1.24 g of 50% aqueous solution) in 5 ml of water and 2-nitrobenzoyl chloride (0.96 g). The resulting mixture was stirred at 23° C. overnight. Water was added and the mixture was extracted with ether. A second extraction was performed with methylene chloride and the combined organic extracts were dried over magnesium sulfate. Evaporation afforded 0.4 g of N'-t-butyl-N-(2-pyridinecarbonyl)-N'-(2-nitrobenzoyl)hydrazine as a yellow solid. m.p. 137–140° C.

EXAMPLE 729

Preparation of N'-t-butyl-N-(2-pyridine-carbonyl)-N'-(2-bromobenzoyl)hydrazine

An aqueous solution of sodium hydroxide (1.24 g of 50% NaOH diluted with 5 ml of water) was added to a solution of N'-t-butyl-N-(2-pyridinecarbonyl)hydrazine (1.0 g, 0.00518 mol) in 20 ml of toluene at 23° C. The mixture was cooled and treated with 2-bromobenzoyl chloride (1.137 g, 0.00518 mol). The mixture was then stirred at 23° C. overnight. The solids were removed by filtration, washed with water and dried to afford 0.96 g of N'-t-butyl-N-(2-pyridinecarbonyl)-N'-(2-bromobenzoyl)hydrazine as a white solid. m.p. 179–180° C.

EXAMPLE 733

Preparation of N'-t-butyl-N-(2-pyridine-carbonyl)-N'-(3,4-dichlorobenzoyl)hydrazine A solution of N'-t-butyl-N-(2-pyridinecarbonyl)-hydrazine (0.5 g) in 10 ml of toluene was treated with 50% sodium hydroxide (0.61 g). 3,4-dichlorobenzoyl chloride (0.6 g) was added and the mixture was stirred rapidly for 4 hours at 23° C. and then was allowed to stand for 48 hours. The solids were removed by filtration and washed with water to afford 0.75 g of N'-t-butyl-N-(2-pyridinecarbonyl)-N'-(3,4-dichlorobenzoyl)hydrazine as a white solid. m.p. 175–178° C.

EXAMPLE 737

Preparation of N'-t-butyl-N-(5-bromo-nicotinoyl-N'-(4-chlorobenzoyl)hydrazine

N'-t-butyl-N'-(4-chlorobenzoyl)hydrazine was prepared substantially according to the procedured for preparing N'-t-butyl-N'-benzoylhydrazine described for Example 220 step 3 except 4-chlorobenzoyl chloride was used in place of benzoyl chloride.

A solution of N'-t-butyl-N'-(4-chlorobenzoyl)-hydrazine (0.5 g, 0.0022 mol) and 5-bromonicotinic acid (0.44 g, 0.0022 mol) in 10 ml of methylene chloride containing triethylamine (0.33 g) was added to a solution of methanesulfonyl chloride (0.25 g, 0.0022 mol) in 10 ml of methylene chloride at 0° C. The resulting mixture was stirred at 23° C. for 2 hours and then was allowed to stand overnight at 23° C. Aqueous sodium bicarbonate was added and the layers were separated. The aqueous layer was re-extracted with methylene chloride. The organic extracts were evaporated to give a yellow solid which was triturated with hexane/methylene chloride to afford N'-t-butyl-N-(5-bromonicotinoyl)-N'-(4-chlorobenzoyl)hydrazine as an off-white solid. m.p. 193–197° C.

EXAMPLE 738

Preparation of N'-t-butyl-N-(pyrazine-carbonyl)-N'-benzoylhydrazine

To a mechanically stirred solution of t-butylhydrazine hydrochloride (51 g, 0.41 mol) in dioxane (100 ml) and water (50 ml), cooled in an ice bath was treated with 50% sodium hydroxide (32 g). The resulting mixture was treated dropwise with di-t-butyl-dicarbonate (92 g, 0.42 mol) over about one-half of an hour. After complete addition, the reaction mixture was warmed to room temperature and stirred for 2 hours. The resulting white solid was filtered off, washed with water and air-dried to afford 74 g of N'-t-butyl-N-t-butoxycarbonylhydrazine, mp. 69–71° C.

A mechanically stirred solution of N'-t-butyl-N-t-butoxycarbonylhydrazine (61 g, 0.32 mol) in toluene (120 ml) cooled in an ice bath, was treated dropwise and simultaneously with 50% sodium hydroxide (31 g) in water (50 ml) and benzoyl chloride (45 g). The addition was complete in 20 minutes and the resulting mixture was warmed to room temperature and allowed to stir for one hour. The resulting white solid was filtered, washed with water and air dried to afford 94 g of N-t-butoxycarbonyl-N'-benzoyl-N'-t-butylhydrazine, mp. 167–170° C.

To a mechanically stirred solution of N-t-butoxycarbonyl-N'-benzoyl-N'-t-butylhydrazine (52 g, 0.18 mol) in methanol (100 ml) was added concentrated hydrochloric acid (35 ml). The resulting mixture was stirred at room temperature for 4 days and then neutralized with saturated aqueous sodium bicarbonate. The resulting white solid was filtered, washed with water and dried under vacuum to afford N'-t-butyl-N'-benzoylhydrazine (39 g) mp. 124–125° C.

Triethylamine (1.0 g, 0.01 mol) was added to a solution of N'-t-butyl-N'-benzoylhydrazine (0.86 g, 0.0031 mol) and pyrazine carboxylic acid (0.56 g, 0.0045 mol) in 10 ml of methylene chloride at 23° C. This mixture was added to a solution of methanesulfonyl chloride (0.6 g, 0.0052 mol) in 10 ml of methylene chloride at 0° C. The mixture was stirred at 23° C. for 3 hours and then allowed to stand at 23° C. overnight. Aqueous sodium bicarbonate was added and the layers were separated. The organic extracts were evaporated to give crude product which was triturated with ether to afford N'-t-butyl-N-(pyrazinecarbonyl)-N'-benzoylhydrazine as a white solid. m.p. 181–183° C.

EXAMPLE 739

Preparation of N'-t-butyl-N-isonicotinoyl-N'-benzoylhydrazine

A solution of N'-t-butyl-N'-benzoylhydrazine (0.5 g, 0.00026 mol) in 10 ml of toluene was treated with 50% sodium hydroxide (0.6 g) followed by isonicotinyl chloride hydrochloride (0.47 g, 0.0026 mol). The mixture was stirred at 23° C. overnight. The solids were removed by filtration and washed with water followed by ether to afford N'-t-butyl-N-isonicotinyl-N'-benzoylhydrazine.

EXAMPLE 743

Preparation of N'-t-butyl-N-(2-pyridine-carbonyl)-N'-(4-fluorobenzoyl)hydrazine)

By substantially following the procedures described above for Example 2, except using 4-fluorobenzoyl chloride rather than benzoyl chloride, N'-t-butyl-N-(2-pyridinecarbonyl)-N'-(4-fluorobenzoyl)hydrazine was afforded.

EXAMPLES 754 AND 755

Preparation of N'-t-butyl-N'-(2-pyridinecarbonyl)-N-benzoylhydrazine

To a suspension of 2-picolinic acid (12.8 g, 0.104 mol.) in methylene chloride (80 ml) were added dropwise triethylamine (14 g, 0.139 mol.) in 10 ml methylene chloride followed by methanesulfonyl chloride (13 g, 0.113 mol.) in 10 ml methylene chloride at 0° C. The resulting mixture was stirred for half an hour before the dropwise addition of N'-t-butyl-N-benzoylhydrazine (20.0 g, 0.10 mole) in 80 ml methylene chloride at 0° C. to 23° C. The final dark brown mixture was allowed to stir at 23° C. for one hour, and to stand at 23° C. overnight.

Aqueous sodium bicarbonate was added and the layers were separated. The aqueous layer was re-extracted with methylene chloride. The organic extracts were combined, and dried over magnesium sulfate. Evaporation under reduced pressure gave 25 g of a light green, brown solid. Recrystalization on a steam bath with ethyl acetate:hexane (80:20 v/v) afforded a light yellow solid.

Column chromatography on silica gel, eluted first with methylene chloride and ether and then with ethyl acetate afforded two separate isomers of N'-t-butyl-N'-(2-pyridinecarbonyl)-N-benzoylhydrazine.

EXAMPLE 764

Preparation of N'-t-butyl-N-benzoyl-N'-(2-furoyl)hydrazine

N'-t-butyl-N-benzoylhydrazine (1 g) was dissolved in 20 ml toluene. Water (5 ml) and 50% aqueous sodium hydroxide (1.25 g) was added followed by 2-furoylchloride (0.68 g). After stirring for 7 hours at room temperature, 0.3 g 2-furoylchloride was added. and the mixture stirred for a further 6 hours. The solid product, N'-t-butyl-N-benzoyl-N'-(2-furoyl)hydrazine, was removed by filtration and washed with water. m.p. 155–175° C.

EXAMPLE 765

Preparation of N'-t-butyl-N-benzoyl-N'-(2-thiophenecarbonyl)hydrazine

N'-t-butyl-N-benzoylhydrazine (1.0 g) was dissolved in 20 ml toluene. 50% aqueous sodium hydroxide (1.25 g) was added followed by 2-thiophene-carbonylchloride (0.76 g). The mixture was stirred at room temperature for 14 hours. The solid product, N'-t-butyl-N-benzoyl-N'-(2-thiophenecarbonyl)hydrazine, was removed by filtration and washed with water. m.p. >200° C.

EXAMPLE 766

Preparation of N'-t-butyl-N-(2-thiophene-carbonyl)-N'-benzoylhydrazine

N'-t-butyl-N-(2-thiophenecarbonyl)hydrazine (1 g) was dissolved in 10 ml toluene and treated with 50% aqueous sodium hydroxide (1.0 g) and water (2 ml) followed by benzoylchloride (0.8 g). After stirring for 14 hours at room temperature, the solid product, N'-t-butyl-N-(2-thiophenecarbonyl)-N'-benzoylhydrazine, was removed by filtration and washed with water. m.p. >190° C.

EXAMPLE 767

Preparation of N'-t-butyl-N-(2-furoyl)-N'-benzoylhydrazine

N'-t-butyl-N-(2-furoyl)hydrazine (1.0 g) was dissolved in 10 ml toluene and 2 ml water. 50% aqueous sodium hydroxide (1.0 g) was added followed by benzoylchloride (0.8 g). After stirring for 14 hours at room temperature, the solid product, N'-t-butyl-N-(2-furoyl)-N'-benzoylhydrazine, was removed by filtration and washed with water. m.p. 160–162° C.

EXAMPLE 772

Preparation of N'-t-butyl-N-(4-methyl-benzoyl)-N'-(2,5-dichlorothiophene-3-carbonyl)-hydrazine N'-t-butyl-N-4-methylbenzoylhydrazine (0.7 g) was dissolved in 35 ml toluene. Water (5 ml) and 50% aqueous sodium hydroxide (0.8 g) were added followed by 2,5-dichlorothiophene-3-carbonylchloride (2.0 g). After stirring for 3 hours at room temperature, ether was added and the organic layer separated. Evaporation afforded a solid which was triturated with 10% ether-hexane to afford N'-t-butyl-N-(4-methylbenzoyl)-N'-(2,5-dichlorothiophene-3-carbonyl)hydrazine. m.p. 163–165° C.

EXAMPLE 778

Preparation of N'-t-butyl-N-(N-methyl-2-pyrrolecarbonyl)-N'-benzoylhydrazine

N'-t-butyl-N-(N-methyl-2-carbonylpyrrole)hydrazine (0.8 g) was dissolved in 10 ml toluene and 1 ml water. 50% aqueous sodium hydroxide (10 drops) was added followed by benzoylchloride (1.2 g). After 14 hours stirring at room temperature, ether was added and the product, N'-t-butyl-N-(N-methyl-2-pyrrolecarbonyl)-N'-benzoylhydrazine, was isolated by filtration and washed with ether. m.p. 182–185° C.

EXAMPLE 787

Preparation of N'-t-butyl-N-(1,2,3-triazole-4-carbonyl)-N'-(3-methylbenzoyl)hydrazine 1,2,3-triazole-4-carboxylic acid (1.0 g) and triethylamine (0.9 g) were dissolved in 40 ml methylene chloride and cooled in an ice bath. Methanesulfonylchloride (1.0 g) was added dropwise. After addition was complete, the reaction mixture was stirred for 0.5 hours. N'-t-butyl-N'-(3-methylbenzoyl)hydrazine (1.84 g) in 10 ml CH$_2$Cl$_2$ was added dropwise. The resulting mixture was allowed to stand for 14 hours. Aqueous sodium bicarbonate was added. The organic layer was dried over anhydrous magnesium sulfate, filtered and evaporated to give a yellow oil. Chromatography on silica gel using acetone as eluant afforded N'-t-butyl-N-1,2,3-triazole-4-carbonyl-N'-(3-methylbenzoyl)hydrazine.

EXAMPLE 802

Preparation of N'-(1-cyano-1-methyl-)ethyl-N,N'-dibenzoylhydrazine

To a suspension of benzoylhydrazine (13.6 g, 0.1 mole) in deionized water (50 ml) at 5° C. with stirring was dropwise added concentrated hydrogen chloride (9.8 g, 0.1 mole). To the resulting clear solution was added sodium cyanide (5.2 g, 0.1 mole) and acetone (6.5 g, 0.11 mole). A white and thick precipitate appeared. The cooling bath was removed and the reaction flask was stoppered tightly. The reaction mixture was stirred for 18 hours. The precipitate was collected by suction-filtration and was washed with a small amount of water to give 17.5 g (86.2% yielded) of the desired intermediate, N'-(1-cyano-1-methyl)ethyl-N-benzoic acid hydrazide, as the starting material for the next step. (m.p. 82–92° C.)

To the solution of N'-(1-cyano-1-methyl)ethyl-N-benzoic acid hydrazide (2 g, 0.01 mole) in dry methylene chloride (25 ml) under nitrogen at room temperature with stirring was added benzoyl chloride (2.02 g, 0.014 mole). To the above mixture was dropwise added triethylamine (1.31 g, 0.013 mole). The reaction mixture was stirred at room temperature for 5 hours. The reaction mixture was diluted with methylene chloride (50 ml), washed with water and brine. The organic layer was dried over MgSO$_4$ and the solvent was evaporated at reduced pressure to give a residue. The residue was treated with ethyl acetate/hexane mixture (1:1) affording a crude solid product which was collected by suction-filtration (1 g, 33% yield). An analytical sample was obtained by crystallization from ethyl acetate/hexane (4:1), m.p. 202–204° C. NMR and IR spectra showed the desired product.

EXAMPLE 809

Preparation of N'-(1-cyano-1-methyl-)ethyl-N,N'-di-4-tolylhydrazine

To the suspension of 4-toluic acid hydrazide (15.0 g, 0.1 mole) in water (150 ml) and ethanol (20 ml) at 5° C. with stirring was dropwise added concentrated hydrogen chloride (10 g, 0.1 mole). To the above suspension was carefully added sodium cyanide (5.3 g, 0.1 mole) and acetone (6.6 g, 0.11 mole). The reaction flask was stoppered tightly and the cooling bath was removed. The resulting viscous reaction mixture was stirred at room temperature for more than 24 hours. The precipitate was collected by suction-filtration and was washed with a small amount of diluted hydrogen chloride and water affording 14.6 g. (64.8%) of N'-(1-cyano-1-methyl)ethyl-4-toluic acid hydrazide as the starting material for the next step. Analytical sample was obtained by crystallization from ethyl acetate/hexane (3:1), m.p. 146–148° C.

To the solution of N'-(1-cyano-1-methyl)ethyl-4-toluic acid hydrazide (2.17 g, 0.01 mole) in dry methylene chloride (65 ml) under nitrogen with magnetic stirring was added 4-dimethylaminopyridine catalyst (1.34 g, 0.011 mole) followed by 4-methylbenzoyl chloride (2.52 g, 0.017 mole). To the above mixture was dropwise added triethylamine (1.1 g, 0.011 mole). The reaction mixture was slightly exothermic. After stirring at room temperature for 40 minutes the reaction mixture was diluted with methylene chloride (50 ml), washed with diluted HCl solution (2×50 ml), dil NaOH (50 ml), H$_2$O (50 ml) and brine. The organic layer was dried over MgSO$_4$, and the solvent was evaporated under reduced pressure to give a residue. The residue was treated with ethyl acetate/hexane mixture (1:1) and the resulting solid was collected by suction-filtration and affording 2.75 g (82% yield) of almost pure product. (m.p. 192–198° C.) NMR and IR spectra showed the desired product.

EXAMPLE NO. 822

Preparation of N'-(1,1-dimethyl-3-butenyl)-N, N'dibenzoylhydrazine

To a gently refluxing solution of allyl magnesium bromide (380 ml of 1M solution) was added acetone azine (20 g) dissolved in diethyl ether (200 ml). The solution was refluxed for three days. Upon cooling, a saturated solution of ammonium chloride (50 ml) was added. The aqueous layer was separated and washed twice with diethyl ether (200 ml). The combined ether extracts were dried over anhydrous magnesium sulfate, filtered and the ether removed at reduced pressure. The product was distilled through a vigreux column at 3.1 torr and collected in a dry ice/acetone cooled receiving flask. The boiling point was 60–65° C. 15 g of product was collected.

Oxalic acid (16.7 g) was dissolved in a solution of ethanol:diethyl ether (1:1) (150 ml) and water (3.3 g) was added. To this acid solution was added the hydrazone (13 g) dissolved in diethyl ether (75 ml). The solution was stirred for 24 hours then filtered. The solid is washed once with diethyl ether. The filtrate was concentrated and combined with the solid to afford a 71% yield (17.2 g) of the hydrazine oxalate.

The 1,1-dimethyl-3-butenylhydrazine oxalate (2 g) was dissolved in toluene and neutralized with 50% aqueous sodium hydroxide. To this solution was added benzoyl chloride (2.8 g) and sodium hydroxide (50% Aq. solution) (3.2 g) at 25° C. The reaction mixture was warmed to room temperature and stirred. The mixture was diluted with hexane and filtered to afford an oily product which solidified upon standing. (m.p. 105–112° C.)

EXAMPLE NO. 829

Preparation of N'-t-butyl-N-benzoyl-N'-benzylhydrazine

Benzyl bromide (0.9 g), 1-benzoyl-2-t-butyl hydrazine (1 g) and triethylamine (0.52 g) were warmed in dimethylformamide (50 ml) at 50° C. for 2 hours. The reaction mixture was cooled to room temperature, diluted with diethylether (100 ml) and washed three times with 25 ml of water. The organic layer was dried over magnesium sulfate, filtered, and the solvent removed in vacuo to afford the product as a white solid. The product was chromatographed on silica gel (G:70 to 230 mesh) using methylene chloride as eluent to afford a 75% yield of a white solid: m.p. 147–149.

EXAMPLE NO. 837

Preparation of N'-t-butyl-N-furoyl-N'-benzylhydrazine

Benzyl bromide (1.8 g), 1-furoyl-2-t-butyl hydrazine (2 g) and excess powdered potassium carbonate were stirred in dimethylformamide (50 ml) at 50° C. for 2 hours. The reaction mixture was cooled to room temperature, diluted with diethyl ether and washed several times with water. The organic layer was dried over magnesium sulfate, filtered, and the solvent removed in vacuo. The white solid product was chromatographed on silica gel (G:70–230 mesh) using methylene chloride as eluent to afford the product in good yield: m.p. 152–153.

EXAMPLE NO. 853

Preparation of N'-t-butyl-N-benzoyl-N'-methylpyridinylhydrazine

N'-t-butyl-N-benzoyl hydrazine (1.2 g), 2-chloromethyl pyridine (1.0 g) and triethylamine (2 equivalents) were stirred in dimethyl sulfoxide (15 ml) at room temperature for 2 hours. The reaction mixture was then warmed to 50° C. for 2 hours. The mixture was diluted with ether and washed with water. The organic layer was dried over magnesium sulfate, filtered and rotavapped to afford a yellow oil. The oil was chromatographed on silica gel (G:70–230 mesh) using a methylene chloride-ether mixture (1:1) as eluent to afford the purified product as a yellow gum in approximately 20% yield.

EXAMPLE NO. 855

Preparation of N'-t-butyl-N-benzyl-N'-benzoylhydrazine

N'-t-butyl-N'-benzoyl benzaldehyde hydrazone (1.8 g) and sodium cyanoborohydride (1.5 equivalents) were stirred in dry methanol (30 ml) at room temperature. Ten percent HCl was added to bring the pH of the reaction mixture to pH 3–4 and stirred at room temperature for 1 hour. The methanol was removed in vacuo and the residue was dissolved in methylene chloride. The methylene chloride layer was washed with saturated aqueous sodium bicarbonate and then with water. The organic layer was dried over magnesium sulfate, filtered and the solvent removed in vacuo to afford in good yield a white solid: m.p. 110–115.

EXAMPLE NO. 864

Preparation of N'-t-butyl-N'-benzoyl-benzaldehyde hydrazone

Benzaldehyde (10.6 g), t-butylhydrazine, hydrochloride (12.4 g) and triethylamine (10.1 g) were stirred in toluene (150 ml) at room temperature. The reaction mixture was washed with water and dried over magnesium sulfate. The mixture was filtered and the solvent was removed in vacuo to afford N'-t-butyl benzaldehyde hydrazone as a yellow oil in good yield.

The N'-t-butyl benzaldehyde hydrazone (1.76 g) and benzoyl chloride (1.4 g) were stirred in a pyridine-methylene chloride solvent system (1:1, 50 ml), diluted with methylene chloride and washed several times with 10% HCl. The organic layer was dried over magnesium sulfate, filtered and the solvent removed in vacuo to afford a low melting solid in good yield: m.p. 69–72° C.

EXAMPLE NO. 870

Preparation of N-benzoyl-N'-t-butyl-N'-phenylethylhydrazine

N'-t-butyl-N-benzoylhydrazine (2.2 g), powdered potassium carbonate (5 g) and beta-phenethyl bromide (1.8 g) were stirred in dimethylformamide (15 ml) at 60° for 18 hours. The reaction mixture was cooled, and diluted with ether and water. The white solid product was filtered off and

EXAMPLE NO. 871

Preparation of N-benzoyl-N'-t-butyl-N'-(ethoxycarbonyl)methylhydrazine

N'-t-butyl-N-benzoylhydrazine (2.0 g), powdered potassium carbonate (5 g) and bromoethyl acetate (1.6 g) were stirred in dimethylformamide (20 ml) at 60° C. for 14 hours. The reaction mixture was diluted with water and ether, and the organic layer was separated. The organic layer was washed several times with water, dried over magnesium sulfate and rotavapped to afford an oil. Chromatographic purification gave the pure oil product (0.25 g).

EXAMPLE NO. 872

Preparation of N'-t-butyl-N'-benzoyl-N-[N-(4-tolyl) aminocarbonyl]hydrazine

N't-butyl-N'-benzoylhydrazine (0.8 g) and p-methylphenylisocyanate (0.9 g) were stirred in diethylether (10 ml) at 23° C. for 15 hours. The reaction mixture was diluted with ether and filtered to afford 0.5 g of solid product: m.p. 208–210° C.

EXAMPLE NO. 873

Preparation of N'-t-butyl-N'-benzoyl-carbonyl-N-benzoylhydrazine

N'-t-butyl-N'-benzoylhydrazine (1 g), benzoyl formic acid (0.7 g) and methanesulfonyl chloride (0.7 g) were stirred in toluene (30 ml) and saturated sodium bicarbonate (10 ml) at approximately 5° C. Triethylamine was added slowly, dropwise to the reaction mixture and stirred 1 hour at room temperature. After stirring for 1 hour, the reaction mixture was diluted with toluene (25 ml) and washed with water several times. The organic layers were dried over magnesium sulfate, filtered and the toluene rotavapped off to afford a white solid. After column chromatography, the product was obtained as a white solid in approximately 70% yield.

EXAMPLE NO. 878

Preparation of N'-t-butyl-N-benzoyl-carbonyl-N'-benzoylhydrazine

N'-t-butyl-N-benzoylhydrazine (1 g), benzoyl formic acid (1 g), and methanesulfonyl chloride (0.7 g) were stirred in toluene (35 ml) and saturated sodium bicarbonate (15 ml) at approximately 5° C. Triethylamine was added slowly, dropwise to the reaction mixture, and slowly warmed to room temperature. After stirring for 1 hour, the reaction mixture was diluted with toluene (20 ml) and the organic layer was washed several times with water. The organic layers were dried over magnesium sulfate, filtered and the toluene rotavapped off to afford a white gum. The crude product was chromatographed on silica gel (G:230–400 mesh) using a methylene chloride ether solvent system as eluent to afford a 65% yield of a white solid.

EXAMPLE NO. 880

Preparation of N'-t-butyl-N-(1,2,3,4-tetrahydronaphthyl-2-carbonyl)-N'-(3-toluoyl) hydrazine To a stirred suspension of N'-t-butyl-N'-(3-toluoyl) hydrazine (1.2 g) in toluene (10 ml) and aqueous sodium hydroxide (3 ml of 50% solution) was added 1,2,3,4-tetrahydronaphthyl-2-carbonyl chloride (0.007 mol). After stirring 1 hour, hexane and ether were added and the solids filtered off and dried by vacuum oven at 45° C.

EXAMPLE NO. 882

Preparation of N'-t-butyl-N-benzoyl-N'-(alpha-chlorophenylacetylhydrazine)

N'-t-butyl-N-benzoylhydrazine (10 g) was stirred in toluene (100 ml) and saturated sodium bicarbonate (50 ml) at approximately 5–10° C. Alpha-chlorophenylacetylchloride (9.8 g) in toluene (20 ml) was added slowly, dropwise to the cooled reaction mixture, warmed to room temperature and stirred several hours. Hexane (100 ml) was added to the reaction mixture and the solid product was filtered. The filter cake was washed several times with hexane and then water. The product was air dried to afford a 92% yield.

EXAMPLE NO. 883

Preparation of N'-t-butyl-N-benzoyl-N'-phenylacetylhydrazine

N'-t-butyl-N-benzoylhydrazine (2 g) was stirred in toluene (35 ml) and 50% aqueous sodium hydroxide (1 g) at 5° C. Phenylacetylchloride (1.5 g) was added slowly, dropwise to the reaction mixture, warmed to room temperature and stirred 1 hour. The reaction mixture was diluted with hexane (50 ml) and filtered off to yield a solid product. The filter cake was washed with hexane and water and allowed to air dry. The white solid product obtained in 90% yield melted at 167–169° C.

EXAMPLE NO. 893

Preparation of N'-t-butyl-N'-benzoyl-alpha-furoyloxybenzaldehyde hydrazone

N'-benzoyl-N'-t-butyl hydrazine (1.5 g) was stirred in a two-phase solvent system consisting of toluene (20 ml) and 50% aqueous sodium hydroxide (10 ml). First, a phase transfer catalyst, (n-Bu)$_4$N+-I (25–50 mg) was added and then 2-furoyl chloride was added dropwise. After the addition, the suspended white solid hydrazine went slowly into solution as it reacted to form the acylated product. After stirring at room temperature for 1 hour, the reaction mixture was diluted with 35 ml water and 30 ml of ethyl acetate. The layers were separated and the organic layer was washed several times with water, dried over magnesium sulfate, filtered and concentrated in vacuo to afford the product as a clear oil. The product was chromatographed on silica gel (G:230–400 mesh) using methylene chloride as the eluting solvent affording a clear, colorless oil (85% yield).

EXAMPLE NO. 905

Preparation of N'-t-butyl-N'-2,4-dichlorobenzoyl-alpha-methoxy-2,3-dimethylbenzaldehyde hydrazone To a stirred solution of N'-t-butyl-N-(2,3-dimethylbenzoyl)hydrazine (4.2 g) and triphenylphosphine (5.5 g) in dry acetonitrile (60 ml) at room temperature under nitrogen was dropwise added carbon tetrachloride (3.5 g). The reaction mixture was stirred overnight at room temperature. The acetonitrile was removed in vacuo and the crude reaction mixture was chromatographed on silica gel (6, 230–400 mesh) using hexane/ethyl acetate (3:1) to afford the corresponding hydrazinoyl chloride as a yellow oil.

To a stirred suspension of powdered potassium carbonate (2 g) in methanol (75 ml) was added dropwise a solution of the above hydrazinoyl chloride (2.2 g) in methanol (40 ml). The reaction mixture was stirred overnight at room temperature, concentrated in vacuo and the carbonate was filtered off. The filtrate was rotavapped to afford methoxyhydrazine as a while solid (1.9 g).

To a stirred solution of the methoxyhydrazine (1.5 g) in toluene (25 ml) and 50% sodium hydroxide (2 g diluted with 8 g of water) was added 2,4-dichlorobenzoyl chloride (2.5 g) dropwise while the reaction mixture was kept at approximately 0° C. After warming to room temperature, the reaction mixture was diluted with ether and the layers separated. The organic layer was washed twice with water, once with saturated sodium chloride solution and dried over sodium sulfate. Concentration of the reaction gave a product which was chromatographed on silica gel (6, 230–400 mesh) using a hexane/ethyl acetate (4:1) solvent system.

EXAMPLE NO. 914

Preparation of N'-t-butyl-N-benzene-sulfonyl-N'-benzoylhydrazine

N'-t-butyl-N'-benzoylhydrazine (0.4 g) was stirred in pyridine (3 ml) at room temperature. Benzenesulfonyl chloride (0.5 g) was added slowly, dropwise and stirred for 2 hours, diluted with diethyl ether (20 ml) and washed several times with a 10% HCl solution and then water. The organic layer was dried over magnesium sulfate, filtered and the solvent rotavapped off to afford a white solid in good yield.

EXAMPLE NO. 918

Preparation of N'-t-butyl-N-benzoyl-N'-benzenesulfonylhydrazine

N-benzoyl-N'-t-butyl hydrazine (0.8 g) was stirred in pyridine (2 ml) at room temperature. Benzenesulfonyl chloride (0.8 g) was added slowly dropwise, stirred about 1 hour, diluted with diethyl ether (10 ml) and washed several times with a 10% HCl solution and then water. The organic layer was dried over magnesium sulfate. The mixture was filtered and the solvent rotavapped off to afford a white solid in good yield.

EXAMPLE NO. 922

Preparation of N'-t-butyl-N'-[methyl-(2-chlorophenylamino)phosphinyl]-N-benzoylhydrazine Methyl dichlorophosphine (1.3 g) in ether (10 ml) and triethylamine (2 ml) were added to a stirred solution of N-benzoyl-N'-t-butyl hydrazine (1.0 g) in methylene chloride (3 ml). After stirring 5 minutes at room temperature, o-chloroaniline was added neat producing a mild exotherm. The reaction was quenched 2 minutes later with water (20 ml) and ether (20 ml), separated and the organic washed with 0.1N HCl, dried over MgSO$_4$, filtered and rotavapped to a colorless oil weighing 0.5 g.

EXAMPLE NO. 923

Preparation of N'-t-butyl-N-methyl-phenylphosphinyl-N'-benzoylhydrazine

Triethylamine (7 ml) and t-butyl hydrazine.HCl (4 g) were stirred in methylene chloride (20 ml) at about 0° C. To this was added, slowly, methylphenylphosphinyl chloride (0.03 mol). The mixture was stirred at 0° C. for 15 minutes and quenched with a sodium bicarbonate solution. The reaction mixture was extracted with diethyl ether, washed with water and dried over magnesium sulfate. After filtering the drying agent, the solvent was removed in vacuo to afford an oily product which was used directly in the subsequent step.

N'-t-butyl-N-(methylphenyl)phosphinylhydrazine (0.7 g) and triethylamine (3 ml) were stirred in diethyl ether (30 ml) at room temperature. Slowly, dropwise benzoyl chloride (1.2 g) was added to the reaction mixture. After stirring 1 hour at room temperature, the reaction mixture was diluted with hexane and the solid product filtered off. The white solid melted at 175–178° C.

EXAMPLE NO. 933

Preparation of N'-t-butyl-N-(2-phenyl-3-methylpentanoyl)-N'-(3-toluoyl)hydrazine To a stirred suspension of N'-t-butyl-N'-(3-toluoyl) hydrazine (0.7 g) in toluene (10 ml) and aqueous sodium hydroxide (12 drops of 50% aqueous sodium hydroxide) was added dropwise 2-phenyl-3-methyl-pentanoyl chloride (1.0 g). The reaction mixture was stirred overnight, diluted with hexanes and the solids filtered. The solids were washed with hexane and air dried.

EXAMPLE NO. 941

Preparation of N'-t-butyl-N-phenyl-propiolyl-N'-(3-toluoyl)hydrazine

To a stirred solution of N'-(3-toluoyl)-N'-t-butyl hydrazine (1.0 g) in toluene (15 ml) and aqueous sodium hydroxide was added phenylpropiolyl chloride (0.01 mol) dropwise at room temperature. After stirring the reaction mixture for 3 hours, hexane and ether were added and the solids filtered. The solids were vacuum dried at 60° C.

EXAMPLE NO. 942

Preparation of N'-t-butyl-N-(2,3-di-methylbenzoyl)-N'-phenylpropiolylhydrazine

To a stirred solution of N-(2,3-dimethylbenzoyl)-N'-t-butyl hydrazine (1.0 g) in toluene (15 ml) and aqueous sodium hydroxide was added phenylpropiolyl chloride (0.006 mol) dropwise. After stirring 15 minutes at room temperature, ether and hexane were added and the solid product was filtered off.

EXAMPLE NO. 944

Preparation of N'-t-butyl-N-(3,4-epoxy-cyclohexane carbonyl)-N'-(3-toluoyl)hydrazine To a stirred solution of N'-t-butyl-N'-(3-toluoyl)hydrazine (20 g) in toluene (150 ml) and aqueous sodium hydroxide at 10° C. was added 3-cyclohexenecarbonyl chloride (14.3 g) dropwise at a rate which maintained the temperature at or below 10° C. After stirring at room temperature for 2 hours, hexane was added and the solids filtered. The filler cake was washed with hexane and water and —N'-(3-toluoyl) hydrazine (2 g) and m-chloroperbenzoic acid (1.1 mol equivalents of 80% material) was stirred in methylene chloride (50 ml) overnight. The reaction mixture was diluted with methylene chloride (50 ml) and washed with saturated aqueous sodium bicarbonate solution (3×25 ml), dried over magnesium sulfate, filtered and rotavapped to afford the white solid epoxide in 78% overall yield.

EXAMPLE 948

Preparation of N'-t-butyl-N-pyrenone-carbonyl-N'-(3-toluoyl)hydrazine

To a stirred suspension of t-butyl hydrazine hydrochloride (0.02 mol) in toluene (20 ml) and aqueous hydroxide (5 ml of 50% solution) at room temperature was added pyrenonecarbonyl chloride (0.01 mol). After stirring the reaction mixture for 20 minutes, ether and hexane were added and the solid product was filtered and washed with water. The solid product (0.5 g) was stirred in toluene (10 ml) and aqueous sodium hydroxide and m-toluoyl chloride (0.8 g) was added dropwise. After stirring for 5 hours, hexane and ether were added and the solid product filtered and air dried.

EXAMPLE NO. 1002

Preparation of 1-t-butyl-1-(3- toluoyl)-4-(4-chlorobenzenesulfonyl)semicarbazide To a solution of N'-t-butyl-N'-3-toluoyl hydrazine (4.03 g, 0.02 mole) in methylene chloride (25 ml) under nitrogen was added 4-chlorobenzenesulfonyl isocyanate (5 g, 80%, 0.02 mole) at room temperature. The exothermic reaction mixture was stirred at room temperature for 30 minutes. The solvent was evaporated under reduced pressure to give an oil. A precipitate appeared after treating with ether. The pure product was collected by suction-filtration and washed with a small amount of ether affording 4.8 g of 1-t-butyl-1-(3-toluoyl)-4-(4-chlorobenzenesulfonyl)semicarbazide as a white solid. m.p. 184–188° C.

EXAMPLE NO. 1008

Preparation of N'-(1-methyl-1-carbamyl)ethyl-N'-3-toluoyl-N-4-chlorobenzoyl hydrazine To concentrated hydrochloric acid (10 ml) at 0–5° C. was added N'-(1-methyl-1-cyano)ethyl-N'-3-toluoyl-N-4-chlorobenzoyl hydrazine (0.8 g, 2.25 mmole) in one portion with stirring. After stirring for 40 minutes at a temperature below 20° C., the reaction mixture was diluted with water (50 ml) and hexane (50 ml). The resultant suspension was suction-filtered to give the product, N'-(1-methyl-1-carbamyl)ethyl-N'-3-toluoyl-N-4-chlorobenzoyl hydrazine, as a white solid. m.p. 213–218° C. Yield is 0.5 g (59%).

EXAMPLE NO. 1013

Preparation of N'-t-butyl-N'-3-toluoyl-mucochloric acid hydrazone

To a solution of N'-t-butyl-N'-3-toluoylhydrazine (1.03 g, 5 mmole) in 80% methanol (25 ml) was added mucochloric acid (0.85 g, 5 mmole). The reaction mixture was held at room temperature for 2 hours with occasional shaking. The resultant viscous suspension was suction-filtered and washed with water. After air-drying overnight, the product, N'-t-butyl-3-toluoyl mucochloric acid hydrazone, weighed 1.50 g. m.p. 167–168° C.

EXAMPLE NO. 1015

Preparation of N'-t-butyl N'-3-toluoyl-ethylpyruvate hydrazone

To a solution of N'-t-butyl-N'-3-toluoyl hydrazine (2.06 g, 10 mmole) in methylene chloride (20 ml) and water (20 ml) at room temperature with stirring was added ethylpyruvate (2.4 g, 21 mmole). The reaction mixture was stirred at room temperature for 16 hours. The reaction mixture turned to two phases. The aqueous phase was extracted with methylene chloride (2×50 ml) and the extracts were combined with the organic phase. The combined organic solution was washed with water and brine, dried over magnesium sulfate, filtered and evaporated to give a liquid product. The product was further dried in vacuum to give 1.9 g of N'-t-butyl-N'-3-toluoyl ethylpyruvate hydrazone as an oil.

EXAMPLE NO. 1016

Preparation of N'-t-butyl-N'-3-toluoyl-acetone hydrazone

To a solution of t-butyl acetone hydrazone (5 g, 39 mmole) in methylene chloride (50 ml) at 0° C. under nitrogen was added 3-toluoyl chloride (6.1 g, 39 mmole), followed by slowly adding triethylamine (3.94 g, 39 mmole). After the addition the reaction mixture was stirred at between 0–5° C. for one hour. The reaction mixture was diluted with methylene chloride (100 ml) and washed subsequently with water, dilute HCl, water, and brine. The organic layer was dried over MgSO4 and filtered. The solvent was evaporated under a reduced pressure to give a light brown liquid. The desired product, N'-t-butyl-N'-3-toluoyl acetone hydrazone, was obtained (2.45 g) by a vacuum distillation. b.p. 96–104° C. at 0.05 mm Hg.

EXAMPLE NO. 1017

Preparation of N'-t-butyl-N'-3-toluoyl-N-isopropylhydrazine

To a solution of N'-t-butyl-N'-3-toluoyl acetone hydrazone (1.5 g, 6.08 mmole) in methanol (50 ml) at room temperature with stirring was added, in small portions, sodium borocyanohydride (0.5 g, 8 mmole). To the above reaction mixture was added 10% HCl (5 ml) and the mixture stirred for 10 minutes. A white precipitate appeared. To this was added water (50 ml) and dilute NaOH until the solution turned basic. The resultant white solid was collected by suction-filtration and washed with water. The product was further dried in vacuum to give 0.9 g (60%) of N'-t-butyl-N'-3-toluoyl-N-isopropylhydrazine as a fluffy white powder. m.p. 107–109° C.

EXAMPLE NO. 1018

Preparation of N'-t-butyl-N'-benzoyl-N-(1-cyano-1-methyl)ethylhydrazine

To a suspension of N'-t-butyl-N'-benzoyl- hydrazine (1.92 g, 10 mmole) in water (30 ml) at 0–5° C. was added concentrated HCl (1 g, 10 mmole), followed by NaCN (0.52 g, 10.6 mmole) and acetone (0.75 g, 12.9 mmole). After the addition, the reaction flask was stoppered tightly and the reaction mixture was stirred at room temperature for 16 hours. The resultant suspension was suction-filtered and washed with water. The product, N'-t-butyl-N'-benzoyl-N-(1-cyano-1-methyl)ethylhydrazine, was further dried in vacuum to give 2.1 g as a white powder. m.p. 117–120° C.

By following substantially the procedures in Examples 1 and 3 and using the reactants shown below in Table II the products of Example Nos. 2, 4 through 12, 14, 19, 20, 32, 37, 55, 98 through 101, 145, 169, 174, 181, 234, 250, 260, 264, 289, 295, 298, 308, 364, 390, 391, 394, 449, 613, 632, 924 through 928, 937, 938, 939, 943, 949, 950, 951, 954, 959, 961, 963, 964, 965, 967, 968, 990 and 996 were prepared.

TABLE II

| Ex. No. | Compound of Formula III or VI | Compound of Formula IV | Base | Solvents |
|---|---|---|---|---|
| 3 | 3-chlorobenzoyl chloride | t-butylhydrazine hydrochloride | sodium hydroxide | toluene and water |
| 4 | 3,4-dichlorobenzoyl chloride | t-butylhydrazine hydrochloride | sodium hydroxide | toluene and water |
| 5 | 4-methylbenzoyl chloride | t-butylhydrazine hydrochloride | sodium hydroxide | toluene and water |
| 6 | 4-nitrobenzoyl chloride | t-butylhydrazine hydrochloride | sodium hydroxide | toluene and water |
| 7 | 4-methoxybenzoyl chloride | t-butylhydrazine hydrochloride | sodium hydroxide | toluene and water |
| 8 | 3-nitrobenzoyl chloride | t-butylhydrazine hydrochloride | sodium hydroxide | toluene and water |
| 9 | 3-methoxybenzoyl chloride | t-butylhydrazine hydrochloride | sodium hydroxide | toluene and water |
| 10 | 2-nitrobenzoyl chloride | t-butylhydrazine hydrochloride | sodium hydroxide | toluene and water |
| 11 | 2-chlorobenzoyl chloride | t-butylhydrazine hydrochloride | sodium hydroxide | toluene and water |
| 12 | 2-methoxybenzoyl chloride | t-butylhydrazine hydrochloride | sodium hydroxide | toluene and water |
| 14 | 4-cyanobenzoyl chloride | t-butylhydrazine hydrochloride | sodium hydroxide | toluene and water |
| 19 | 3-methylbenzoyl chloride | t-butylhydrazine hydrochloride | sodium hydroxide | toluene and water |
| 20 | 2-methylbenzoyl chloride | t-butylhydrazine hydrochloride | sodium hydroxide | toluene and water |
| 32 | 4-t-butylbenzoyl chloride | t-butylhydrazine hydrochloride | sodium hydroxide | toluene and water |
| 37 | 3,5-dichlorobenzoyl-chloride | t-butylhydrazine hydrochloride | sodium hydroxide | toluene and water |
| 55 | 1-naphthoylchloride | t-butylhydrazine hydrochloride | sodium hydroxide | toluene and water |
| 98 | 4-fluorobenzoyl chloride | t-butylhydrazine hydrochloride | sodium hydroxide | toluene and water |
| 99 | 3-fluorobenzoyl chloride | t-butylhydrazine hydrochloride | sodium hydroxide | toluene and water |
| 100 | 2-fluorobenzoyl chloride | t-butylhydrazine hydrochloride | sodium hydroxide | toluene and water |
| 101 | 2-naphthoylchloride | t-butylhydrazine hydrochloride | sodium hydroxide | toluene and water |
| 145 | 4-biphenylbenzoyl chloride | t-butylhydrazine hydrochloride | sodium hydroxide | toluene and water |
| 169 | 2-chloromethyl-benzoyl chloride | t-butylhydrazine hydrochloride | sodium hydroxide | toluene and water |
| 174 | 2-bromobenzoyl chloride | t-butylhydrazine hydrochloride | sodium hydroxide | toluene and water |
| 181 | 4-ethylbenzoyl chloride | t-butylhydrazine hydrochloride | sodium hydroxide | toluene and water |
| 234 | 3-methoxy benzoyl chloride | t-butylhydrazine hydrochloride | sodium hydroxide | toluene and water |
| 250 | benzoyl chloride | 2,2-dimethyl-pentylhydrazine oxalic acid salt | sodium hydroxide | toluene and water |
| 260 | 2-nitro-4-chloro-benzoyl chloride | t-butylhydrazine hydrochloride | sodium hydroxide | toluene and water |
| 264 | 2,6-difluorobenzoyl chloride | t-butylhydrazine hydrochloride | sodium hydroxide | toluene and water |
| 289 | 4-vinylbenzoyl chloride | t-butylhydrazine hydrochloride | sodium hydroxide | toluene and water |
| 295 | benzoyl chloride | 2,2-dimethyl-propylhydrazine oxalic acid salt | sodium hydroxide | toluene and water |
| 298 | 2-bromobenzoyl chloride | 2,2-dimethyl-propylhydrazine oxalic acid salt | sodium hydroxide | toluene and water |
| 308 | 4-(1-propenyl)-benzoyl chloride | t-butylhydrazine hydrochloride | sodium hydroxide | toluene and water |
| 364 | 4-bromobenzoyl chloride | t-butylhydrazine hydrochloride | sodium hydroxide | toluene and water |
| 390 | 3,5-dimethyl-benzoyl chloride | t-butylhydrazine hydrochloride | sodium hydroxide | toluene and water |
| 391 | 2,4-dichlorobenzoyl chloride | t-butylhydrazine hydrochloride | sodium hydroxide | toluene and water |
| 394 | 2,3-dimethyl-benzoyl chloride | t-butylhydrazine hydrochloride | sodium hydroxide | toluene and water |
| 449 | 3,4-dimethyl-benzoyl chloride | t-butylhydrazine hydrochloride | sodium hydroxide | toluene and water |
| 613 | 2-acetoxybenzoyl chloride | t-butylhydrazine hydrochloride | NaHCO$_3$ i.e. sodium bicarbonate | toluene and water |
| 632 | 2-methyl-3-chloro-benzoyl chloride | t-butylhydrazine hydrochloride | sodium hydroxide | toluene and water |
| 924 | 4-chlorobenzoyl chloride | methylhydrazine | sodium hydroxide | toluene |
| 925 | 3,5-dichlorobenzoyl chloride | methylhydrazine | sodium hydroxide | toluene |
| 926 | n-pentanoylchloride | t-butylhydrazine hydrochloride | sodium hydroxide | toluene and water |
| 927 | n-heptanoyl chloride | t-butylhydrazine hydrochloride | sodium hydroxide | toluene and water |
| 928 | chloroacetyl chloride | t-butylhydrazine hydrochloride | sodium hydroxide | toluene and water |
| 937 | ,-dimethyl acryloyl chloride | t-butylhydrazine hydrochloride | sodium hydroxide | toluene and water |
| 938 | 2,3,3-trichloro-acryloyl chloride | t-butylhydrazine hydrochloride | sodium hydroxide | toluene and water |
| 939 | cinnamoyl chloride | t-butylhydrazine hydrochloride | sodium hydroxide | toluene and water |
| 943 | cyclohexanecarbonyl chloride | t-butylhydrazine hydrochloride | sodium hydroxide | toluene and water |
| 949 | 2-furoylchloride | t-butylhydrazine hydrochloride | sodium hydroxide | toluene and water |
| 950 | 2-thiophene carboxylic acid chloride | t-butylhydrazine hydrochloride | sodium hydroxide | toluene and water |
| 951 | pyrrolidine carbonylchloride | t-butylhydrazine hydrochloride | sodium hydroxide | toluene and water |
| 954 | N,N-diethylcarbamoyl chloride | t-butylhydrazine hydrochloride | sodium hydroxide | toluene and water |
| 959 | benzoylchloride | 2-tolylhydrazine | sodium hydroxide | toluene and water |
| 961 | benzoylchloride | phenylhydrazine | sodium hydroxide | toluene and water |
| 963 | benzoylchloride | 2-chlorophenyl hydrazine | sodium hydroxide | toluene and water |
| 964 | benzoylchloride | 4-chlorophenyl hydrazine | sodium hydroxide | toluene and water |
| 965 | benzoylchloride | benzylhydrazine | sodium hydroxide | toluene and water |
| 967 | 3,5-dichlorobenzoyl chloride | benzylhydrazine | sodium hydroxide | toluene and water |
| 968 | benzoylchloride | 4-chloropyrazinyl hydrazine | sodium hydroxide | toluene and water |
| 990 | n-butanoyl chloride | t-butylhydrazine hydrochloride | sodium hydroxide | toluene and water |
| 996 | benzoyl chloride | N'-(1,1-dimethyl) benzyl-N-benzoyl hydrazine | sodium hydroxide | toluene and water |

By following substantially the procedures in Example 16 and using the reactants shown below in Table III, the products of Example Nos. 13, 15, 17, 18, 21 through 31, 33 through 36, 38, 40 through 43, 45, 47 through 54, 56, 57 through 62, 64 through 97, 104 through 109, 113, 117, 118, 119, 121, 122, 123, 125, 126, 130 through 135, 137 through 142, 146, 147, 150, 152 through 154, 160, 163, 167, 173, 175 through 180, 182, 183, 184, 190, 194 through 202, 204 through 211, 214 through 219, 224 through 231, 235 through 249, 251 through 259, 261 through 263, 265 through 270, 272 through 284, 287, 288, 290 through 292, 296, 297, 299 through 307, 309 through 322, 325, 327, 328, 334, 341 through 343, 346 through 348, 355 through 357, 370, 371, 377, 378, 380, 381, 387 through 389, 392, 393, 395, 396, 401 through 413, 419, 420, 422 through 424, 426 through 433, 437 through 448, 450 through 452, 454 through 457, 459 through 469, 474 through 483, 485 through 540, 542 through 545, 548 through 612, 615 through 624, 626 through 631, 633, 929 through 932, 934, 935, 936, 940, 946, 947, 952, 953, 962, 966, 993, 994, 995, 997 and 998 were prepared.

TABLE III

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| 13 | 4-toluoyl chloride | benzoylchloride | t-butylhydrazine hydrochloride |
| 15 | 4-toluoyl chloride | 4-chlorobenzoyl chloride | t-butylhydrazine hydrochloride |
| 17 | benzoylchloride | 3-chlorobenzoyl chloride | t-butylhydrazine hydrochloride |
| 18 | benzoylchloride | 2-chlorobenzoyl chloride | t-butylhydrazine hydrochloride |
| 21 | benzoylchloride | 4-methylbenzoyl chloride | t-butylhydrazine hydrochloride |
| 22 | benzoylchloride | 3-methylbenzoyl chloride | t-butylhydrazine hydrochloride |
| 23 | benzoylchloride | 2-methylbenzoyl chloride | t-butylhydrazine hydrochloride |
| 24 | benzoylchloride | 4-methoxybenzoyl chloride | t-butylhydrazine hydrochloride |
| 25 | benzoylchloride | 3-methoxybenzoyl chloride | t-butylhydrazine hydrochloride |
| 26 | benzoylchloride | 2-methoxybenzoyl chloride | t-butylhydrazine hydrochloride |
| 27 | benzoylchloride | 4-t-butylbenzoyl chloride | t-butylhydrazine hydrochloride |
| 28 | benzoylchloride | 4-cyanobenzoyl chloride | t-butylhydrazine hydrochloride |
| 29 | benzoylchloride | 4-nitrobenzoyl chloride | t-butylhydrazine hydrochloride |
| 30 | benzoylchloride | 3-nitrobenzoyl chloride | t-butylhydrazine hydrochloride |
| 31 | benzoylchloride | 2-nitrobenzoyl chloride | t-butylhydrazine hydrochloride |
| 33 | 4-methylbenzoyl chloride | 3,4-dichlorobenzoyl chloride | t-butylhydrazine hydrochloride |
| 34 | benzoylchloride | 4-fluorobenzoyl chloride | t-butylhydrazine hydrochloride |
| 35 | benzoylchloride | 3-fluorobenzoyl chloride | t-butylhydrazine hydrochloride |
| 36 | benzoylchloride | 2-fluorobenzoyl chloride | t-butylhydrazine hydrochloride |
| 38 | benzoylchloride | 2,4-dichlorobenzoyl chloride | t-butylhydrazine hydrochloride |
| 40 | benzoylchloride | 4-trifluoromethyl benzoylchloride | t-butylhydrazine hydrochloride |
| 41 | benzoylchloride | 3-trifluoromethyl benzoylchloride | t-butylhydrazine hydrochloride |
| 42 | benzoylchloride | 2-trifluoromethyl benzoylchloride | t-butylhydrazine hydrochloride |
| 43 | benzoylchloride | 2,5-difluorobenzoyl chloride | t-butylhydrazine hydrochloride |
| 45 | benzoylchloride | 3-cyanobenzoyl chloride | t-butylhydrazine hydrochloride |
| 47 | benzoylchloride | 2,6-difluorobenzoyl chloride | t-butylhydrazine hydrochloride |
| 48 | 4-chlorobenzoyl chloride | benzoylchloride | t-butylhydrazine hydrochloride |
| 49 | benzoylchloride | 3,4-dichlorobenzoyl chloride | t-butylhydrazine hydrochloride |
| 50 | benzoylchloride | 3,5-dichlorobenzoyl chloride | t-butylhydrazine hydrochloride |
| 51 | benzoylchloride | 2,6-dichlorobenzoyl chloride | t-butylhydrazine hydrochloride |
| 52 | 4-t-butylbenzoyl chloride | benzoylchloride | t-butylhydrazine hydrochloride |
| 53 | 2-chlorobenzoyl chloride | benzoylchloride | t-butylhydrazine hydrochloride |
| 54 | 1-naphthoylchloride | benzoylchloride | t-butylhydrazine hydrochloride |
| 56 | 3-chlorobenzoyl chloride | benzoylchloride | t-butylhydrazine hydrochloride |
| 57 | 4-chlorobenzoyl chloride | 3,4-dichlorobenzoyl chloride | t-butylhydrazine hydrochloride |
| 58 | 2-chlorobenzoyl chloride | 3,4-dichlorobenzoyl chloride | t-butylhydrazine hydrochloride |
| 59 | 2-methylbenzoyl chloride | benzoylchloride | t-butylhydrazine hydrochloride |
| 60 | benzoylchloride | 2-chloro-4-nitro benzoylchloride | t-butylhydrazine hydrochloride |
| 61 | benzoylchloride | 3,5-dinitrobenzoyl chloride | t-butylhydrazine hydrochloride |
| 62 | benzoylchloride | 2,3-dichlorobenzoyl chloride | t-butylhydrazine hydrochloride |
| 64 | benzoylchloride | 2-chloro-5-methyl benzoylchloride | t-butylhydrazine hydrochloride |
| 65 | benzoylchloride | 3,5-dimethylbenzoyl chloride | t-butylhydrazine hydrochloride |
| 66 | benzoylchloride | 2-nitro-5-methyl benzoylchloride | t-butylhydrazine hydrochloride |
| 67 | benzoylchloride | 2-methyl-3-chloro benzoylchloride | t-butylhydrazine hydrochloride |
| 68 | benzoylchloride | 3-chloro-4-methyl benzoylchloride | t-butylhydrazine hydrochloride |
| 69 | benzoylchloride | 2-nitro-3-chloro benzoylchloride | t-butylhydrazine hydrochloride |
| 70 | benzoylchloride | 3-methoxy-4-nitro benzoylchloride | t-butylhydrazine hydrochloride |
| 71 | benzoylchloride | 2-nitro-3-methoxy benzoylchloride | t-butylhydrazine hydrochloride |
| 72 | benzoylchloride | 2,4-dinitrobenzoyl chloride | t-butylhydrazine hydrochloride |
| 73 | 4-chlorobenzoyl chloride | 2-chlorobenzoyl chloride | t-butylhydrazine hydrochloride |
| 74 | 4-chlorobenzoyl chloride | 3-chlorobenzoyl chloride | t-butylhydrazine hydrochloride |
| 75 | 4-chlorobenzoyl chloride | 4-methylbenzoyl chloride | t-butylhydrazine hydrochloride |
| 76 | 4-chlorobenzoyl chloride | 3,5-dichlorobenzoyl chloride | t-butylhydrazine hydrochloride |
| 77 | 4-chlorobenzoyl chloride | 2,4-dichlorobenzoyl chloride | t-butylhydrazine hydrochloride |
| 78 | 4-chlorobenzoyl chloride | 4-trifluoromethyl benzoylchloride | t-butylhydrazine hydrochloride |
| 79 | benzoylchloride | 4-methanesulfonyl benzoylchloride | t-butylhydrazine hydrochloride |
| 80 | benzoylchloride | 4-isopropylbenzoyl chloride | t-butylhydrazine hydrochloride |
| 81 | benzoylchloride | 2-acetoxybenzoyl chloride | t-butylhydrazine hydrochloride |
| 82 | benzoylchloride | 4-ethylbenzoyl chloride | t-butylhydrazine hydrochloride |
| 83 | benzoylchloride | 2-bromobenzoyl chloride | t-butylhydrazine hydrochloride |
| 84 | benzoylchloride | 4-hydroxybenzoyl chloride | t-butylhydrazine hydrochloride |
| 85 | 4-methylbenzoyl chloride | 2-methylbenzoyl chloride | t-butylhydrazine hydrochloride |
| 86 | 4-methylbenzoyl chloride | 3-methylbenzoyl chloride | t-butylhydrazine hydrochloride |
| 87 | 4-methylbenzoyl chloride | 2,4-dichlorobenzoyl chloride | t-butylhydrazine hydrochloride |
| 88 | 4-methylbenzoyl chloride | 3,5-dichlorobenzoyl chloride | t-butylhydrazine hydrochloride |
| 89 | 4-methylbenzoyl chloride | 2-chlorobenzoyl chloride | t-butylhydrazine hydrochloride |
| 90 | 4-methylbenzoyl chloride | 4-flourobenzoyl chloride | t-butylhydrazine hydrochloride |

TABLE III-continued

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| 91 | 4-methylbenzoyl chloride | 4-trifluoromethyl chloride | t-butylhydrazine hydrochloride |
| 92 | 4-methylbenzoyl chloride | 3-chlorobenzoyl chloride | t-butylhydrazine hydrochloride |
| 93 | 4-chlorobenzoyl chloride | 3-chloromethyl chloride | t-butylhydrazine hydrochloride |
| 94 | 4-chlorobenzoyl chloride | 4-chloromethyl chloride | t-butylhydrazine hydrochloride |
| 95 | 4-chlorobenzoyl chloride | 2-methylbenzoyl chloride | t-butylhydrazine hydrochloride |
| 96 | 4-chlorobenzoyl chloride | 3-methoxybenzoyl chloride | t-butylhydrazine hydrochloride |
| 97 | 4-chlorobenzoyl chloride | 3-methylbenzoyl chloride | t-butylhydrazine hydrochloride |
| 104 | benzoylchloride | 4-bromobenzoyl hydrochloride | t-butylhydrazine hydroxide |
| 105 | benzoylchloride | 3-bromobenzoyl chloride | t-butylhydrazine hydrochloride |
| 106 | benzoylchloride | 4-n-butylbenzoyl chloride | t-butylhydrazine hydrochloride |
| 107 | 4-ethylbenzoyl chloride | benzoylchloride | t-butylhydrazine hydrochloride |
| 108 | 3,4-dichloro-benzoylchloride | benzoylchloride | t-butylhydrazine hydrochloride |
| 109 | benzoylchloride | 4-acetylbenzoyl chloride | t-butylhydrazine hydrochloride |
| 113 | benzoylchloride | 2-iodobenzoyl chloride | t-butylhydrazine hydrochloride |
| 117 | benzoylchloride | 4-phenoxybenzoyl chloride | t-butylhydrazine hydrochloride |
| 118 | 4-trifluoromethyl-benzoylchloride | benzoylchloride | t-butylhydrazine hydrochloride |
| 119 | 4-trifluoromethyl-benzoylchloride | 3,4-dichlorobenzozyl-chloride | t-butylhydrazine hydrochloride |
| 121 | benzoylchloride | 2-chloro-4-bromo-benzoylchloride | t-butylhydrazine hydrochloride |
| 122 | benzoylchloride | 4-phenylbenzoyl chloride | t-butylhydrazine hydrochloride |
| 123 | benzoylchloride | 3,4,5-trimethoxy-benzoylchloride | t-butylhydrazine hydrochloride |
| 125 | benzoylchloride | 3-thiocyanomethyl-benzoylchloride | t-butylhydrazine hydrochloride |
| 126 | benzoylchloride | 3-cyanomethyl-benzoylchloride | t-butylhydrazine hydrochloride |
| 130 | 4-ethylbenzoyl chloride | 3-toluoylchloride | t-butylhydrazine hydrochloride |
| 131 | 4-ethylbenzoyl chloride | 4-chlorobenzoyl chloride | t-butylhydrazine hydrochloride |
| 132 | 4-ethylbenzoyl chloride | 2-nitrobenzoyl chloride | t-butylhydrazine hydrochloride |
| 133 | benzoylchloride | 3-ethylbenzoyl chloride | t-butylhydrazine hydrochloride |
| 134 | 4-ethylbenzoyl chloride | 3-bromobenzoyl chloride | t-butylhydrazine hydrochloride |
| 135 | 4-ethylbenzoyl chloride | 2-iodobenzoyl chloride | t-butylhydrazine hydrochloride |
| 137 | benzoylchloride | 4-carbomethoxy benzoylchloride | t-butylhydrazine hydrochloride |
| 138 | 2-bromobenzoyl chloride | benzoylchloride | t-butylhydrazine hydrochloride |
| 139 | 2-trifluoromethyl-benzoylchloride | benzoylchloride | t-butylhydrazine hydrochloride |
| 140 | benzoylchloride | 3-iodobenzoyl chloride | t-butylhydrazine hydrochloride |
| 141 | benzoylchloride | 2-ethylbenzoyl chloride | t-butylhydrazine hydrochloride |
| 142 | benzoylchloride | 3-methoxymethyl benzoylchloride | t-butylhydrazine hydrochloride |
| 146 | benzoylchloride | 2-nitro-4-(2-chloro -4-trifluoro-methyl phenoxy) benzoylchloride | t-butylhydrazine hydrochloride |
| 147 | 2-nitro-4-(2-chloro -4-trifluoromethyl phenoxy) benzoyl chloride | benzoylchloride | t-butylhydrazine hydrochloride |
| 150 | benzoylchloride | 4-methylthio-benzoylchloride | t-butylhydrazine hydrochloride |
| 152 | benzoylchloride | 3-bromo-4-methyl benzoylchloride | t-butylhydrazine hydrochloride |
| 153 | benzoylchloride | 3-methyl-4-bromo benzoylchloride | t-butylhydrazine hydrochloride |
| 154 | benzoylchloride | 2,4-dibromo benzoylchloride | t-butylhydrazine hydrochloride |
| 160 | benzoylchloride | 3-phenoxy benzoylchloride | t-butylhydrazine hydrochloride |
| 163 | benzoylchloride | 4-formyl benzoyl chloride | t-butylhydrazine hydrochloride |
| 167 | benzoylchloride | 2-acetoxybenzoyl chloride | t-butylhydrazine hydrochloride |
| 173 | 2-methyl-5-tri-fluoromethyl benzoylchloride | 2-toluoyl chloride | t-butylhydrazine hydrochloride |
| 175 | 4-ethylbenzoyl chloride | 3-ethyl benzoylchloride | t-butylhydrazine hydrochloride |
| 176 | benzoylchloride | 4-n-propyl benzoylchloride | t-butylhydrazine hydrochloride |
| 177 | 4-toluoyl chloride | 3-bromo benzoylchloride | t-butylhydrazine hydrochloride |
| 178 | 4-toluoyl chloride | 3,5-dimethyl benzoylchloride | t-butylhydrazine hydrochloride |
| 179 | benzoylchloride | 4-iodobenzoyl chloride | t-butylhydrazine hydrochloride |
| 180 | 4-toluoyl chloride | 4-ethyl benzoyl chloride | t-butylhydrazine hydrochloride |
| 182 | 4-toluoyl chloride | 3-ethyl benzoyl chloride | t-butylhydrazine hydrochloride |
| 183 | benzoylchloride | 2-isopropylbenzoyl chloride | t-butylhydrazine hydrochloride |
| 184 | 3-ethyl benzoyl chloride | benzoylchloride | t-butylhydrazine hydrochloride |
| 190 | 3-ethyl benzoyl chloride | 2,4-dichloro benzoylchloride | t-butylhydrazine hydrochloride |
| 194 | 4-methoxybenzoyl chloride | 3-toluoyl chloride | t-butylhydrazine hydrochloride |
| 195 | 4-methoxybenzoyl chloride | benzoylchloride | t-butylhydrazine hydrochloride |
| 196 | 2-chlorobenzoyl chloride | 3-toluoyl chloride | t-butylhydrazine hydrochloride |
| 197 | 2-chlorobenzoyl chloride | 2-nitrobenzoyl chloride | t-butylhydrazine hydrochloride |
| 198 | 2-chlorobenzoyl chloride | 4-toluoyl chloride | t-butylhydrazine hydrochloride |
| 199 | 2-chlorobenzoyl chloride | 4-ethyl benzoyl chloride | t-butylhydrazine hydrochloride |
| 200 | 4-ethyl benzoyl chloride | 3,5-dimethyl benzoylchloride | t-butylhydrazine hydrochloride |
| 201 | 4-ethyl benzoyl chloride | 2-chloro-4-methyl benzoylchloride | t-butylhydrazine hydrochloride |
|  | benzoylchloride | 3-acetoxybenzoyl chloride | t-butylhydrazine hydrochloride |
| 204 | 4-ethyl benzoyl chloride | 2-nitro-3-methyl benzoylchloride | t-butylhydrazine hydrochloride |
| 205 | 4-methoxybenzoyl chloride | 3,5-dimethyl benzoylchloride | t-butylhydrazine hydrochloride |
| 206 | 4-methoxybenzoyl chloride | 2,4-dichloro benzoylchloride | t-butylhydrazine hydrochloride |
| 207 | 2-chlorobenzoyl | 2,6-dichloro | t-butylhydrazine |

TABLE III-continued

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| | chloride | benzoylchloride | hydrochloride |
| 208 | 2-chlorobenzoyl chloride | 2-bromobenzoyl benzoylchloride | t-butylhydrazine hydrochloride |
| 209 | 2-chlorobenzoyl chloride | 2,5-difluoro benzoylchloride | t-butylhydrazine hydrochloride |
| 210 | 2-chlorobenzoyl chloride | 4-methoxy benzoylchloride | t-butylhydrazine hydrochloride |
| 211 | 2-chlorobenzoyl chloride | 2-toluoyl chloride | t-butylhydrazine hydrochloride |
| 214 | 2-chlorobenzoyl chloride | 2,4-dichlorobenzoyl chloride | t-butylhydrazine hydrochloride |
| 215 | 2-chlorobenzoyl chloride | 3-methoxy benzoylchloride | t-butylhydrazine hydrochloride |
| 216 | 2-chlorobenzoyl chloride | 3-chlorobenzoyl chloride | t-butylhydrazine hydrochloride |
| 217 | 2-chlorobenzoyl chloride | 2-trifluoromethyl benzoylchloride | t-butylhydrazine hydrochloride |
| 218 | 2-chlorobenzoyl chloride | 3-trifluoromethyl benzoylchloride | t-butylhydrazine hydrochloride |
| 219 | 2-chlorobenzoyl chloride | 4-trifluoromethyl benzoylchloride | t-butylhydrazine hydrochloride |
| 224 | 2-chlorobenzoyl chloride | 4-cyanobenzoyl benzoylchloride | t-butylhydrazine hydrochloride |
| 225 | 2-chlorobenzoyl chloride | 4-fluorobenzoyl benzoylchloride | t-butylhydrazine hydrochloride |
| 226 | 2-chlorobenzoyl chloride | 4-bromobenzoyl benzoylchloride | t-butylhydrazine hydrochloride |
| 227 | 2-chlorobenzoyl chloride | 4-chloro benzoylchloride | t-butylhydrazine hydrochloride |
| 228 | 2-chlorobenzoyl chloride | 2-methoxy benzoylchloride | t-butylhydrazine hydrochloride |
| 229 | 2-chlorobenzoyl chloride | 4-nitro benzoylchloride | t-butylhydrazine hydrochloride |
| 230 | 2-chlorobenzoyl chloride | 2-fluoro benzoylchloride | t-butylhydrazine hydrochloride |
| 231 | 2-chlorobenzoyl chloride | 2,6-difluoro benzoylchloride | t-butylhydrazine hydrochloride |
| 235 | 3-methoxybenzoyl chloride | 2,5-difluoro benzoylchloride | t-butylhydrazine hydrochloride |
| 236 | 3-methoxybenzoyl chloride | 4-chlorobenzoyl benzoylchloride | t-butylhydrazine hydrochloride |
| 237 | 3-methoxybenzoyl chloride | 3,4-dichloro benzoylchloride | t-butylhydrazine hydrochloride |
| 238 | 3-methoxybenzoyl chloride | benzoylchloride | t-butylhydrazine hydrochloride |
| 239 | 3-methoxybenzoyl chloride | 3-toluoyl chloride | t-butylhydrazine hydrochloride |
| 240 | 3-methoxybenzoyl chloride | 3,4-dichloro benzoylchloride | t-butylhydrazine hydrochloride |
| 241 | 3-methoxybenzoyl chloride | 4-chlorobenzoyl chloride | t-butylhydrazine hydrochloride |
| 242 | 3-methoxybenzoyl chloride | 2-nitrobenzoyl chloride | t-butylhydrazine hydrochloride |
| 243 | benzoylchloride | 4-trifluoromethoxy benzoylchloride | t-butylhydrazine hydrochloride |
| 244 | 4-trifluoromethoxy benzoylchloride | benzoylchloride | t-butylhydrazine hydrochloride |
| 245 | 4-trifluoromethoxy benzoylchloride | 3-toluoyl chloride | t-butylhydrazine hydrochloride |
| 246 | 4-trifluoromethoxy benzoylchloride | 4-chloro benzoyl chloride | t-butylhydrazine hydrochloride |
| 247 | 4-trifluoromethoxy benzoylchloride | 3,4-dichloro benzoylchloride | t-butylhydrazine hydrochloride |
| 248 | 4-trifluoromethoxy benzoylchloride | 4-chlorobenzoyl chloride | t-butylhydrazine hydrochloride |
| 249 | 4-trifluoromethoxy benzoylchloride | 3-toluoyl chloride | t-butylhydrazine hydrochloride |
| 251 | 4-ethoxybenzoyl chloride | 3-toluoyl chloride | t-butylhydrazine hydrochloride |
| | 4-ethoxybenzoyl chloride | 3,5-dimethyl benzoylchloride | t-butylhydrazine hydrochloride |
| 253 | 4-ethoxybenzoyl chloride | benzoylchloride | t-butylhydrazine hydrochloride |
| 254 | 4-ethoxybenzoyl chloride | 2-nitro-4-chloro benzoylchloride | t-butylhydrazine hydrochloride |
| 255 | 3-chloro-4-methoxy-benzoylchloride | benzoylchloride | t-butylhydrazine hydrochloride |
| 256 | 4-methylthio benzoylchloride | benzoylchloride | t-butylhydrazine hydrochloride |
| 257 | 4-n-butyloxy benzoylchloride | 4-chlorobenzoyl chloride | t-butylhydrazine hydrochloride |
| 258 | 2-methylthio-benzoylchloride | benzoylchloride | t-butylhydrazine hydrochloride |
| 259 | 2-nitro-4-chloro-benzoylchloride | benzoylchloride | t-butylhydrazine hydrochloride |
| 261 | 2-nitro-4-chloro-benzoylchloride | 4-t-butylbenzoyl chloride | t-butylhydrazine hydrochloride |
| — | 2-nitro-4-chloro-benzoylchloride | 4-chlorobenzoyl chloride | t-butylhydrazine hydrochloride |
| 263 | 4-toluoyl chloride | 2-chloro-5-methyl benzoylchloride | t-butylhydrazine hydrochloride |
| 265 | 4-phenoxybenzoyl chloride | benzoylchloride | t-butylhydrazine hydrochloride |
| 266 | 4-phenoxybenzoyl chloride | 4-toluoyl chloride | t-butylhydrazine hydrochloride |
| 267 | 4-n-butylbenzoyl chloride | benzoylchloride | t-butylhydrazine hydrochloride |
| 268 | 4-n-butylbenzoyl chloride | 4-chlorobenzoyl chloride | t-butylhydrazine hydrochloride |
| 269 | 4-isopropylbenzoyl chloride | benzoylchloride | t-butylhydrazine hydrochloride |
| 270 | 4-isopropylbenzoyl chloride | 3-toluoyl chloride | t-butylhydrazine hydrochloride |
| 271 | 4-cyanobenzoyl chloride | benzoylchloride | t-butylhydrazine hydrochloride |
| 273 | 4-cyanobenzoyl chloride | 3-toluoyl chloride | t-butylhydrazine hydrochloride |
| 274 | 2-methyl-4-chloro-benzoylchloride | benzoylchloride | t-butylhydrazine hydrochloride |
| 275 | 4-ethylbenzoyl chloride | 4-trifluoromethoxy benzoylchloride | t-butylhydrazine hydrochloride |
| 276 | benzoylchloride | 2,3,4,5,6-penta-fluoro benzoyl chloride | t-butylhydrazine hydrochloride |
| 277 | 2,3,4,5,6-penta-fluoro benzoyl chloride | benzoylchloride | t-butylhydrazine hydrochloride |
| 278 | 4-cyanobenzoyl chloride | 3,4-dichlorobenzoyl chloride | t-butylhydrazine hydrochloride |
| 279 | 2-methyl-4-chloro-benzoylchloride | 3-toluoyl chloride | t-butylhydrazine hydrochloride |
| 280 | 4-trifluoromethyl benzoylchloride | 3,5-dimethylbenzoyl chloride | t-butylhydrazine hydrochloride |
| 281 | 2-methyl-4-chloro-benzoylchloride | 3,5-dimethylbenzoyl chloride | t-butylhydrazine hydrochloride |
| 282 | benzoylchloride | 3-vinylbenzoyl chloride | t-butylhydrazine hydrochloride |
| 283 | 4-ethylbenzoyl chloride | 3-vinylbenzoyl chloride | t-butylhydrazine hydrochloride |
| 284 | 4-trifluoromethyl-benzoylchloride | 3-vinylbenzoyl chloride | t-butylhydrazine hydrochloride |
| 287 | 4-n-propylbenzoyl chloride | 3,4-dichloro-benzoylchloride | t-butylhydrazine hydrochloride |
| 288 | 4-n-propylbenzoyl chloride | 3-toluoyl chloride | t-butylhydrazine hydrochloride |
| 290 | 4-vinylbenzoyl chloride | 3-toluoyl chloride | t-butylhydrazine hydrochloride |
| 291 | 2,6-difluoro- | 3,4-dichloro- | t-butylhydrazine |

TABLE III-continued

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| | benzoylchloride | benzoylchloride | hydrochloride |
| 292 | 2,6-difluoro-benzoylchloride | 3-toluoyl chloride | t-butylhydrazine hydrochloride |
| 296 | 4-chlorobenzoyl chloride | 2-bromobenzoyl chloride | t-butylhydrazine hydrochloride |
| 297 | 4-toluoyl chloride | 3-toluoyl chloride | 2,2-dimethylpropylhydrazine oxalic acid salt |
| 299 | 4-chlorobenzoyl chloride | 3,5-dimethylbenzoylchloride | t-butylhydrazine hydrochloride |
| 300 | 3-methoxybenzoyl chloride | 3,5-dimethylbenzoyl chloride | t-butylhydrazine hydrochloride |
| 301 | 4-chlorobenzoyl chloride | 4-fluorobenzoyl chloride | t-butylhydrazine hydrochloride |
| 302 | 4-n-propylbenzoyl chloride | 3,5-dimethylbenzoyl chloride | t-butylhydrazine hydrochloride |
| 303 | 4-vinylbenzoyl chloride | 3,5-dimethylbenzoyl chloride | t-butylhydrazine hydrochloride |
| 304 | 4-acetoxybenzoyl chloride | 3,5-dimethylbenzoyl chloride | t-butylhydrazine hydrochloride |
| 305 | 3,5-dimethyl-benzoylchloride | benzoylchloride | t-butylhydrazine hydrochloride |
| 306 | 3,5-dimethyl-benzoylchloride | 3-toluoyl chloride | t-butylhydrazine hydrochloride |
| 307 | 3,5-dimethyl-benzoylchloride | 4-ethylbenzoyl chloride | t-butylhydrazine hydrochloride |
| 309 | 4-isopropyl-benzoylchloride | 3,5-dimethyl benzoylchloride | t-butylhydrazine hydrochloride |
| 310 | 4-ethylbenzoyl chloride | 2-bromobenzoyl chloride | t-butylhydrazine hydrochloride |
| 311 | 3-chloro-4-methyl-benzoylchloride | benzoylchloride | t-butylhydrazine hydrochloride |
| 312 | 3-chloro-4-methyl-benzoylchloride | benzoylchloride | t-butylhydrazine hydrochloride |
| 313 | 3-chloro-4-methyl-benzoylchloride | 3-toluoyl chloride | t-butylhydrazine hydrochloride |
| 314 | 3-chloro-4-methyl-benzoylchloride | 3,4-dichlorobenzoyl chloride | t-butylhydrazine hydrochloride |
| 315 | 4-ethylbenzoyl chloride | 2-nitrobenzoyl chloride | 2,2-dimethyl-propylhydrazine oxalic acid salt |
| 316 | 2,6-difluoro-benzoylchloride | 2-chlorobenzoyl chloride | t-butylhydrazine hydrochloride |
| 317 | 2,6-difluoro-benzoylchloride | 3-chlorobenzoyl chloride | t-butylhydrazine hydrochloride |
| 318 | 2,6-difluoro-benzoylchloride | 4-chlorobenzoyl chloride | t-butylhydrazine hydrochloride |
| 319 | 2,6-difluoro-benzoylchloride | 3,5-dimethylbenzoyl chloride | t-butylhydrazine hydrochloride |
| 320 | 4-ethylbenzoyl chloride | 3,5-dimethylbenzoyl chloride | 2,2-dimethylpropylhydrazine oxalic acid salt |
| 321 | 3-trifluoromethyl-benzoylchloride | 4-chlorobenzoyl chloride | t-butylhydrazine hydrochloride |
| 322 | 3-trifluoromethyl-benzoylchloride | 3,5-dimethyl-benzoylchloride | t-butylhydrazine hydrochloride |
| 325 | 2-nitro-3-methoxy-benzoylchloride | 3-toluoyl chloride | t-butylhydrazine hydrochloride |
| 327 | 4-chlorobenzoyl chloride | 4-carboxymethyl-benzoylchloride | t-butylhydrazine hydrochloride |
| 328 | 4-ethylbenzoyl chloride | 4-carboxymethyl-benzoylchloride | t-butylhydrazine hydrochloride |
| 334 | 4-ethylbenzoyl chloride | 3,5-dichloro-benzoylchloride | t-butylhydrazine hydrochloride |
| 341 | 4-chlorobenzoyl chloride | 2-fluorobenzoyl chloride | t-butylhydrazine hydrochloride |
| 342 | 4-ethylbenzoyl chloride | 3,4-dichloro-benzoylchloride | t-butylhydrazine hydrochloride |
| 343 | 4-ethylbenzoyl | 2-fluorobenzoyl | t-butylhydrazine |
| | chloride | chloride | hydrochloride |
| 346 | 4-carboxymethyl-benzoylchloride | 4-chlorobenzoyl chloride | t-butylhydrazine hydrochloride |
| 347 | 4-carboxymethyl-benzoylchloride | 3,5-dimethyl-benzoylchloride | t-butylhydrazine hydrochloride bonate |
| 348 | 4-carboxymethyl-benzoylchloride | 3-toluoyl chloride | t-butylhydrazine hydrochloride bonate |
| 355 | 3-phenoxybenzoyl chloride | benzoylchloride | t-butylhydrazine hydrochloride |
| 356 | 3-phenoxybenzoyl chloride | 3-toluoyl chloride | t-butylhydrazine hydrochloride |
| 357 | 4-acetylbenzoyl chloride | 3-toluoyl chloride | t-butylhydrazine hydrochloride |
| 370 | 4-biphenylbenzoyl chloride | 3-toluoyl chloride | t-butylhydrazine hydrochloride |
| 371 | 3-cyanobenzoyl chloride | 3-toluoyl chloride | t-butylhydrazine hydrochloride |
| 377 | 3-chloromethyl-benzoylchloride | 3-toluoyl chloride | t-butylhydrazine hydrochloride |
| 378 | 4-ethylbenzoyl chloride | 2,3-dimethylbenzoyl chloride | t-butylhydrazine hydrochloride |
| 380 | benzoylchloride | 2,3-dimethylbenzoyl chloride | t-butylhydrazine hydrochloride |
| 381 | 4-toluoyl chloride | 2,3-dimethylbenzoyl chloride | t-butylhydrazine hydrochloride |
| 387 | benzoylchloride | 1-naphthoyl chloride | t-butylhydrazine hydrochloride |
| 388 | 1-naphthoyl chloride | 3-toluoyl chloride | t-butylhydrazine hydrochloride |
| 389 | 4-isothiocyanato-benzoylchloride | 3-toluoyl chloride | t-butylhydrazine hydrochloride |
| 392 | 2-fluorobenzoyl chloride | 2-bromobenzoyl chloride | t-butylhydrazine hydrochlorider |
| 393 | 2-fluorobenzoyl chloride | 3-toluoyl chloride | t-butylhydrazine hydrochloride |
| 395 | 2-fluorobenzoyl chloride | 2-nitrobenzoyl chloride | t-butylhydrazine hydrochloride |
| 396 | 2-fluorobenzoyl chloride | benzoylchloride | t-butylhydrazine hydrochloride |
| 401 | 4-bromobenzoyl chloride | benzoylchloride | t-butylhydrazine hydrochloride |
| 402 | 2,3-dichloro-benzoylchloride | 2-bromobenzoyl chloride | t-butylhydrazine hydrochloride |
| 403 | 2,3-dichloro-benzoylchloride | benzoylchloride | t-butylhydrazine hydrochloride |
| 404 | 2-fluorobenzoyl chloride | 3,5-dimethyl-benzoylchloride | t-butylhydrazine hydrochloride |
| 405 | 2,3-dichloro-benzoylchloride | 3-toluoyl chloride | t-butylhydrazine hydrochloride |
| 406 | benzoylchloride | 2-naphthoyl chloride | t-butylhydrazine hydrochloride |
| 407 | 2-naphthoyl chloride | 3-toluoyl chloride | t-butylhydrazine hydrochloride |
| 408 | benzoylchloride | 3-trifluoromethoxy-benzoylchloride | t-butylhydrazine hydrochloride |
| 409 | 4-isothiocyanato-benzoylchloride | benzoylchloride | t-butylhydrazine hydrochloride |
| 410 | 2,6-difluoro-benzoylchloride | 2,4-difluoro-benzoylchloride | t-butylhydrazine hydrochloride |
| 411 | 2,6-difluoro-benzoylchloride | 3,5-dichloro-benzoylchloride | t-butylhydrazine hydrochloride |
| 412 | 4-toluoyl chloride | 3,5-bis-(trifluoromethyl)benzoyl | t-butylhydrazine hydrochloride |
| 413 | benzoylchloride | 3,5-bis-(trifluoromethyl)benzoyl chloride | t-butylhydrazine hydrochloride |
| 419 | benzoylchloride | 3-chloro-4-fluoro- | t-butylhydrazine |

TABLE III-continued

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| 420 | 4-chlorobenzoyl chloride | benzoylchloride | t-butylhydrazine hydrochloride |
| 422 | 4-chlorobenzoyl chloride | 3-chloro-4-fluoro-benzoylchloride | t-butylhydrazine hydrochloride |
| 423 | 2,3-dimethyl-benzoylchloride | 3,5-bis-(trifluoromethyl)benzoyl chloride | t-butylhydrazine hydrochloride |
| 424 | 4-toluoyl chloride | 3,4-dichloro-benzoylchloride | t-butylhydrazine hydrochloride |
| 426 | 2,6-dimethyl-benzoylchloride | 3-chloro-2-methyl-hydrochloride | t-butylhydrazine hydroxide |
| 427 | 2,6-dimethyl-benzoylchloride | 3-toluoyl chloride | t-butylhydrazine hydrochloride |
| 428 | 2,3-dimethyl-benzoylchloride | 3,5-dimethyl-benzoylchloride | t-butylhydrazine hydrochloride |
| 429 | 2,3-dimethyl-benzoylchloride | 2-bromobenzoyl chloride | t-butylhydrazine hydrochloride |
| 430 | 2,3-dimethyl-benzoylchloride | 3,5-dimethyl-benzoylchloride | t-butylhydrazine hydrochloride |
| 431 | 3-trifluoro-methoxybenzoyl chloride | 3-chlorobenzoyl chloride | t-butylhydrazine hydrochloride |
| 432 | 3-trifluoro-methoxybenzoyl chloride | benzoylchloride | t-butylhydrazine hydrochloride |
| 433 | 2,3-dimethyl-benzoylchloride | 3-toluoyl chloride | t-butylhydrazine hydrochloride |
| 437 | 2,6-difluoro-benzoylchloride | 2-methyl-3-chloro-benzoylchloride | t-butylhydrazine hydrochloride |
| 438 | 2-methyl-3-chloro-benzoylchloride | 2-bromobenzoyl chloride | t-butylhydrazine hydrochloride |
| 439 | 2-methyl-3-chloro-benzoylchloride | 3,5-dimethyl-benzoylchloride | t-butylhydrazine hydrochloride |
| 440 | 2,3-dimethyl-benzoylchloride | 3-chloro-4-fluoro-benzoylchloride | t-butylhydrazine hydrochloride |
| 441 | 4-ethylbenzoyl chloride | 3-chloro-4-fluoro-benzoylchloride | t-butylhydrazine hydrochloride |
| 442 | 3,4-dimethyl benzoylchloride | 3-chloro-4-fluoro-benzoylchloride | t-butylhydrazine hydrochloride |
| 443 | 3,4-dimethyl-benzoylchloride | benzoylchloride | t-butylhydrazine hydrochloride |
| 444 | 3,4-dimethyl-benzoylchloride | 3-toluoyl chloride | t-butylhydrazine hydrochloride |
| 445 | 3,4-dimethyl-benzoylchloride | 2-chlorobenzoyl chloride | t-butylhydrazine hydrochloride |
| 446 | 3,4-dimethyl-benzoylchloride | 2,4-dichloro-benzoylchloride | t-butylhydrazine hydrochloride |
| 447 | 3,4-dimethyl-benzoylchloride | 2-bromobenzoyl chloride | t-butylhydrazine hydrochloride |
| 448 | 3,4-dimethyl-benzoylchloride | 3,5-dimethyl-benzoylchloride | t-butylhydrazine hydrochloride |
| 450 | benzoylchloride | 2-nitrobenzoyl chloride | t-butylhydrazine hydrochloride |
| 451 | 4-ethylbenzoyl chloride | 3,4-dimethyl-benzoylchloride | t-butylhydrazine hydrochloride |
| 452 | 2-fluoro-6-chloro-benzoylchloride | 3,4-dimethyl-benzoylchloride | t-butylhydrazine hydrochloride |
| 454 | 4-chloromethyl benzoylchloride | 3-toluoyl chloride | t-butylhydrazine hydrochloride |
| 455 | 2,3-dimethoxy-benzoylchloride | benzoylchloride | t-butylhydrazine hydrochloride |
| 456 | 2,3-dimethoxy-benzoylchloride | benzoylchloride | t-butylhydrazine hydrochloride |
| 457 | 2,3-dimethoxy-benzoylchloride | 4-chlorobenzoyl chloride | t-butylhydrazine hydrochloride |
| 459 | 4-t-butylbenzoyl chloride | 2-bromobenzoyl chloride | t-butylhydrazine hydrochloride |
| 460 | 4-t-butylbenzoyl chloride | 3,4-dimethyl-benzoylchloride | t-butylhydrazine hydrochloride |
| 461 | 4-t-butylbenzoyl chloride | 3,5-dimethyl-benzoylchloride | t-butylhydrazine hydrochloride |
| 461 | 4-t-butylbenzoyl chloride | 2,4-dichloro-benzoylchloride | t-butylhydrazine hydrochloride |
| 462 | 4-t-butylbenzoyl chloride | 2-nitrobenzoyl chloride | t-butylhydrazine hydrochloride |
| 463 | 4-t-butylbenzoyl chloride | 2-bromobenzoyl chloride | t-butylhydrazine hydrochloride |
| 464 | 4-t-butylbenzoyl chloride | 3-toluoyl chloride | t-butylhydrazine hydrochloride |
| 465 | 4-t-butylbenzoyl chloride | 2-chlorobenzoyl chloride | t-butylhydrazine hydrochloride |
| 466 | 4-t-butylbenzoyl chloride | 3,4-dichloro-benzoylchloride | t-butylhydrazine hydrochloride |
| 467 | 3,4-dimethyl-benzoylchloride | 3,4-dichloro-benzoylchloride | t-butylhydrazine hydrochloride |
| 468 | 3,4-dimethyl-benzoylchloride | 4-fluorobenzoyl chloride | t-butylhydrazine hydrochloride |
| 469 | 4-t-butylbenzoyl chloride | 4-fluorobenzoyl chloride | t-butylhydrazine hydrochloride |
| 474 | 1-naphthoyl chloride | 2,4-dichloro-benzoylchloride | t-butylhydrazine hydrochloride |
| 475 | 1-naphthoyl chloride | 2-bromobenzoyl chloride | t-butylhydrazine hydrochloride |
| 476 | 2-methyl-3-nitro-benzoylchloride | benzoylchloride | t-butylhydrazine hydrochloride |
| 477 | 2-methyl-3-nitro-benzoylchloride | 3-toluoyl chloride | t-butylhydrazine hydrochloride |
| 478 | 2-methyl-3-nitro-benzoylchloride | 4-chlorobenzoyl chloride | t-butylhydrazine hydrochloride |
| 479 | 2-methyl-3-nitro-benzoylchloride | 2,4-dichloro-benzoylchloride | t-butylhydrazine hydrochloride |
| 480 | 3-bromo-2-methyl-benzoylchloride | benzoylchloride | t-butylhydrazine hydrochloride |
| 481 | 3-bromo-2-methyl-benzoylchloride | 3-toluoylchloride | t-butylhydrazine hydrochloride |
| 482 | 3-bromo-2-methyl-benzoylchloride | 4-chlorobenzoyl chloride | t-butylhydrazine hydrochloride |
| 483 | 3-bromo-2-methyl-benzoylchloride | 2,4-dichlorobenzoyl chloride | t-butylhydrazine hydrochloride |
| 485 | 2-toluoyl chloride | 2-bromobenzoyl chloride | t-butylhydrazine hydrochloride |
| 486 | 2-toluoyl chloride | 2-nitrobenzoyl chloride | t-butylhydrazine hydrochloride |
| 487 | 2-toluoyl chloride | 3-nitrobenzoyl chloride | t-butylhydrazine hydrochloride |
| 488 | 2-toluoyl chloride | 4-chlorobenzoyl chloride | t-butylhydrazine hydrochloride |
| 489 | 2-toluoyl chloride | 3-toluoyl chloride | t-butylhydrazine hydrochloride |
| 490 | 2-toluoyl chloride | 3,5-dimethyl-benzoylchloride | t-butylhydrazine hydrochloride |
| 491 | 2-toluoyl chloride | 3,4-dichloro-benzoylchloride | t-butylhydrazine hydrochloride |
| 492 | 2-toluoyl chloride | 3,5-dichloro-benzoylchloride | t-butylhydrazine hydrochloride |
| 493 | 2-methyl-3-fluoro-chloride | benzoylchloride | t-butylhydrazine hydrochloride |
| 494 | 2-methyl-3-fluoro-benzoylchloride | 3-toluoyl chloride | t-butylhydrazine hydrochloride |
| 495 | 2-fluoro-6-chloro-benzoylchloride | benzoylchloride | t-butylhydrazine hydrochloride |
| 496 | 2-fluoro-6-chloro-benzoylchloride | 2,4-dichloro-benzoylchloride | t-butylhydrazine hydrochloride |
| 497 | 2-fluoro-6-chloro-benzoylchloride | 4-fluorobenzoyl chloride | t-butylhydrazine hydrochloride |
| 498 | 4-(2-chloroethyl)-benzoylchloride | 3,5-dimethyl-benzoylchloride | t-butylhydrazine hydrochloride |
| 499 | 2,4,6-trifluoro-benzoylchloride | benzoylchloride | t-butylhydrazine hydrochloride |

TABLE III-continued

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| 500 | 2,4,6-trifluoro-benzoylchloride | 2,4-dichloro-benzoylchloride | t-butylhydrazine hydrochloride |
| 501 | 2,4,6-trifluoro-benzoylchloride | 2-bromobenzoyl chloride | t-butylhydrazine hydrochloride |
| 502 | 2,4,6-trifluoro-benzoylchloride | 3,5-dimethyl benzoylchloride | t-butylhydrazine hydrochloride |
| 503 | 2-nitro-3-chloro-benzoylchloride | | t-butylhydrazine hydrochloride |
| 503 | 2-nitro-3-chloro-benzoylchloride | 2-bromobenzoyl chloride | t-butylhydrazine hydrochloride |
| 504 | 2-nitro-3-chloro-benzoylchloride | 2-nitrobenzoyl chloride | t-butylhydrazine hydrochloride |
| 505 | 2-nitro-3-chloro-benzoylchloride | 3-toluoyl chloride | t-butylhydrazine hydrochloride |
| 506 | 2-nitro-3-chloro-benzoylchloride | 3-chlorobenzoyl chloride | t-butylhydrazine hydrochloride |
| 507 | 2-nitro-3-chloro-benzoylchloride | 2,4-dichloro-benzoylchloride | t-butylhydrazine hydrochloride |
| 508 | 2-nitro-3-chloro-benzoylchloride | 3,5-dichloro-benzoylchloride | t-butylhydrazine hydrochloride |
| 509 | 2-nitro-3-chloro-benzoylchloride | 3,5-dimethyl-benzoylchloride | t-butylhydrazine hydrochloride |
| 510 | 4-ethylbenzoyl chloride | 2,3-difluoro-benzoylchloride | t-butylhydrazine hydrochloride |
| 511 | 4-ethylbenzoyl chloride | 2,3-dichloro-benzoylchloride | t-butylhydrazine hydrochloride |
| 512 | 2,3-difluoro-benzoylchloride | | t-butylhydrazine hydrochloride |
| 513 | 2,3-dichloro-benzoylchloride | 2-nitrobenzoyl chloride | t-butylhydrazine hydrochloride |
| 514 | benzoylchloride | 2,3-difluoro-benzoylchloride | t-butylhydrazine hydrochloride |
| 516 | 2,3-dichloro-benzoylchloride | 3,5-dimethyl-benzoylchloride | t-butylhydrazine hydrochloride |
| 517 | 2,3-dichloro-benzoylchloride | 2,4-dichloro-benzoylchloride | t-butylhydrazine hydrochloride |
| 518 | 2,3-dichloro-benzoylchloride | 3,5-dichloro-benzoylchloride | t-butylhydrazine hydrochloride |
| 519 | 2,3-dichloro-benzoylchloride | 3-chlorobenzoyl chloride | t-butylhydrazine hydrochloride |
| 520 | 2,3-dichloro-benzoylchloride | 2,3-dimethyl-benzoylchloride | t-butylhydrazine hydrochloride |
| 521 | 2,3-difluoro-benzoylchloride | 2-bromobenzoyl chloride | t-butylhydrazine hydrochloride |
| 522 | 2,3-dimethyl-benzoylchloride | 4-chlorobenzoyl chloride | t-butylhydrazine hydrochloride |
| 523 | 2,3-dimethyl-benzoylchloride | 2,4-dichloro-benzoylchloride | t-butylhydrazine hydrochloride |
| 524 | 2,3-dimethyl-benzoylchloride | 2,6-difluoro-benzoylchloride | t-butylhydrazine hydrochloride |
| 525 | 2,3-dimethyl-benzoylchloride | 2,4-difluoro-benzoylchloride | t-butylhydrazine hydrochloride |
| 526 | 2,3-dimethyl-benzoylchloride | 3-methoxybenzoyl chloride | t-butylhydrazine hydrochloride |
| 527 | 2,3-dimethyl-benzoylchloride | 2-methoxybenzoyl chloride | t-butylhydrazine hydrochloride |
| 528 | 2,3-dimethyl-benzoylchloride | 2-toluoyl chloride | t-butylhydrazine hydrochloride |
| 529 | 2,3-dimethyl-benzoylchloride | 4-toluoyl chloride | t-butylhydrazine hydrochloride |
| 530 | 2-methyl-3-chloro-benzoylchloride | 2,4-dichlorobenzoyl chloride | t-butylhydrazine hydrochloride |
| 531 | 4-(2-chloro-ethyl)benzoyl chloride | benzoylchloride | t-butylhydrazine hydrochloride |
| 532 | 4-(2-chloro-ethyl)benzoyl chloride | 2,4-dichloro-benzoylchloride | t-butylhydrazine hydrochloride |
| 533 | 3-fluoro-4-methyl-benzoylchloride | 3,5-dimethyl-benzoylchloride | t-butylhydrazine hydrochloride |
| 534 | 3-fluoro-4-methyl-benzoylchloride | 3,5-difluoro-benzoylchloride | t-butylhydrazine hydrochloride |
| 535 | 3-fluoro-4-methyl-benzoylchloride | 3-toluoyl chloride | t-butylhydrazine hydrochloride |
| 536 | 3-fluoro-4-methyl-benzoylchloride | 3,5-dichloro-benzoylchloride | t-butylhydrazine hydrochloride |
| 537 | 3-fluoro-4-methyl-benzoylchloride | 2-nitrobenzoyl chloride | t-butylhydrazine hydrochloride |
| 538 | 3-fluoro-4-methyl-benzoylchloride | 2,4-dichloro-benzoylchloride | t-butylhydrazine hydrochloride |
| 539 | 4-ethylbenzoyl chloride | 3,5-difluoro-benzoylchloride | t-butylhydrazine hydrochloride |
| 540 | 2,3-dimethyl-benzoylchloride | 2-iodobenzoyl chloride | t-butylhydrazine hydrochloride |
| 542 | 2,6-difluoro-3-methylbenzoyl chloride | benzoylchloride | t-butylhydrazine hydrochloride |
| 543 | 2,6-difluoro-3-methylbenzoyl chloride | 3-toluoyl chloride | t-butylhydrazine hydrochloride |
| 544 | 2,6-difluoro-3-methylbenzoyl chloride | 2,4-dichloro- | t-butylhydrazine hydrochloride |
| 545 | 4-chlorobenzoyl chloride | 2,3-dimethyl-benzoylchloride | t-butylhydrazine hydrochloride |
| 548 | 2-fluoro-6-chloro-benzoylchloride | 2,3-difluorobenzoyl chloride | t-butylhydrazine hydrochloride |
| 549 | 2,3-difluoro-benzoylchloride | 2-nitrobenzoyl chloride | t-butylhydrazine hydrochloride |
| 550 | 2,3-difluoro-benzoylchloride | 3-toluoyl chloride | t-butylhydrazine hydrochloride |
| 551 | 2,3-difluoro-benzoylchloride | 3,5-dimethyl-benzoylchloride | t-butylhydrazine hydrochloride |
| 552 | 2,3-difluoro-benzoylchloride | 2,4-dichloro-benzoylchloride | t-butylhydrazine hydrochloride |
| 553 | 2,3-dimethyl-benzoylchloride | 2,3-difluoro-benzoylchloride | t-butylhydrazine hydrochloride |
| 554 | 2,3-dimethyl-benzoylchloride | 2,3-dichloro-benzoylchloride | t-butylhydrazine hydrochloride |
| 555 | 2,3-dimethyl-benzoylchloride | 3,4-dimethyl-benzoylchloride | t-butylhydrazine hydrochloride |
| 556 | 2,3-dimethyl-benzoylchloride | 2-nitrobenzoyl chloride | t-butylhydrazine hydrochloride |
| 557 | 4-ethylbenzoyl chloride | 2-methyl-5-chloro-benzoylchloride | t-butylhydrazine hydrochloride |
| 558 | 2,3-dimethyl-benzoylchloride | benzoylchloride | t-butylhydrazine hydrochloride |
| 559 | benzoylchloride | 2-methyl-5-chloro-benzoylchloride | t-butylhydrazine hydroxide |
| 560 | 2,6-difluoro-benzoylchloride | 2-methyl-5-chloro-benzoylchloride | t-butylhydrazine hydrochloride |
| 561 | 2,3-dimethyl-benzoylchloride | 2-methyl-5-chloro-benzoylchloride | t-butylhydrazine hydrochloride |
| 562 | 2-methyl-3-chloro-benzoylchloride | 2-methyl-5-chloro-benzoylchloride | t-butylhydrazine hydrochloride |
| 563 | 2,6-difluoro-benzoylchloride | 2-chloro-5-methyl-benzoylchloride | t-butylhydrazine hydrochloride |
| 564 | 2,3-dimethyl-benzoylchloride | 2-chloro-5-methyl-benzoylchloride | t-butylhydrazine hydrochloride |
| 565 | 2-methyl-3-chloro-benzoylchloride | 2-chloro-5-methyl-benzoylchloride | t-butylhydrazine hydrochloride |
| 566 | 4-chlorobenzoyl chloride | 2-methyl-5-chloro-benzoylchloride | t-butylhydrazine hydrochloride |
| 567 | 4-chlorobenzoyl chloride | 2-chloro-5-methyl-benzoylchloride | t-butylhydrazine hydrochloride |
| 568 | 2-flouro-4-chloro-benzoylchloride | benzoylchloride | t-butylhydrazine hydrochloride |
| 569 | 2-flouro-4-chloro- | 3-tolyl chloride | t-butylhydrazine |

TABLE III-continued

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| | benzoylchloride | | hydrochloride |
| 570 | 2-flouro-4-chloro-benzoylchloride | 3,5-dimethyl benzoylchloride | t-butylhydrazine hydrochloride |
| 571 | 2-flouro-4-chloro-benzoylchloride | 3,5-dichloro-benzoylchloride | t-butylhydrazine hydrochloride |
| 572 | 2-flouro-4-chloro-benzoylchloride | 2-bromobenzoyl chloride | t-butylhydrazine hydrochloride |
| 573 | 2-flouro-4-chloro-benzoylchloride | 2-nitrobenzoyl chloride | t-butylhydrazine hydrochloride |
| 574 | 2-chloro-3-methyl-benzoylchloride | 2,4-dichloro-benzoylchloride | t-butylhydrazine hydrochloride |
| 575 | 2-chloro-3-methyl-benzoylchloride | benzoylchloride | t-butylhydrazine |
| 576 | 2-chloro-3-methyl-benzoylchloride | 3-toluoyl chloride | t-butylhydrazine hydrochloride |
| 577 | 2-chloro-3-methyl-benzoylchloride | 3,5-dimethyl-benzoylchloride | t-butylhydrazine hydrochloride |
| 578 | 2-chloro-3-methyl-benzoylchloride | 3,5-dichloro-benzoylchloride | t-butylhydrazine hydrochloride |
| 579 | 2-bromo-3-methyl-benzoylchloride | 3,5-dimethyl-benzoylchloride | t-butylhydrazine hydrochloride |
| 580 | 2-bromo-3-methyl-benzoylchloride | 2,4-dichloro-benzoylchloride | t-butylhydrazine hydrochloride |
| 581 | 2-bromo-3-methyl-benzoylchloride | 3-toluoyl chloride | t-butylhydrazine hydrochloride |
| 582 | 2-bromo-3-methyl-benzoylchloride | 3,5-dichloro-benzoylchloride | t-butylhydrazine hydrochloride |
| 583 | 2-bromo-3-methyl-benzoylchloride | 2-bromobenzoyl chloride | t-butylhydrazine hydrochloride |
| 584 | 2,3-dimethyl-benzoylchloride | 2-chlorobenzoyl chloride | t-butylhydrazine hydrochloride |
| 585 | 2,3-dimethyl-benzoylchloride | 2-trifluoromethyl-benzoylchloride | t-butylhydrazine hydrochloride |
| 586 | 2,3-dimethyl-benzoylchloride | 4-ethylbenzoyl chloride | t-butylhydrazine hydrochloride |
| 587 | 2,3-dimethyl-benzoylchloride | 3,5-dichloro-benzoylchloride | t-butylhydrazine hydrochloride |
| 588 | 2,6-difluoro-benzoylchloride | 3-chloro-4-fluoro-benzoylchloride | t-butylhydrazine hydrochloride |
| 589 | 4-chlorobenzoyl chloride | 3,5-difluoro-benzoylchloride | t-butylhydrazine hydrochloride |
| 590 | 2,3-dimethyl-benzoylchloride | 3,5-difluoro-benzoylchloride | t-butylhydrazine hydrochloride |
| 591 | 2-methyl-3-chloro-benzoylchloride | 3,5-difluoro-benzoylchloride | t-butylhydrazine hydrochloride |
| 592 | benzoylchloride | 3,5-difluoro-benzoylchloride | t-butylhydrazine hydrochloride |
| 593 | 4-ethylbenzoyl chloride | 2,5-dimethyl-benzoylchloride | t-butylhydrazine hydrochloride |
| 594 | 2,6-difluoro-benzoylchloride | 3,5-difluoro-benzoylchloride | t-butylhydrazine hydrochloride |
| 595 | 2-methyl-3-chloro-benzoylchloride | 3,5-dichloro-benzoylchloride | t-butylhydrazine hydrochloride |
| 596 | 2,3-dimethyl-benzoylchloride | 2,5-dimethyl-benzoylchloride | t-butylhydrazine hydrochloride |
| 597 | 2-bromobenzoyl chloride | 3,5-dimethyl-benzoylchloride | t-butylhydrazine hydrochloride |
| 598 | 2-bromo-3-methyl-benzoylchloride | 3-chlorobenzoyl chloride | t-butylhydrazine hydrochloride |
| 599 | 2-chloro-3-methyl-benzoylchloride | 3-chlorobenzoyl chloride | t-butylhydrazine hydrochloride |
| 600 | 2-chloro-3-methyl-benzoylchloride | 3-chlorobenzoyl chloride | t-butylhydrazine hydrochloride |
| 601 | 2-chloro-3-methyl-benzoylchloride | 2-nitrobenzoyl chloride | t-butylhydrazine hydrochloride |
| 602 | 2,3-dimethyl-benzoylchloride | 2-nitro-3-methyl-benzoylchloride | t-butylhydrazine hydrochloride |
| 603 | 2,3-dimethyl-benzoylchloride | 2-nitro-5-methyl-benzoylchloride | t-butylhydrazine hydrochloride |
| 604 | 2,6-difluoro-benzoylchloride | benzoylchloride | t-butylhydrazine hydrochloride |
| 605 | 2,6-dimethyl-benzoylchloride | 2,4-dichloro-benzoylchloride | t-butylhydrazine hydrochloride |
| 606 | 2,4,6-trimethyl-benzoylchloride | 3,5-dimethyl-benzoylchloride | t-butylhydrazine hydrochloride |
| 607 | 2,4,6-trimethyl-benzoylchloride | 2,4-dichloro-benzoylchloride | t-butylhydrazine hydrochloride |
| 608 | 2,6-difluoro-benzoylchloride | 4-toluoyl chloride | t-butylhydrazine |
| 609 | 2,6-difluoro-benzoylchloride | 2,5-dichloro-benzoylchloride | t-butylhydrazine hydrochloride |
| 610 | 2,4,6-trimethyl-benzoylchloride | 4-chlorobenzoyl chloride | t-butylhydrazine hydrochloride |
| 611 | 2,4,6-trimethyl-benzoylchloride | 3-toluoyl chloride | t-butylhydrazine hydrochloride |
| 612 | 2,4,6-trimethyl-benzoylchloride | 3,4-dichloro-benzoylchloride | t-butylhydrazine hydrochloride |
| 615 | 2,4-dimethyl-benzoylchloride | 3-toluoyl chloride | t-butylhydrazine hydrochloride |
| 616 | 2,4-dimethyl-benzoylchloride | 2,4-dichloro-benzoylchloride | t-butylhydrazine hydrochloride |
| 617 | 2,4-dimethyl-benzoylchloride | 3,5-dimethyl-benzoylchloride | t-butylhydrazine hydrochloride |
| 618 | 2,4-dimethyl-benzoylchloride | 3,5-dichloro-benzoylchloride | t-butylhydrazine hydrochloride |
| 619 | 2,4-dimethyl-benzoylchloride | 3-bromobenzoyl chloride | t-butylhydrazine hydrochloride |
| 620 | 2,4-dimethyl-benzoylchloride | 3,4-dichloro-benzoylchloride | t-butylhydrazine hydrochloride |
| 621 | 2-bromo-3-methyl-benzoylchloride | 2-nitrobenzoyl chloride | t-butylhydrazine hydrochloride |
| 622 | piperonyl chloride | benzoylchloride | t-butylhydrazine hydrochloride |
| 623 | piperonyl chloride | 4-chlorobenzoyl chloride | t-butylhydrazine hydrochloride |
| 624 | piperonyl chloride | 3-toluoyl chloride | t-butylhydrazine hydrochloride |
| 626 | 2-pyrrolobenzoyl chloride | benzoylchloride | t-butylhydrazine hydrochloride |
| 627 | 2-pyrrolobenzoyl chloride | 3-toluoyl chloride | t-butylhydrazine hydrochloride |
| 628 | 2,3-dimethyl-benzoylchloride | 2-bromo-5-methyl-benzoylchloride | t-butylhydrazine hydrochloride |
| 629 | 2-methyl-3-chloro-benzoylchloride | 3-chlorobenzoyl chloride | t-butylhydrazine hydrochloride |
| 630 | 2-methyl-3-chloro-benzoylchloride | 4-fluorobenzoyl chloride | t-butylhydrazine hydrochloride |
| 631 | 2-methyl-3-chloro-benzoylchloride | 2-bromobenzoyl chloride | t-butylhydrazine hydrochloride |
| 633 | 2-methyl-3-chloro-benzoylchloride | 3,5-dimethyl-4 chlorobenzoyl chloride | t-butylhydrazine hydrochloride |
| 929 | n-pentanoyl chloride | 2-furoylchloride | t-butylhydrazine hydrochloride |
| 930 | ethylchloroformate | n-pentanoylchloride | t-butylhydrazine hydrochloride |
| 931 | ethylchloroformate | 4-chlorobenzoyl | t-butylhydrazine hydrochloride |
| 932 | benzoylchloride | ethylchoro formate hydrochloride | t-butylhydrazine hydroxide |
| 934 | phenylchloro-formate | benzoylchloride | t-butylhydrazine hydrochloride |
| 935 | benzoylchloride | phenylchloro formate | t-butylhydrazine hydrochloride |
| 936 | benzoylchloride | 4-nitrophenyl chloroformate | t-butylhydrazine hydrochloride |
| 940 | 4-ethylbenzoyl chloride | phenylpropiolyl chloride | t-butylhydrazine hydrochloride |

TABLE III-continued

Base = Sodium hydroxide except for examples 243 and 408 which had no added base, examples 346, 347, 348, 462, and 486 which used sodium bicarbonate, and 953 which used no base.
Solvent = toluene and water except for examples 243 and 408 which used pyridine, examples 509–515 which used toluene only, and example 953 which used methylene chloride only.

| Ex. No. | Compound of Formula III | Compound of Formula VI | Compound of Formula IV |
|---|---|---|---|
| 945 | 4-chlorobenzoyl chloride | 4-phenylbenzoyl chloride | t-butylhydrazine hydrochloride |
| 946 | benzoylchloride | 1,2,3,4-tetrahydro-2-naphthoylchloride | t-butylhydrazine hydrochloride |
| 947 | prolinecarboxylic acid chloride | 3-toluoyl chloride | t-butylhydrazine |
| 952 | benzoylchloride | N,N-diethylcarbamoyl chloride | t-butylhydrazine hydrochloride |
| 953 | benzoylchloride | p-chlorophenyl isocyanate | t-butylhydrazine hydrochloride |
| 962 | 3,5-dichlorobenzoyl chloride | chloroacetyl chloride | phenylhydrazine |
| 966 | 3,5-dichlorobenzoyl chloride | chloroacetyl chloride | benzylhydrazine |
| 993 | n-pentanoyl | ethylchloro formate | t-butylhydrazine hydrochloride |
| 994 | 4-chlorobenzoyl-chloride | ethylchloro formate | t-butylhydrazine hydrochloride |
| 995 | 2,6-difluoro-benzoylchloride | ethylchloro formate | t-butylhydrazine hydrochloride |
| 997 | benzoylchloride | 3-chlorobenzoyl chloride | N'-(1,1-di-methyl)benzyl-N-benzoyl hydrazine |
| 998 | benzoylchloride | 2,3-dichloro-benzoylchloride | N'-(1,1-di-methyl)benzyl-N-benzoyl hydrazine |

By following substantially the procedures in Example 44 and using the reactants shown below in Table IV, the products of Example Nos. 39, 46, 63, 110, 111, 112, 114, 115, 116, 120, 124, 127, 128, 129, 136, 143, 155 through 158, 185 through 189, 332, 336 through 340, 382, 383, 384, 399, 400, 414 through 418, 421, 434, 435, 436, 453, 470, 471, 472, 546, 547, 634 and 955 through 960 were prepared.

TABLE IV

| Ex. No. | Reactants | |
|---|---|---|
| 39 | Compound of Formula VII: | Benzoylhydrazine |
| | Compound of Formula VIII: | Dimethyl ketone |
| | Solvent: | Methanol |
| | Catalyst: | Acetic acid |
| | Compound of Formula IX: | Benzoylhydrazone of acetone |
| | Reducing Agent: | Sodium cyanoborohydride |
| | Solvent: | Methanol |
| | Catalyst: | Acetic acid |
| | Compound of Formula X: | 2-isopropyl-1-benzoylhydrazine |
| | Compound of Formula VI: | Benzoylchloride |
| | Base: | Sodium hydroxide |
| | Solvent: | Toluene and water |
| 46 | Compound of Formula VII: | Benzoylhydrazine |
| | Compound of Formula VII: | Methylethyl ketone |
| | Solvent: | Methanol |
| | Catalyst: | Acetic acid |
| | Compound of Formula IX: | Benzoylhydrazone of 2-butanone |
| | Reducing Agent: | Sodium cyanoborohydride |
| | Solvent: | Methanol |
| | Catalyst: | Acetic acid |
| | Compound of Formula X: | 2-sec-butyl-1-benzoylhydrazine |
| | Compound of Formula VI: | Benzoylchloride |
| | Base: | Sodium hydroxide |

TABLE IV-continued

| Ex. No. | Reactants | |
|---|---|---|
| | Solvent: | Toluene and water |
| 63 | Compound of Formula VII: | Benzoylhydrazine |
| | Compound of Formula VIII: | Methyl-t-butyl ketone |
| | Solvent: | Methanol |
| | Catalyst: | Acetic acid |
| | Compound of Formula IX: | Benzoylhydrazone of methyl-t-butylketone |
| | Reducing Agent: | Sodium cyanoborohydride |
| | Solvent: | Methanol |
| | Catalyst: | Acetic acid |
| | Compound of Formula X: | 2-(1,2,2-trimethylpropyl)-1-benzoylhydrazine |
| | Compound of Formula VI: | Benzoylchloride |
| | Base: | Sodium hydroxide |
| | Solvent: | Toluene and water |
| 110 | Compound of Formula VII: | Benzoylhydrazine |
| | Compound of Formula VIII: | 1,1,1-trimethylacetaldehyde |
| | Solvent: | Methanol |
| | Catalyst: | Acetic acid |
| | Compound of Formula IX: | Benzoylhydrazone of 1,1,1-trimethylacetaldehyde |
| | Reducing Agent: | Sodium cyanoborohydride |
| | Solvent: | Methanol |
| | Catalyst: | Acetic acid |
| | Compound of Formula X: | 2-neopentyl-1-benzoylhydrazine |
| | Compound of Formula VI: | 2-bromobenzoylchloride |
| | Base: | Sodium hydroxide |
| | Solvent: | Toluene and water |
| 111 | Compound of Formula VII: | Benzoylhydrazine |
| | Compound of Formula VIII: | 1,1,1-trimethylacetaldehyde |
| | Solvent: | Methanol |
| | Catalyst: | Acetic acid |
| | Compound of Formula IX: | Benzoylhydrazone of 1,1,1-trimethylacetaldehyde |
| | Reducing Agent: | Sodium cyanoborohydride |
| | Solvent: | Methanol |
| | Catalyst: | Acetic acid |
| | Compound of Formula X | 2-neopentyl-1-benzoylhydrazine |
| | Compound of Formula VI: | 2-nitrobenzoylchloride |
| | Base: | Sodium hydroxide |
| | Solvent: | Toluene and water |
| 112 | Compound of Formula VII: | Benzoylhydrazine |
| | Compound of Formula VIII: | 1,1,1-trimethylacetaldehyde |
| | Solvent: | Methanol |
| | Catalyst: | Acetic acid |
| | Compound of Formula IX: | Benzoylhydrazone of 1,1,1-trimethylacetaldehyde |
| | Reducing Agent: | Sodium cyanoborohydride |
| | Solvent: | Methanol |
| | Catalyst: | Acetic acid |
| | Compound of Formula X: | 2-neopentyl-1-benzoylhydrazine |
| | Compound of Formula VI: | 2-anisoyl chloride |
| | Base: | Sodium hydroxide |
| | Solvent: | Toluene and water |
| 114 | Compound of Formula VII. | Benzoylhydrazine |
| | Compound of Formula VIII: | Isobutyraldehyde |
| | Solvent: | Methanol |
| | Catalyst: | Acetic acid |
| | Compound of Formula IX: | Benzoylhydrazone of isobutyr-aldehyde |
| | Reducing Agent: | Sodium cyanoborohydride |
| | Solvent: | Methanol |
| | Catalyst: | Acetic Acid |
| | Compound of Formula X: | 2-isobutyl-1-benzoylhydrazine |
| | Compound of Formula VI: | Benzoylchloride |
| | Base: | Sodium hydroxide |
| | Solvent: | Toluene and water |
| 115 | Compound of Formula VII: | Benzoylhydrazine |
| | Compound of Formula VIII: | Acetone |
| | Solvent: | Methanol |
| | Catalyst: | Acetic acid |
| | Compound of Formula IX: | Benzoylhydrazone of acetone |
| | Reducing Agent: | Sodium cyanoborohydride |
| | Solvent: | Methanol |
| | Catalyst: | Acetic acid |
| | Compound of Formula X: | 2-isopropyl-1-benzoylhydrazine |

TABLE IV-continued

| Ex. No. | Reactants | |
|---|---|---|
| | Compound of Formula VI: | 2-bromobenzoylchloride |
| | Base: | Sodium hydroxide |
| | Solvent: | Toluene and water |
| 116 | Compound of Formula VII: | Benzoylhydrazine |
| | Compound of Formula VIII: | Acetone |
| | Solvent: | Methanol |
| | Catalyst: | Acetic acid |
| | Compound of Formula IX: | Benzoylhydrazone of acetone |
| | Reducing Agent: | Sodium cyanoborohydride |
| | Solvent: | Methanol |
| | Catalyst: | Acetic acid |
| | Compound of Formula X: | 2-isopropyl-1-benzoylhydrazine |
| | Compound of Formula VI: | 3,4-dichlorobenzoylchloride |
| | Base: | Sodium hydroxide |
| | Solvent: | Toluene and water |
| 120 | Compound of Formula VII: | Benzoylhydrazine |
| | Compound of Formula VIII: | Dicyclopropylketone |
| | Solvent: | Methanol |
| | Catalyst: | Acetic Acid |
| | Compound of Formula IX: | Benzoylhydrazone of dicyclopropylketone |
| | Reducing Agent: | Sodium cyanoborohydride |
| | Solvent: | Methanol |
| | Catalyst: | Acetic acid |
| | Compound of Formula X: | 2-dicyclopropylmethyl-1-benzoylhydrazine |
| | Compound of Formula VI: | Benzoylchloride |
| | Base: | Sodium hydroxide |
| | Solvent: | Toluene and water |
| 124 | Compound of Formula VII: | Benzoylhydrazine |
| | Compound of Formula VIII: | Methyl-t-butyl ketone |
| | Solvent: | Methanol |
| | Catalyst: | Acetic acid |
| | Compound of Formula IX: | Benzoylhydrazone of methyl-t-butylketone |
| | Reducing Agent: | Sodium cyanoborohydride |
| | Solvent: | Methanol |
| | Catalyst: | Acetic acid |
| | Compound of Formula X: | 2-(1,2,2-trimethylpropyl)-1-benzoylhydrazine |
| | Compound of Formula VI: | 2-nitrobenzoylchloride |
| | Base: | Sodium hydroxide |
| | Solvent: | Toluene and water |
| 127 | Compound of Formula VII: | Benzoylhydrazine |
| | Compound of Formula VIII: | Methyl-t-butyl ketone |
| | Solvent: | Methanol |
| | Catalyst: | Acetic acid |
| | Compound of Formula IX: | Benzoylhydrazone of methyl-t-butylketone |
| | Reducing Agent: | Sodium cyanoborohydride |
| | Solvent: | Methanol |
| | Catalyst: | Acetic acid |
| | Compound of Formula X: | 2-(1,2,2-trimethylpropyl)-1-benzoylhydrazine |
| | Compound of Formula VI: | Benzoylchloride |
| | Base: | Sodium hydroxide |
| | Solvent: | Toluene and water |
| 128 | Compound of Formula VII: | Benzoylhydrazine |
| | Compound of Formula VIII: | Diisopropyl ketone |
| | Solvent: | Methanol |
| | Catalyst: | Acetic acid |
| | Compound of Formula IX: | Benzoylhydrazone of diisopropylketone |
| | Reducing Agent: | Sodium cyanoborohydride |
| | Solvent: | Methanol |
| | Catalyst: | Acetic acid |
| | Compound of Formula X: | 2-diisopropylmethyl-1-benzoyl hydrazine |
| | Compound of Formula VI: | Benzoylchloride |
| | Base: | Sodium hydroxide |
| | Solvent: | Toluene and water |
| 129 | Compound of Formula VII: | Benzoylhydrazine |
| | Compound of Formula VIII: | Cyclopropylmethyl ketone |
| | Solvent: | Methanol |
| | Catalyst: | Acetic acid |
| | Compound of Formula IX: | Benzoylhydrazone of cyclopropylmethylketone |
| | Reducing Agent: | Sodium cyanoborohydride |
| | Solvent: | Methanol |
| | Catalyst: | Acetic acid |
| | Compound of Formula X: | 2-(1-cyclopropylethyl)-1-benzoylhydrazine |
| | Compound of Formula VI: | Benzoylchloride |
| | Base: | Sodium hydroxide |
| | Solvent: | Toluene and water |
| 136 | Compound of Formula VII: | Benzoylhydrazine |
| | Compound of Formula VIII: | Methyl-t-butylketone |
| | Solvent: | Methanol |
| | Catalyst: | Acetic acid |
| | Compound of Formula IX: | Benzoylhydrazone of methyl-t-butylketone |
| | Reducing Agent: | Sodium cyanoborohydride |
| | Solvent: | Methanol |
| | Catalyst: | Acetic acid |
| | Compound of Formula X: | 2-(1-methyl)neopentyl-1-benzoylhydrazine |
| | Compound of Formula VI: | 2-bromobenzoylchloride |
| | Base: | Sodium hydroxide |
| | Solvent: | Toluene and water |
| 143 | Compound of Formula VII: | Benzoylhydrazine |
| | Compound of Formula VIII: | Methyl cyclohexyl ketone |
| | Solvent: | Methanol |
| | Catalyst: | Acetic acid |
| | Compound of Formula IX: | Benzoylhydrazone of methyl cyclohexyl ketone |
| | Reducing Agent: | Sodium cyanoborohydride |
| | Solvent: | Methanol |
| | Catalyst: | Acetic acid |
| | Compound of Formula X: | 1-benzoyl-2-(1-cyclohexylethyl)hydrazine |
| | Compound of Formula VI: | benzoylchloride |
| | Base: | Sodium hydroxide |
| | Solvent: | Toluene and water |
| 155 | Compound of Formula VII: | Benzoylhydrazine |
| | Compound of Formula VIII: | Acetone |
| | Solvent: | Methanol |
| | Catalyst: | Acetic acid |
| | Compound of Formula IX: | Benzoylhydrazone of acetone |
| | Reducing Agent: | Sodium cyanoborohydride |
| | Solvent: | Methanol |
| | Catalyst: | Acetic acid |
| | Compound of Formula X: | 1-benzoyl-2-isopropyl hydrazine |
| | Compound of Formula VI: | 2,6-dichlorobenzoylchloride |
| | Base: | Sodium hydroxide |
| | Solvent: | Toluene and water |
| 156 | Compound of Formula VII: | Benzoylhydrazine |
| | Compound of Formula VIII: | Trimethylacetaldehyde |
| | Solvent: | Methanol |
| | Catalyst: | Acetic acid |
| | Compound of Formula IX: | Benzoylhydrazone of trimethyl acetaldehyde |
| | Reducing Agent: | Sodium cyanoborohydride |
| | Solvent: | Methanol |
| | Catalyst: | Acetic acid |
| | Compound of Formula X: | 1-benzoyl-2-(2,2-dimethylpropyl) hydrazine |
| | Compound of Formula VI: | 3,4-dichlorobenzoylchloride |
| | Base: | Sodium hydroxide |
| | Solvent: | Toluene and water |
| 157 | Compound of Formula VII: | Benzoylhydrazine |
| | Compound of Formula VIII: | Pinacolone |
| | Solvent: | Methanol |
| | Catalyst: | Acetic acid |
| | Compound of Formula IX: | Benzoylhydrazone of pinacolone |
| | Reducing Agent: | Sodium cyanoborohydride |
| | Solvent: | Methanol |
| | Catalyst: | Acetic acid |
| | Compound of Formula X: | 1-benzoyl-2-(1,2,2-trimethylpropyl)hydrazine |
| | Compound of Formula VI: | 4-cyanobenzoylchloride |
| | Base: | Sodium hydroxide |

TABLE IV-continued

| Ex. No. | Reactants | |
|---|---|---|
| 158 | Solvent: | Toluene and water |
| | Compound of Formula VII: | Benzoylhydrazine |
| | Compound of Formula VIII: | Trimethylacetaldehyde |
| | Solvent: | Methanol |
| | Catalyst: | Acetic acid |
| | Compound of Formula IX: | Benzoylhydrazone of trimethyl acetaldehyde |
| | Reducing Agent: | Sodium cyanoborohydride |
| | Solvent: | Methanol |
| | Catalyst: | Acetic acid |
| | Compound of Formula X: | 1-benzoyl-2-(2,2-dimethylpropyl)hydrazine |
| | Compound of Formula VI: | 4-ethylbenzoylchloride |
| | Base: | Sodium hydroxide |
| | Solvent: | Toluene and water |
| 185 | Compound of Formula VII: | Benzoylhydrazine |
| | Compound of Formula VIII: | Pinacolone |
| | Solvent: | Methanol |
| | Catalyst: | Acetic acid |
| | Compound of Formula IX: | Benzoylhydrazone of pinacolone |
| | Reducing Agent: | Sodium cyanoborohydride |
| | Solvent: | Methanol |
| | Catalyst: | Acetic acid |
| | Compound of Formula X: | 1-benzoyl-2-(1,2,2-trimethyl-propyl)hydrazine |
| | Compound of Formula VI: | 3-nitrobenzoylchloride |
| | Base: | Sodium hydroxide |
| | Solvent: | Toluene and water |
| 186 | Compound of Formula VII: | Benzoylhydrazine |
| | Compound of Formula VIII: | Trimethylacetaldehyde |
| | Solvent: | Methanol |
| | Catalyst: | Acetic acid |
| | Compound of Formula IX: | Benzoylhydrazone of trimethyl acetaldehyde |
| | Reducing Agent: | Sodium cyanoborohydride |
| | Solvent: | Methanol |
| | Catalyst: | Acetic acid |
| | Compound of Formula X: | 1-benzoyl-2-(2,2-dimethylpropyl)hydrazine |
| | Compound of Formula VI: | 3-nitrobenzoylchloride |
| | Base: | Sodium hydroxide |
| | Solvent: | Toluene and water |
| 187 | Compound of Formula VII: | Benzoylhydrazine |
| | Compound of Formula VIII: | Trimethylacetaldehyde |
| | Solvent: | Methanol |
| | Catalyst: | Acetic acid |
| | Compound of Formula IX: | Benzoylhydrazone of trimethyl acetaldehyde |
| | Reducing Agent: | Sodium cyanoborohydride |
| | Solvent: | Methanol |
| | Catalyst: | Acetic acid |
| | Compound of Formula X: | 1-benzoyl-2-(2,2-dimethylpropyl)hydrazine |
| | Compound of Formula VI: | 3-toluoyl chloride |
| | Base: | Sodium hydroxide |
| | Solvent: | Toluene and water |
| 188 | Compound of Formula VII: | Benzoylhydrazine |
| | Compound of Formula VIII: | Trimethylacetaldehyde |
| | Solvent: | Methanol |
| | Catalyst: | Acetic acid |
| | Compound of Formula IX: | Benzoylhydrazone of trimethyl acetaldehyde |
| | Reducing Agent: | Sodium cyanoborohydride |
| | Solvent: | Methanol |
| | Catalyst: | Acetic acid |
| | Compound of Formula X: | 1-benzoyl-2-(2,2-dimethylpropyl)hydrazine |
| | Compound of Formula VI: | 4-chlorobenzoylchloride |
| | Base: | Sodium hydroxide |
| | Solvent: | Toluene and water |
| 189 | Compound of Formula VII: | Benzoylhydrazine |
| | Compound of Formula VIII: | Trimethylacetaldehyde |
| | Solvent: | Methanol |
| | Catalyst: | Acetic acid |
| | Compound of Formula IX: | Benzoylhydrazone of trimethyl acetaldehyde |
| | Reducing Agent: | Sodium cyanoborohydride |
| | Solvent: | Methanol |
| | Catalyst: | Acetic acid |
| | Compound of Formula X: | 1-benzoyl-2-(2,2-dimethylpropyl)hydrazine |
| | Compound of Formula VI: | 2,4-dinitrobenzoylchloride |
| | Base: | Sodium hydroxide |
| | Solvent: | Toluene and water |
| 332 | Compound of Formula VII: | 4-toluoylhydrazine |
| | Compound of Formula VIII: | Pinacolone |
| | Solvent: | Methanol |
| | Catalyst: | Acetic acid |
| | Compound of Formula IX: | 4-toluoyl hydrazone of pinacolone |
| | Reducing Agent: | Sodium cyanoborohydride |
| | Solvent: | Methanol |
| | Catalyst: | Acetic acid |
| | Compound of Formula X: | 1-(4-toluoyl)-2-(1,2,2-trimethylpropyl)hydrazine |
| | Compound of Formula VI: | 2-nitrobenzoylchloride |
| | Base: | Sodium hydroxide |
| | Solvent: | Toluene and water |
| 336 | Compound of Formula VII: | 4-toluoylhydrazine |
| | Compound of Formula VIII: | Pinacolone |
| | Solvent: | Methanol |
| | Catalyst: | Acetic acid |
| | Compound of Formula IX: | 4-toluoyl hydrazone of pinacolone |
| | Reducing Agent: | Sodium cyanoborohydride |
| | Solvent: | Methanol |
| | Catalyst: | Acetic acid |
| | Compound of Formula X: | 1-(4-toluoyl)-2-(1,2,2-trimethylpropyl)hydrazine |
| | Compound of Formula VI: | 3,5-dimethylbenzoylchloride |
| | Base: | Sodium hydroxide |
| | Solvent: | Toluene and water |
| 337 | Compound of Formula VII: | 4-toluoylhydrazine |
| | Compound of Formula VIII: | Pinacolone |
| | Solvent: | Methanol |
| | Catalyst: | Acetic acid |
| | Compound of Formula IX: | 4-toluoyl hydrazone of pinacolone |
| | Reducing Agent: | Sodium cyanoborohydride |
| | Solvent: | Methanol |
| | Catalyst: | Acetic acid |
| | Compound of Formula X: | 1-(4-toluoyl)-2-(1,2,2-trimethylpropyl)hydrazine |
| | Compound of Formula VI: | 2-nitro-3-methyl benzoyl chloride |
| | Base: | Sodium hydroxide |
| | Solvent: | Toluene and water |
| 338 | Compound of Formula VII: | 4-toluoylhydrazine |
| | Compound of Formula VIII: | Pinacolone |
| | Solvent: | Methanol |
| | Catalyst: | Acetic acid |
| | Compound of Formula IX: | 4-toluoyl hydrazone of pinacolone |
| | Reducing Agent: | Sodium cyanoborohydride |
| | Solvent: | Methanol |
| | Catalyst: | Acetic acid |
| | Compound of Formula X: | 1-(4-toluoyl)-2-(1,2,2-trimethylpropyl)hydrazine |
| | Compound of Formula VI: | 2-nitro-5-methylbenzoyl chloride |
| | Base: | Sodium hydroxide |
| | Solvent: | Toluene and water |
| 339 | Compound of Formula VII: | 4-toluoylhydrazine |
| | Compound of Formula VIII: | Pinacolone |
| | Solvent: | Methanol |
| | Catalyst: | Acetic acid |
| | Compound of Formula IX: | 4-toluoyl hydrazone of pinacolone |
| | Reducing Agent: | Sodium cyanoborohydride |
| | Solvent: | Methanol |
| | Catalyst: | Acetic acid |
| | Compound of Formula X: | 1-(4-toluoyl)-2-(1,2,2-trimethylpropyl)hydrazine |

TABLE IV-continued

| Ex. No. | Reactants | |
|---|---|---|
| | Compound of Formula VI:<br>Base:<br>Solvent: | 3-toluoyl chloride<br>Sodium hydroxide<br>Toluene and water |
| 340 | Compound of Formula VII:<br>Compound of Formula VIII:<br>Solvent:<br>Catalyst:<br>Compound of Formula IX: | 4-toluoylhydrazine<br>Pinacolone<br>Methanol<br>Acetic acid<br>4-toluoyl hydrazone of pinacolone |
| | Reducing Agent:<br>Solvent:<br>Catalyst:<br>Compound of Formula X: | Sodium cyanoborohydride<br>Methanol<br>Acetic acid<br>1-(4-toluoyl)-2-(1,2,2-trimethylpropyl)hydrazine |
| | Compound of Formula VI:<br>Base:<br>Solvent: | 2-iodobenzoyl chloride<br>Sodium hydroxide<br>Toluene and water |
| 382 | Compound of Formula VII:<br>Compound of Formula VIII:<br>Solvent:<br>Catalyst:<br>Compound of Formula IX: | 4-toluoylhydrazine<br>Pinacolone<br>Methanol<br>Acetic acid<br>4-toluoyl hydrazone of pinacolone |
| | Reducing Agent:<br>Solvent:<br>Catalyst:<br>Compound of Formula X: | Sodium cyanoborohydride<br>Methanol<br>Acetic acid<br>1-(4-toluoyl)-2-(1,2,2-trimethylpropyl)hydrazine |
| | Compound of Formula VI:<br>Base:<br>Solvent: | 2-toluoyl chloride<br>Sodium hydroxide<br>Toluene and water |
| 383 | Compound of Formula VII:<br>Compound of Formula VIII:<br>Solvent:<br>Catalyst:<br>Compound of Formula IX: | 4-toluoylhydrazine<br>Pinacolone<br>Methanol<br>Acetic acid<br>4-toluoyl hydrazone of pinacolone |
| | Reducing Agent:<br>Solvent:<br>Catalyst:<br>Compound of Formula X: | Sodium cyanoborohydride<br>Methanol<br>Acetic acid<br>1-(4-toluoyl)-2-(1,2,2-trimethylpropyl)hydrazine |
| | Compound of Formula VI: | 2-trifluoromethylbenzoyl chloride |
| | Base:<br>Solvent: | Sodium hydroxide<br>Toluene and water |
| 384 | Compound of Formula VII:<br>Compound of Formula VIII:<br>Solvent:<br>Catalyst:<br>Compound of Formula IX: | 4-toluoylhydrazine<br>Pinacolone<br>Methanol<br>Acetic acid<br>4-toluoyl hydrazone of pinacolone |
| | Reducing Agent:<br>Solvent:<br>Catalyst:<br>Compound of Formula X: | Sodium cyanoborohydride<br>Methanol<br>Acetic acid<br>1-(4-toluoyl)-2-(1,2,2-trimethylpropyl)hydrazine |
| | Compound of Formula VI:<br>Base:<br>Solvent: | benzoyl chloride<br>Sodium hydroxide<br>Toluene and water |
| 399 | Compound of Formula VII:<br>Compound of Formula VIII:<br>Solvent:<br>Catalyst:<br>Compound of Formula IX: | 4-toluoylhydrazine<br>4,4-dimethyl-2-pentanone<br>Methanol<br>Acetic acid<br>4-toluoyl hydrazone of 3,4-dimethyl-2-pentanone |
| | Reducing Agent:<br>Solvent:<br>Catalyst:<br>Compound of Formula X: | Sodium cyanoborohydride<br>Methanol<br>Acetic acid<br>1-(4-toluoyl)-2-(4,4-dimethyl-2-pentyl)hydrazine |
| | Compound of Formula VI:<br>Base:<br>Solvent: | 3,5-dimethylbenzoyl chloride<br>Sodium hydroxide<br>Toluene and water |
| 400 | Compound of Formula VII:<br>Compound of Formula VIII: | 4-toluoylhydrazine<br>4,4-dimethyl-2-pentanone |

TABLE IV-continued

| Ex. No. | Reactants | |
|---|---|---|
| | Solvent:<br>Catalyst:<br>Compound of Formula IX: | Methanol<br>Acetic acid<br>4-toluoyl hydrazone of 4,4-dimethyl-2-pentanone |
| | Reducing Agent:<br>Solvent:<br>Catalyst:<br>Compound of Formula X: | Sodium cyanoborohydride<br>Methanol<br>Acetic acid<br>1-(4-toluoyl)-2-(4,4-dimethyl-2-pentyl)hydrazine |
| | Compound of Formula VI:<br>Base:<br>Solvent: | 3,4-dichlorobenzoyl chloride<br>Sodium hydroxide<br>Toluene and water |
| 414 | Compound of Formula VII:<br>Compound of Formula VIII:<br>Solvent:<br>Catalyst:<br>Compound of Formula IX: | 4-toluoylhydrazine<br>3-methyl-3-ethyl-2-pentanone<br>Methanol<br>Acetic acid<br>4-toluoyl hydrazone of 3-methyl-3-ethyl-2-pentanone |
| | Reducing Agent:<br>Solvent:<br>Catalyst:<br>Compound of Formula X: | Sodium cyanoborohydride<br>Methanol<br>Acetic acid<br>1-(4-toluoyl)-2-(3-methyl-3-ethylpent-2-yl)hydrazine |
| | Compound of Formula VI:<br>Base:<br>Solvent: | benzoyl chloride<br>Sodium hydroxide<br>Toluene and water |
| 415 | Compound of Formula VII:<br>Compound of Formula VIII:<br>Solvent:<br>Catalyst:<br>Compound of Formula IX: | 4-toluoylhydrazine<br>3-methyl-3-ethyl-2-pentanone<br>Methanol<br>Acetic acid<br>4-toluoyl hydrazone of 3-methyl-3-ethyl-2-pentanone |
| | Reducing Agent:<br>Solvent:<br>Catalyst:<br>Compound of Formula X: | Sodium cyanoborohydride<br>Methanol<br>Acetic acid<br>1-(4-toluoyl)-2-(3-methyl-3-ethylpent-2-yl)hydrazine |
| | Compound of Formula VI:<br>Base:<br>Solvent: | 3,5-dimethylbenzoyl chloride<br>Sodium hydroxide<br>Toluene and water |
| 416 | Compound of Formula VII:<br>Compound of Formula VIII:<br>Solvent:<br>Catalyst:<br>Compound of Formula IX: | 4-toluoylhydrazine<br>3-methyl-3-ethyl-2-pentanone<br>Methanol<br>Acetic acid<br>4-toluoyl hydrazone of 3-methyl-3-ethyl-2-pentanone |
| | Reducing Agent:<br>Solvent:<br>Catalyst:<br>Compound of Formula X: | Sodium cyanoborohydride<br>Methanol<br>Acetic acid<br>1-(4-toluoyl)-2-(3-methyl-3-ethylpent-2-yl)hydrazine |
| | Compound of Formula VI:<br>Base:<br>Solvent: | 2-nitrobenzoyl chloride<br>Sodium hydroxide<br>Toluene and water |
| 417 | Compound of Formula VII:<br>Compound of Formula VIII:<br>Solvent:<br>Catalyst:<br>Compound of Formula IX: | 4-ethylbenzoyl hydrazine<br>Pinacolone<br>Methanol<br>Acetic acid<br>4-ethylbenzoyl hydrazone of pinacolone |
| | Reducing Agent:<br>Solvent:<br>Catalyst:<br>Compound of Formula X: | Sodium cyanoborohydride<br>Methanol<br>Acetic acid<br>1-(4-ethylbenzoyl)-2-(1,2,2-trimethylpropyl)hydrazine |
| | Compound of Formula VI:<br>Base:<br>Solvent: | 3,5-dimethylbenzoyl chloride<br>Sodium hydroxide<br>Toluene and water |
| 418 | Compound of Formula VII:<br>Compound of Formula VIII:<br>Solvent:<br>Catalyst:<br>Compound of Formula IX: | 4-ethylbenzoyl hydrazine<br>Pinacolone<br>Methanol<br>Acetic acid<br>4-ethylbenzoyl hydrazone of pinacolone |
| | Reducing Agent:<br>Solvent: | Sodium cyanoborohydride<br>Methanol |

TABLE IV-continued

| Ex. No. | | Reactants |
|---|---|---|
| | Catalyst: | Acetic acid |
| | Compound of Formula X: | 1-(4-ethylbenzoyl)-2-(1,2,2-trimethylpropyl)hydrazine |
| | Compound of Formula VI: | 2-nitro-5-methylbenzoyl chloride |
| | Base: | Sodium hydroxide |
| | Solvent: | Toluene and water |
| 421 | Compound of Formula VII: | 4-ethylbenzoyl hydrazine |
| | Compound of Formula VIII: | Acetone |
| | Solvent: | Methanol |
| | Catalyst: | Acetic acid |
| | Compound of Formula IX: | 4-ethylbenzoyl hydrazone of acetone |
| | Reducing Agent: | Sodium cyanoborohydride |
| | Solvent: | Methanol |
| | Catalyst: | Acetic acid |
| | Compound of Formula X: | 1-(4-ethylbenzoyl)-2-isopropyl hydrazine |
| | Compound of Formula VI: | 3,5-dimethylbenzoyl chloride |
| | Base: | Sodium hydroxide |
| | Solvent: | Toluene and water |
| 434 | Compound of Formula VII: | 4-ethylbenzoyl hydrazine |
| | Compound of Formula VIII: | Pinacolone |
| | Solvent: | Methanol |
| | Catalyst: | Acetic acid |
| | Compound of Formula IX: | 4-ethylbenzoyl hydrazone of pinacolone |
| | Reducing Agent: | Sodium cyanoborohydride |
| | Solvent: | Methanol |
| | Catalyst: | Acetic acid |
| | Compound of Formula X: | 1-(4-ethylbenzoyl)-2-(1,2,2-trimethylpropyl)hydrazine |
| | Compound of Formula VI: | 2,4-dichlorobenzoyl chloride |
| | Base: | Sodium hydroxide |
| | Solvent: | Toluene and water |
| 435 | Compound of Formula VII: | 4-toluoylhydrazine |
| | Compound of Formula VIII: | 3-methyl-3-ethyl-2-pentanone |
| | Solvent: | Methanol |
| | Catalyst: | Acetic acid |
| | Compound of Formula IX: | 4-toluoylhydrazone of 3-methyl-3-ethyl-2-pentanone |
| | Reducing Agent: | Sodium cyanoborohydride |
| | Solvent: | Methanol |
| | Catalyst: | Acetic acid |
| | Compound of Formula X: | 1-(4-toluoyl)-2-(3-methyl-3-ethylpent-2-yl)hydrazine |
| | Compound of Formula VI: | 2-nitro-5-methylbenzoyl chloride |
| | Base: | Sodium hydroxide |
| | Solvent: | Toluene and water |
| 436 | Compound of Formula VII: | 4-toluoylhydrazine |
| | Compound of Formula VIII: | 3-methyl-3-ethyl-2-pentanone |
| | Solvent: | Methanol |
| | Catalyst: | Acetic acid |
| | Compound of Formula IX: | 4-toluoylhydrazone of 3-methyl-3-ethyl-2-pentanone |
| | Reducing Agent: | Sodium cyanoborohydride |
| | Solvent: | Methanol |
| | Catalyst: | Acetic acid |
| | Compound of Formula X: | 1-(4-toluoyl)-2-(3-methyl-3-ethylpent-2-yl)hydrazine |
| | Compound of Formula VI: | 2-nitro-3-methylbenzoyl chloride |
| | Base: | Sodium hydroxide |
| | Solvent: | Toluene and water |
| 453 | Compound of Formula VII: | 4-toluoylhydrazine |
| | Compound of Formula VIII: | 2,2-dimethyl-3-pentanone |
| | Solvent: | Methanol |
| | Catalyst: | Acetic acid |
| | Compound of Formula IX: | 4-toluoylhydrazone of 2,2-dimethyl-3-pentanone |
| | Reducing Agent: | Sodium cyanoborohydride |
| | Solvent: | Methanol |
| | Catalyst: | Acetic acid |
| | Compound of Formula X: | 1-(4-toluoyl)-2-(2,2-dimethyl-pent-3-yl)hydrazine |
| | Compound of Formula VI: | Benzoyl chloride |
| | Base: | Sodium hydroxide |
| | Solvent: | Toluene and water |
| 470 | Compound of Formula VII: | 4-toluoylhydrazine |
| | Compound of Formula VIII: | 2,2-dimethyl-3-pentanone |
| | Solvent: | Methanol |
| | Catalyst: | Acetic acid |
| | Compound of Formula IX: | 4-toluoylhydrazone of 2,2-dimethyl-3-pentanone |
| | Reducing Agent: | Sodium cyanoborohydride |
| | Solvent: | Methanol |
| | Catalyst: | Acetic acid |
| | Compound of Formula X: | 1-(4-toluoyl)-2-(2,2-dimethylpent-3-yl)hydrazine |
| | Compound of Formula VI: | 2-nitrobenzoyl chloride |
| | Base: | Sodium hydroxide |
| | Solvent: | Toluene and water |
| 471 | Compound of Formula VII: | 4-toluoylhydrazine |
| | Compound of Formula VIII: | 2,2-dimethyl-3-butanone |
| | Solvent: | Methanol |
| | Catalyst: | Acetic acid |
| | Compound of Formula IX: | 4-toluoylhydrazone of 2,2-dimethyl-3-butanone |
| | Reducing Agent: | Sodium cyanoborohydride |
| | Solvent: | Methanol |
| | Catalyst: | Acetic acid |
| | Compound of Formula X: | 1-(4-toluoyl)-2-(2,2-dimethylbut-3-yl)hydrazine |
| | Compound of Formula VI: | 2-nitro-5-methylbenzoyl chloride |
| | Base: | Sodium hydroxide |
| | Solvent: | Toluene and water |
| 472 | Compound of Formula VII: | 4-toluoylhydrazine |
| | Compound of Formula VIII: | 2,2-dimethyl-3-pentanone |
| | Solvent: | Methanol |
| | Catalyst: | Acetic acid |
| | Compound of Formula IX: | 4-toluoylhydrazone of 2,2-dimethyl-3-pentanone |
| | Reducing Agent: | Sodium cyanoborohydride |
| | Solvent: | Methanol |
| | Catalyst: | Acetic acid |
| | Compound of Formula X: | 1-(4-toluoyl)-2-(2,2-dimethylpent-3-yl)hydrazine |
| | Compound of Formula VI: | 3,5-dimethylbenzoyl chloride |
| | Base: | Sodium hydroxide |
| | Solvent: | Toluene and water |
| 546 | Compound of Formula VII: | 2,3-dimethylbenzoyl hydrazine |
| | Compound of Formula VIII: | Pinacolone |
| | Solvent: | Methanol |
| | Catalyst: | Acetic acid |
| | Compound of Formula IX: | (2,3-dimethylbenzoyl)hydrazone of pinacolone |
| | Reducing Agent: | Sodium cyanoborohydride |
| | Solvent: | Methanol |
| | Catalyst: | Acetic acid |
| | Compound of Formula X: | 1-(2,3-dimethylbenzoyl)-2-(1,2,2-trimethylpropyl)hydrazine |
| | Compound of Formula VI: | 3,5-dimethylbenzoyl chloride |
| | Base: | Sodium hydroxide |
| | Solvent: | Toluene and water |
| 547 | Compound of Formula VII: | 2,3-dimethylbenzoyl hydrazine |
| | Compound of Formula VIII: | Pinacolone |
| | Solvent: | Methanol |
| | Catalyst: | Acetic acid |
| | Compound of Formula IX: | (2,3-dimethylbenzoyl)hydrazone of pinacolone |
| | Reducing Agent: | Sodium cyanoborohydride |
| | Solvent: | Methanol |
| | Catalyst: | Acetic acid |
| | Compound of Formula X: | 1-(2,3-dimethylbenzoyl)-(1,2,2-trimethylpropyl)hydrazine |
| | Compound of Formula VI: | 3-toluoyl chloride |
| | Base: | Sodium hydroxide |
| | Solvent: | Toluene and water |
| 634 | Compound of Formula VII: | Benzoylhydrazine |
| | Compound of Formula VIII: | Methyl t-butyl ketone |
| | Solvent: | Methanol |

TABLE IV-continued

| Ex. No. | Reactants | |
|---|---|---|
| | Catalyst: | Hydrochloric acid |
| | Compound of Formula IX: | Benzoylhydrazone of methyl t-butyl ketone |
| | Reducing Agent: | Sodium cyanoborohydride |
| | Solvent: | Methanol |
| | Catalyst: | Hydrochloric acid |
| | Compound of Formula X: | 1-(1,2,2-trimethylpropyl)-2-benzoylhydrazine |
| | Compound of Formula VI: | 2-methyl-3-chlorobenzoyl chloride |
| | Base: | Sodium hydroxide |
| | Solvent: | Toluene and water |
| 955 | Compound of Formula VII: | Benzoylhydrazine |
| | Compound of Formula VIII: | Deoxybenzoin |
| | Solvent: | Methanol |
| | Catalyst: | Hydrochloric acid |
| | Compound of Formula IX: | Benzoylhydrazone of doexybenzoin |
| | Reducing Agent: | Sodium cyanoborohydride |
| | Solvent: | Methanol |
| | Catalyst: | Hydrochloric acid |
| | Compound of Formula X: | 1-(1,2-diphenylethyl)-2-benzoylhydrazine |
| | Compound of Formula VI: | 3-toluoyl chloride |
| | Base: | Sodium hydroxide |
| | Solvent: | Toluene and water |
| 956 | Compound of Formula VII: | Benzoylhydrazine |
| | Compound of Formula VIII: | Cyclopentanone |
| | Solvent: | Methanol |
| | Catalyst: | Hydrochloric acid |
| | Compound of Formula IX: | Benzoylhydrazone of cyclopentanone |
| | Reducing Agent: | Sodium cyanoborohydride |
| | Solvent: | Methanol |
| | Catalyst: | Hydrochloric acid |
| | Compound of Formula X: | 1-cyclopentyl-2-benzoyl hydrazine |
| | Compound of Formula VI: | 3-toluoyl chloride |
| | Base: | Sodium hydroxide |
| | Solvent: | Toluene and water |
| 957 | Compound of Formula VII: | Benzoylhydrazine |
| | Compound of Formula VIII: | Cyclohexanone |
| | Solvent: | Methanol |
| | Catalyst: | Hydrochloric acid |
| | Compound of Formula IX: | Benzoylhydrazone of Cyclohexanone |
| | Reducing Agent: | Sodium cyanoborohydride |
| | Solvent: | Methanol |
| | Catalyst: | Hydrochloric acid |
| | Compound of Formula X: | 1-cyclohexyl-2-benzoyl hydrazine |
| | Compound of Formula VI: | 3-toluoyl chloride |
| | Base: | Sodium hydroxide |
| | Solvent: | Toluene and water |
| 958 | Compound of Formula VII: | Benzoylhydrazine |
| | Compound of Formula VIII: | 2-methyl cyclohexanone |
| | Solvent: | Methanol |
| | Catalyst: | Hydrochloric acid |
| | Compound of Formula IX: | Benzoyl hydrazone of 2-methyl-cyclohexanone |
| | Reducing Agent: | Sodium cyanoborohydride |
| | Solvent: | Methanol |
| | Catalyst: | Hydrochloric acid |
| | Compound of Formula X: | 1-(2-methylcyclohexyl)-2-benzoyl hydrazine |
| | Compound of Formula VI: | 3-toluoyl chloride |
| | Base: | Sodium hydroxide |
| | Solvent: | Toluene and water |
| 960 | Compound of Formula VII: | Benzoylhydrazine |
| | Compound of Formula VIII: | Phenylcyclopentyl ketone |
| | Solvent: | Methanol |
| | Catalyst: | Hydrochloric acid |
| | Compound of Formula IX: | Benzoylhydrazone of phenyl-cyclopentylketone |
| | Reducing Agent: | Sodium cyanoborohydride |
| | Solvent: | Methanol |
| | Catalyst: | Hydrochloric acid |
| | Compound of Formula X: | 1-(alpha-cyclopentylbenzyl)-2-benzoyl hydrazine |
| | Compound of Formula VI: | 3-toluoyl chloride |
| | Base: | Sodium hydroxide |
| | Solvent: | Toluene and water |

By following substantially the procedures in Example 220 and using the reactants shown below in Table V, the products of Examples 168, 170, 171, 172, 191, 192, 193, 213, 221 through 223, 232, 233, 293, 326, 331, 379, 397, 398, 425 and 458 were prepared.

TABLE V

| Ex. No. | Compound of Formula XII | Compound of Formula XIII | Base | Solvent |
|---|---|---|---|---|
| 168 | 3,4-dimethoxy-benzoyl chloride | N'-t-butyl-N'-benzoylhydrazine | sodium hydroxide | toluene and water |
| 170 | 2-chloromethyl-benzoyl chloride | N'-t-butyl-N'-benzoyl hydrazine | sodium hydroxide | toluene and water |
| 171 | 4-n-propylbenzoyl chloride | N'-t-butyl-N'-benzoyl hydrazine | sodium hydroxide | toluene and water |
| 172 | 2-nitrobenzoyl chloride | N'-t-butyl-N'-benzoyl hydrazine | sodium hydroxide | toluene and water |
| 191 | 3,4-dichloro-benzoyl chloride | N'-t-butyl-N'-(4-chlorobenzoyl)hydrazine | sodium hydroxide | toluene and water |
| 192 | 4-n-heptyl-benzoyl chloride | N'-t-butyl-N'-(4-chlorobenzoyl)hydrazine | sodium hydroxide | toluene and water |
| 193 | 4-n-propyl-benzoyl chloride | N'-t-butyl-N'-(4-chlorobenzoyl)hydrazine | sodium hydroxide | toluene and water |
| 212 | 2-fluoro-benzoyl chloride | N'-t-butyl-N'-(4-chlorobenzoyl)hydrazine | sodium hydroxide | toluene and water |
| 213 | 2,4-dichloro-benzoyl chloride | N'-t-butyl-N'-(4-chlorobenzoyl)hydrazine | sodium hydroxide | toluene and water |
| 221 | 3-nitrobenzoyl chloride | N'-t-butyl-N'-benzoylhydrazine | sodium hydroxide | toluene and water |
| 222 | 2,6-dichloro-benzoyl chloride | N'-t-butyl-N' benzoylhydrazine | sodium hydroxide | toluene and water |
| 223 | 2,4-difluoro-benzoyl chloride | N'-t-butyl-N'-benzoylhydrazine | sodium hydroxide | toluene and water |
| 232 | 4-nitrobenzoyl chloride | N'-t-butyl-N'-benzoylhydrazine | sodium hydroxide | toluene and water |
| 233 | 4-cyanobenzoyl chloride | N'-t-butyl-N'-benzoylhydrazine | sodium hydroxide | toluene and water |
| 293 | 2-chloromethyl benzoyl chloride | N'-t-butyl-N'-(4-chlorobenzoyl)hydrazine | sodium hydroxide | toluene and water |
| 326 | 3-bromo-4-methyl-benzoic methane-sulfonic anhydride | N'-t-butyl-N'-benzoylhydrazine | triethyl amine | methylene chloride |
| 331 | 4-fluorobenzoyl chloride | N'-t-butyl-N'-benzoylhydrazine | sodium hydroxide | toluene and water |
| 379 | 2,3-dimethyl benzoylchloride | N'-t-butyl-N'-(3-toluoyl)-hydrazine | sodium hydroxide | toluene and water |
| 397 | 2-methyl-3-chloro-benzoyl chloride | N'-t-butyl-N'-(3-toluoyl)-hydrazine | sodium hydroxide | toluene and water |
| 398 | 2-methyl-3-chloro-benzoyl chloride | N'-t-butyl-N'-benzoylhydrazine | sodium hydroxide | toluene and, water |
| 425 | 3-chloro-4-fluoro-benzoyl chloride | N'-t-butyl-N'-benzoylhydrazine | sodium hydroxide | toluene and water |
| 458 | 3-chloro-4-fluoro-benzoyl chloride | N'-t-butyl-N'-(3,4-dichloro-benzoyl)hydrazine | sodium hydroxide | toluene and water |

Example 324 but using the appropriately substituted reactants, the compounds of Examples 323 and 979 to 989 were prepared.

TABLE IV-continued

| Ex. No. | Reactants | |
|---|---|---|
| | Compound of Formula VI: | 3-toluoyl chloride |
| | Base: | Sodium hydroxide |
| | Solvent: | Toluene and water |

Using a nitrobenzoyl compound of Formula II as a reactant and reducing it, followed in certain cases by an addition reaction (such as alkylation) under the conditions (additional reactant, base or acid, and solvent) set forth in Table VI, the products of Examples 329, 330, 350 through 354, 372, 375, 473 and 484 were prepared.

TABLE VI

| Ex. No. | Compound of Formula II | Reactant | Base or Acid | Solvent |
|---|---|---|---|---|
| 162 | N-benzoyl-N'-t-butyl-N'-(4-formylbenzoyl)-hydrazine | sodium borohydride | | methanol |
| 329 | N-benzoyl-N'-t-butyl-N'-(3-nitrobenzoyl)-hydrazine | zinc dust | | acetic acid |
| 330 | N-benzoyl-N'-t-butyl-N'-(2-nitrobenzoyl)-hydrazine | zinc dust | | acetic acid |
| 350 | N-(2-nitro-3-methoxybenzoyl)-N'-t-butyl-N'-(3-toluoyl)hydrazine | zinc dust | | acetic acid |
| 351 | N-(4-nitrobenzoyl)-N'-t-butyl-N'-(4-chlorobenzoyl)hydrazine | hydrogen, platinum on carbon | | ethyl acetate-methanol |
| 352 | N-(4-aminobenzoyl)-N'-t-butyl-N'-(4-chlorobenzoyl)hydrazine | methyl chloroformate | pyridine | methylene chloride |
| 353 | N-(4-aminobenzoyl)-N'-t-butyl-N'-(4-chlorobenzoyl)hydrazine | acetic anhydride | | |
| 354 | N-(2-nitro-3-methoxybenzoyl)-N'-t-butyl-N'-(3-toluoyl)hydrazine | 1. H₂/catalyst 2. AC₂O | | 1. ethyl acetate 2. none |
| 372 | N-(3-nitrobenzoyl)-N'-t-butyl-N'-(3-toluoyl)-hydrazine | zinc dust | | aqueous acetic acid |
| 375 | N-(3-aminobenzoyl)-N'-t-butyl-N'-(3-toluoyl)-hydrazine | methacryloyl chloride | sodium hydroxide | water |
| 473 | N-(2-nitro-3-methoxybenzoyl)-N'-t-butyl-N'-benzoylhydrazine | zinc dust | ammonium chloride | aqueous ethanol |
| 484 | N-(2-methyl-3-nitro benzoyl)-N'-t-butyl-N'-(3-toluoyl) hydrazine | zinc dust | ammonium chloride | aqueous ethanol |

Using a chloromethylbenzoyl compound of Formula II as a reactant and performing a substitution reaction under the conditions (base or acid, and solvent) set forth in Table VII, the products of Examples 159, 161, 162, 294, 361, 362, 363 and 367 were prepared.

| Ex. No. | Compound of Formula II | Reactant | Base or Acid | Solvent |
|---|---|---|---|---|
| 159 | N-benzoyl-N'-t-butyl-N'-(3-chloromethylbenzoyl) hydrazine | sodium acetate | | N,N-dimethyl-formamide |
| 161 | N-benzoyl-N'-t-butyl-N'-(3-chloromethylbenzoyl) hydrazine | p-thiocresol | sodium hydroxide | toluene-water |
| 294 | N-(2-chloromethyl-benzoyl)-N''-t-butyl-N'-(4-chlorobenzoyl)-hydrazine | diethylamine | | tetra-hydro-furan |
| 361 | N-(4-chloromethyl benzoyl)-N'-t-butyl-N'-benzoyl hydrazine | sodium acetate | | N,N-dimethyl-formamide |
| 362 | N-(4-chloromethyl benzoyl)-N'-t-butyl-N'-benzoyl hydrazine | potassium thiocyanate | | ethanol |
| 363 | N-(4-acetoxymethyl benzoyl)-N'-t-butyl-N'-benzoylhydrazine | | sodium hydroxide | methanol |
| 367 | N-(4-chloromethyl benzoyl)-N'-t-butyl-N'-benzoyl hydrazine | potassium cyanide | | dimethyl formamide |

Using an acetyloxybenzoyl compound of Formula II as a reactant and performing a hydrolysis, under the conditions (base and solvent) set forth in Table VIII, the products of Examples 151, 165, 203, 271, 285, 333, 349 and 614 were prepared.

TABLE VIII

| Ex. No. | Compound of Formula II | Reactant | Base or Acid | Solvent |
|---|---|---|---|---|
| 151 | N-benzoyl-N'-t-butyl-N'-(2-acetoxybenzoyl)-hydrazine | | sodium hydroxide | methanol |
| 165 | N-benzoyl-N'-(1,2,2-trimethylpropyl)-N'-2-acetoxybenzoyl)hydrazine | | sodium hydroxide | methanol |
| 203 | N-benzoyl-N'-t-butyl-N'-(3-acetoxybenzoyl) hydrazine | | potassium hydroxide | methanol |
| 271 | N-(4-acetoxybenzoyl)-N'-t-butyl-N'-benzoyl hydrazine | | potassium hydroxide | methanol |
| 285 | N-(4-acetoxybenzoyl)-N'-t-butyl-N'-(3-toluoyl) hydrazine | | potassium hydroxide | methanol |
| 333 | N-(3-acetoxybenzoyl)-N'-t-butyl-N'-benzoyl hydrazine | | potassium hydroxide | methanol |
| 349 | N-(4-carbomethoxy benzoyl)-N'-t-butyl-N'-(3-toluoyl)hydrazine | | sodium hydroxide | aqueous tetra-hydro-furan |
| 614 | N,N'-bis-(2-acetoxy-benzoyl)-N'-t-butyl hydrazine | | sodium hydroxide | methanol |

Using a hydroxybenzoyl compound of Formula II as a reactant and performing an alkylation or esterification, under the conditions (base and solvent) set forth in Table IX, the products of Examples 144, 286, 335, 345, 358, 359, 360, 365, 366 and 385 were prepared.

TABLE IX

| Ex. No. | Compound of Formula II | Reactant | Base | Solvent |
|---|---|---|---|---|
| 144 | N-benzoyl-N'-t-butyl-N'-(4-hydroxybenzoyl)-hydrazine | allyl bromide | potassium t-butoxide | tetra-hydro-furan |
| 286 | N-(4-hydroxybenzoyl)-N'-t-butyl-N'-benzoyl-hydrazine | allyl bromide | potassium t-butoxide | tetra-hydro-furan |
| 335 | N(3hydroxybenzoyl)-N'-t-butyl-N'-benzoyl-hydrazine | allyl bromide | sodium hydride | dimethyl-formamide |
| 345 | N-(3-hydroxybenzoyl)-N'-t-butyl-N'-benzoyl-hydrazine | vinyl chloroformate | potassium t-butoxide | tetra-hydro-furan |
| 358 | N-(4-hydroxybenzoyl)-N'-t-butyl-N'-benzoyl-hydrazine | chloromethyl-methyl ether | potassium t-butoxide | tetra-hydro-furan |
| 359 | N-(4-hydroxybenzoyl)-N'-t-butyl-N benzoyl-hydrazine | N,N-dimethyl-carbamoyl chloride | potassium t-butoxide | tetra-hydro-furan |

TABLE IX-continued

| Ex. No. | Compound of Formula II | Reactant | Base | Solvent |
|---|---|---|---|---|
| 360 | N-(4-hydroxybenzoyl)-N'-t-butyl-N'-benzoylhydrazine | ethyl bromoacetate | potassium t-butoxide | tetrahydrofuran |
| 365 | N-(4-hydroxybenzoyl)-N'-t-butyl-N'-benzoylhydrazine | chloromethylmethyl sulfide | sodium hydride | dimethylformamide |
| 366 | N-(4-hydroxybenzoyl)-N'-t-butyl-N'-benzoylhydrazine | isobutyl bromide | potassium t-butoxide | dimethyl formamide |
| 385 | N-(4-hydroxybenzoyl)-N'-t-butyl-N'-benzoylhydrazine | chloromethylmethyl ether | potassium t-butoxide | tetrahydrofuran |

Using a compound of Formula II as a reactant and performing the stated reaction under the conditions (additional reactant, base or acid, and solvent) set forth in Table X, the products of Examples 149, 164, 166, 368, 369, 373, 374, 376, 386 and 541 were prepared.

TABLE X

| Ex. No. | Compound Prepared. Reactants. Reaction Conducted and Conditions |
|---|---|
| 149 | N-benzoyl-N'-t-butyl-N'-(4-methanesulfonylbenzoyl)hydrazine was prepared from N-benzoyl-N'-t-butyl-N'-(4-methylthiobenzoyl)hydrazine using meta-chloroperbenzoic acid in methylene chloride in an oxidation reaction. |
| 164 | N-benzoyl-N'-t-butyl-N'-(4-carboxybenzoyl)hydrazine was prepared from N-benzoyl-N'-t-butyl-N'-(4-methoxycarbonyl-benzoyl)hydrazine sodium hydroxide as a base and methanol as solvent in a hydrolysis reaction. |
| 166 | N-benzoyl-N'-t-butyl-N'-(4-(2,2-dichloroethenyl)benzoyl)hydrazine was prepared from N-benzoyl-N'-t-butyl-N'-(4-formylbenzoyl)hydrazine using triphenylphosphine in carbon tetrachloride as solvent in a Wittig-type reaction. |
| 368 | N-(4-(1,2-epoxypropyl)benzoyl)-N'-t-butyl-N'-benzoylhydrazine was prepared from N-(4-(1-propenyl)benzoyl)-N'-t-butyl-N'-benzoylhydrazine using meta-chloroperbenzoic acid in methylene chloride as solvent in an oxidation reaction. |
| 369 | N-(4-acetylsemicarbazone)-N'-t-butyl-N-(3-toluoyl)hydrazine was prepared from N-(4-acetylbenzoyl)-N'-t-butyl-N'-(3-toluoyl)hydrazine using semicarbazide in ethanol solvent with hydrochloric acid catalyst in a condensation reaction. |
| 373 | N-(4-(2-hydroxy-1,1-dimethylethylamino-carbonyl)benzoyl)-N'-t-butyl-N'-(3-toluoyl)-hydrazine was prepared from N-(4-methoxycarbonylbenzoyl)-N'-t-butyl-N'-(3-toluoyl)hydrazine using 2-amino-2-methylpropanol in a condensation reaction. |
| 374 | N-(4-(2-hydroxyethyl)benzoyl)-N'-t-butyl-N'-(3-toluoyl)hydrazine was prepared from N-(4-acetylbenzoyl)-N'-t-butyl-N'-(3-toluoyl)hydrazine using sodium borohydride in methanol solvent in a reduction reaction. |
| 376 | N-(3-carboxybenzoyl)-N'-t-butyl-N'-(3-toluoyl)hydrazine was prepared from N-(3-cyanobenzoyl)-N'-t-butyl-N'-(3-toluoyl)hydrazine using potassium hydroxide as base in methanol solvent in a hydrolysis reaction. |
| 386 | N-(4-(1-methylethenyl)benzoyl)-N'-t-butyl-N'-(3-toluoyl)hydrazine was prepared from N-(4-acetylbenzoyl)-N'-t-butyl-N'-(3-toluoyl)hydrazine using methyltriphenylphosphonium bromide and n-butyl lithium as base and tetrahydrofuran solvent in a Wittig reaction. |
| 541 | N-(4-(2-hydroxyethyl)benzoyl)-N'-t-butyl-N'-(3,5-dimethylbenzoyl)hydrazine was prepared from N-(4-(2-acetoxyethyl)benzoyl)-N'-t-butyl-N'-(3,5-dimethylbenzoyl)hydrazine using sodium hydroxide as base and methanol as solvent in a hydrolysis. |

By following substantially the process for preparing the compounds of the present invention as described above and as exemplified by the illustrative preparation of the compounds of Examples 635 to 639 and 642 and using the appropriately substituted reactants, the compounds of Examples 640, 641 and 643 to 645 were prepared.

By following substantially the processes for preparing the compounds as described above and as exemplified by the illustrative preparation of the compounds of Examples 646, 648, 654, 656, 659 and 660 and using the appropriately substituted reactants, the compounds of Examples 647, 649 to 653, 655, 657, 658 and 661 to 681 were prepared.

By following substantially the procedures in processes described above as exemplified above by the preparation of the compounds of Examples 682, 683, 688, 689, 691, 699 and 702 and using the appropriately substituted reactants, the compounds of Examples 684 to 687, 690, 692 to 698, 700, 701, 703 to 721 and 991 were prepared.

By following substantially the procedures in the processes described above and as exemplified by the preparation of the compounds of Examples 722, 723, 724, 727, 729, 733, 737, 738, 739, 743, 754 and 755 and using the appropriately substituted reactants, the compounds of Examples 725, 726, 728, 730 to 732, 734 to 736, 740 to 742, 744 to 753, 756 and 992 were prepared.

By following substantially the procedures in the processes described above and as exemplified by the preparation of the compounds of Examples 764, 765, 766, 767, 772, 778 and 787 and using the appropriately substituted reactants, the compounds of Examples 768 to 771, 773 to 777, 779 to 786 and 788 to 794 were prepared.

By following substantially the procedures in Example 802 (without catalyst) or 809 (with catalyst) and using the reactants shown below in Table XI, the products of Examples 802 to 818 were prepared.

TABLE XI

| Ex. No. | Compound of Formula VII | Compound of Formula VIIIa | Compound of Formula VI |
|---|---|---|---|
| 802 | benzoylhydrazine | acetone | benzoyl chloride |
| 803 | benzoylhydrazine | acetone | 4-chlorobenzoyl chloride |
| 804 | 4-toluoylhydrazine | acetone | 3-methylbenzoyl chloride |
| 805 | benzoylhydrazine | acetone | 3-methylbenzoyl chloride |
| 806 | 4-chlorobenzoylhydrazine | acetone | 4-chlorobenzoyl chloride |
| 807 | 4-toluoylhydrazine | acetone | 3,5-dimethylbenzoyl chloride |
| 808 | 4-toluoylhydrazine | acetone | 4-fluorobenzoyl chloride |
| 809 | 4-toluoylhydrazine | acetone | 4-methylbenzoyl chloride |

TABLE XI-continued

| Ex. No. | Compound of Formula VII | Compound of Formula VIIIa | Compound of Formula VI |
|---|---|---|---|
| 810 | benzoylhydrazine | methylethyl-ketone | benzoyl chloride |
| 811 | thienoylhydrazine | acetone | 3-methylbenzoyl chloride |
| 812 | 4-ethylbenzoyl-hydrazine | acetone | 3,5-dimethylbenzoyl chloride |
| 813 | 2-toluoylhydrazine | acetone | 3,5-dimethylbenzoyl chloride |
| 814 | 4-chlorobenzoyl-hydrazine | acetone | 3-methylbenzoyl chloride |
| 815 | 2,4-difluorobenzoyl-hydrazine | acetone | 4-chlorobenzoyl chloride |
| 816 | 2-toluoylhydrazine | acetone | 3-methylbenzoyl chloride |
| 817 | 2-nitrobenzoyl-hydrazine | acetone | 3-methylbenzoyl chloride |
| 818 | 2-chlorobenzoyl-hydrazine | acetone | 3-methylbenzoyl chloride |

Examples 820 and 821 were made generally in accordance with the procedures for Example 822 above.

The (trimethylsilylmethyl)hydrazine, trifluoroalkyl hydrazine and (2-carbomethoxy-2-propyl)hydrazine were made generally in accordance with the procedures from Noll, J. E.; Sprier, J. L.; Daubert, B. F.; JACS 73, 3867, 1951; Hung, S. C.; Le; Breton, G. C.; JOC 46, 5413, 1981; and Organic Synthesis Vol 5, pg. 43, respectively. From these starting materials Examples 795–801, 819 and 823–828 were made generally in accordance with the procedure for Example 822 above.

The reactants shown below in Table XII were used to prepare Examples 795–801, 819–828 and 969–978.

TABLE XII

| Ex. No. | Compound of Formula III | Compound of Formula IV | Compound of Formula VI |
|---|---|---|---|
| 795 | 2,3-dimethyl benzoylchloride | (1-methyl-2,2,2-trifluoroethyl)hydrazine | 2,4-dichloro benzoylchloride |
| 796 | 2,3-dimethyl benzoylchloride | (1-methyl-2,2,2-trifluoroethyl)hydrazine | 3,5-dimethyl benzoylchloride |
| 797 | 2,3-dimethyl benzoylchloride | (1-methyl-2,2,2-trifluoroethyl)hydrazine | 2-nitro-5-toluoylchloride |
| 798 | benzoylchloride | (1-methyl-2,2,2-trifluoroethyl)hydrazine | benzoylchloride |
| 799 | 3,4-dichloro benzoylchloride | (2,2,2-trifluoroethyl)hydrazine | 3,4-dichloro benzoylchloride |
| 800 | 4-chlorobenzoyl chloride | (2,2,2-trifluoroethyl)hydrazine | 4-chlorobenzoyl chloride |
| 801 | benzoylchloride | (2,2,2-trifluoroethyl)hydrazine | benzoylchloride |
| 819 | benzoylchloride | (1-carbmethoxy-1-methylethyl)hydrazine | benzoylchloride |
| 820 | 4-toluoylchloride | (1,1-dimethyl-3-butenyl)hydrazine | 4-toluoylchloride |
| 821 | 3-toluoylchloride | (1,1-dimethyl-3-butenyl)hydrazine | 3-toluoylchloride |
| 822 | benzoylchloride | (1,1-dimethyl-3-butenyl)hydrazine | benzoylchloride |
| 823 | 4-ethylbenzoyl chloride | (trimethylsilylmethyl)hydrazine | 2-nitro-5-toluoyl chloride |
| 824 | 4-chlorobenzoyl chloride | (trimethylsilylmethyl)hydrazine | 4-chlorobenzoyl chloride |
| 825 | 2-toluoyl chloride | (trimethylsilylmethyl)hydrazine | 2-toluoyl chloride |
| 826 | 2-nitrobenzoyl chloride | (trimethylsilylmethyl)hydrazine | 2-nitrobenzoyl chloride |
| 827 | benzoyl chloride | (trimethylsilylmethyl)hydrazine | benzoyl chloride |
| 828 | 4-ethylbenzoyl chloride | (trimethylsilylmethyl)hydrazine | 3,5-dimethyl benzoylchloride |
| 969 | 4-toluoyl chloride | (2-methyl-2-propenyl)hydrazine | benzoylchloride |
| 970 | 4-toluoyl chloride | (2-methyl-2-propenyl)hydrazine | 3-toluoylchloride |
| 971 | benzoyl chloride | (1,5-dimethyl-1-heptenyl)hydrazine | 2-bromobenzoyl chloride |
| 972 | benzoyl chloride | (1,5-dimethyl-1-heptenyl)hydrazine | 2-nitrobenzoyl chloride |
| 973 | 4-methylbenzoyl chloride | (2-bromo-2,2-dimethyl ethyl)hydrazine | 3-toluoylchloride |
| 974 | 4-toluoyl chloride | (1-carbethoxyethyl)hydrazine | benzoylchloride |
| 975 | 4-toluoyl chloride | (1-carbethoxyethyl)hydrazine | 2-nitrobenzoyl chloride |
| 976 | 4-toluoyl chloride | (2-dimethylamino-1-methylethyl)hydrazine | 3,5-dimethyl benzoylchloride |
| 977 | 4-toluoyl chloride | (2-hydroxy-2,2-dimethylethyl)hydrazine | benzoylchloride |
| 978 | 4-toluoyl chloride | (2-hydroxy-2,2-dimethylethyl)hydrazine | 3,5-dimethyl benzoylchloride |

By following substantially the procedures in Examples 829, 837 and 853 and using the reactants shown in Table XIII, the products of Example Nos. 830–836, 838–852 and 854 were prepared.

TABLE XIII

| Ex. No. | Halide | Hydrazine | Base | Solvent |
|---|---|---|---|---|
| 830 | 4-chlorobenzyl bromide | N'-t-butyl-N-benzoyl hydrazine | triethylamine | dimethylformamide |
| 831 | 2,4-dichloro-benzyl bromide | N'-t-butyl-N-benzoyl hydrazine | triethylamine | dimethylformamide |
| 832 | 3,4-dichloro-benzyl bromide | N'-t-butyl-N-benzoyl hydrazine | triethylamine | dimethylformamide |
| 833 | 4-trifluoromethyl-benzyl bromide | N'-t-butyl-N-benzoyl hydrazine | triethylamine | dimethyl-formamide |
| 834 | 4-methoxycarbonyl benzyl bromide | N'-t-butyl-N-benzoyl hydrazine | triethylamine | dimethylformamide |
| 835 | 2-nitrobenzyl | N'-t-butyl-N-benzoyl | triethylamine | dimethylformamide |

TABLE XIII-continued

| Ex. No. | Halide | Hydrazine | Base | Solvent |
|---|---|---|---|---|
| | bromide | hydrazine | | |
| 836 | 4-fluorobenzyl bromide | N'-t-butyl-N-benzoyl hydrazine | triethylamine | dimethylformamide |
| 838 | 2-bromobenzyl bromide | N'-t-butyl-N-benzoyl hydrazine | triethylamine | dimethylformamide |
| 839 | 2-cyanobenzyl bromide | N'-t-butyl-N-benzoyl hydrazine | triethylamine | dimethylformamide |
| 840 | benzyl bromide | N'-t-butyl-N-thienoyl hydrazine | triethylamine | dimethylformamide |
| 841 | 4-cyanobenzyl bromide | N'-t-butyl-N-(4-methylbenzoyl) hydrazine | triethylamine | dimethylformamide |
| 842 | benzyl bromide | N'-t-butyl-N-(4-methylbenzoyl) hydrazine | triethylamine | dimethylformamide |
| 843 | 3-nitrobenzyl bromide | N'-t-butyl-N-benzoyl hydrazine | triethylamine | dimethylformamide |
| 844 | 4-methoxybenzyl bromide | N'-t-butyl-N-benzoyl hydrazine | triethylamine | dimethylformamide |
| 845 | 3-methoxybenzyl bromide | N'-t-butyl-N-benzoyl hydrazine | triethylamine | dimethylformamide |
| 846 | 3-methylbenzyl bromide | N'-t-butyl-N-benzoyl hydrazine | triethylamine | dimethylformamide |
| 847 | 3-methylbenzyl bromide | N'-t-butyl-N-(4-methylbenzoyl) hydrazine | triethylamine | dimethylformamide |
| 848 | 4-methylbenzyl bromide | N'-t-butyl-N-benzoyl hydrazine | triethylamine | dimethylformamide |
| 849 | 4-methylbenzyl bromide | N'-t-butyl-N-(4-methylbenzoyl) hydrazine | triethylamine | dimethylformamide |
| 850 | benzyl bromide | N'-t-butyl-N-(3,4-dichlorobenzoyl) hydrazine | triethylamine | dimethylformamide |
| 851 | 4-methylbenzyl bromide | N'-t-butyl-N-(3,4-dichlorobenzoyl) hydrazine | triethylamine | dimethylformamide |
| 852 | benzyl bromide | N'-t-butyl-N-(2-pyridinyl) hydrazine | triethylamine | dimethylformamide |
| 854 | 2-methylbenzyl bromide | N'-t-butyl-N-benzoyl hydrazine | triethylamine | dimethylformamide |

By following substantially the procedures in Example 855 and using the reactants shown in Table XIV, the products of Example Nos. 856–863 were prepared.

TABLE XIV

| Ex. No. | Hydrazone | Base | Solvent |
|---|---|---|---|
| 856 | N'-t-butyl-N'-(4-fluorobenzoyl)-benzaldehyde hydrazone | sodium cyanoborohydride | dry methanol |
| 857 | N'-t-butyl-N'-(2-bromobenzoyl)-benzaldehyde hydrazone | sodium cyanoborohydride | dry methanol |
| 858 | N'-t-butyl-N'-(3,4-dichloro-benzoyl) benzaldehyde hydrazone | sodium cyanoborohydride | dry methanol |
| 859 | N'-t-butyl-N'-(2-methylbenzoyl) benzaldehyde hydrazone | sodium cyanoborohydride | dry methanol |
| 860 | N'-t-butyl-N'-(3,4-dichloro-benzoyl)-3-methylbenzaldehyde hydrazone | sodium cyanoborohydride | dry methanol |
| 861 | N'-t-butyl-N'-benzoyl-3-methyl-benzaldehyde hydrazone | sodium cyanoborohydride | dry methanol |
| 862 | N'-t-butyl-N'-2-thienoyl-3-methylbenzaldehyde hydrazone | sodium cyanoborohydride | dry methanol |
| 863 | N'-t-butyl-N'-benzoyl-methyl-2-pyridinylbenzaldehyde hydrazone | sodium cyanoborohydride | dry methanol |

By following substantially the procedures in Example 864 and using the reactants shown in Table XV, the products of Example Nos. 865–869 were prepared.

TABLE XV

| Ex. No. | Benzaldehyde | Halide | Base | Solvent | Solvent System |
|---|---|---|---|---|---|
| 865 | benzaldehyde | 4-fluorobenzoyl chloride | triethyl-amine | toluene | pyridine/methylene chloride |
| 866 | benzaldehyde | 3,4-dichloro-benzoyl chloride | triethyl-amine | toluene | pyridine/methylene chloride |
| 867 | benzaldehyde | 2-bromobenzoyl chloride | triethyl-amine | toluene | pyridine/methylene chloride |
| 868 | 3-methyl-benzaldehyde | benzoyl chloride | triethyl-amine | toluene | pyridine/methylene chloride |
| 869 | benzaldehyde | 2-thienoyl chloride | triethyl-amine | toluene | pyridine/methylene chloride |

Example 874 was prepared by following substantially the procedures in Example 873 and using N'-t-butyl-N'-benzoylhydrazine, 3-methylbenzoyl formic acid, methanesulfonyl chloride in toluene and saturated sodium bicarbonate.

By following substantially the procedures in Example 878 and using the hydrazine shown in Table XVI and the reactants in Example 878, the products of Example Nos. 875–877 were prepared.

TABLE XVI

| Ex. No. | Hydrazine |
|---|---|
| 875 | N'-t-butyl-N-(2,3-dimethylbenzoyl) hydrazine |
| 876 | N'-t-butyl-N-(4-methylbenzoyl) hydrazine |
| 877 | N'-t-butyl-N-(4-ethylbenzoyl) hydrazine |

By following substantially the procedure in Example Nos. 882 and 883 and using the reactants shown in Table XVII, the products of Example Nos. 879–881 and 884–886, were prepared.

TABLE XVII

| Ex. No. | Hydrazine | Base | Solvent | Halide |
|---|---|---|---|---|
| 879 | N'-t-butyl-N-(2,3-dimethyl-benzoyl)hydrazine | sodium hydroxide | toluene | alpha-isopropyl-4-chlorophenylacetyl chloride |
| 881 | N'-t-butyl-N-(4-chlorobenzoyl) hydrazine | sodium hydroxide | toluene | phenylactyl chloride |
| 884 | N'-t-butyl-N-(4-chlorobenzoyl) hydrazine | sodium bicarbonate | toluene | alpha-chlorophenyl-acetyl chloride |
| 885 | N'-t-butyl-N-(2,3-dimethyl-benzoyl) hydrazine | sodium hydroxide | toluene | phenylacetyl chloride |
| 886 | N'-t-butyl-N-(4-ethylbenzoyl) hydrazine | sodium hydroxide | toluene | phenylacetyl chloride |

By following substantially the procedure in Example 893 and using the hydrazine and halide shown in Table XVIII and the other reactants in Example 893, the products of Example Nos. 887–892, 894–903 and 907–913 were prepared.

TABLE XVIII

| Ex. No. | Hydrazine | Halide |
|---|---|---|
| 887 | N,N'-benzoyl-N'-t-butyl hydrazine | acetyl chloride |
| 888 | N,N'-benzoyl-N'-t-butyl hydrazine | methylchloroformate |
| 889 | N,N'-benzoyl-N'-t-butyl hydrazine | methoxyacetyl chloride |
| 890 | N,N'-benzoyl-N'-t-butyl hydrazine | vinyl chloroformate |
| 891 | N,N'-benzoyl-N'-t-butyl hydrazine | crotonyl chloride |
| 892 | N,N'-benzoyl-N'-t-butyl hydrazine | tigloyl chloride |
| 894 | N'-t-butyl-N-4-ethylbenzoyl-N'-3,5-dimethylbenzoyl hydrazine | methylacryloyl chloride |
| 895 | N'-t-butyl-N-4-ethylbenzoyl-N'-3,5-dimethylbenzoyl hydrazine | acetyl chloride |
| 896 | N'-t-butyl-N-4-ethylbenzoyl-N'-3,5-dimethylbenzoyl hydrazine | methylchloroformate |
| 897 | N'-t-butyl-N-4-ethylbenzoyl-N'-3,5-dimethylbenzoyl hydrazine | methoxyacetyl chloride |
| 898 | N'-t-butyl-N-4-ethylbenzoyl-N'-3,5-dimethylbenzoyl hydrazine | vinyl chloroformate |
| 899 | N'-t-butyl-N-4-ethylbenzoyl-N'-3,5-dimethylbenzoyl hydrazine | 2-furoyl chloride |
| 900 | N'-t-butyl-N-4-ethylbenzoyl-N'-3,5-dimethylbenzoyl hydrazine | propionyl chloride |
| 901 | N'-t-butyl-N-2,3-dimethylbenzoyl-N'-3-methylbenzoyl hydrazine | acetyl chloride |
| 902 | N'-t-butyl-N-2,3-dimethylbenzoyl-N'-3-methylbenzoyl hydrazine | methacryloyl chloride |
| 903 | N'-t-butyl-N-2,3-dimethylbenzoyl-N'-3-methylbenzoyl hydrazine | 2-furoyl chloride |
| 907 | N'-t-butyl-N-4-ethylbenzoyl-N'-2,3-dimethylbenzoyl hydrazine | acryloyl chloride |
| 908 | N,N'-benzoyl-N'-t-butyl hydrazine | acryloyl chloride |
| 909 | N,N'-benzoyl-N'-t-butyl hydrazine | 4-ethylbenzoyl chloride |
| 910 | N,N'-benzoyl-N'-t-butyl hydrazine | 4-pentenoyl chloride |
| 911 | N,N'-benzoyl-N'-t-butyl hydrazine | tigloyl chloride |
| 912 | N'-t-butyl-N-benzoyl-N'-2,4-dichlorobenzoyl hydrazine | acetyl chloride |
| 913 | N'-t-butyl-N-benzoyl-N'-2,4-dichlorobenzoyl hydrazine | methacryloyl chloride |

Examples 904 and 906 were prepared by following substantially the procedures in Example 905 and using N'-t-butyl-N-(2,3-dimethylbenzoyl)hydrazine and ethanol, and N'-t-butyl-N-benzoylhydrazine and methanol, respectively.

Examples 915 and 916 were prepared by following substantially the procedures in Example 914 and using 4-methylbenzene sulfonyl and 4-fluorobenzene sulfonyl, respectively.

Examples 917 and 919–921 were prepared by following substantially the procedures in Example 918 except using the hydrazine and halide shown in Table XIX.

TABLE XIX

| Ex. No. | Hydrazine | Halide |
|---|---|---|
| 917 | N'-t-butyl-N-benzoyl hydrazine | 4-fluorobenzene sulfonyl chloride |
| 919 | N'-t-butyl-N-benzoyl hydrazine | 4-methylbenzene sulfonyl chloride |
| 920 | N'-t-butyl-N-(2-pyridinoyl) hydrazine | benzene sulfonyl chloride |
| 921 | N'-t-butyl-N-benzoyl hydrazine | 2-thienyl sulfonyl chloride |

Example 1014 was prepared by following substantially the procedure in example 1013 and using mucobromic acid.

Example Nos. 999 to 1007 and 1012 were prepared by following substantially the procedure of Example 872 and using the appropriately substituted reactants.

Example Nos. 1009 to 1011 were prepared by following substantially the procedure of Example 1008 and using the appropriately substituted reactants.

It will be appreciated by those skilled in the art that compounds of Formula I can be used as precursors for preparing other compounds of Formula I by procedures well known to those skilled in the art. For example, a suitable compound of Formula I can be reduced, alkylated, substituted, esterified, hydrolyzed or the like.

As previously noted, the compounds of the present invention exhibit excellent insecticidal activity and are most active against insects of the orders Lepidoptera and Coleoptera.

In general, for the control of insects in agriculture, horticulture and forestry, the compounds of the present invention may be used at a dosage corresponding to from about 10 grams to about 10 kilograms of the active substance per hectare and from about 100 grams to about 5 kilograms per hectare of the active substance is preferred. The exact amount of dosage for a given situation can be routinely determined and depends on a variety of factors, for example, the substance used, the kind of insect, the formulation used, the state of the crop infested with the insect and the prevailing weather conditions. The term "insecticidal" as employed in the specification and claims of this application is to be construed as any means which adversely affects the existence or growth of the target insects at any stage in their life cycle. Such means can comprise a complete killing action, eradication, arresting in growth, inhibition, reducing in number, reproductive inhibition (such as ovicidal or chemisterilant) or any combination thereof. The term "control" as employed in the specification and claims of this application is to be construed as meaning "insecticidal" or protecting plants from insect damage. By "insecticidally effective amount" is meant that dosage of active substance sufficient to exert insect "control."

The compounds of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations," (1973), edited by Wade Van Valkenburg. In these compositions and formulations, the active substance or substances are mixed with conventional inert agronomically acceptable (i.e., plant compatible and/or pesticidally inert) diluents or extenders such as solid carrier material or liquid carrier material, of the type usable in conventional compositions or formulations. By agronomically acceptable carrier is meant any substance which can be used to dissolve, disperse or diffuse the active ingredient in the composition without impairing the active ingredient's effectiveness and which by itself has no significant detrimental effect on the soil, equipment, desirable plants or agronomic environment. If desired, conventional adjuvants such as surfactants, stabilizers, antifoam agents and antidrift agents may also be added.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparation, which are diluted with water before or during use.

Baits are preparations generally comprising a food or other substance attractive to the target pest, that includes at least one lethal or non-lethal toxicant. Lethal toxicants kill the pest upon ingesting the bait while non-lethal toxicants change the behavior, feeding habits and physiology of the pest for the purpose of control.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cottonseed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or nonionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolysates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1% and 99% by weight, and preferably between about 1% and 75% by weight, of the mixture. Carrier composition mixtures suitable for direct application or field application generally contemplate those in which the active compound is used in an amount substantially between about 0.0001% and 5%, preferably between about 0.001% and 3%, by weight of the mixture. Thus the present invention contemplates overall formulations and compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant (e.g., a surface-active agent, such as an emulsifying agent and/or a dispersing agent), and an amount of the active compound generally, between about 0.0001% and about 99% by weight of the composition, preferably between about 0.001% and about 90% by weight of the composition, and more preferably between about 0.01% and about 75% by weight of the composition, which is effective for the purpose in question.

The active compounds can be applied as sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and often amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of killing, combatting or controlling insects, which comprises contacting insects with a correspondingly combative or toxic amount (i.e., an insecticidally effective amount) of at least one active compound of the invention alone or together with a carrier vehicle (composition or formulation) as noted above. The term "contacting" as employed in the specification and claims of this application is to be construed as applying to at least one of (a) such insects and (b) the corresponding habitat thereof (i.e., the locus to be protected, for example, to a growing crop or to an area where a crop is to be grown) the active compound of this invention alone or as a constituent of a composition or formulation. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example, pumice and attaclay), or chopped tobacco stems or the like.

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and similar substances. Alternatively organic carrier materials such as, for example, ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance optionally dissolved in a volatile solvent such as acetone, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products. In the case of flowables, a liquid inert carrier such as water is also included.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight depending upon toxicant solubility. A suitable liquid highly concentrated primary composition other than an emulsifiable concentrate is a solution of the active substance in a liquid which is readily miscible with water, for example, acetone, to which solution a dispersant and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e., preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients, the preparations according to the invention may also contain other substances commonly used in preparations of this kind.

For example, a lubricant, such as calcium stearate or magnesium stearate, may be added to a wettable powder or to a mixture to be granulated. Furthermore, there may, for example, be added "adhesives" such as polyvinylalcohol-cellulose derivatives or other colloidal materials, such as casein, to improve the adherence of this pesticide to the surface to be protected.

Representative preparation of compositions and formulations including the compounds of the present invention are set forth below as Examples A through I by way of illustration but not limitation.

Example A

| Granular | |
|---|---|
| Ingredient | %/wt. |
| Toxicant and toxicant impurities | 0.25 |
| Triton ® X-305 (binder) (Octylphenyl-30-ethylene oxide ethanol) | 0.25 |
| Agsorb 24/48 (diluent) (Montmorillonite clay) | 99.50 |

Preparation: The toxicant and Triton® X-305 are dissolved into methylene chloride and the mixture is added to the Agsorb® with continuous mixing. The methylene chloride is then allowed to evaporate.

Example B

| Dust | |
|---|---|
| Ingredient | %/wt. |
| Toxicant and toxicant impurities | 1.0 |
| Talc | 99.0 |

Preparation: Toxicant is dissolved in excess acetone and the mixture is impregnated onto the talc. The acetone is then permitted to evaporate.

Example C

| Wettable Powder | |
|---|---|
| Ingredient | %/wt. |
| Toxicant and toxicant impurities | 31.3 |
| Duponal? WA Dry (wetter) (Sodium lauryl sulfate) | 2.0 |
| Reax? 45A (dispersant) (Sodium lignin sulfonate) | 5.0 |
| Barden clay (diluent) | 31.7 |
| HiSil? 233 (diluent) (Sodium silica) | 30.0 |

Preparation: The toxicant, optionally dissolved in a volatile solvent, is absorbed onto the Barden clay and HiSil® carriers. The Duponal® and Reax® are then added and the entire dry mixture blended until homogeneous. The composition is then micronized to a fine particle size.

Example D

| Emulsifiable Concentrate | |
|---|---|
| Ingredient | %/wt. |
| Toxicant and toxicant impurities | 15.0 |
| Sponto? 232T (emulsifier) (Anionic and nonionic blend of the following surfactants: calcium dodecyl benzene sulfonate; and ethoxylated alkylphenol) | 6.0 |
| Sponto? 234T (emulsifier) (Anionic and nonionic blend of the following surfactants: calcium dodecyl benzene sulfonate; and ethoxylated alkylphenol) | 4.0 |
| Cyclohexanone (solvent) | 22.5 |
| Tenneco? 500-100 (solvent) (Aromatic solvent mixture principally comprising xylene, cumene and ethyl benzene having a boiling point range of 290–345° F.) | 52.5 |

Preparation: All ingredients are mixed together with continuous agitation until a homogeneous clear solution is obtained.

Example E

| Aerosol | |
|---|---|
| Ingredient | %/wt. |
| Toxicant and toxicant impurities | 0.5 |
| Freon 12 | 99.5 |

Preparation: The components are mixed and packaged under pressure in a suitable container equipped with a release spray valve.

Example F

| Fumigating Candle or Fumigating Powder | |
|---|---|
| Ingredient | %/wt. |
| Toxicant and toxicant impurities | 1.0 |
| Wood dust | 96.0 |
| Starch | 3.0 |

Preparation: Toxicant, wood dust, and starch are blended together and then molded into a candle using a small amount of water to activate the starch.

Example G

| Bait | |
|---|---|
| Method A | |
| Ingredient | %/wt. |
| Toxicant and toxicant impurities | 1.00 |
| Wheat Bran (carrier and attractant) | 89.95 |

-continued

Bait

| Method A Ingredient | %/wt. |
|---|---|
| Corn Syrup (attractant) | 7.00 |
| Corn Oil (attractant) | 2.00 |
| Kathon ® 4200 (preservative) (2-n-octyl-4-isothiazolin-3-one) | 0.05 |

Preparation: The corn oil and corn syrup are added to the wheat bran with adequate mixing. The toxicant and Kathon® are premixed with excess acetone and this solution is added to the wheat bran base with continued mixing. The acetone is then permitted to evaporate.

| Method B Ingredient | %/wt. |
|---|---|
| Toxicant and toxicant impurities | 0.06 |
| Granulated Sugar (carrier and attractant) | 99.94 |

Example H

Pellet

Same as Example G, Method A, with this addition: the bait composition is formed into ¼" diameter by ⅜" long pellets using a suitable die and press apparatus

Example I

| Flowable Ingredient | %/wt. |
|---|---|
| Toxicant and toxicant impurities | 31.3 |
| Duponal? WA Dry (wetter) (Sodium lauryl sulfate) | 2.0 |
| Reax? 45A (dispersant) (Sodium lignin sulfonate) | 5.0 |
| HiSil? 233 (diluent) (Sodium silica) | 30.0 |
| Kelzan? (thickener) (Xanthan gum) | 0.5 |
| Water | 31.2 |

Preparation: The toxicant is absorbed onto the HiSil® carrier. The Duponal® and Reax® are then added and the entire dry mixture blended until homogeneous. The composition is then micronized to a fine particle size. The resulting powder is suspended in water and the Kelzan® added.

Compositions and formulations according to the present invention may also include known pesticidal compounds. This expands the spectrum of activity of the preparations and may give rise to synergism.

The following known insecticidal, fungicidal and acaricidal compounds are suitable for use in such a combined preparation.

Insecticides such as: achloroepoxyoctahydrodimethanonaphthalene; Carbamates, for example, N-methyl-1-naphthylcarbamate; Dinitrophenols, for example, 2-methyl-4,6-dinitrophenol and 2-(2-butyl)-4,6-dinitrophenyl-3,3-dimethylacrylate; Organic phosphorus compounds, such as dimethyl-2-methoxy-3-carbonyl-1-methylvinyl phosphate, 0,0-diethyl-0-p-nitrophenylphosphorothioate; N-monomethylamide of 0,0-dimethyldithiophosphorylacetic acid; Diphenylsulfides, for example, p-chlorobenzyl or p-chlorophenyl sulfide and 2,4,4',5-tetrachlorodiphenylsulfide; Diphenylsulfonates, for example, p-chlorophenylbenzenesulfonate; Methylcarbinols, for example, 4,4-dichloro-1-trichloromethylbenzhydrol; Quinoxaline compounds, such as methylquinoxaline dithiocarbonate; Amidines such as N'-(4-chloro-2-methylphenyl) N,N-dimethylformamidine; Pyrethroids such as Allethrin; Biologicals such as *Bacillus thuringiensis* preparations; Organic tin compounds such as tricyclohexyltin hydroxide; Synergists such as piperonyl butoxide; Insect growth regulators such as N-benzoyl-phenyl ureas, for example, diflubenzuron.

Fungicides such as: Organic mercury compounds, for example, phenylmercuryacetate and methylmercurycyanoguanide; Organic tin compounds, for example, triphenyltin hydroxide and triphenyltin acetate; Alkylenebisdithiocarbamates, for example, zinc ethylenebisthiocarbamate and manganese ethylenebisdithiocarbamate; and 2,4-dinitro-6-(2-octyl-phenylcrotonate), 1-bis(dimethylamino)phosphoryl-3-phenyl-5-amino-1,2,4-triazole, 6-methylquinoxaline-2,3-dithiocarbonate, 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

Biological Activity

It has been found by biological evaluation that compounds according to the present invention have pesticidal activity and are capable of controlling larvae and adult forms of pests, especially insects from the orders Lepidoptera and Coleoptera and most especially insects from the order Lepidoptera. One skilled in the art will know how to determine the activity of a given compound against a given insect and the dosage required to obtain general or selective insecticidal effects. The compounds of the present invention in part affect the normal development of insects, particularly insects from the order Lepidoptera, by directly and/or indirectly influencing the moulting process.

As previously noted, the compounds of the present invention are particularly suitable for controlling plant destructive insects in crops of cultivated plants, such as, but not limited to, cotton, vegetables, corn and other cereals and the like; forestry, such as, but not limited to, birch, spruce, pine, fir and the like; and ornamental plants, flowers and trees. Compounds of the present invention are also particularly suitable for controlling insects destructive to stored commodities such as seeds and the like; fruit crops, such as, but not limited to fruit and/or citrus trees, raspberry bushes and the like; and turf, such as, but not limited to, lawns, sod and the like.

In evaluating the pesticidal activity of the compounds of this invention, the following test procedures were employed.

Unless a different application rate is indicated in Table XX, a test solution containing 600 parts per million (ppm) was made by dissolving the test compound in a solvent (acetone:methanol, 1:1), adding water to give an acetone:methanol:water system of 5:5:90 and then a surfactant. A 1:1 mixture of an alkylarylpolyetheralcohol (sold under the trademark Triton® X-155) and a modified phthalic glycerol alkyl resin (sold under the trademark Triton® B-1956) was utilized at the equivalent of 1 ounce per 100 gal. of test solution as a surfactant.

Initial evaluations were made on one or more of the following pests:

| | Code | |
|---|---|---|
| Symbol | Common Name | Latin Name |
| SAW | Southern Armyworm | *Spodoptera eridania* |
| MBB | Mexican Bean Beetle | *Epilachna varivestis* |
| BW | Boll Weevil | *Anthonomus grandis grandis* |

For the foliar bean beetle and armyworm tests, individual bean (*Phaseolus limensis* var. Woods' Prolific leaves are placed on moistened pieces of filter paper in Petri dishes. The leaves are then sprayed with the test solution using a rotating turntable and allowed to dry. The dishes are infested with 10 third instar larvae of Southern armyworm or Mexican bean beetle. The dishes are then covered.

For the Boll Weevil test ten adult weevils are placed in a 0.5 pint glass Mason jar containing a small cube of apple. The weevils are confined to the jars by fiberglass screen mesh secured by a screw-type rim cap. The jars are then sprayed with the test solution using a rotating turntable, directing the spray through the mesh into the jar.

The rotating turntable consists of a fixed, continuously operating spray nozzle under which targets are rotated at a fixed speed and distance. If the target is a Petri dish (such as for the armyworm), the distance from the nozzle is 15 inches. If the target is a Mason jar, the distance between the screened lid and the nozzle is 6 inches (10 inches from the base of the jar to the nozzle). The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and No. 70 air cap. At the 10 psig air pressure used and with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

All treatments are maintained at 75–80° F. under continuous fluorescent light in a well-ventilated room.

For soil treatment (systemic) trials, a portion of the 600 ppm test solution is diluted to 150 ppm. Ten (10) ml of the 150 ppm test solution is pipetted into soil (approximately 200 g of standard greenhouse soil) in a 3-inch pot containing a lima bean seedling. This results in a soil concentration of approximately 8 ppm. Treated plants are maintained under existing greenhouse conditions for one week. Two bean leaves are removed and placed individually on moist filter paper in Petri dishes. One leaf is infested with 10 third instar larvae of Mexican bean beetle. The other leaf is infested with 10 third instar larvae of Southern armyworm. The dishes are then covered and held for 3 days at which time the percent control (mortality) is determined. A second observation may be made 6 days after infesting the dishes if the experimenter feels the effect may not be complete or moribund insects appear to evidence signs of some recovery. Where necessary, untreated bean leaves are introduced into dishes held for a second observation to preclude insect starvation.

The results of the initial insecticidal evaluations are given in Table XX.

Armyworm and bean beetle spray (foliar) results are 96 hour observations unless otherwise noted. Boll weevil spray results are 48 hour observations unless, in the discretion of the experimenter, particular evaluations were held for 96 hour observations if it is believed the effect of a test compound may not be complete or moribund insects appear to evidence some signs of recovery. If, after 96 hours, there was a change in the percent control, it is shown in parentheses. Soil treatment results are 72 hour observations. At the discretion of the experimenter, particular evaluations were held for 144 hour observations. If, after 144 hours, there was a change in the percent control, it is shown in parentheses. Evaluations are based on a scale of 0–100 percent in which 0 equals no activity and 100 equals total kill.

TABLE XX

Initial Biological Evaluations

| Ex. No. | Foliar Application Test Species | | | Soil Application Test Species | |
|---|---|---|---|---|---|
| | SAW | MBB | BW | MBB | SAW |
| 1 | 100$^a$ | 0 | 0 | 80 | 0 |
| 2 | 100 | 0 | 0 | 20 | 0 |
| 3 | 100 | 60$^a$ | 0 | 100 | 100 |
| 4 | 100 | 0 | 0 | 60 | 0 |
| 5 | 100 | 0 | 0 | 50 | 0 |
| 6 | 40 | 0 | 0 | —$^b$ | — |
| 7 | 100 | 0 | 0 | 50 | 0 |
| 8 | 10 | 0 | 0 | — | — |
| 9 | 100 | 0 | 0 | 70 | 100 |
| 10 | 100 | 0 | 0 | 60 | 0 |
| 11 | 100 | 0 | 0 | 20 | 100 |
| 12 | 20$^d$ | 100 | 0 | 50 | 0 |
| 13 | 100 | 0 | 0 | 20 | 100 |
| 14 | 20$^d$ | 0$^d$ | 60$^d$ | 0$^d$ | 0$^d$ |
| 15 | 100 | 0 | 0 | 20 | 0 |
| 16 | 100 | 0 | 0 | 30 | 100 |
| 17 | 100 | 0 | 0 | 40 | 100 |
| 18 | 100 | 100 | 0 | 100 | 100 |
| 19 | 100 | 0 | 100 | 20 | 0 |
| 20 | 100 | 0 | 0 | — | — |
| 21 | 100 | 0 | 0 | — | — |
| 22 | 100 | 0 | 0 | 40 | 100 |
| 23 | 100 | 0 | 100 | — | — |
| 24 | 100 | 0 | 80 | — | — |
| 25 | 100 | 0 | 0 | — | — |
| 26 | 100 | 100 | 0 | 0 | 100 |
| 27 | 100$^d$ | 0$^d$ | 20$^d$ | 20(40)$^d$ | 70$^d$ |
| 28 | 10 | 0 | 0 | — | — |
| 29 | 100 | 0 | 0 | 0 | 40 |
| 30 | 100 | 0 | 0 | 0 | 10 |
| 31 | 100 | 100 | 0 | 40 | 100 |
| 32 | 0$^d$ | 20a,c | 20$^c$ | — | — |
| 33 | 100 | 40 | 0 | 20 | 0 |
| 34 | 100 | 20 | 0 | 70 | 100 |
| 35 | 100 | 100 | 0 | 100 | 100 |
| 36 | 100 | 100 | 20 | 90 | 100 |
| 37 | 100 | 0 | 0 | — | — |
| 38 | 100 | 90 | 20 | 0(60) | 100 |
| 39 | 100 | 0 | 0 | 0 | 20 |
| 40 | 40 | 20 | 20 | 0 | 0 |
| 41 | 100 | 0 | 20 | 20 | 100 |
| 42 | 100 | 100 | 0 | 100 | 100 |
| 43 | 100 | 100 | 0 | 100 | 100 |
| 44 | 100 | 10 | 0 | 0(20) | 0 |
| 45 | 100 | 0 | 0 | 0(40) | 0(40) |
| 46 | 100 | 0 | 60 | 40(80) | 60(80) |
| 47 | 100 | 100 | 0 | 80(90) | 100 |
| 48 | 100 | 100 | 0(40) | 40(60) | 100 |
| 49 | 100 | 100 | 40(80) | 10(60) | 100 |
| 50 | 100 | 0 | 40(80) | 40(70) | 0(10) |
| 51 | 100 | 100 | 0 | 70(100) | 30 |
| 52 | 100 | 100 | 0 | 20(30) | 20(50) |
| 53 | 100 | 0 | 40 | 20(60) | 100 |

TABLE XX-continued

Initial Biological Evaluations

| Ex. No. | Foliar Application Test Species | | | Soil Application Test Species | |
|---|---|---|---|---|---|
| | SAW | MBB | BW | MBB | SAW |
| 54 | 100 | 20 | 0 | 0 | 0 |
| 55 | 100 | 10 | 0 | 0 | 0 |
| 56 | 100 | 100 | 0 | 60(80) | 100 |
| 57 | 100 | 0 | 0 | 40(60) | 0 |
| 58 | 100 | 20 | 0 | 20 | 0 |
| 59 | 100 | 70 | 20 | 20 | 100 |
| 60 | 100 | 40 | 0 | 0 | 0 |
| 61 | 80[d] | 0 | 0 | 60(80) | 0 |
| 62 | 100 | 40 | 0 | 20 | 100 |
| 63 | 100 | 10 | 0 | 20 | 0 |
| 64 | 100 | 20 | 0 | 0(100) | 10(50) |
| 65 | 100 | 20 | 0 | 0(40) | 100 |
| 66 | 100 | 70 | 0 | 40(80) | 40(50) |
| 67 | 100 | 40 | 0 | 20(80) | 100 |
| 68 | 100 | 10 | 20 | 20 | 0 |
| 69 | 100 | 40 | 0 | 20 | 0 |
| 70 | 100 | 40 | 20 | 0(20) | 0 |
| 71 | 100[c] | 60 | 0 | 0(20) | 0 |
| 72 | 60 | 0 | 0 | 20 | 0 |
| 73 | 100 | 100 | 0 | 40(80) | 100 |
| 74 | 100 | 80 | 0 | 20 | 0 |
| 75 | 100 | 60 | 0 | 0 | 0 |
| 76 | 100 | 60 | 0 | 0(20) | 0 |
| 77 | 100 | 100 | 0 | 0 | 0 |
| 78 | 90 | 40 | 0 | 20 | 0 |
| 79 | 0[d] | 0 | 20 | 0 | 0 |
| 80 | 20[d] | 0 | 20 | 0 | 0 |
| 81 | 100 | 0 | 20 | 0 | 20 |
| 82 | 100 | 0 | 0 | 0 | 0 |
| 83 | 100 | 100 | 0 | 60(100) | 100 |
| 84 | 10 | 0 | 0 | 0 | 0 |
| 85 | 100 | 30 | 0 | 0 | 20 |
| 86 | 100 | 30 | 20 | 0 | 80(100) |
| 87 | 100 | 40 | 40 | 0 | 40(50) |
| 88 | 100 | 20 | 0 | 0 | 0 |
| 89 | 100 | 0 | 0 | 0 | 100 |
| 90 | 100 | 0 | 0 | 0 | 90 |
| 91 | 100a,c | 0 | 40 | 0 | 0 |
| 92 | 100 | 50 | 0 | 0 | 90(100) |
| 93 | 100 | 0 | 0 | 0 | 0 |
| 94 | 0[d] | 10 | 0 | 0 | 0 |
| 95 | 100 | 100 | 20 | 40(100) | 100 |
| 96 | 100 | 30 | 0 | 0 | 0 |
| 97 | 100 | 0 | 20 | 0 | 0 |
| 98 | 100 | 0 | 0 | 0 | 100 |
| 99 | 100 | 60 | 0 | 40(80) | 100 |
| 100 | 100 | 100 | 0 | 80(100) | 100 |
| 101 | 100 | 0 | 0 | 20 | 0 |
| 102 | 100 | 0 | 0 | 20 | 0(40) |
| 103 | 100 | 100 | 0 | 0(60) | 100 |
| 104 | 100 | 0 | 0(20) | 0 | 40(100) |
| 105 | 100 | 0 | 40 | 0 | 100 |
| 106 | 80 | 0 | 60 | 0 | 0(100) |
| 107 | 100 | 0 | 0 | 0(40) | 100 |
| 108 | 100 | 0 | 0 | 0 | 0 |
| 109 | 100 | 20 | 0 | 0(100) | 100 |
| 110 | 100 | 70 | 0 | 100 | 90(100) |
| 111 | 100 | 100 | 0 | 0 | 0 |
| 112 | 100 | 100 | 20 | 20(40) | 90(100) |
| 113 | 100 | 100 | 0 | 100 | 100 |
| 114 | 100 | 0 | 0 | 0 | 10 |
| 115 | 100 | 100 | 0 | 20(60) | 90(100) |
| 116 | 100 | 10 | 0 | 0 | 0 |
| 117 | 100 | 10 | 0 | 40(80) | 100 |
| 118 | 100 | 10 | 0 | 0 | 90(100) |
| 119 | 100 | 0 | 0 | 0 | 0 |
| 120 | 100 | 30 | 20 | 0 | 0 |
| 121 | 100 | 100 | 0 | 20(40) | 100 |
| 122 | 70 | 20 | 0 | 0 | 20(50) |
| 123 | 100 | 0 | 0 | 0(100) | 100 |
| 124 | 100 | 100 | 0 | 0 | 20(30) |
| 125 | 100 | 0 | 0 | 0 | 0 |
| 126 | 100 | 10 | 0 | 0 | 0 |
| 127 | 100 | 10 | 0 | 20 | 0 |
| 128 | 100 | 0 | 0 | 0 | 0 |
| 129 | 100 | 40 | 40(60) | 100(80) | 80(100) |
| 130 | 100 | 0 | 0 | 0(20) | 100 |
| 131 | 100 | 0 | 0 | 0 | 100 |
| 132 | 100 | 0 | 0 | 20(40) | 0 |
| 133 | 100 | 10 | 0 | 0 | 0 |
| 134 | 100 | 10 | 0 | 0 | 10(30) |
| 135 | 100 | 0 | 0 | 20(40) | 60 |
| 136 | 100 | 70 | 0 | 20 | 30(50) |
| 137 | 100 | 10 | 0 | 40(60) | 0 |
| 138 | 100 | 0 | 0 | 0 | 90(100) |
| 139 | 100 | 0 | 0 | 0(20) | 0 |
| 140 | 100 | 0 | 0 | 20 | 0 |
| 141 | 100 | 100 | 0 | 20(100) | 100 |
| 142 | 100 | 0 | 0 | 20 | 40 |
| 143 | 0[d] | 0 | 0 | 20 | 0 |
| 144 | 0[d] | 10a,c | 20[c] | 0 | 0 |
| 145 | 30[c] | 0 | 0[c] | 0 | 0 |
| 146 | 100 | 20 | 40(60) | 0 | 0 |
| 147 | 0[d] | 20[d] | 20[d] | 0[d] | 0[d] |
| 148 | 60[d] | 0 | 40 | 0 | 20(0) |
| 149 | 20[c] | 20a,c | 0[c] | 0 | 0 |
| 150 | 20[c] | 0 | 0[c] | 0 | 0 |
| 151 | 0 | 0 | 0 | 0 | 0 |
| 152 | 100 | 0 | 0 | 0 | 0 |
| 153 | 100 | 0 | 0 | 0 | 80(90) |
| 154 | 100 | 10 | 0 | 0 | 0 |
| 155 | 0[d] | 30 | 0 | 0(20) | 0 |
| 156 | 10[c] | 0 | 0[c] | 0 | 0 |
| 157 | 0[d] | 10 | 20 | 0 | 0 |
| 158 | 20 | 0 | 0 | 0 | 0 |
| 159 | 10 | 0 | 0 | 0 | 0 |
| 160 | 20[d] | 0 | 0 | 20 | 0 |
| 161 | 30 | 0 | 0 | 0(20) | 0 |
| 162 | 70 | 20 | 0 | 40(60) | 0 |
| 163 | 20 | 20 | 0 | 0(20) | 0 |
| 164 | 100[d] | 0 | 20 | 40 | 0 |
| 165 | 20[c] | 10 | 0 | 0 | 0 |
| 166 | 10 | 10 | 0 | 0 | 0 |
| 167 | 30 | 0 | 0 | 0 | 0 |
| 168 | 10 | 40 | 0 | 0 | 0 |
| 169 | 0[d] | 30 | 0 | 0 | 0 |
| 170 | 0[d] | 10 | 0 | 0 | 0 |
| 171 | 100 | 40 | 0 | 0 | 0 |
| 172 | 100 | 0 | 0 | 0 | 0 |
| 173 | 60 | 30 | 20 | 0 | 0 |
| 174 | 100 | 0 | 0 | 0 | 80(100) |
| 175 | 100 | 0 | 0 | 0 | 0 |
| 176 | 0[d] | 10 | 0 | 0 | 0 |
| 177 | 100 | 30 | 0 | 0 | 10 |
| 178 | 100 | 10 | 0 | 0 | 10 |
| 179 | 90 | 0 | 20 | 0 | 0 |
| 180 | 100 | 0 | 0 | 0 | 0 |
| 181 | 100 | 10 | 0 | 0 | 0 |
| 182 | 100 | 0 | 0 | 0 | 0 |
| 183 | 30 | 80 | 0 | 0(100) | 0(100) |
| 184 | 100 | 10 | 0 | 0 | 0 |
| 185 | 30[c] | 20a,c | 0[c] | 0 | 0 |
| 186 | 30[c] | 10[d] | 30[d] | 20[d] | 0[d] |
| 187 | 100 | 0 | 0 | 0(20) | 0(10) |
| 188 | 100[c] | 0 | 0[c] | 0 | 0 |
| 189 | 100[c] | 0 | 20 | 0 | 0 |
| 190 | 100 | 0 | 0 | 0(40) | 20(60) |
| 191 | 90 | 0 | 0 | 0 | 0 |
| 192 | 20 | 0 | 0 | 0 | 0 |
| 193 | 100 | 0 | 0 | 0 | 0 |
| 194 | 100 | 80 | 20 | 20(60) | 100 |
| 195 | 100 | 80 | 0 | 80(100) | 100 |
| 196 | 100 | 0 | 0 | 0 | 100 |
| 197 | 100 | 0 | 20 | 0(20) | 100 |

TABLE XX-continued

Initial Biological Evaluations

| Ex. No. | Foliar Application Test Species | | | Soil Application Test Species | |
|---|---|---|---|---|---|
| | SAW | MBB | BW | MBB | SAW |
| 198 | 100 | 0 | 0 | 20 | 90(100) |
| 199 | 20 | 10 | 0 | 20 | 30 |
| 200 | 100 | 0 | 0 | 0(20) | 90 |
| 201 | 100 | 0 | 0(60) | 0 | 20(30) |
| 202 | 40 | 20 | 0 | 40 | 0 |
| 203 | 60 | 0 | 20(60) | 0 | 0 |
| 204 | 50 | 0 | 0 | 0 | 0 |
| 205 | 100 | 10 | 0 | 20 | 100 |
| 206 | 100 | 10 | 0 | 0 | 100 |
| 207 | 0[d] | 20[d] | 20[d] | 0[d] | 0(10)[d] |
| 208 | 100 | 0 | 0 | 0(20) | 90 |
| 209 | 100 | 10 | 0 | 60(20) | 100 |
| 210 | 20[c] | 10 | 40 | 0 | 0 |
| 211 | 20 | 10 | 0 | 0 | 0 |
| 212 | 100 | 0 | 0 | 0 | 90(100) |
| 213 | 100 | 0 | 40 | 0 | 0 |
| 214 | 100 | 0 | 0 | 0 | 40(60) |
| 215 | 100 | 10 | 0 | 0(20) | 100 |
| 216 | 100 | 0 | 20 | 20 | 50(60) |
| 217 | 100 | 60 | 0 | 20 | 100 |
| 218 | 90 | 10 | 0 | 0 | 0 |
| 219 | 60[c] | 0[c] | 0[c] | 0 | 0 |
| 220 | 100 | 0 | 0 | 0 | 100 |
| 221 | 60 | 10 | 0 | 20 | 0 |
| 222 | 100 | 10a,c | 0[c] | 0 | 0 |
| 223 | 100 | 10 | 0 | 40 | 100 |
| 224 | 40 | 10 | 20 | 0 | 0 |
| 225 | 100 | 20 | 0 | 0(20) | 100 |
| 226 | 100 | 10 | 0 | 0 | 0 |
| 227 | 100 | 0 | 0 | 0 | 30(40) |
| 228 | 100 | 0 | 20 | 0(40) | 100 |
| 229 | 60 | 20 | 0 | 0 | 0 |
| 230 | 100 | 50 | 0 | 60(80) | 100 |
| 231 | 60 | 20 | 0 | 40 | 60 |
| 232 | 100 | 0 | 0 | 20 | 0 |
| 233 | 100 | 0 | 0 | 40 | 60 |
| 234 | 100 | 10 | 0 | 0 | 100 |
| 235 | 100 | 60 | 0 | 100 | 100 |
| 236 | 100 | 10 | 0 | 0 | 30 |
| 237 | 100 | 20 | 0 | 0 | 0 |
| 238 | 90 | 60 | 0 | 0 | 0 |
| 239 | 100 | 0 | 0 | 0 | 0 |
| 240 | 30 | 10 | 0 | 0 | 0 |
| 241 | 100 | 0 | 0 | 0 | 0 |
| 242 | 50 | 30 | 0 | 0 | 0 |
| 243 | 10 | 20 | 0 | 0 | 0 |
| 244 | 100 | 0 | 0 | 0 | 70(80) |
| 245 | 100 | 0 | 0 | 0 | 80(90) |
| 246 | 100 | 10 | 0 | 0 | 0 |
| 247 | 100 | 0 | 0 | 0 | 0 |
| 248 | 100 | 0 | 0 | 0 | 0 |
| 249 | 100 | 0 | 0 | 0 | 0 |
| 250 | 80 | 50 | 0 | 0 | 10 |
| 251 | 100 | 20 | 20 | 20(40) | 60 |
| 252 | 100 | 0 | 0 | 0(20) | 100 |
| 253 | 100 | 10 | 20(40) | 0 | 20(30) |
| 254 | 100 | 0 | 0 | 0 | 0 |
| 255 | 100 | 100 | 0 | 0 | 0 |
| 256 | 100 | 0 | 0 | 0 | 0 |
| 257 | 100 | 0 | 0 | 20 | 20 |
| 258 | 40[c] | 90 | 40 | 100 | 0 |
| 259 | 100 | 10 | 0 | 0 | 0 |
| 260 | 100 | 20 | 0 | 0 | 0 |
| 261 | 0[d] | 10 | 0 | 0 | 0 |
| 262 | 60 | 0 | 0 | 0 | 0 |
| 263 | 100 | 30 | 0 | 20 | 40 |
| 264 | 80 | 0 | 80(100) | 0 | 10(30) |
| 265 | 0[c] | 10 | 0 | 0 | 0 |
| 266 | 0[d] | 10 | 0 | 0 | 0 |
| 267 | 100 | 0 | 0 | 0 | 0 |
| 268 | 40 | 0 | 0 | 0 | 0 |
| 269 | 100 | 0 | 60(80) | 0 | 0 |
| 270 | 100 | 0 | 0 | 20(40) | 0 |
| 271 | 100 | 10 | 0 | 20(0) | 70 |
| 272 | 40 | 10 | 0 | 0 | 0 |
| 273 | 100 | 0 | 40(100) | 0 | 0 |
| 274 | 100 | 0 | 0 | 20 | 50(90) |
| 275 | 40[c] | 30a,c | 0[c] | 0 | 0 |
| 276 | 100 | 10 | 20(60) | 0 | 0 |
| 277 | 100 | 30 | 0 | 20 | 0 |
| 278 | 60 | 0 | 0 | 0 | 0 |
| 279 | 100 | 10 | 0 | 0 | 0 |
| 280 | 100 | 10 | 20(80) | 0 | 0 |
| 281 | 100 | 0 | 0 | 0 | 0 |
| 282 | 100 | 30 | 0 | 0 | 0 |
| 283 | 100 | 0 | 0 | 0 | 0 |
| 284 | 90 | 50 | 0 | 0 | 0 |
| 285 | 100 | 50 | 0 | 0 | 0 |
| 286 | 100 | 0 | 0 | 0 | 0 |
| 287 | 100 | 10 | 0 | 0 | 0 |
| 288 | 100 | 0 | 0 | 0 | 0 |
| 289 | 100 | 40 | 0 | 20 | 0 |
| 290 | 100 | 50 | 0 | 0 | 0 |
| 291 | 100 | 30 | 0 | 0 | 80(90) |
| 292 | 100 | 10 | 0 | 0 | 100 |
| 293 | 20 | 30 | 20 | 0 | 0 |
| 294 | 0[d] | 10a,c | 0[c] | 0 | 0 |
| 295 | 100 | 100 | 0 | 0 | 60(80) |
| 296 | 100 | 50 | 0 | 60(100) | 100 |
| 297 | 100 | 40 | 0 | 0 | 0 |
| 298 | 80 | 30 | 0 | 0 | 0 |
| 299 | 100 | 20 | 0 | 0 | 0 |
| 300 | 100 | 0 | 0 | 0(20) | 100 |
| 301 | 100 | 0 | 0 | 0 | 70(100) |
| 302 | 100 | 0 | 0 | 0 | 0 |
| 303 | 100 | 30 | 0 | 0 | 0 |
| 304 | 70 | 90 | 0 | 0 | 0 |
| 305 | 100 | 40 | 0 | 0 | 60(100) |
| 306 | 100 | 40 | 0 | 0 | 0 |
| 307 | 100 | 60 | 0 | 0 | 0 |
| 308 | 0[d] | 40 | 0 | 0 | 0 |
| 309 | 100 | 60 | 0 | 0 | 0 |
| 310 | 100 | 40 | 0 | 0 | 0 |
| 311 | 100 | 100 | 0 | 40(60) | 90(100) |
| 312 | 100 | 0 | 0 | 0 | 10 |
| 313 | 100 | 20 | 0 | 0 | 0 |
| 314 | 100 | 0 | 0 | 0 | 0 |
| 315 | 100 | 0 | 0 | 20(40) | 0 |
| 316 | 100 | 0 | 0 | 20 | 100 |
| 317 | 100 | 20 | 0 | 0 | 80(100) |
| 318 | 100 | 20 | 0 | 0 | 90(100) |
| 319 | 100 | 20 | 0 | 0 | 100 |
| 320 | 100 | 0 | 0 | 40 | 0 |
| 321 | 80 | 0 | 0 | — | — |
| 322 | 100 | 0 | 0 | — | — |
| 323 | 100 | 20 | 0 | — | — |
| 324 | 100 | 20 | 0 | — | — |
| 325 | 100 | 10 | 0 | — | — |
| 326 | 100 | 30 | 0 | — | — |
| 327 | 30 | 30 | 0 | — | — |
| 328 | 0[d] | 50 | 0 | — | — |
| 329 | 100 | 30 | 0 | — | — |
| 330 | 100 | 30 | 0 | — | — |
| 331 | 100 | 30 | 0 | — | — |
| 332 | 100 | 70 | 0 | — | — |
| 333 | 30 | 0 | 0 | — | — |
| 334 | 100 | 0 | 0 | — | — |
| 335 | 90 | 70 | 0 | — | — |
| 336 | 100 | 30 | 0 | — | — |
| 337 | 50[c] | 30 | 0 | — | — |
| 338 | 100 | 40 | 0 | — | — |
| 339 | 100 | 0 | 20(80) | — | — |
| 340 | 100 | 0 | 0 | — | — |
| 341 | 100 | 100 | 0 | — | — |

TABLE XX-continued

Initial Biological Evaluations

| Ex. No. | Foliar Application Test Species | | | Soil Application Test Species | |
|---|---|---|---|---|---|
| | SAW | MBB | BW | MBB | SAW |
| 342 | 100 | 0 | 0 | — | — |
| 343 | 100 | 10 | 20(60) | — | — |
| 344 | 0[e] | 0 | 40 | — | — |
| 345 | 20 | 0 | 0 | — | — |
| 346 | 40[e] | 10a,c | 0[e] | — | — |
| 347 | 100 | 20 | 0 | — | — |
| 348 | 100[e] | 0 | 0[e] | — | — |
| 349 | 60 | 0 | 0 | — | — |
| 350 | 100 | 20 | 0 | — | — |
| 351 | 100 | 0 | 0 | — | — |
| 352 | 50 | 20 | 0 | — | — |
| 353 | 100 | 0 | 0 | — | — |
| 354 | 100 | 30 | 0 | — | — |
| 355 | 100[e] | 90 | 0 | — | — |
| 356 | 40[e] | 0 | 0[e] | — | — |
| 357 | 100 | 20 | 0 | — | — |
| 358 | 100 | 0 | 0 | — | — |
| 359 | 100 | 0 | 0 | — | — |
| 360 | 70[e] | 0 | 0[e] | — | — |
| 361 | 100 | 10 | 0 | — | — |
| 362 | 100 | 70 | 0 | — | — |
| 363 | 100 | 20 | 0 | — | — |
| 364 | 100 | 10 | 0 | — | — |
| 365 | 100 | 0 | 0 | — | — |
| 366 | 100 | 40 | 0 | — | — |
| 367 | 100 | 30 | 0 | — | — |
| 368 | 100 | 0 | 0 | — | — |
| 369 | 100 | 0 | 0 | — | — |
| 370 | 30 | 30 | 0 | — | — |
| 371 | 100 | 10 | 20 | — | — |
| 372 | 30 | 0 | 0 | — | — |
| 373 | 90 | 10 | 0 | — | — |
| 374 | 100 | 10 | 0 | — | — |
| 375 | 100[d] | 10 | 0 | — | — |
| 376 | 100[e] | 20 | 0 | — | — |
| 377 | 100 | 20 | 0 | — | — |
| 378 | 100 | 20 | 0 | — | — |
| 379 | 100 | 20 | 0 | — | — |
| 380 | 100 | 10 | 0 | — | — |
| 381 | 100 | 30 | 0 | — | — |
| 382 | 100 | 0 | 20 | — | — |
| 383 | 100 | 20 | 0 | — | — |
| 384 | 80 | 20 | 0 | — | — |
| 385 | 100 | 100 | 0 | — | — |
| 386 | 100 | 20 | 20 | — | — |
| 387 | 100 | 0 | 0 | — | — |
| 388 | 100 | 30 | 20(40) | — | — |
| 389 | 0[d] | 70 | 0 | — | — |
| 390 | 100 | 30 | 0 | — | — |
| 391 | 100 | 0 | 20(60) | — | — |
| 392 | 100 | 100 | 0 | — | — |
| 393 | 100 | 20 | 0 | — | — |
| 394 | 100 | 0 | 0 | — | — |
| 395 | 100 | 70 | 0 | — | — |
| 396 | 100 | 100 | 0 | — | — |
| 397 | 100 | 0 | 0 | — | — |
| 398 | 100 | 40 | 0 | — | — |
| 399 | 100 | 0 | 0 | — | — |
| 400 | 90 | 0 | 0 | — | — |
| 401 | 100 | 70 | 0 | — | — |
| 402 | 100 | 40 | 0 | — | — |
| 403 | 100 | 0 | 0 | — | — |
| 404 | 100 | 20 | 20(40) | — | — |
| 405 | 100 | 10 | 0 | — | — |
| 406 | 100 | 0 | 20 | — | — |
| 407 | 100 | 20 | 0 | — | — |
| 408 | 90 | 60 | 0 | — | — |
| 409 | 40 | 0 | 0 | — | — |
| 410 | 100 | 90 | 0 | — | — |
| 411 | 100 | 10 | 0 | — | — |
| 412 | 30 | 30 | 0 | — | — |
| 413 | 100 | 10 | 0 | — | — |
| 414 | 60 | 50 | 40 | — | — |
| 415 | 60 | 20 | 20(60) | — | — |
| 416 | 100 | 30 | 0 | — | — |
| 417 | 100 | 20 | 0 | — | — |
| 418 | 100 | 0 | 20 | — | — |
| 419 | 100 | 10 | 0 | — | — |
| 420 | 100 | 0 | 40 | — | — |
| 421 | 100 | 10 | 0 | — | — |
| 422 | 100 | 0 | 0 | — | — |
| 423 | 100 | 0 | 0 | — | — |
| 424 | 100 | 10 | 0 | — | — |
| 425 | 100 | 70 | 0 | — | — |
| 426 | 100 | 0 | 0 | — | — |
| 427 | 100 | 20 | 0 | — | — |
| 428 | 100 | 10 | 20(80) | — | — |
| 429 | 100 | 20 | 0 | — | — |
| 430 | 100 | 0 | 0 | — | — |
| 431 | 90 | 40 | 0 | — | — |
| 432 | 100 | 20 | 0 | — | — |
| 433 | 100 | 0 | 0 | — | — |
| 434 | 100 | 10 | 20 | — | — |
| 435 | 100 | 20 | 0 | — | — |
| 436 | 0[d] | 30 | 0 | — | — |
| 437 | 100 | 10 | 0 | — | — |
| 438 | 100 | 40 | 0 | — | — |
| 439 | 100 | 0 | 0 | — | — |
| 440 | 100 | 20 | 0 | — | — |
| 441 | 100 | 20 | 0 | — | — |
| 442 | 100 | 30 | 0 | — | — |
| 443 | 100 | 20 | 0 | — | — |
| 444 | 100 | 0 | 0 | — | — |
| 445 | 100 | 20 | 0 | — | — |
| 446 | 100 | 20 | 20 | — | — |
| 447 | 100 | 20 | 0 | — | — |
| 448 | 100 | 20 | 0 | — | — |
| 449 | 100 | 20 | 0 | — | — |
| 450 | 100 | 20 | 0 | — | — |
| 451 | 100 | 50 | 0 | — | — |
| 452 | 100 | 30 | 0 | — | — |
| 453 | 100 | 30 | 0 | — | — |
| 454 | 100 | 0 | 0 | — | — |
| 455 | 100 | 50 | 0 | — | — |
| 456 | 100 | 20 | 0 | — | — |
| 457 | 100 | 50 | 0 | — | — |
| 458 | 100 | 0 | 0 | — | — |
| 459 | 100 | 0 | 20 | — | — |
| 460 | 100 | 0 | 0 | — | — |
| 461 | 0[d] | 10a,c | 0[e] | — | — |
| 462 | 40 | 20 | 0 | — | — |
| 463 | 50 | 10 | 0 | — | — |
| 464 | 100 | 10 | 0 | — | — |
| 465 | 70 | 0 | 0 | — | — |
| 466 | 100 | 0 | 40 | — | — |
| 467 | 100 | 0 | 0 | — | — |
| 468 | 100 | 10 | 0 | — | — |
| 469 | 60[e] | 20 | 0 | — | — |
| 470 | 100 | 10 | 0 | — | — |
| 471 | 100 | 10 | 0 | — | — |
| 472 | 100 | 0 | 0 | — | — |
| 473 | 100 | 20 | 0 | — | — |
| 474 | 100[e] | 20 | 0 | — | — |
| 475 | 50[e] | 0 | 0[e] | — | — |
| 476 | 100 | 0 | 0 | — | — |
| 477 | 100 | 10 | 20 | — | — |
| 478 | 100 | 20 | 0 | — | — |
| 479 | 100 | 0 | 0 | — | — |
| 480 | 100 | 20 | 0 | — | — |
| 481 | 100 | 0 | 0 | — | — |
| 482 | 100 | 20 | 0 | — | — |
| 483 | 100 | 10 | 0 | — | — |
| 484 | 100 | 20 | 0 | — | — |
| 485 | 100 | 40 | 0 | — | — |

TABLE XX-continued

Initial Biological Evaluations

| Ex. No. | Foliar Application Test Species | | | Soil Application Test Species | |
|---|---|---|---|---|---|
| | SAW | MBB | BW | MBB | SAW |
| 486 | 100 | 20 | 0 | — | — |
| 487 | 100 | 50 | 0 | — | — |
| 488 | 100 | 0 | 0 | — | — |
| 489 | 100 | 40 | 20 | — | — |
| 490 | 100 | 0 | 0 | — | — |
| 491 | 60 | 20 | 0 | — | — |
| 492 | 100 | 0 | 0 | — | — |
| 493 | 100 | 20 | 0 | — | — |
| 494 | 100 | 0 | 0 | — | — |
| 495 | 100 | 10 | 0 | — | — |
| 496 | 100 | 0 | 0 | — | — |
| 497 | 100 | 10 | 0 | — | — |
| 498 | 100 | 0 | 60(80) | — | — |
| 499 | 100 | 40 | 0 | — | — |
| 500 | 100 | 10 | 0 | — | — |
| 501 | 100 | 30 | 0 | — | — |
| 502 | 100 | 10 | 20 | — | — |
| 503 | 90 | 30 | 0 | — | — |
| 504 | 100 | 40 | 0 | — | — |
| 505 | 100 | 30 | 20 | — | — |
| 506 | 100 | 0 | 0 | — | — |
| 507 | 60 | 20 | 0 | — | — |
| 508 | 100 | 0 | 0 | — | — |
| 509 | 100 | 70 | 0 | — | — |
| 510 | 100 | 10 | 0 | — | — |
| 511 | 100 | 10 | 0 | — | — |
| 512 | 90 | 20 | 0 | — | — |
| 513 | 100 | 10 | 0 | — | — |
| 514 | 100 | 30 | 0 | — | — |
| 515 | 100 | 100 | 0 | — | — |
| 516 | 100 | 10 | 0 | — | — |
| 517 | 100 | 10 | 0 | — | — |
| 518 | 100 | 30 | 0 | — | — |
| 519 | 100 | 10 | 0 | — | — |
| 520 | 100 | 30 | 0 | — | — |
| 521 | 100 | 50 | 0 | — | — |
| 522 | 100 | 10 | 0 | — | — |
| 523 | 100 | 10 | 0 | — | — |
| 524 | 90 | 30 | 0 | — | — |
| 525 | 100 | 30 | 0 | — | — |
| 526 | 100 | 10 | 0 | — | — |
| 527 | 100 | 0 | 0 | — | — |
| 528 | 100 | 0 | 0 | — | — |
| 529 | 100 | 10 | 0 | — | — |
| 530 | 100 | 10 | 0 | — | — |
| 531 | 100 | 10 | 0 | — | — |
| 532 | 100 | 20 | 0 | — | — |
| 533 | 100 | 0 | 0 | — | — |
| 534 | 100 | 10 | 0 | — | — |
| 535 | 100 | 0 | 0 | — | — |
| 536 | 100 | 10 | 0 | — | — |
| 537 | 100 | 0 | 0 | — | — |
| 538 | 100 | 20 | 0 | — | — |
| 539 | 100 | 0 | 0 | — | — |
| 540 | 100 | 10 | 0 | — | — |
| 541 | 100 | 0 | 0 | — | — |
| 542 | 100 | 0 | 0 | — | — |
| 543 | 100 | 0 | 0 | — | — |
| 544 | 100 | 0 | 0 | — | — |
| 545 | 100 | 0 | 0 | — | — |
| 546 | 100 | 0 | 0 | — | — |
| 547 | 100 | 0 | 0 | — | — |
| 548 | 100 | 30 | 20 | — | — |
| 549 | 100 | 30 | 0 | — | — |
| 550 | 100 | 40 | 0 | — | — |
| 551 | 100 | 0 | 0 | — | — |
| 552 | 100 | 30 | 20 | — | — |
| 553 | 100 | 40 | 0 | — | — |
| 554 | 100 | 20 | 0 | — | — |
| 555 | 100 | 20 | 0 | — | — |
| 556 | 100 | 10 | 0 | — | — |
| 557 | 30 | 30 | 0 | — | — |
| 558 | 100 | 20 | 0 | — | — |
| 559 | 100 | 50 | 0 | — | — |
| 560 | 90 | 0 | 0 | — | — |
| 561 | 100 | 30 | 20 | — | — |
| 562 | 100 | 0 | 0 | — | — |
| 563 | 100 | 10 | 0 | — | — |
| 564 | 100 | 0 | 0 | — | — |
| 565 | 100 | 0 | 0 | — | — |
| 566 | 40 | 70 | 0 | — | — |
| 567 | 100 | 40 | 20 | — | — |
| 568 | 100 | 0 | 0 | — | — |
| 569 | 100 | 20 | 0 | — | — |
| 570 | 100 | 10 | 0 | — | — |
| 571 | 100 | 50 | 0 | — | — |
| 572 | 100 | 80 | 0 | — | — |
| 573 | 100 | 20 | 0 | — | — |
| 574 | 100 | 0 | 0 | — | — |
| 575 | 100 | 0 | 20 | — | — |
| 576 | 100 | 20 | 0 | — | — |
| 577 | 100 | 0 | 0 | — | — |
| 578 | 100 | 40 | 0 | — | — |
| 579 | 100 | 40 | 0 | — | — |
| 580 | 100 | 0 | 0 | — | — |
| 581 | 100 | 0 | 0 | — | — |
| 582 | 100 | 0 | 0 | — | — |
| 583 | 100 | 30 | 0 | — | — |
| 584 | 100 | 0 | 0 | — | — |
| 585 | 100 | 0 | 0 | — | — |
| 586 | 100 | 0 | 0 | — | — |
| 587 | 100 | 10 | 0 | — | — |
| 588 | 100 | 40 | 0 | — | — |
| 589 | 100 | 40 | 0 | — | — |
| 590 | 100 | 30 | 0 | — | — |
| 591 | 100 | 0 | 0 | — | — |
| 592 | 100 | 40 | 0 | — | — |
| 593 | 100 | 40 | 0 | — | — |
| 594 | 100 | 10 | 0 | — | — |
| 595 | 100 | 10 | 20 | — | — |
| 596 | 100 | 80 | 0 | — | — |
| 597 | 100 | 40 | 0 | — | — |
| 598 | 100 | 10 | 20 | — | — |
| 599 | 100 | 40 | 0 | — | — |
| 600 | 100 | 30 | 0 | — | — |
| 601 | 100 | 10 | 0 | — | — |
| 602 | 100 | 10 | 0 | — | — |
| 603 | 100 | 20 | 0 | — | — |
| 604 | 100 | 10 | 0 | — | — |
| 605 | 100 | 20 | 20(80) | — | — |
| 606 | 80[d] | 20 | 0 | — | — |
| 607 | 80 | 10 | 0 | — | — |
| 608 | 100 | 30 | 0 | — | — |
| 609 | 100 | 20 | 0 | — | — |
| 610 | 0[d] | 20 | 0 | — | — |
| 611 | 30 | 30 | 0 | — | — |
| 612 | 0(30)[a] | 20 | 0 | — | — |
| 613 | 0(70)[a] | 50 | 0 | — | — |
| 614 | 10 | 20 | 0 | — | — |
| 615 | 100 | 20 | 0 | — | — |
| 616 | 100 | 0 | 0 | — | — |
| 617 | 100 | 10 | 0 | — | — |
| 618 | 100 | 10 | 0 | — | — |
| 619 | 100 | 0 | 0 | — | — |
| 620 | 70 | 30 | 20(40) | — | — |
| 621 | 100 | 10 | 0 | — | — |
| 622 | 100 | 70 | 0 | 60(100) | 100 |
| 623 | 100 | 0 | 0 | 0 | 20(50) |
| 624 | 100 | 80 | 0 | 0 | 80(100) |
| 625 | 100 | 10 | 20 | — | — |
| 626 | 100 | 90 | 0 | — | — |
| 627 | 100 | 0 | 0 | — | — |
| 628 | 100 | 40 | 0 | — | — |
| 629 | 100 | 0 | 0 | — | — |

TABLE XX-continued

Initial Biological Evaluations

| Ex. No. | Foliar Application Test Species | | | Soil Application Test Species | |
|---|---|---|---|---|---|
| | SAW | MBB | BW | MBB | SAW |
| 630 | 100 | 0 | 0 | — | — |
| 631 | 100 | 0 | 0 | — | — |
| 632 | 100 | 30 | 0 | — | — |
| 633 | 100 | 10 | 0 | — | — |
| 634 | 100 | 90 | 0 | — | — |
| 635 | $0^d$ | 100 | 0 | 0 | 0 |
| 636 | $80^d$ | 100 | 0 | 0 | 0 |
| 637 | 100 | 100 | 0 | 20(60) | 100 |
| 638 | 100 | 10 | 20 | — | — |
| 639 | 10 | 20 | 0 | — | — |
| 640 | 100 | 80 | 0 | 0 | 0 |
| 641 | 100 | 30 | 0 | — | — |
| 642 | 100 | 100 | 0 | — | — |
| 643 | 100 | 20 | 0 | — | — |
| 644 | 100 | 40 | 0 | — | — |
| 645 | 100 | 20 | 0 | — | — |
| 646 | 100 | 0 | 0 | 20 | 100 |
| 647 | 100 | 60 | 20 | 20 | 40(60) |
| 648 | 70 | 100 | 0 | 80(20) | 40(100) |
| 649 | 100 | 40 | 0 | 40 | 0(80) |
| 650 | $100^c$ | 10 | 0 | 0(40) | 0(20) |
| 651 | 90 | 60 | 40 | 80(60) | 0(20) |
| 652 | 20 | 10 | 0 | 0(40) | 40(60) |
| 653 | $0^d$ | 0 | 0 | 0(20) | 0 |
| 654 | 70 | 100 | 0 | 20(40) | 0 |
| 655 | 80 | 70 | 0 | 40(100) | 40(80) |
| 656 | 100 | 0 | 0 | 0 | 100 |
| 657 | 30 | 0 | 0 | 0 | 0 |
| 658 | $40^c$ | 90 | 20 | 80(100) | 0 |
| 659 | $30^c$ | 80 | 0 | 0(80) | 0 |
| 660 | $80^c$ | 70 | 0 | 0 | 0 |
| 661 | 100 | 20 | 0 | 0 | 0 |
| 662 | 70 | 40 | 20 | 0 | 0 |
| 663 | 100 | 0 | 0 | — | — |
| 664 | $100^c$ | 0 | 0 | 0 | 0 |
| 665 | 60 | 30 | 20(40) | 0(20) | 0 |
| 666 | 100 | 0 | 0 | — | — |
| 667 | 100 | 0 | 0 | — | — |
| 668 | $60^d$ | 20 | 0 | — | — |
| 669 | $20^d$ | 30 | 0 | — | — |
| 670 | 90 | 40 | 0 | — | — |
| 671 | 100 | 30 | 0 | — | — |
| 672 | 100 | 100 | 0 | — | — |
| 673 | 20 | 40 | 0 | — | — |
| 674 | 100 | 50 | 80 | — | — |
| 675 | 100 | 30 | 0 | — | — |
| 676 | $100^c$ | 80 | 0 | — | — |
| 677 | $70^c$ | 40 | 0 | — | — |
| 678 | 50 | 30 | 0 | — | — |
| 679 | 100 | 30 | 0 | — | — |
| 680 | 100 | 10 | 0 | — | — |
| 681 | 100 | 100 | 0 | — | — |
| 682 | 10 | 40 | 0 | — | — |
| 683 | 100 | 0 | 0 | 0 | 20 |
| 684 | $20^a$ | $100^a$ | 0 | — | — |
| 685 | $10^c$ | $10a,c$ | 40 | — | — |
| 686 | $20^c$ | $0a,c$ | 0 | — | — |
| 687 | $0^d$ | $30a,c$ | 0 | — | — |
| 688 | 100 | 100 | 0 | 60(100) | 100 |
| 689 | 90 | 50 | 0 | 40(100) | 0(20) |
| 690 | $0^d$ | $10^d$ | $0^d$ | $0^d$ | $0^d$ |
| 691 | $30^c$ | 10 | 0 | 0 | 0 |
| 692 | 80 | $0^a$ | 0 | — | — |
| 693 | $0^d$ | 20 | 0 | 0 | 0 |
| 694 | 80 | 80 | 40 | 0 | 0 |
| 695 | $60^d$ | 30 | 0 | 0 | 0 |
| 696 | $0^d$ | 40 | 20 | 20 | 0 |
| 697 | $20^c$ | 0 | 0 | 0 | 0 |
| 698 | 100 | 0 | 20 | 0 | 100 |
| 699 | 100 | 100 | 0 | 60(100) | 90 |
| 700 | $0^d$ | $100a,c$ | 0 | 0 | 0 |
| 701 | $90^c$ | 10 | 20 | 40(20) | 0 |
| 702 | $0^d$ | 100 | 0 | 0 | 0 |
| 703 | $10^a$ | $0^a$ | 0 | — | — |
| 704 | $0^d$ | 30 | 0 | — | — |
| 705 | 80 | 0 | 0 | — | — |
| 706 | 30 | 30 | 20 | — | — |
| 707 | 100 | 40 | 0 | — | — |
| 708 | 100 | 10 | 0 | — | — |
| 709 | $80^d$ | 100 | 20(40) | — | — |
| 710 | 100 | 30 | 0 | — | — |
| 711 | 100 | 30 | 0 | — | — |
| 712 | 100 | 20 | 0 | — | — |
| 713 | 100 | 60 | 0 | — | — |
| 714 | 100 | 40 | 0 | — | — |
| 715 | 100 | 20 | 0 | — | — |
| 716 | 100 | 0 | 0 | — | — |
| 717 | 100 | 40 | 0 | — | — |
| 718 | $10^d$ | 70 | 0 | — | — |
| 719 | $0^d$ | 20 | 0 | — | — |
| 720 | 100 | 0 | 0 | — | — |
| 721 | 100 | 30 | 0 | — | — |
| 722 | 50 | 0 | 40 | 0 | 0 |
| 723 | 100 | 80 | 40 | 60(100) | 90(100) |
| 724 | 90 | 10 | 0 | 0(20) | 0 |
| 725 | 100 | 0 | 0 | 0 | 0 |
| 726 | 100 | 30 | 0 | 20 | 100 |
| 727 | 100 | 30 | 0 | 100 | 100 |
| 728 | $0^d$ | $20^d$ | | $0^d$ | $0^d$ |
| 729 | 100 | 70 | 0 | 100 | 100 |
| 730 | 70 | 50 | 0 | 40(20) | 50(60) |
| 732 | 100 | 0 | 20 | 0 | 100 |
| 733 | 100 | 50 | 0 | 0 | 80(100) |
| 734 | $10^c$ | 0 | 20 | 0 | 0 |
| 735 | 100 | 10 | 0 | 20 | 80(100) |
| 736 | 100 | 0 | 0 | 0 | 90(100) |
| 737 | 100 | 0 | 0 | 0 | 0 |
| 738 | 100 | 80 | 0 | 80 | 100 |
| 739 | 100 | 20 | 0 | 0 | 0 |
| 740 | 30 | 30 | 0 | 0 | 0 |
| 741 | 100 | 0 | 0 | — | 0 |
| 742 | 100 | 0 | 0 | — | 0 |
| 743 | 100 | 40 | 0 | — | 0 |
| 744 | 100 | 20 | 0 | — | 0 |
| 745 | 100 | 10 | 0 | — | 0 |
| 746 | 100 | 0 | 0 | — | 0 |
| 747 | 70 | 20 | 0 | — | 0 |
| 748 | $100^d$ | $100^d$ | $0^d$ | $0^d$ | $0(10)^d$ |
| 749 | 100 | 0 | 0 | — | 0 |
| 750 | 20 | 30 | 0 | — | 0 |
| 751 | 100 | 0 | 20 | — | 0 |
| 752 | 10 | 20 | 0 | — | 0 |
| 753 | 100 | 20 | 0 | — | 0 |
| 754 | 100 | 70 | 0 | — | 0 |
| 755 | 100 | 10 | 0 | — | 0 |
| 756 | 100 | 0 | 0 | 0 | — |
| 757 | 100 | 0 | 0 | — | — |
| 758 | 100 | 100 | 0 | — | — |
| 759 | 100 | 10 | 0 | — | — |
| 760 | $100^c$ | 40 | 20(40) | — | — |
| 761 | $0^d$ | 90 | 0 | — | — |
| 762 | 100 | 40 | 0 | — | — |
| 763 | 100 | 90 | 0 | — | — |
| 764 | 80 | 80 | 0 | 0 | 50(90) |
| 765 | 100 | 10 | 0 | 40(100) | 100 |
| 766 | 100 | 20 | 20 | 0(20) | 100 |
| 767 | 100 | 0 | 0 | 0 | 0 |
| 768 | 50 | 10 | 40 | 0 | 0 |
| 769 | 100 | 20 | 20 | 0(20) | 0 |
| 770 | 50 | 30 | 20 | 0(20) | 0 |
| 771 | $50^c$ | 0 | 0 | 0(20) | 0 |
| 772 | 90 | 10 | 0 | 0(20) | 0 |
| 773 | 20 | 40 | 0 | 0 | 0 |
| 774 | 100 | 0 | 20 | 20 | 90 |

TABLE XX-continued

Initial Biological Evaluations

| Ex. No. | Foliar Application Test Species | | | Soil Application Test Species | |
|---|---|---|---|---|---|
| | SAW | MBB | BW | MBB | SAW |
| 775 | 100 | 30 | 0 | 0 | 20(30) |
| 776 | 40 | 0 | 0 | 0 | 0 |
| 777 | 60c | 30a,c | 20c | 0 | 0 |
| 778 | 100 | 10 | 0 | 0 | 0 |
| 779 | 90 | 20 | 0 | 0 | 0 |
| 780 | 100 | 0 | 0 | 0 | 0 |
| 781 | 100 | 80 | 0 | 40(100) | 100 |
| 782 | 40 | 70 | 0 | 0(20) | 40 |
| 783 | 100 | 10 | 0 | 0 | 10 |
| 784 | 100 | 30 | 0 | 0 | 0 |
| 785 | 100 | 20 | 0 | 40(0) | 80(100) |
| 786 | 60 | 0 | 0 | 0 | 0 |
| 787 | 30 | 30 | 0 | — | — |
| 788 | 70 | 30 | 0 | — | — |
| 789 | 100 | 0 | 0 | — | — |
| 790 | 100 | 90 | 0 | — | — |
| 791 | 20c | 10 | 0 | 0 | 0 |
| 792 | 0d | 10a,c | 0c | 0 | 0 |
| 793 | 20 | 0 | 0 | — | — |
| 794 | 0d | 10 | 0 | 0 | 0 |
| 795 | 100 | 30 | 0 | — | — |
| 796 | 100 | 30 | 0 | — | — |
| 797 | 100 | 0 | 0 | — | — |
| 798 | 100 | 10 | 0 | — | — |
| 799 | 0a | 0a | 0 | 0 | 0 |
| 800 | 30a | 30a | 20 | 0 | 0 |
| 801 | 20c | 10 | 0 | 0 | 0 |
| 802 | 100 | 40 | 0 | 80 | 80(100) |
| 803 | 100 | 60 | 0 | 0 | 0 |
| 804 | 100 | 30 | 0 | 0 | 0 |
| 805 | 100 | 30 | 0 | — | — |
| 806 | 100 | 20 | 0 | — | — |
| 807 | 100 | 0 | 0 | — | — |
| 808 | 100 | 20 | 0 | — | — |
| 809 | 100 | 0 | 0 | — | — |
| 810 | 100 | 50 | 0 | — | — |
| 811 | 50 | 0 | 0 | — | — |
| 812 | 100 | 0 | 60 | — | — |
| 813 | 100 | 0 | 0 | — | — |
| 814 | 100 | 20 | 20 | — | — |
| 815 | 100 | 0 | 0 | — | — |
| 816 | 100 | 0 | 0 | — | — |
| 817 | 100 | 30 | 0 | — | — |
| 818 | 100 | 40 | 0 | — | — |
| 819 | 30 | 10 | 0 | 0(20) | 0 |
| 820 | 100 | 0a | 0 | 0(20) | 0 |
| 821 | 100a | 70 | 0 | 0(20) | 0 |
| 822 | 100a | 100 | 40(100) | 0(100) | 100 |
| 823 | 100a | 0a | 0 | — | — |
| 824 | 0d | 10 | 0 | — | — |
| 825 | 100a | 30 | 0 | — | — |
| 826 | 100a | 0a | 0 | — | — |
| 827 | 60 | 10a | 0 | — | — |
| 828 | 0a | 0a | 20 | — | — |
| 829 | 100 | 100 | 0 | 20(80) | 80(90) |
| 830 | 0 | 10 | 0 | 0 | 20 |
| 831 | 100 | 0 | 0 | 0 | 0 |
| 832 | 100 | 0 | 0 | 0 | 0 |
| 833 | 60 | 0 | 0 | 0 | 20 |
| 834 | 0 | 0 | 40 | 0 | 0 |
| 835 | 100 | 90 | 0 | 60 | 100 |
| 836 | 0 | 50 | 0 | 0 | 0 |
| 837 | 0 | 0 | 20 | 0 | 0 |
| 838 | 0 | 100 | 0 | 0 | 70 |
| 839 | 100 | 40 | 0 | 0 | 100 |
| 840 | 0 | 0 | 0 | 0 | 0 |
| 841 | 0 | 0 | 20 | 0(20) | 0 |
| 842 | 10 | 20 | 0 | 0(20) | 0 |
| 843 | 40 | 50 | 0 | 20(60) | 50(90) |
| 844 | 0 | 10 | 0 | 0 | 0 |
| 845 | 70 | 10 | 0 | 0(40) | 0 |
| 846 | 40 | 0 | 40 | 20 | 0 |
| 847 | 0 | 30 | 0 | 20 | 0 |
| 848 | 40 | 30 | 20 | 0(60) | 20(80) |
| 849 | 0 | 10 | 40 | 0 | 0 |
| 850 | 10 | 0 | 0 | 0 | 0 |
| 851 | 0 | 0 | 0 | 20 | 0 |
| 852 | 0 | 0 | 0 | 20(40) | 0 |
| 853 | 0 | 0 | 0 | 0 | 0 |
| 854 | 0 | 60 | 0 | 60 | 0 |
| 855 | 0 | 90 | 0 | 0 | 0 |
| 856 | 100 | 0 | 0 | 0 | 0 |
| 857 | 50 | 20 | 20 | 0(20) | 0 |
| 858 | 0 | 10 | 0 | 0 | 0 |
| 859 | 0 | 60 | 0 | 60 | 0 |
| 860 | 0 | 10 | 0 | 0 | 0 |
| 861 | 0 | 10 | 0 | 0 | 0 |
| 862 | 0 | 10 | 0 | 0(40) | 0 |
| 863 | 0 | 20 | 0 | 0 | 0 |
| 864 | 40 | 0 | 0 | 0 | 0 |
| 865 | 100 | 50 | 0 | 0 | 0(20) |
| 866 | 0 | 100 | 0 | 0 | 0 |
| 867 | 0 | 100 | 0 | 0 | 0 |
| 868 | 10 | 0 | 20 | 0 | 0 |
| 869 | 0 | 0 | 0 | 40 | 0 |
| 870 | 100 | 10 | 0 | 0 | 80(90) |
| 871 | 0 | 0 | 0 | 0 | 0 |
| 872 | 0 | 10 | 20 | 0 | 0 |
| 873 | 0 | 20 | 0 | — | — |
| 874 | 100 | 0 | 0 | — | — |
| 875 | 20 | 20 | 0 | — | — |
| 876 | 100 | 20 | 0 | — | — |
| 877 | 80 | 10 | 0 | — | — |
| 878 | 100 | 10 | 0 | — | — |
| 879 | 100 | 10 | 0 | — | — |
| 880 | 100 | 10 | — | — | — |
| 881 | 80 | 80 | 40 | 0 | 0 |
| 882 | 100 | 0 | 0 | — | — |
| 883 | 90 | 50 | 0 | 0(20) | 40(100) |
| 884 | 0 | 0 | 0 | — | — |
| 885 | 90 | 30 | 0 | — | — |
| 886 | 100 | 10 | 0 | — | — |
| 887 | 100 | 100 | 0 | — | — |
| 888 | 30 | 100 | 0 | — | — |
| 889 | 100 | 40 | 0 | — | — |
| 890 | 100 | 70 | 0 | — | — |
| 891 | 100 | 20 | 0 | — | — |
| 892 | 100 | 30 | 20 | — | — |
| 893 | 0 | 40 | 0 | — | — |
| 894 | 100 | 0 | 0 | — | — |
| 895 | 100 | 20 | 0 | — | — |
| 896 | 100 | 30 | 0 | — | — |
| 897 | 100 | 0 | 0 | — | — |
| 898 | 100 | 30 | 0 | — | — |
| 899 | 100 | 10 | 0 | — | — |
| 900 | 100 | 0 | 0 | — | — |
| 901 | 100 | 10 | 0 | — | — |
| 902 | 100 | 0 | 0 | — | — |
| 903 | 100 | 30 | 0 | — | — |
| 904 | 100 | 0 | 0 | — | — |
| 905 | 100 | 0 | 0 | — | — |
| 906 | 0 | 10 | 0 | — | — |
| 907 | 100 | 0 | 0 | — | — |
| 908 | 100 | 30 | 40 | — | — |
| 909 | 100 | 30 | 0 | — | — |
| 910 | 100 | 50 | 0 | — | — |
| 911 | 100 | 0 | 0 | — | — |
| 912 | 100 | 10 | 0 | — | — |
| 913 | 100 | 0 | 0 | — | — |
| 914 | 0 | 0 | 0 | 0 | 0 |
| 915 | 90 | 10 | 0 | 0 | 0 |
| 916 | 0 | 0 | 0 | 0 | 0 |
| 917 | 0 | 0 | 20 | 0 | 0 |
| 918 | 0 | 0 | 0 | 0 | 0 |

TABLE XX-continued

Initial Biological Evaluations

| Ex. No. | Foliar Application Test Species | | | Soil Application Test Species | |
|---|---|---|---|---|---|
| | SAW | MBB | BW | MBB | SAW |
| 919 | 100 | 40 | 20 | 0(20) | 0 |
| 920 | 0 | 0 | 0 | 0 | 0 |
| 921 | 0 | 90 | 20 | 20 | 0 |
| 922 | 0 | 0 | 0(40) | 0 | 0 |
| 923 | 0 | 30 | 0 | — | — |
| 924 | 0[a] | 10[a] | 0 | — | — |
| 925 | — | — | — | — | — |
| 926 | 0 | 100 | 20 | 0 | 60(100) |
| 927 | 0 | 0 | 0 | 0 | 20 |
| 928 | 20 | 30 | 0 | 0 | 20 |
| 929 | 0 | 60 | 0 | 0 | 0(20) |
| 930 | 0 | 80 | 0 | 0 | 0 |
| 931 | 0 | 100 | 0 | 20(20) | 20 |
| 932 | 100 | 40 | 0 | 40 | 0(20) |
| 933 | 0 | 0 | — | — | — |
| 934 | 100 | 100 | 0 | 20 | 0 |
| 935 | 0 | 0 | 0 | — | — |
| 936 | 0 | 40 | 0 | 0 | 40 |
| 937 | 0 | 10 | 0 | 0 | 40 |
| 938 | 0 | 0 | 0 | 0 | 20 |
| 939 | 0 | 0 | 0 | 0 | 0 |
| 940 | 10 | 10 | — | — | — |
| 941 | 0 | 10 | — | — | — |
| 942 | 0 | 0 | — | — | — |
| 943 | 0 | 0 | 0 | — | — |
| 944 | 0 | 0 | — | — | — |
| 945 | 0 | 0 | 0 | 0 | 0 |
| 946 | 0 | 20 | — | — | — |
| 947 | 0 | 20 | 0 | — | — |
| 948 | 0 | 20 | — | — | — |
| 949 | 0 | 10 | 0 | 0 | 20 |
| 950 | 0 | 0 | 0 | 0 | 0 |
| 951 | 0 | 0 | 0 | 0 | 20(40) |
| 952 | 0 | 20 | 0 | 0 | 0 |
| 953 | 0 | 0 | 0 | — | — |
| 954 | 0 | 0 | 20 | 0 | 0 |
| 955 | 0 | 0 | 20 | 0 | 20(40) |
| 956 | 40 | 10 | 0(20) | 0 | 0 |
| 957 | 40 | 60 | 0 | 0 | 0 |
| 958 | 0 | 0 | 0 | 0 | 0 |
| 959 | 0 | 0 | 0 | 0 | 20 |
| 960 | 0 | 0 | 0 | 0 | 0 |
| 961 | 0 | 100 | 40 | 0(20) | 0 |
| 962 | — | — | — | — | — |
| 963 | 0 | 50 | 0 | 20 | 0 |
| 964 | 20 | 100 | 0 | 20 | 0 |
| 965 | 0 | 60 | 60 | 20(40) | 0 |
| 966 | 0[a] | 0[a] | 0 | — | — |
| 967 | 0[a] | 0[a] | 0 | — | — |
| 968 | 0 | 30 | 0 | 0 | 20 |
| 969 | 0 | — | — | — | — |
| 970 | 0 | — | — | — | — |
| 971 | 0 | — | — | — | — |
| 972 | 0 | — | — | — | — |
| 973 | 0 | — | — | — | — |
| 974 | 0 | — | — | — | — |
| 975 | 0 | — | — | — | — |
| 976 | 10 | — | — | — | — |
| 977 | 0 | — | — | — | — |
| 978 | 60 | — | — | — | — |
| 979 | 100(80) | 0(20) | 0 | — | — |
| 980 | 100 | 0(30) | 0 | — | — |
| 981 | 100 | 0 | 0 | — | — |
| 982 | 100 | 10(40) | 0 | — | — |
| 983 | 0(30) | 10(20) | 0 | — | — |
| 984 | 30 | 10 | 0 | — | — |
| 985 | 0 | 20 | 0 | — | — |
| 986 | 0 | 0 | 0 | — | — |
| 987 | 0 | 0 | 0 | — | — |
| 988 | 0 | 0 | 0 | — | — |
| 989 | 0 | 0 | 0 | — | — |
| 990 | 0 | 30 | 0 | — | — |
| 991 | 0 | 0 | 0 | — | — |
| 992 | 0 | 0 | 0 | — | — |
| 993 | 0 | 0 | 0 | — | — |
| 994 | 0 | 0 | 0 | — | — |
| 995 | 0 | 0 | 0 | — | — |
| 996 | 20 | 20 | 0 | — | — |
| 997 | 0 | 30 | 0 | — | — |
| 998 | 0 | 0 | 0 | — | — |
| 999 | 0 | 0 | 0 | — | — |
| 1000 | 0 | 0 | 0 | — | — |
| 1001 | 0 | 10 | 0 | — | — |
| 1002 | 0 | 0 | 20 | — | — |
| 1003 | 0 | 10 | 0 | — | — |
| 1004 | 0 | 0 | 0 | — | — |
| 1005 | 0 | — | — | — | — |
| 1006 | 0 | — | — | — | — |
| 1007 | 100 | 0 | 0 | — | — |
| 1008 | 0 | 20 | 0 | — | — |
| 1009 | 0 | 30 | 0 | — | — |
| 1010 | 0 | 20 | 0 | — | — |
| 1011 | 0 | 0 | 0 | — | — |
| 1012 | 0 | 0 | 0 | — | — |
| 1013 | 0 | 40 | 0 | — | — |
| 1014 | 0 | 0 | 20 | — | — |
| 1015 | 0 | 10 | 0 | — | — |
| 1016 | 100 | 0 | 0 | — | — |
| 1017 | 100 | 40 | 0 | — | — |
| 1018 | 10 | 0 | 20 | — | — |

Not all compounds were tested by soil application. The results of the compounds tested are reported.

It should be understood that the instant specification and examples are set forth by way of illustration and not limitation, and that various modifications and changes may be made without departing from the spirit and scope of the present invention as defined by the appended claims.

We claim:

1. A compound of the formula

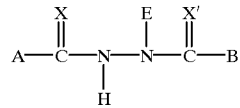

wherein

X and X' are independently selected from O, S and NR, wherein R is selected from hydrogen and $(C_1-C_6)$alkyl;

E is selected from;

1) an unsubstituted tertiary-carbon containing $(C_4-C_{10})$ alkyl or substituted tertiary-carbon containing $(C_3-C_{10})$ alkyl wherein the substituents are independently selected from 1 to 4 alkenyl, cyano, cycloalkyl, halogen, and phenyl and wherein the sum of non-hydrogen atoms in E is from 4 to 14, E does not have a chain length of non-hydrogen atoms greater than 5, and E does not contain more than one cyano group; and 2) an unsubstituted or substituted non-tertiary-carbon containing $(C_4-C_{10})$ alkyl wherein the substituents are independently selected from 1 to 4 alkenyl, cyano, cycloalkyl, halogen, phenyl, and trimethylsilyl and wherein the sum of non-hydrogen atoms in E is from 5 to 14, E does not have a chain length of non-hydrogen atoms greater than 5, and E does not contain more than one cyano group;

A and B are independently selected from;
1) unsubstituted or substituted naphthyl wherein the substituents are independently selected from 1 to 3 halo; nitro; $(C_1-C_4)$alkoxy; $(C_1-C_4)$alkyl; and amino;
2) unsubstituted or substituted phenyl wherein the substituents are independently selected from 1 to 5 halo; nitro; cyano; hydroxy; $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; $(C_1-C_6)$haloalkoxy; $(C_1-C_6)$alkoxy$(C_1-C_6)$alkyl; $(C_1-C_6)$alkoxy$(C_1-C_6)$alkoxy; $(C_1-C_6)$alkylthio$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$alkyl, or $(C_1-C_4)$alkoxy; $(C_2-C_6)$alkenyloxy; $(C_2-C_6)$alkenylcarbonyl; $(C_2-C_6)$alkenyloxycarbonyloxy; $(C_2-C_6)$alkynyl optionally substituted with halo or $(C_1-C_4)$alkyl; carboxy; $(C_1-C_6)$alkylcarboxy$(C_1-C_6)$alkyl); $(C_1-C_6)$alkylcarbonyl; $(C_1-C_6)$haloalkylcarbonyl; $(C_1-C_6)$alkoxycarbonyl; $(C_1-C_6)$haloalkoxycarbonyl; $(C_1-C_6)$alkanoyloxy (—OCOR); $(C_1-C_6)$alkoxycarbonyl$(C_1-C_6)$alkoxy; amino (—NRR'); carboxamido (—CONRR'); $(C_2-C_6)$alkenylcarbonylamino; $(C_1-C_6)$hydroxyalkylaminocarbonyl; aminocarbonyloxy (—OCONRR'); amido (—NRCOR); alkoxycarbonylamino (—NRCO_2R'); thiocyanato; isothiocyanato; $(C_1-C_6)$thiocyanatoalkyl; $(C_1-C_6)$alkylthio; sulfoxide (—S(O)R); sulfonyl (—SO_2R); alkylsulfonyloxy (—OSO_2R); sulfonamide (—SO_2NRR'); alkylthiocarbonyl (—CSR); thioamido (—NRCSR'); unsubstituted or substituted phenyl wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino, and $(C_1-C_4)$dialkylamino having independently the stated number of carbon atoms in each alkyl group; unsubstituted or substituted phenoxy wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino, and $(C_1-C_4)$dialkylamino having independently the stated number of carbon atoms in each alkyl group; unsubstituted or substituted benzoyl wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino and $(C_1-C_4)$dialkylamino having independently the stated number of carbon atoms in each alkyl group; benzoyloxy$(C_1-C_6)$alkyl; phenylthio$(C_1-C_6)$alkyl wherein the phenyl ring is unsubstituted or substituted with 1 to 3 substituents independently selected from halo, cyano, nitro, $(C_1-C_4)$alkyl, $(C_1-C_4)$haloalkyl, $(C_1-C_4)$alkoxy, carboxy, amino, $(C_1-C_4)$alkylamino, and $(C_1-C_4)$dialkylamino having independently the stated number of carbon atoms in each alkyl group; imino (—CR=N—R^2) wherein R^2 is selected from hydroxy, $(C_1-C_4)$alkyl, $(C_1-C_4)$alkoxy, amino (—NRR'), phenylamino, carbonyl (—COR), and benzoyl; acetylthiosemicarbazone; or when two adjacent positions on the phenyl ring are substituted with alkoxy groups, these groups, together with the carbon atoms to which they are attached, may be joined to form a 5 or 6 membered dioxolano or dioxano heterocyclic ring; and
3) unsubstituted or substituted five-membered heterocycle selected from furyl, thienyl, triazolyl, pyrrolyl, isopyrrolyl, pyrazolyl, isoimidazolyl, thiazolyl, isothiazolyl, oxazolyl, and isooxazolyl wherein the substituents are independently selected from 1 to 3 halo; nitro; hydroxy; $(C_1-C_6)$alkyl; $(C_1-C_6)$alkoxy; carboxy; $(C_1-C_6)$alkoxycarbonyl (—CO_2R); $(C_1-C_6)$alkylcarboxy$(C_1-C_6)$alkyl (—RCO_2R'); carboxamido (—CONRR'); amino (—NRR'); amido (—NRCOR'); $(C_1-C_6)$alkylthio; or unsubstituted or substituted phenyl wherein the substituents are independently selected from one to three halo, nitro, $(C_1-C_6)$alkyl, $(C_1-C_6)$haloalkyl; $(C_1-C_6)$alkoxy; $(C_1-C_6)$haloalkoxy; carboxy, $(C_1-C_4)$alkoxycarbonyl (—CO_2R); or amino (—NRR');

wherein R, R' and R'' are selected from hydrogen and $(C_1-C_6)$alkyl;

and agronomically acceptable salts thereof;
provided that:
1) when X and X' are O and A and B are unsubstituted phenyl, then E is other than 2-methylpropyl (—CH_2CH(CH_3)_2); 3-methylbutyl (—CH_2CH_2CH(CH_3)_2); neopentyl (2,2-dimethylpropyl; —CH_2C(CH_3)_3) or cyclohexylmethyl (—CH_2C_6H_{11}); or
2) when X and X' are O, and A is unsubstituted phenyl or phenyl substituted with 1 to 2 substituents independently selected from $(C_1-C_6)$alkyl and halo, and B is unsubstituted phenyl or phenyl substituted with 1 to 2 substituents independently selected from halo, nitro, and $(C_1-C_6)$alkyl, then E is other than halo $(C_2-C_6)$alkyl; or
3) when X and X' are O, and E is t-butyl (—C(CH_3)_3), and A is unsubstituted phenyl, then B is other than 4-nitrophenyl; or
4) when one of A and B is an unsubstituted or substituted five-membered heterocycle then the other of A and B is other than an unsubstituted or substituted five-membered heterocycle; or
5) when A is phenyl substituted with from two to three substituents in the 2, 3, and 4 positions wherein the 3 substituent is $(C_1-C_6)$alkoxy, the 2 substituent is selected from halo and $(C_1-C_6)$alkyl, and, when substituted, the 4 substituent is $(C_1-C_6)$alkyl then B is other than unsubstituted phenyl or phenyl substituted with from one to four substituents in the 2, 3, 4, and 5 positions wherein the 2 substituent is selected from halo, and $(C_1-C_6)$alkyl and the 3, 4, and 5 substituents are independently selected from bromo, chloro, fluoro, and $(C_1-C_6)$alkyl.

2. The compound of claim 1 wherein

X and X' are independently selected from O and S;

E is selected from
(1) an unsubstituted or substituted tertiary-carbon containing $(C_3-C_{10})$ alkyl wherein the substituents are independently selected from 1 to 4 alkenyl, cyano, cycloalkyl, halogen, and phenyl and wherein the sum of non-hydrogen atoms in E is from 4 to 14, E does not have a chain length of non-hydrogen atoms greater than 5, and E does not contain more than one cyano group; and
(2) an unsubstituted or substituted non-tertiary-carbon containing $(C_4-C_{10})$ alkyl wherein the substituents are independently selected from 1 to 4 alkenyl, cyano, cycloalkyl, halogen, phenyl, and trimethylsilyl and wherein the sum of non-hydrogen atoms in E is from 5 to 14; and A and B are independently selected from (1) unsubstituted or substituted naphthyl wherein the substituents are independently selected from 1 to 3 halo; nitro; $(C_1-C_4)$alkoxy; $(C_1-C_4)$alkyl; and amino; and (2) unsubstituted or substituted phenyl wherein the substituents are independently selected from 1 to 5 halo; nitro; cyano; hydroxy; $(C_1-C_6)$alkyl; $(C_1-C_6)$haloalkyl; $(C_1-C_6)$cyanoalkyl; $(C_1-C_6)$hydroxyalkyl; $(C_1-C_6)$alkoxy; $(C_1-C_6)$haloalkoxy; $(C_1-C_6)$alkoxy$(C_1-C_6)$alkyl; $(C_1-C_6)$alkoxy$(C_1-C_6)$alkoxy; $(C_1-C_6)$alkylthio$(C_1-C_6)$alkoxy; $(C_1-C_6)$alkanoyloxy$(C_1-C_6)$alkyl; $(C_2-C_6)$alkenyl optionally substituted with halo, cyano, $(C_1-C_4)$alkyl, or $(C_1-C_4)$alkoxy; $(C_2-C_6)$alkenyloxy; $(C_2-C_6)$alkenylcarbonyl; $(C_2-C_6)$alkenyloxycarbonyloxy; $(C_2-C_6)$alkynyl optionally substituted with halo or $(C_1-C_4)$alkyl; carboxy; $(C_1-C_6)$alkylcarboxy$(C_1-C_6)$alkyl); $(C_1-C_6)$alkylcarbonyl; $(C_1-C_6)$haloalkylcarbonyl; $(C_1-C_6)$alkoxycarbonyl; $(C_1-C_6)$haloalkoxycarbonyl; $(C_1-C_6)$alkanoyloxy (—OCOR); $(C_1-C_6)$alkoxycarbonyl$(C_1-C_6)$alkoxy; amino (—NRR'); carboxamido (—CONRR'); $(C_2-C_6)$alkenylcarbonylamino; $(C_1-C_6)$hydroxyalkylaminocarbonyl; aminocarbonyloxy (—OCONRR'); amido (—NRCOR'); alkoxycarbonylamino (—NRCO$_2$R'); thiocyanato; isothiocyanato; $(C_1-C_6)$thiocyanatoalkyl; $(C_1-C_6)$alkylthio; sulfoxide (—S(O)R); sulfonyl (—SO$_2$R); alkylsulfonyloxy (—OSO$_2$R); sulfonamide (—SO$_2$NRR'); alkylthiocarbonyl (—CSR); thioamido (—NRCSR'); unsubstituted or substituted phenyl wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino, and $(C_1-C_4)$dialkylamino having independently the stated number of carbon atoms in each alkyl group; unsubstituted or substituted phenoxy wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino, and $(C_1-C_4)$dialkylamino having independently the stated number of carbon atoms in each alkyl group; unsubstituted or substituted benzoyl wherein the substituents are independently selected from 1 to 3 halo, cyano, nitro, $(C_1-C_4)$alkyl, $(C_1-C_4)$haloalkyl, $(C_1-C_4)$alkoxy, carboxy, amino, $(C_1-C_4)$alkylamino and $(C_1-C_4)$dialkylamino having independently the stated number of carbon atoms in each alkyl group; benzoyloxy$(C_1-C_6)$alkyl; phenylthio$(C_1-C_6)$alkyl wherein the phenyl ring is unsubstituted or substituted with 1 to 3 substituents independently selected from halo, cyano, nitro, $(C_1-C_4)$alkyl, $(C_1-C_4)$haloalkyl, $(C_1-C_4)$alkoxy, carboxy, amino, $(C_1C_4)$alkylamino, and $(C_1-C_4)$dialkylamino having independently the stated number of carbon atoms in each alkyl group; imino (—CR=N—R$^2$) wherein R$^2$ is selected from hydroxy, $(C_1-C_4)$alkyl, $(C_1-C_4)$alkoxy, amino (—NRR'), phenylamino, carbonyl (—COR), and benzoyl; acetylthiosemicarbazone; or when two adjacent positions on the phenyl ring are substituted with alkoxy groups, these groups, together with the carbon atoms to which they are attached, may be joined to form a 5 or 6 membered dioxolano or dioxano heterocyclic ring;

or agronomically acceptable salts thereof.

3. The compound of claim 1 wherein

X and X' are O or S;

E is branched $(C_3-C_8)$alkyl; and

A and B are the same or different unsubstituted naphthyl or unsubstituted or substituted phenyl wherein the substituents are independently selected from 1 to 5 halo; nitro; cyano; $(C_1-C_4)$alkyl; $(C_1-C_4)$haloalkyl; $(C_1-C_4)$cyanoalkyl; $(C_1-C_4)$alkoxy; $(C_1-C_4)$alkoxyalkyl having independently the stated number of carbon atoms in each alkyl group; carbonyl (—COR); $(C_1-C_4)$alkoxycarbonyl; $(C_1-C_4)$alkanoyloxy; thiocyanato; unsubstituted or substituted phenyl having one or two of the same or different halo, nitro, $(C_1-C_4)$alkyl, $(C_1-C_4)$alkoxy, carboxy, amino, $(C_1-C_4)$alkylamino or $(C_1-C_4)$dialkylamino having independently the stated number of carbon atoms in each alkyl group; or phenoxy where the phenyl ring is unsubstituted or substituted with one or two of the same or different halo, nitro, $(C_1-C_4)$alkyl, $(C_1-C_4)$alkoxy, carboxy, amino, $(C_1-C_4)$alkylamino or $(C_1-C_4)$dialkylamino having independently the stated number of carbon atoms in each alkyl group where R is hydrogen or $(C_1-C_4)$alkyl;

or agronomically acceptable salts thereof.

4. The compound of claim 1 wherein

X and X' are O;

E is branched $(C_4-C_7)$alkyl; and

A and B are independently selected from unsubstituted or substituted phenyl wherein the substituents are independently selected from 1 to 3 halo, nitro, $(C_1-C_4)$alkyl, $(C_1-C_4)$alkoxy, or $(C_1-C_4)$haloalkyl;

or agronomically acceptable salts thereof.

5. The compound of claim 1 wherein

X and X' are O;

E is selected from tertiary butyl, neopentyl (2,2-dimethylpropyl), and 1,2,2-trimethylpropyl; and A and B are independently selected from unsubstituted phenyl or substituted phenyl wherein the substituents are independently selected from 1 to 3 chloro, fluoro, bromo, iodo, nitro, methyl, ethyl, methoxy, and trifluoromethyl;

or agronomically acceptable salts thereof.

6. The compound of claim 3 wherein

A is a substituted phenyl wherein the substituents are selected from 1 substituent in the 4-position and 1 substituent in each of the 2 and 3-positions; and B is phenyl substituted with from 1 to 3 substituents.

7. The compound of claim 3 wherein

A is a substituted phenyl wherein the substituents are selected from 1 substituent in the 4-position and 1 substituent in each of the 2 and 3-positions; and B is phenyl substituted with 1 substituent in each of the 3 and 5-positions.

8. A compound of the formula

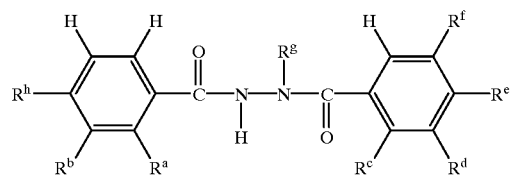

wherein $R^a$ is selected from hydrogen, halo and $(C_1-C_6)$alkyl;

$R^b$ is selected from hydrogen, unsubstituted $(C_1-C_6)$alkoxy, and halo substituted $(C_1-C_6)$alkoxy;

$R^c$ is selected from hydrogen, halo, $(C_1-C_6)$alkyl, $(C_1-C_6)$alkoxy, $(C_1-C_6)$alkoxy$(C_1-C_6)$alkyl, and nitro;

$R^d$, $R^e$, and $R^f$ are independently selected from hydrogen, bromo, chloro, fluoro, $(C_1-C_6)$alkyl, $(C_1-C_6)$alkoxy, and $(C_1-C_6)$alkoxy$(C_1-C_6)$alkyl;

$R^g$ is a branched $(C_4-C_6)$alkyl; and $R^h$ is selected from hydrogen, $(C_1-C_6)$alkoxy, $(C_1-C_6)$alkyl, and, when taken together with $R^b$, methylenedioxy, 1,2-ethylenedioxy, 1,2-ethyleneoxy, and 1,3-propyleneoxy wherein an oxo atom is located at the $R^b$ position; and the substituent pairs selected from $R^c$ and $R^d$, and $R^d$ and $R^e$, and $R^e$ and $R^f$ when taken together can be methylenedioxy or 1,2-ethylenedioxy;

provided that;

one of $R^a$ and $R^b$ and $R^h$ must be other than hydrogen and one of $R^c$ and $R^d$ and $R^e$ and $R^f$ must be other than hydrogen; and when $R^b$ is $(C_1-C_6)$alkoxy, and $R^a$ is selected from halo and $(C_1-C_6)$alkyl, and $R^h$ is selected from hydrogen and $(C_1-C_6)$alkyl then the phenyl ring substituted with $R^c$, $R^d$, $R^e$, and $R^f$ is other than substituted phenyl wherein $R^c$ is selected from hydrogen, halo, and $(C_1-C_6$alkyl and $R^d$, $R^e$, and $R^f$ are independently selected from hydrogen, bromo, chloro, fluoro, and $(C_1-C_6)$alkyl;

and agronomically acceptable salts thereof.

9. The compound of claim 8 wherein $R^a$ and $R^b$ are other than hydrogen and $R^h$ is hydrogen or $R^h$ is other than hydrogen and $R^a$ and $R^b$ are hydrogen.

10. The compound of claim 8 wherein $R^c$ and $R^e$ are hydrogen; and $R^d$ and $R^f$ are other than hydrogen.

11. The compound of claim 8 wherein $R^a$ and $R^b$ are other than hydrogen and $R^h$ is hydrogen or $R^h$ is other than hydrogen and $R^a$ and $R^b$ are hydrogen;

$R^c$ and $R^e$ are hydrogen; and $R^d$ and $R^f$ are other than hydrogen.

12. The compound of claim 8 wherein $R^a$ and $R^b$ are hydrogen, $R^c$ is hydrogen, $R^d$ is methyl, $R^e$ is hydrogen, $R^f$ is methyl, $R^g$ is t-butyl, and $R^h$ is ethyl; or $R^a$, $R^b$, $R^c$, $R^d$, $R^e$, and $R^f$ are hydrogen, $R^g$ is t-butyl, and $R^h$ is chloro.

* * * * *